US008993847B2

(12) United States Patent
Allen et al.

(10) Patent No.: US 8,993,847 B2
(45) Date of Patent: Mar. 31, 2015

(54) DROUGHT TOLERANT PLANTS AND RELATED CONSTRUCTS AND METHODS INVOLVING GENES ENCODING FERROCHELATASES

(75) Inventors: Stephen M. Allen, Wilmington, DE (US); Stanley Luck, Wilmington, DE (US); Jeffrey Mullen, Maple Plain, MN (US); Hajime Sakai, Newark, DE (US); Sobhana Sivasankar, Urbandale, IA (US); Scott V. Tingey, Wilmington, DE (US); Robert Wayne Williams, Hockessin, DE (US)

(73) Assignees: Pioneer Hi Bred International Inc., Johnston, IA (US); E I du Pont de Nemours and Company, Wilmington, DE (US)

( * ) Notice: Subject to any disclaimer, the term of this patent is extended or adjusted under 35 U.S.C. 154(b) by 426 days.

(21) Appl. No.: 13/430,732

(22) Filed: Mar. 27, 2012

(65) Prior Publication Data
US 2012/0180159 A1    Jul. 12, 2012

Related U.S. Application Data

(62) Division of application No. 12/887,724, filed on Sep. 22, 2010, now Pat. No. 8,158,859, which is a division of application No. 12/326,206, filed on Dec. 2, 2008, now Pat. No. 7,812,223.

(60) Provisional application No. 60/991,859, filed on Dec. 3, 2007.

(51) Int. Cl.
*A01H 5/00* (2006.01)
*C12N 9/88* (2006.01)
*C12N 15/82* (2006.01)
*A01H 1/00* (2006.01)
*C07H 21/04* (2006.01)
*C07K 14/415* (2006.01)
*C12N 15/00* (2006.01)
*C12N 15/63* (2006.01)

(52) U.S. Cl.
CPC .............. *C12N 9/88* (2013.01); *C12N 15/8273* (2013.01); *C12Y 499/01001* (2013.01)
USPC ........................................................ 800/295

(58) Field of Classification Search
None
See application file for complete search history.

(56) References Cited

U.S. PATENT DOCUMENTS 7,625,738 B1    12/2009  CaJacob et al.
2004/0010815 A1  1/2004  Lange et al.
2004/0031072 A1  2/2004  LaRosa et al.
2004/0034888 A1  2/2004  Liu et al.
2006/0150283 A1  7/2006  Alexandrov et al.

FOREIGN PATENT DOCUMENTS

JP    2001190168        7/2001
JP    2005185101        7/2005
WO    2007/030001 A1    3/2007

OTHER PUBLICATIONS

Jaillon et al., Nature 449:463-467, Sep. 2007, UniProt Database, Acc. No. D7SWL7.*
Cushman et al., Genomic Approaches to Plant Stress Tolerance. Curr. Opin. Plant Biol., vol. 3(2), p. 117-124, 2000.
Bray et al., Molecular Responses to Water Deficit. Plant Physiol., vol. 103, p. 1035-1040, 1993.
Zhu et al., Molecular Aspects of Osmotic Stress in Plants. Critical Reviews in Plant Sciences, vol. 16(3), p. 253-277, 1997.
Thomashow, Plant Cold Acclimation: Freezing Tolerance Genes and Regulatory Mechanisms. Annu Rev Plant Physiol. Plant Mol. Biol., vol. 50, p. 571-599, 1999.
Xiong et al., Molecular and Genetic Aspects of Plant Responses to Osmotic Stress. Plant, Cell and Environment, vol. 25, p. 131-139, 2002.
Weigel et al., Activation Tagging in *Arabidopsis*. Plant Physiol., vol. 122, p. 1003-1013, 2000.
National Center for Biotechnology Information General Identifier No. 511080, Accession No. X73417, Apr. 18, 2005, Smith et al., Isolation of a cDNA Encoding Chloroplast Ferrochelatase from *Arabidopsis thaliana* by Functional Complementation of a Yeast Mutant.
National Center for Biotechnology Information General Identifier No. 511081, Accession No. CAA51819, Apr. 18, 2005, Smith et al., Isolation of a cDNA Encoding Chloroplast Ferrochelatase from *Arabidopsis thaliana* by Functional Complementation of a Yeast Mutant.
National Center for Biotechnology Information General Identifier No. 30684569, Accession No. NM_128592, May 22, 2008, *Arabidopsis thaliana* Ferrochelatase II mRNA, Complete cds.
National Center for Biotechnology Information General Identifier No. 15227742, Accession No. NP_180598, May 22, 2008, Ferrochelatase II (*Arabidopsis thaliana*).
National Center for Biotechnology Information General Identifier No. 2623989, Accession No. Y13156, Apr. 18, 2005, Chow et al., Ferrochelatase is Encoded by two Genes in *Arabidopsis*.
National Center for Biotechnology Information General Identifier No. 2623990, Accession No. CAA73614, Apr. 18, 2005, Chow et al., Ferrochelatase is Encoded by Two Genes in *Arabidopsis*.
National Center for Biotechnology Information General Identifier No. 2460251, Accession No. AAB71887, Oct. 2, 1997, Hansson et al., Six Barley Genes Encoding Enzymes Involved in Chlorophyll and Heme Synthesis: Chromosomal Locations and Genomic Sequence of the Ferrochelatase Gene.

(Continued)

*Primary Examiner* — Phuong Bui

(57) ABSTRACT

Isolated polynucleotides and polypeptides and recombinant DNA constructs useful for conferring drought tolerance, compositions (such as plants or seeds) comprising these recombinant DNA constructs, and methods utilizing these recombinant DNA constructs. The recombinant DNA construct comprises a polynucleotide operably linked to a promoter that is functional in a plant, wherein said polynucleotide encodes a ferrochelatase.

8 Claims, 27 Drawing Sheets

(56) References Cited

OTHER PUBLICATIONS

National Center for Biotechnology Information General Identifier No. 113631036, Accession No. BAF24717, May 19, 2007, Matsumoto et al., The Rice Annotation Project Database (RAP-DB): Hub for *Oryza sativa* ssp.Japonica Genome Information.

National Center for Biotechnology Information General Identifier No. 147818793, Accession No. CAN67281, Feb. 5, 2008, Velasco et al., A High Quality Draft Consensus Sequence of the Genome of a Heterozygous Grapevine Variety.

National Center for Biotechnology Information General Identifier No. 115463419, Accession No. NP_001055309, Feb. 14, 2008, Ohyanagi et al., The Rice Annotation Project Database (RAP-DB): Hub for *Oryza sativa*.

National Center for Biotechnology Information General Identifier No. 12082085, Accession No. BAB20760, Feb. 14, 2002, Suzuki et al., Two Types of Ferrochelatase in Photosynthetic and Nonphotosynthetic Tissues of Cucumber: Their Difference in Phylogeny, Gene Expression and Localization.

National Center for Biotechnology Information General Identifier No. 15147828, Accession No. CAC50871, Aug. 17, 2005, Papenbrock et al., Impaired Expression of the Plastidic Ferrochelatase by Antisense RNA Synthesis Leads to a Necrotic Phenotype of Transformed Tobacco Plants.

National Center for Biotechnology Information General Identifier No. 1708186, Accession No. P54225, Jan. 20, 2009, Kaneko et al., Sequence Analysis of the Genome of the Unicellular *Cyanobacterium synechocystis* sp. Strain PCC6803. I. Sequence Features in the 1 Mb Region from Map Positions 64% to 92% of the Genome.

Suzuki et al., Two Types of Ferrochelatase in Photosynthetic and Nonphotosynthetic Tissues of Cucumber, The Journal of Biological Chemistry, vol. 277, p. 4731-4737, 2002.

Smith et al., Isolation of a cDNA Encoding Chloroplast Ferrochelatase from *Arabidopsis thaliana* by Functional Complementation of a Yeast Mutant, The Journal of Biological Chemistry, vol. 269, p. 13405-13413, 1994.

Chow et al., Two Different Genes Encode Ferrochelatase in *Arabidopsis*: Mapping, Expression and Subcellular Targeting of the Precursor Proteins, The Plant Journal, vol. 15, p. 531-541, 1998.

Miyamoto et al., Nucleotide Sequences of cDNA Clones Encoding Ferrochelatase from Barley and Cucumber, Plant Physiology, vol. 105, p. 769-770, 1994.

Chow et al., A Single Precursor Protein for Ferrochelatase-I from *Arabidopsis* is Imported in Vitro into both Chloroplasts and Mitchondria, The Journal of Biological Chemistry, vol. 272, p. 27565-27571, 1997.

The Future of Agricultural Biotechnology, Environmental Effects of Transgenic Plants: The Scope and Adequacy of Regulation, Board on Agriculture and Natural Resources (BANR); Chapter 7, 2002.

Shinozaki et al., Gene Expression and Signal Transduction in Water-Stress Response. Plant Physiology, vol. 115, p. 327-334, 1997.

Jagdish P. Singh et al., Investigatin of the Effects of Atmospheric Conditions on the Quantification of Metal Hydrides Using Laser Induced Breakdown Spectroscopy, Society for Applied Spectroscopy, Jun. 1, 1996, pp. 764-773, vol. 50, No. 6.

Database EMBL, Accession No. D26105, Jan. 6, 1994, XP002517106.

Database EMBL, Accession No. D26106, Jan. 6, 1994, XP002517107.

\* cited by examiner

FIG. 10A
Multiple Alignment of Ferrochelatase-I Proteins

FIG. 10B
Multiple Alignment of Ferrochelatase-I Proteins

FIG. 10C
Multiple Alignment of Ferrochelatase-I Proteins

Percent Sequence Identities Between Ferrochelatase-I Proteins

FIG. 12A
Multiple Alignment of Ferrochelatase-II Proteins

FIG. 12B
Multiple Alignment of Ferrochelatase-II Proteins

FIG. 12C
Multiple Alignment of Ferrochelatase-II Proteins

Percent Sequence Identities Between Ferrochelatase-II Proteins

FIG. 14A
Evaluation of Individual Gaspe Flint Derived Maize Lines Transformed with PHP31419*

| Treatment | Event name | % area chg_start chronic - acute2 | % area chg_start chronic - end chronic | % area chg_start chronic - harvest | % area chg_start chronic - recovery 24hr | fv/fm_acute1 | fv/fm_acute2 |
|---|---|---|---|---|---|---|---|
| Reduce Water | EA2392.498.1.2 | ns | ns | ns | ns | ns | ns |
| Reduce Water | EA2392.498.1.3 | ns | ns | ns | ns | 0.089 | ns |
| Reduce Water | EA2392.498.1.5 | ns | ns | ns | ns | ns | ns |
| Reduce Water | EA2392.498.1.6 | 0.034 | 0.072 | 0.0004 | 0.079 | 0.014 | 0.003 |
| Well Water | EA2392.498.1.2 | ns | 0.037 | ns | 0.085 | ns | 0.030 |
| Well Water | EA2392.498.1.3 | ns | ns | 0.093 | (0.032) | ns | ns |
| Well Water | EA2392.498.1.5 | ns | 0.083 | ns | ns | 0.016 | ns |
| Well Water | EA2392.498.1.6 | 0.051 | ns | ns | ns | 0.001 | ns |

* Significant positive effect has P-value less than or equal to 0.1; significant negative effect is in parenthesis; "ns" when difference not significant

FIG. 14B
Evaluation of Individual Gaspe Flint Derived Maize Lines Transformed with PHP31419*

| Treatment | Event name | leaf rolling_harvest | leaf rolling_recovery 24hr | psii_acute1 | psii_acute2 | sgr - r2 > 0.9 | shoot dry weight | shoot fresh weight |
|---|---|---|---|---|---|---|---|---|
| Reduce Water | EA2392.498.1.2 | 0.065 | ns | ns | ns | 0.046 | (0.028) | ns |
| Reduce Water | EA2392.498.1.3 | ns | 0.019 | 0.024 | ns | ns | ns | (0.037) |
| Reduce Water | EA2392.498.1.5 | ns | 0.011 | ns | ns | ns | ns | ns |
| Reduce Water | EA2392.498.1.6 | 0.068 | 0.083 | 0.072 | 0.003 | 0.015 | ns | 0.009 |
| Well Water | EA2392.498.1.2 | ns | ns | ns | ns | ns | ns | ns |
| Well Water | EA2392.498.1.3 | ns | ns | 0.022 | ns | ns | (0.047) | (0.031) |
| Well Water | EA2392.498.1.5 | ns | ns | 0.007 | ns | ns | ns | ns |
| Well Water | EA2392.498.1.6 | ns | ns | ns | ns | ns | ns | ns |

* Significant positive effect has P-value less than or equal to 0.1; significant negative effect is in parenthesis; "ns" when difference not significant FIG. 15
Summary Evaluation of Gaspe Flint Derived Maize Lines Transformed with PHP31419*

| Treatment | % area chg_start chronic - acute2 | % area chg_start chronic - end chronic | % area chg_start chronic - harvest | % area chg_start chronic - recovery 24hr | fv/fm_ acute1 | fv/fm_ acute2 | leaf rolling_ harvest | leaf rolling_ recovery 24hr | psii_ acute1 | psii_ acute2 | sgr - r2 > 0.9 | shoot dry weight | shoot fresh weight |
|---|---|---|---|---|---|---|---|---|---|---|---|---|---|
| Reduce Water | 0.093 | ns | 0.043 | ns | 0.054 | ns | 0.059 | 0.001 | 0.015 | 0.069 | 0.008 | (0.025) | ns |
| Well Water | 0.078 | ns | ns | ns | ns | ns | ns | ns | 0.011 | ns | ns | ns | ns |

* Significant positive effect has P-value less than or equal to 0.1; significant negative effect is in parenthesis; "ns" when difference not significant

FIG. 16A
Evaluation of Individual Gaspe Flint Derived Maize Lines Transformed with PHP33089*

| Treatment | Event name | % area chg_ start chronic - end chronic | % area chg_ start chronic - end severe | % area chg_ start chronic - recovery 48hr | Psii_ end severe | psii_ recovery 48hr | psii_ start severe | fv/fm_ end severe | fv/fm_ recovery 48hr | fv/fm_ start severe |
|---|---|---|---|---|---|---|---|---|---|---|
| Reduce Water | EA2534.088.2.2 | ns | (0.076) | ns | (0.016) | ns | ns | (0.074) | ns | ns |
| Reduce Water | EA2534.088.2.4 | 0.095 | Ns | ns | ns | 0.043 | ns | (0.025) | 0.041 | ns |
| Reduce Water | EA2534.088.2.5 | 0.068 | 0.063 | ns | 0.008 | ns | 0.022 | 0.065 | ns | 0.036 |
| Reduce Water | EA2534.088.2.8 | ns | (0.012) | (0.032) | (0.011) | ns | ns | ns | ns | ns |
| Well Water | EA2534.088.2.2 | ns | Ns | ns | ns | ns | 0.058 | ns | ns | ns |
| Well Water | EA2534.088.2.4 | 0.030 | Ns | ns | ns | (0.017) | (0.060) | ns | ns | ns |
| Well Water | EA2534.088.2.5 | ns | Ns | ns | 0.006 | ns | ns | 0.01 | ns | ns |
| Well Water | EA2534.088.2.8 | ns | Ns | ns | ns | (0.048) | (0.029) | ns | (0.012) | ns |

* Significant positive effect has P-value less than or equal to 0.1; significant negative effect is in parenthesis; "ns" when difference not significant

FIG. 16B
Evaluation of Individual Gaspe Flint Derived Maize Lines Transformed with PHP33089*

| Treatment | Event name | leaf rolling_ recovery 48hr | sgr - r2 > 0.9 | shoot dry weight | shoot fresh weight |
|---|---|---|---|---|---|
| Reduce Water | EA2534.088.2.2 | ns | ns | ns | ns |
| Reduce Water | EA2534.088.2.4 | ns | ns | ns | ns |
| Reduce Water | EA2534.088.2.5 | ns | ns | ns | ns |
| Reduce Water | EA2534.088.2.8 | ns | ns | 0.005 | ns |
| Well Water | EA2534.088.2.2 | ns | ns | ns | ns |
| Well Water | EA2534.088.2.4 | 0.072 | ns | ns | ns |
| Well Water | EA2534.088.2.5 | (0.051) | ns | ns | ns |
| Well Water | EA2534.088.2.8 | ns | ns | ns | ns |

* Significant positive effect has P-value less than or equal to 0.1; significant negative effect is in parenthesis; "ns" when difference not significant

FIG. 17

Summary Evaluation of Gaspe Flint Derived Maize Lines Transformed with PHP33089*

| Treatment | % area chg_ start chronic - end chronic | % area chg_ start chronic - end severe | % area chg_ start chronic - recovery48hr | fv/fm_ end severe | fv/fm_ recovery 48hr | fv/fm_ start severe | leaf rolling_ recovery 48hr | psii_ end severe | psii_ recovery 48hr | psii_ start severe | sgr - r2 > 0.9 | shoot dry weight | shoot fresh weight |
|---|---|---|---|---|---|---|---|---|---|---|---|---|---|
| Reduce Water Well Water | ns 0.076 | ns ns | ns ns | ns ns | ns (0.032) | ns ns | ns ns | ns ns | ns (0.087) | ns ns | ns ns | 0.027 ns | ns ns |

* Significant positive effect has P-value less than or equal to 0.1; significant negative effect is in parenthesis; "ns" when difference not significant

FIG. 18A
Evaluation of Individual Gaspe Flint Derived Maize Lines Transformed with PHP30829*

| Treatment | Event name | % area chg_start chronic - end chronic | leaf rolling_recovery 24hr | leaf rolling_recovery 48hr | % area chg_start chronic - harvest | % area chg_start chronic - recovery 24hr | % area chg_start chronic - recovery 48hr | fv/fm_acute1 | fv/fm_acute2 |
|---|---|---|---|---|---|---|---|---|---|
| Reduce Water | EA2391.472.1.10 | (0.013) | ns | (0.012) | (0.002) | ns | (0.002) | ns | ns |
| Reduce Water | EA2391.472.1.2 | ns | ns | ns | ns | ns | ns | ns | (0.028) |
| Reduce Water | EA2391.472.1.3 | (0.036) | ns | (0.096) | ns | ns | ns | ns | ns |
| Reduce Water | EA2391.472.1.4 | ns | (0.081) | ns | ns | ns | ns | ns | 0.0022 |
| Well Water | EA2391.472.1.10 | ns | ns | ns | 0.001 | ns | ns | (0.007) | ns |
| Well Water | EA2391.472.1.2 | ns | ns | 0.069 | 0.058 | ns | ns | 0.008 | 0.001 |
| Well Water | EA2391.472.1.3 | ns | 0.091 | ns | 0.059 | ns | ns | ns | ns |
| Well Water | EA2391.472.1.4 | ns | ns | ns | ns | ns | ns | 0.006 | 0.095 |

* Significant positive effect has P-value less than or equal to 0.1; significant negative effect is in parenthesis; "ns" when difference not significant

FIG. 18B
Evaluation of Individual Gaspe Flint Derived Maize Lines Transformed with PHP30829*

| Treatment | Event name | psii_acute1 | psii_acute2 | sgr - r2 > 0.9 | shoot dry weight | shoot fresh weight |
|---|---|---|---|---|---|---|
| Reduce Water | EA2391.472.1.10 | ns | ns | (0.025) | ns | ns |
| Reduce Water | EA2391.472.1.2 | ns | (0.021) | ns | ns | ns |
| Reduce Water | EA2391.472.1.3 | ns | ns | ns | (0.079) | (0.056) |
| Reduce Water | EA2391.472.1.4 | (0.018) | 0.012 | (0.058) | ns | ns |
| Well Water | EA2391.472.1.10 | 0.026 | (0.071) | 0.034 | (0.046) | 0.012 |
| Well Water | EA2391.472.1.2 | ns | 0.016 | ns | ns | ns |
| Well Water | EA2391.472.1.3 | ns | ns | ns | ns | ns |
| Well Water | EA2391.472.1.4 | 0.04 | ns | ns | ns | ns |

* Significant positive effect has P-value less than or equal to 0.1; significant negative effect is in parenthesis; "ns" when difference not significant FIG. 19
Summary Evaluation of Gaspe Flint Derived Maize Lines Transformed with PHP30829

| Treatment | % area chg_ start chronic -end chronic | % area chg_ start chronic - harvest chronic | % area chg_ start chronic - recovery 24hr | % area chg_ start chronic - recovery 48hr | fv/fm_ acute1 | fv/fm_ acute2 | leaf rolling_ recovery 24hr | leaf rolling_ recovery 48hr | psii_ acute1 | psii_ acute2 | sgr - r2 > 0.9 | shoot dry weight | shoot fresh weight |
|---|---|---|---|---|---|---|---|---|---|---|---|---|---|
| Reduce Water | (0.056) | ns | ns | (0.087) | ns | ns | ns | (0.087) | ns | ns | (0.056) | ns | ns |
| Well Water | 0.032 | 0.0002 | ns | ns | 0.027 | ns | ns | ns | ns | ns | 0.081 | ns | ns |

* Significant positive effect has P-value less than or equal to 0.1; significant negative effect is in parenthesis; "ns" when difference not significant

FIG. 20A
Evaluation of Individual Gaspe Flint Derived Maize Lines Transformed with PHP30745*

| Treatment | Event name | % area chg_ start chronic - end chronic | % area chg_start chronic - end severe | % area chg_start chronic - recovery 48hr | fv/fm_ end severe | fv/fm_ recovery 48hr | fv/fm_ start severe |
|---|---|---|---|---|---|---|---|
| Reduce Water | EA2392.447.1.1 | ns | ns | ns | (0.071) | 0.039 | ns |
| Reduce Water | EA2392.447.1.3 | ns | ns | ns | ns | (0.087) | ns |
| Reduce Water | EA2392.447.1.5 | ns | ns | ns | ns | ns | ns |
| Reduce Water | EA2392.447.1.9 | (0.059) | ns | ns | (0.091) | ns | 0.003 |
| Well Water | EA2392.447.1.1 | 0.003 | 0.007 | 0.007 | ns | ns | ns |
| Well Water | EA2392.447.1.3 | (0.054) | (0.037) | (0.025) | ns | (0.004) | (0.001) |
| Well Water | EA2392.447.1.5 | 0.098 | ns | ns | ns | ns | ns |
| Well Water | EA2392.447.1.9 | 0.001 | 0.002 | 0.005 | ns | ns | ns |

* Significant positive effect has P-value less than or equal to 0.1; significant negative effect is in parenthesis; "ns" when difference not significant

FIG. 20B
Evaluation of Individual Gaspe Flint Derived Maize Lines Transformed with PHP30745*

| Treatment | Event name | leaf rolling_ recovery 48hr | psii_end severe | psii_recovery 48hr | psii_start severe | shoot dry weight | shoot fresh weight |
|---|---|---|---|---|---|---|---|
| Reduce Water | EA2392.447.1.1 | ns | ns | 0.01 | 0.054 | ns | 0.006 |
| Reduce Water | EA2392.447.1.3 | ns | ns | ns | ns | (0.028) | (0.081) |
| Reduce Water | EA2392.447.1.5 | ns | ns | ns | ns | ns | ns |
| Reduce Water | EA2392.447.1.9 | ns | ns | ns | 0.019 | (0.096) | (0.012) |
| Well Water | EA2392.447.1.1 | ns | ns | ns | ns | 0.051 | ns |
| Well Water | EA2392.447.1.3 | ns | ns | (0.051) | (0.0003) | 0.0012 | 0.003 |
| Well Water | EA2392.447.1.5 | ns | ns | 0.002 | ns | (0.026) | ns |
| Well Water | EA2392.447.1.9 | ns | ns | (0.014) | ns | ns | 0.066 |

* Significant positive effect has P-value less than or equal to 0.1; significant negative effect is in parenthesis; "ns" when difference not significant

FIG. 21

Summary Evaluation of Gaspe Flint Derived Maize Lines Transformed with PHP30745*

| Treatment | % area chg_start chronic - end chronic | % area chg_start chronic - end severe | % area chg_start chronic - recovery 48hr | fv/fm_end severe | fv/fm_recovery 48hr | fv/fm_start severe | leaf rolling_recovery 48hr | psii_end severe | psii_recovery 48hr | psii_start severe | shoot dry weight | shoot fresh weight |
|---|---|---|---|---|---|---|---|---|---|---|---|---|
| Reduce Water | ns | ns | ns | ns | ns | 0.081 | ns | ns | 0.035 | 0.091 | ns | ns |
| Well Water | ns | ns | ns | 0.034 | (0.098) | ns | ns | 0.083 | ns | ns | ns | ns |

* Significant positive effect has P-value less than or equal to 0.1; significant negative effect is in parenthesis; "ns" when difference not significant

FIG. 22A
Evaluation of Individual Gaspe Flint Derived Maize Lines Transformed with PHP30761*

| Treatment | Event name | % area chg_ start chronic - end chronic | % area chg_ start chronic - end severe | % area chg_ start chronic - recovery 48hr | fv/fm_ end severe | fv/fm_ recovery 48hr | fv/fm_ start severe |
|---|---|---|---|---|---|---|---|
| Reduce Water | EA2392.441.1.1 | ns | ns | ns | ns | ns | ns |
| Reduce Water | EA2392.441.1.2 | ns | ns | ns | ns | ns | ns |
| Reduce Water | EA2392.441.1.4 | ns | ns | ns | 0.02 | 0.038 | ns |
| Reduce Water | EA2392.441.1.7 | (0.034) | (0.054) | ns | 0.047 | 0.042 | ns |
| Well Water | EA2392.441.1.1 | ns | ns | ns | ns | ns | ns |
| Well Water | EA2392.441.1.2 | ns | ns | ns | ns | ns | 0.03 |
| Well Water | EA2392.441.1.4 | (0.004) | ns | ns | 0.000 | 0.008 | 0.001 |
| Well Water | EA2392.441.1.7 | ns | ns | ns | ns | ns | ns |

* Significant positive effect has P-value less than or equal to 0.1; significant negative effect is in parenthesis; "ns" when difference not significant

FIG. 22B
Evaluation of Individual Gaspe Flint Derived Maize Lines Transformed with PHP30761*

| Treatment | Event name | leaf rolling_ recovery 48hr | psii_ end severe | psii_ recovery 48hr | psii_ start severe | sgr - r2 > 0.9 | shoot dry weight | shoot fresh weight |
|---|---|---|---|---|---|---|---|---|
| Reduce Water | EA2392.441.1.1 | ns | ns | ns | ns | ns | ns | ns |
| Reduce Water | EA2392.441.1.2 | ns | ns | ns | ns | ns | ns | ns |
| Reduce Water | EA2392.441.1.4 | 0.058 | 0.071 | 0.072 | ns | ns | ns | ns |
| Reduce Water | EA2392.441.1.7 | ns | 0.098 | 0.037 | 0.068 | ns | (0.001) | ns |
| Well Water | EA2392.441.1.1 | ns | ns | ns | ns | ns | (0.048) | ns |
| Well Water | EA2392.441.1.2 | ns | ns | ns | ns | ns | 0.1 | ns |
| Well Water | EA2392.441.1.4 | 0.001 | 0.002 | 0.000 | 0.006 | (0.0002) | (0.050) | ns |
| Well Water | EA2392.441.1.7 | ns | ns | ns | ns | ns | ns | ns |

* Significant positive effect has P-value less than or equal to 0.1; significant negative effect is in parenthesis; "ns" when difference not significant

FIG. 23

Summary Evaluation of Gaspe Flint Derived Maize Lines Transformed with PHP30761*

| Treatment | % area chg_start chronic - end chronic | % area chg_start chronic severe | % area chg_start chronic - recovery 48hr | fv/fm_end severe | fv/fm_recovery 48hr | fv/fm_start severe | leaf rolling_recovery 48hr | psii_end severe | psii_recovery 48hr | psii_start severe | sgr - r2 > 0.9 | shoot dry weight | shoot fresh weight |
|---|---|---|---|---|---|---|---|---|---|---|---|---|---|
| Reduce Water | (0.050) | ns | ns | 0.065 | 0.000 | ns | ns | ns | 0.000 | 0.024 | ns | ns | ns |
| Well Water | (0.001) | (0.063) | ns | ns | ns | ns | 0.032 | ns | ns | 0.071 | (0.002) | (0.005) | ns |

* Significant positive effect has P-value less than or equal to 0.1; significant negative effect is in parenthesis; "ns" when difference not significant

SEQUENCE LISTING

```
<160> NUMBER OF SEQ ID NOS: 63

<210> SEQ ID NO 1
<211> LENGTH: 1867
<212> TYPE: DNA
<213> ORGANISM: Arabidopsis thaliana

<400> SEQUENCE: 1
agtaatttag cttcattctc tctctctctc tctcacaatt actgatcggt tctgaaattt      60
gtagctatgc aggcaacggc tttatcatct gggttcaatc ctctaacgaa acgtaaagat     120
cacagatttc ccaggtcatg ctctcagaga aattctctgt ctttgattca atgcgatata     180
aaagagagat ctttcggaga gtctatgacg atcacgaatc gtggattgag ttttaagacg     240
aatgtgtttg agcaagctcg ttctgtgact ggagactgtt cttatgatga aacttcagca     300
aaagcacgtt ctcatgttgt tgcagaagat aagattggtg tcttgctttt gaatttaggt     360
ggtcctgaaa ctcttaacga tgttcaacct ttcttgtata atctctttgc tgatccggat     420
attataaggc ttcctagacc atttcagttt cttcaaggga ctatagctaa gtttatatct     480
gttgttcgtg ctccgaaatc taaagaaggg tatgctgcta ttggtggtgg ctctcctttg     540
cgtaaaataa ctgatgagca agcggatgct attaagatgt ctttgcaagc gaagaacatt     600
gctgctaatg tctatgttgg tatgcggtat tggtatccgt tcactgagga ggctgttcag     660
cagataaaga aggacaaaat tactagactt gttgtactgc cattgtatcc tcagtattct     720
atctctacaa cgggttcaag catacgcgtt ctccaagatt tattcaggaa agatccgtac     780
ctagctggag tgccggtagc tattataaag tcctggtacc aaaggcgagg ctatgtcaat     840
tctatggctg acctcattga gaaggagctt caaactttct ctgatcctaa ggaggttatg     900
atattcttca gtgcccatgg tgttccggtc agctacgtag agaatgctgg agatccgtac     960
cagaagcaga tggaagagtg tattgacttg ataatggaag agctaaaagc cagaggggtt    1020
cttaacgacc ataaattggc ataccagagt cgtgttggcc ctgttcaatg gctgaagcca    1080
tacaccgatg aggttcttgt cgaccttggt aagagtggtg ttaagagtct actagccgtt    1140
ccagtcagtt tcgtgagtga gcacattgag acacttgagg agatagacat ggagtatagg    1200
```

-continued

```
gaattagctc ttgagtcagg ggtagagaac tggggacggg tacccgcgct aggtctcaca    1260
ccatccttca tcaccgactt agctgatgca gtgatagaat cacttccttc agcagaagca    1320
atgtcaaacc caaatgcagt ggttgactca aagatagcg agtcgtcaga tgctttcagt     1380
tacattgtca agatgttctt cggttcgatt ctggctttcg tcctacttct ctccccaaag    1440
atgttccatg cgttccggaa cctatagaat ctcgttggtt ttgtgttaag tcttttcttg    1500
gagaaatgtc ttggttaaat tcaatatata tagtccaatc tattgaagta ctagtacacc    1560
agctctaata agctgatgtg ggtaagtagt tcaatagatt ggactatgta tattaaattt    1620
gactaagaga taaactagag aatgggataa agatgagaac ggtattagaa agttctttga    1680
ggaaatttag atgtatttta aattgaagat gcatttagct ataaacatag tggctacgtt    1740
cctcttagag atgaggagag aattatattc tattattatt tggtttcttt tcttcgtttt    1800
tgtatggttt caatacttaa ttgtcaaaag tatcctataa ttttgttaaa aaaaaaaaa     1860 aaaaaaa                                                              1867
```

<210> SEQ ID NO 2
<211> LENGTH: 466
<212> TYPE: PRT
<213> ORGANISM: Arabidopsis thaliana

<400> SEQUENCE: 2

```
Met Gln Ala Thr Ala Leu Ser Ser Gly Phe Asn Pro Leu Thr Lys Arg
1               5                   10                  15

Lys Asp His Arg Phe Pro Arg Ser Cys Ser Gln Arg Asn Ser Leu Ser
            20                  25                  30

Leu Ile Gln Cys Asp Ile Lys Glu Arg Ser Phe Gly Glu Ser Met Thr
        35                  40                  45

Ile Thr Asn Arg Gly Leu Ser Phe Lys Thr Asn Val Phe Glu Gln Ala
    50                  55                  60

Arg Ser Val Thr Gly Asp Cys Ser Tyr Asp Glu Thr Ser Ala Lys Ala
65                  70                  75                  80

Arg Ser His Val Val Ala Glu Asp Lys Ile Gly Val Leu Leu Leu Asn
                85                  90                  95

Leu Gly Gly Pro Glu Thr Leu Asn Asp Val Gln Pro Phe Leu Tyr Asn
            100                 105                 110

Leu Phe Ala Asp Pro Asp Ile Ile Arg Leu Pro Arg Pro Phe Gln Phe
        115                 120                 125

Leu Gln Gly Thr Ile Ala Lys Phe Ile Ser Val Val Arg Ala Pro Lys
    130                 135                 140

Ser Lys Glu Gly Tyr Ala Ala Ile Gly Gly Gly Ser Pro Leu Arg Lys
145                 150                 155                 160

Ile Thr Asp Glu Gln Ala Asp Ala Ile Lys Met Ser Leu Gln Ala Lys
                165                 170                 175

Asn Ile Ala Ala Asn Val Tyr Val Gly Met Arg Tyr Trp Tyr Pro Phe
            180                 185                 190

Thr Glu Glu Ala Val Gln Gln Ile Lys Lys Asp Lys Ile Thr Arg Leu
        195                 200                 205

Val Val Leu Pro Leu Tyr Pro Gln Tyr Ser Ile Ser Thr Thr Gly Ser
    210                 215                 220

Ser Ile Arg Val Leu Gln Asp Leu Phe Arg Lys Asp Pro Tyr Leu Ala
225                 230                 235                 240

Gly Val Pro Val Ala Ile Ile Lys Ser Trp Tyr Gln Arg Arg Gly Tyr
                245                 250                 255
```

```
Val Asn Ser Met Ala Asp Leu Ile Glu Lys Glu Leu Gln Thr Phe Ser
            260                 265                 270
Asp Pro Lys Glu Val Met Ile Phe Phe Ser Ala His Gly Val Pro Val
        275                 280                 285
Ser Tyr Val Glu Asn Ala Gly Asp Pro Tyr Gln Lys Gln Met Glu Glu
    290                 295                 300
Cys Ile Asp Leu Ile Met Glu Glu Leu Lys Ala Arg Gly Val Leu Asn
305                 310                 315                 320
Asp His Lys Leu Ala Tyr Gln Ser Arg Val Gly Pro Val Gln Trp Leu
                325                 330                 335
Lys Pro Tyr Thr Asp Glu Val Leu Val Asp Leu Gly Lys Ser Gly Val
            340                 345                 350
Lys Ser Leu Leu Ala Val Pro Val Ser Phe Val Ser Glu His Ile Glu
        355                 360                 365
Thr Leu Glu Glu Ile Asp Met Glu Tyr Arg Glu Leu Ala Leu Glu Ser
    370                 375                 380
Gly Val Glu Asn Trp Gly Arg Val Pro Ala Leu Gly Leu Thr Pro Ser
385                 390                 395                 400
Phe Ile Thr Asp Leu Ala Asp Ala Val Ile Glu Ser Leu Pro Ser Ala
                405                 410                 415
Glu Ala Met Ser Asn Pro Asn Ala Val Val Asp Ser Glu Asp Ser Glu
            420                 425                 430
Ser Ser Asp Ala Phe Ser Tyr Ile Val Lys Met Phe Phe Gly Ser Ile
        435                 440                 445
Leu Ala Phe Val Leu Leu Leu Ser Pro Lys Met Phe His Ala Phe Arg
    450                 455                 460
Asn Leu
465

<210> SEQ ID NO 3
<211> LENGTH: 1848
<212> TYPE: DNA
<213> ORGANISM: Beta vulgaris

<400> SEQUENCE: 3
gacttgtaat attatttat  atgcccatca aaatccctaa aaattcctcc tttcaacagc      60
ctaaactgcc ttacaggctt ctggatttct gggtatctca taattaacgc catggatgca    120
accacaagct ctgccatgtt ttcgcagata agattatcat ctccctccct tcgaaatttc    180
agaactagat tctttcagtc atgcccacaa acgagagctc acatgcctcc ttgtagatat    240
acatgtaggc attcttcaat tggttcatat gcactattgc cttccaacct tgttgaaatt    300
caaagcagca aaatcagtgg attttcttat tgtcaaccag agaagaaaag acttggagtg    360
gggaaaactt tttgttctgc tgctatacag acaagcacat acaacgagaa cttggctata    420
gctccttcac atgttgcaga ggaaaagatt ggggtgcttc ttttgaattt aggaggaccc    480
gaaactctta tgatgtcca  accgttcttg tttaatctat tgctgacccc agacatcatt    540
cgccttccta tgttgttccg tttttctgcaa aggcctctag ctcaattgat ttctaagctt    600
agagccccta aaagcaaaga aggatatgct tctataggag ggggttcacc attgcgaaag    660
ataactgacg agcaggcaaa tgcacttaag ttggccttgg aagcaaagaa aaagaatgta    720
tctgtctacg ttgccatgag gtactggtac ccgttacag  aggaggcagt tcagcagata    780
aagaaagacg aggtcacaag gcttgtcgtt cttcctctct atcctcagtt ttctatatct    840
```

```
acaacaggtt ctagcctccg cgttctcgaa acatttttca ggaaggatgc atatctatct    900
caccttccca tcgctatcat ccagtcctgg taccagcgag aaggttatgt caagtccatg    960
gctgacttga ttgagaaaga gctgcagtct ttttctatgc cagatgaggt tatgatattc   1020
ttcagtgctc atggcgtgcc agtaagttat gtggaaaacg ctggagatcc atacaaagat   1080
cagatggagg attgcatttt tttaattatg agagaattaa aatctagagg aatcaacaat   1140
gatcatacac ttgcttacca gagtcgggtt ggtccagtgc aatggctgaa accttatact   1200
gatgaagttc ttgttgagct tggcgaaaaa ggagtcaaga gtctgctagc tgttcctgtg   1260
agctttgtga gtgagcacat tgagacactt gaagagatcg atatggagta caaggaattg   1320
gcgcttgaat ctggcattga aactggggt cgtgttcctg ctcttaactg caattcttct    1380
ttcatcaatg atctagctga tgctgtagct gaagctcttc cttcagcaac tgcaatgtca   1440
actagcacag ctgaagaagt tgataatgat ccagtcaagt atttcataaa attgtttttt   1500
ggttcactgt tggccttcgt cttgcttttg tccccgaaaa tgattttcgc atttaagaac   1560
agccttttgt aaaaatagat ggtagtgttc accagatttt gaagatatac acaaattaga   1620
ctgaaaaatc acactagaat ggatagagga acacaattcg ccacgtaaca tgtagaatta   1680
ctccaagagt atacaacttt gtgtgtacta atttgtagtt tttggattgc gattcacaag   1740
ggatttaatg aattaggtaa caccaaatag cttgtattct tcttaaaaaa aaaaaaaaa    1800
aaaaaaaaaa aaaaaaaaaa aaaaaaaaaa aaaaaaaaaa aaaaaaaa                1848
```

<210> SEQ ID NO 4
<211> LENGTH: 486
<212> TYPE: PRT
<213> ORGANISM: Beta vulgaris

<400> SEQUENCE: 4

```
Met Asp Ala Thr Thr Ser Ser Ala Met Phe Ser Gln Ile Arg Leu Ser
1               5                   10                  15

Ser Pro Ser Leu Arg Asn Phe Arg Thr Arg Phe Phe Gln Ser Cys Pro
            20                  25                  30

Gln Thr Arg Ala His Met Pro Pro Cys Arg Tyr Thr Cys Arg His Ser
        35                  40                  45

Ser Ile Gly Ser Tyr Ala Leu Leu Pro Ser Asn Leu Val Glu Ile Gln
    50                  55                  60

Ser Ser Lys Ile Ser Gly Phe Ser Tyr Cys Gln Pro Glu Lys Lys Arg
65                  70                  75                  80

Leu Gly Val Gly Lys Thr Phe Cys Ser Ala Ala Ile Gln Thr Ser Thr
                85                  90                  95

Tyr Asn Glu Asn Leu Ala Ile Ala Pro Ser His Val Ala Glu Glu Lys
            100                 105                 110

Ile Gly Val Leu Leu Leu Asn Leu Gly Gly Pro Glu Thr Leu Asn Asp
        115                 120                 125

Val Gln Pro Phe Leu Phe Asn Leu Phe Ala Asp Pro Asp Ile Ile Arg
    130                 135                 140

Leu Pro Met Leu Phe Arg Phe Leu Gln Arg Pro Leu Ala Gln Leu Ile
145                 150                 155                 160

Ser Lys Leu Arg Ala Pro Lys Ser Lys Glu Gly Tyr Ala Ser Ile Gly
                165                 170                 175

Gly Gly Ser Pro Leu Arg Lys Ile Thr Asp Glu Gln Ala Asn Ala Leu
            180                 185                 190

Lys Leu Ala Leu Glu Ala Lys Lys Lys Asn Val Ser Val Tyr Val Ala
```

```
            195                 200                 205
Met Arg Tyr Trp Tyr Pro Phe Thr Glu Glu Ala Val Gln Gln Ile Lys
    210                 215                 220

Lys Asp Glu Val Thr Arg Leu Val Val Leu Pro Leu Tyr Pro Gln Phe
225                 230                 235                 240

Ser Ile Ser Thr Thr Gly Ser Ser Leu Arg Val Leu Glu Asn Ile Phe
                245                 250                 255

Arg Lys Asp Ala Tyr Leu Ser His Leu Pro Ile Ala Ile Ile Gln Ser
            260                 265                 270

Trp Tyr Gln Arg Glu Gly Tyr Val Lys Ser Met Ala Asp Leu Ile Glu
        275                 280                 285

Lys Glu Leu Gln Ser Phe Ser Met Pro Asp Glu Val Met Ile Phe Phe
    290                 295                 300

Ser Ala His Gly Val Pro Val Ser Tyr Val Glu Asn Ala Gly Asp Pro
305                 310                 315                 320

Tyr Lys Asp Gln Met Glu Asp Cys Ile Phe Leu Ile Met Arg Glu Leu
                325                 330                 335

Lys Ser Arg Gly Ile Asn Asn Asp His Thr Leu Ala Tyr Gln Ser Arg
            340                 345                 350

Val Gly Pro Val Gln Trp Leu Lys Pro Tyr Thr Asp Glu Val Leu Val
        355                 360                 365

Glu Leu Gly Glu Lys Gly Val Lys Ser Leu Leu Ala Val Pro Val Ser
    370                 375                 380

Phe Val Ser Glu His Ile Glu Thr Leu Glu Glu Ile Asp Met Glu Tyr
385                 390                 395                 400

Lys Glu Leu Ala Leu Glu Ser Gly Ile Glu Asn Trp Gly Arg Val Pro
                405                 410                 415

Ala Leu Asn Cys Asn Ser Ser Phe Ile Asn Asp Leu Ala Asp Ala Val
            420                 425                 430

Ala Glu Ala Leu Pro Ser Ala Thr Ala Met Ser Thr Ser Thr Ala Glu
        435                 440                 445

Glu Val Asp Asn Asp Pro Val Lys Tyr Phe Ile Lys Leu Phe Phe Gly
    450                 455                 460

Ser Leu Leu Ala Phe Val Leu Leu Leu Ser Pro Lys Met Ile Phe Ala
465                 470                 475                 480

Phe Lys Asn Ser Leu Leu
                485

<210> SEQ ID NO 5
<211> LENGTH: 1979
<212> TYPE: DNA
<213> ORGANISM: Brassica napus

<400> SEQUENCE: 5
ttcggcacga ggcctcgtgc cggaaaactg tatggaggcg acggcgttat catctgggct      60
tcgtcctctt ccgaacccta acggttacag actcccgagg tcatgttctc agagaaagtc    120
tctgccttta gctcgattcc attcaaagga gacacctttc aagaaacctc aagggtctct    180
cgcgatcact caccaccgtg ggttgagttt caagacgaac gtcttcgagc aagcgcatca    240
tcctgtagct ggagacctct cttacgatga cactagccgt tctaacgttg ctgaggataa    300
gatcggtgtc ttgcttttga acctaggtgg gcctgagacg cttaacgatg tgcagccttt    360
cttgtataat ctgtttgcag acccggtgag aatcatctat aggcttttg agttttgga     420 gttgttttgg agtgttggtt ttttgatga aatgtggttt gtttgtttgt tgtgttgca     480
```

-continued

```
ggatattata cggcttccta gaccgtttca gtttctccaa ggggctatag caaagttcat    540
atctgtggtt cgcgctccga agtcgaaaga agggtatgct gctattggcg ggggatctcc    600
tttgcgtaag attactgatg agcaagctga tgctattcgg ttggcgttgc aagctaagaa    660
cgtttctgct gatgtctatg ttgggatgcg gtattggttt cctttcactg aggaggctgt    720
ccaacagatt aagaaggata agattacaag acttgttgta ctaccgttgt accctcagta    780
ttctatctcc acgactggct caagcgtccg cgttctccaa gacttattca ggaaagatcc    840
atacctagct agagtgccgg ttgctattat agagtcctgg taccagagaa gaggctatgt    900
caattccatg gctgacctca ttcagaagga gcttcaaact ttctctgatc ctaaggaggt    960
tatggtgttc ttcagtgccc atggtgttcc agttagctat gtagagaact ctggagatcc   1020
ataccagaaa cagatggaag agtgcattga cttgataatg aagagctaa aatccagagg    1080
ggttcaaaac aaccatatct tggcttacca gagtcgtgtt gggcctgttc aatggctgaa   1140
gccatacact gatgaggttc ttgtcgacct tggtaagaat ggtgtcaaga gtctactagc   1200
cgttccagtc agttttgtga gtgagcacat tgagacgctt gaagagatag acatggagta   1260
cagggagcta gctttggagt cagggataga gaactggggg cgtgtcccgg cgctaggtct   1320
gacgccatcc ttcatcaccg acttggctga tgcagtgata gagtcgcttc cttcagcaga   1380
agcaatggtg aacccaccaa gtgctggtgt ctcagaggat agcgagtcat cagacgcttt   1440
cggttacata atgaagatgt tcttcggttc ggttctagcc ttcctactgc ttctctcccc   1500
aaagatgttc catgcattcc gcaaccattt tatctaagaa gaaaacctat cgagaatctc   1560
tggatgaata gttggtttta tgttgttttt ttgttgttgg agaaatgtct tggtgaagtg   1620
taacgtatgt agtccaatct attgaagtac tagcacacca tctctagtga gattatgtgg   1680
ttgagtagtt caatacattg gactacatat attacttttg atcaagatgt aaactaggta   1740
agggaaataa tgagggaaga gacaggattc attttgtttt ttagctatga acatagttcc   1800
tcctagagat gaggtaaagg gaatataatc tattagttat tttggttttc ttaaaagcaa   1860
attgtcaaat gcattctttt gtttattaat caagctgcaa aattcatcac taaaaaaaaa   1920
aaaaaaaaaa aaaaaaaaaa aaaaaaaaaa aaaaaaaaaa aaaaaaaaaa aaaaaaaa    1979
```

<210> SEQ ID NO 6
<211> LENGTH: 469
<212> TYPE: PRT
<213> ORGANISM: Brassica napus

<400> SEQUENCE: 6

Met Glu Ala Thr Ala Leu Ser Ser Gly Leu Arg Pro Leu Pro Asn Pro
1               5                   10                  15

Asn Gly Tyr Arg Leu Pro Arg Ser Cys Ser Gln Arg Lys Ser Leu Pro
            20                  25                  30

Leu Ala Arg Phe His Ser Lys Glu Thr Pro Phe Lys Lys Pro Gln Gly
        35                  40                  45

Ser Leu Ala Ile Thr His His Arg Gly Leu Ser Phe Lys Thr Asn Val
    50                  55                  60

Phe Glu Gln Ala His His Pro Val Ala Gly Asp Leu Ser Tyr Asp Asp
65                  70                  75                  80

Thr Ser Arg Ser Asn Val Ala Glu Asp Lys Ile Gly Val Leu Leu Leu
                85                  90                  95

Asn Leu Gly Gly Pro Glu Thr Leu Asn Asp Val Gln Pro Phe Leu Tyr
            100                 105                 110

Asn Leu Phe Ala Asp Pro Asp Ile Ile Arg Leu Pro Arg Pro Phe Gln
            115                 120                 125

Phe Leu Gln Gly Ala Ile Ala Lys Phe Ile Ser Val Val Arg Ala Pro
        130                 135                 140

Lys Ser Lys Glu Gly Tyr Ala Ala Ile Gly Gly Ser Pro Leu Arg
145                 150                 155                 160

Lys Ile Thr Asp Glu Gln Ala Asp Ala Ile Arg Leu Ala Leu Gln Ala
                165                 170                 175

Lys Asn Val Ser Ala Asp Val Tyr Val Gly Met Arg Tyr Trp Phe Pro
            180                 185                 190

Phe Thr Glu Glu Ala Val Gln Gln Ile Lys Lys Asp Lys Ile Thr Arg
        195                 200                 205

Leu Val Val Leu Pro Leu Tyr Pro Gln Tyr Ser Ile Ser Thr Thr Gly
    210                 215                 220

Ser Ser Val Arg Val Leu Gln Asp Leu Phe Arg Lys Asp Pro Tyr Leu
225                 230                 235                 240

Ala Arg Val Pro Val Ala Ile Ile Glu Ser Trp Tyr Gln Arg Arg Gly
                245                 250                 255

Tyr Val Asn Ser Met Ala Asp Leu Ile Gln Lys Glu Leu Gln Thr Phe
            260                 265                 270

Ser Asp Pro Lys Glu Val Met Val Phe Phe Ser Ala His Gly Val Pro
        275                 280                 285

Val Ser Tyr Val Glu Asn Ser Gly Asp Pro Tyr Gln Lys Gln Met Glu
    290                 295                 300

Glu Cys Ile Asp Leu Ile Met Glu Leu Lys Ser Arg Gly Val Gln
305                 310                 315                 320

Asn Asn His Ile Leu Ala Tyr Gln Ser Arg Val Gly Pro Val Gln Trp
                325                 330                 335

Leu Lys Pro Tyr Thr Asp Glu Val Leu Val Asp Leu Gly Lys Asn Gly
            340                 345                 350

Val Lys Ser Leu Leu Ala Val Pro Val Ser Phe Val Ser Glu His Ile
        355                 360                 365

Glu Thr Leu Glu Glu Ile Asp Met Glu Tyr Arg Glu Leu Ala Leu Glu
    370                 375                 380

Ser Gly Ile Glu Asn Trp Gly Arg Val Pro Ala Leu Gly Leu Thr Pro
385                 390                 395                 400

Ser Phe Ile Thr Asp Leu Ala Asp Ala Val Ile Glu Ser Leu Pro Ser
                405                 410                 415

Ala Glu Ala Met Val Asn Pro Pro Ser Ala Gly Val Ser Glu Asp Ser
            420                 425                 430

Glu Ser Ser Asp Ala Phe Gly Tyr Ile Met Lys Met Phe Phe Gly Ser
        435                 440                 445

Val Leu Ala Phe Leu Leu Leu Leu Ser Pro Lys Met Phe His Ala Phe
    450                 455                 460

Arg Asn His Phe Ile
465

<210> SEQ ID NO 7
<211> LENGTH: 2005
<212> TYPE: DNA
<213> ORGANISM: Zea mays

<400> SEQUENCE: 7
cggaaagcaa atagcagacg gcagacaaca gtcgagggga cacaggaagg cgcgaagaag    60

-continued

```
accgagatcc tcgcccaacg ccatcacgcc actcccccaa tactcaggtg tcaggacagc    120
gagcaggcac aagcagatct cactccacgt tgctccttcc gcccttcctc tccgccgctc    180
cccggaagga tcatggagcg cgggattctt ggctccaggg gcgccgtcca aatcttgggg    240
tcgaagaccg gggccgcgat gtcatgtggc aaaacaacct ctacaagttt tacttgttct    300
accaaacacg agctgaactt gcatgtgaat gttaagccgt tgcaattggc aacagatgga    360
tcctctcgtt tggcatacaa aactccagtg cttaaaaatc agtggaatct ttctgctagt    420
tcttcctctg caaatgtggt taccactttt gatgatgaca aggtgtacc ttccagtttt     480
gctgaagaaa gatcggagt actgttatta atcttggtg gtccagaaac cctagacgat      540
gttcaaccat tcttgttcaa cctatttgct gatccagata tcattcgact gcctaggctc    600
ttcaggttcc ttcaaagacc actggccaaa cttatttcta cttttagagc tcctaagagt    660
aaagaagggt atgcttcaat cggtggtggg tcaccattga ggaaaattac tgatgagcag    720
gcaaatgctt tgaagattgc tctggaaaag aaaaaattga acgcaaatat atatgttggg    780
atgcggtatt ggtatccttt cacagaagaa gccattgatc agattaagaa ggataatatt    840
tccaagctcg ttgttcttcc actctaccct cagtactcca tatcaacaag tgggtcaagc    900
attcgtgttc tccaaaatgt tgtcaaggaa gattcatatt tttctggctt gccaatctcc    960
attatcgaat catggtacca acgtgatggc tatgtgaaat caatggctga cctaattgaa   1020
aaagagctat ctgccttttc caatcctgaa gaggtaatga tattcttcag tgcacatggt   1080
gtgccactta cctatgttca ggatgctgga gatccttaca gagatcagat ggaggattgt   1140
atttctttga tcatggggga gctgagatcc agaggaatct taaatggtca cactttggcg   1200
tatcagagtc gggtgggacc agttcaatgg ctgaagccat atactgatga agttttagta   1260
gaacttggtc agaacggtgt gaagagcctc ctggctgttc agtaagctt cgtgagcgag    1320
cacattgaga cactggaaga aatagacatg gagtacaagg agttggctct ggaatcaggc   1380
attgagaact ggggccgggt ccctgctctt ggatgcactt cgactttcat ctccgacctt   1440
gcagatgcgg ttgtcgaagc cctcccatct gcctcggcgc tgggaaccag aaagcctgaa   1500
gacaccgatt ccagcatgga tctgatgcat tacctgacca gatgttctt cggctcaatc    1560
ttggcattta tcctgctgtt gtcaccaaga ctggtttctg ctttccggaa caccatgctt   1620
taggtggtta ggtaggtaag caaaaggga atggtgtgat aggtaattct aaaaatttg     1680
agattaataa tggaaaaact ggagagagct tggtgatagt aactagagat cctttaggct   1740
ttgtttgggt actctagtat tgaccctaat ccgtgtgttg agatagattg aggtgtaaat   1800
tagtttaagt tatacctcaa ttcagctcag tacatataga ttgagctcaa tactagaata   1860
ctcaaactag gccttagtgc acgaggtagc agcttgtaat ttgctgtttt tgatattgtt   1920
cacaggaaac attggtctca taatgaatc tgtgaaagca cataacgtta caaatcaaaa    1980
aaaaaaaaaa aaaaaaaaaa aaaaa                                        2005
```

<210> SEQ ID NO 8
<211> LENGTH: 476
<212> TYPE: PRT
<213> ORGANISM: Zea mays

<400> SEQUENCE: 8

```
Met Glu Arg Gly Ile Leu Gly Ser Arg Gly Ala Val Gln Ile Leu Gly
1               5                   10                  15

Ser Lys Thr Gly Ala Ala Met Ser Cys Gly Lys Thr Thr Ser Thr Ser
```

-continued

```
                20                  25                  30
Phe Thr Cys Ser Thr Lys His Glu Leu Asn Leu His Val Asn Val Lys
                35                  40                  45
Pro Leu Gln Leu Ala Thr Asp Gly Ser Ser Arg Leu Ala Tyr Lys Thr
 50                  55                  60
Pro Val Leu Lys Asn Gln Trp Asn Leu Ser Ala Ser Ser Ser Ser Ala
 65                  70                  75                  80
Asn Val Val Thr Thr Phe Asp Asp Lys Gly Val Pro Ser Ser Phe
                85                  90                  95
Ala Glu Glu Lys Ile Gly Val Leu Leu Leu Asn Leu Gly Gly Pro Glu
                100                 105                 110
Thr Leu Asp Asp Val Gln Pro Phe Leu Phe Asn Leu Phe Ala Asp Pro
                115                 120                 125
Asp Ile Ile Arg Leu Pro Arg Leu Phe Arg Phe Leu Gln Arg Pro Leu
                130                 135                 140
Ala Lys Leu Ile Ser Thr Phe Arg Ala Pro Lys Ser Lys Glu Gly Tyr
145                 150                 155                 160
Ala Ser Ile Gly Gly Gly Ser Pro Leu Arg Lys Ile Thr Asp Glu Gln
                165                 170                 175
Ala Asn Ala Leu Lys Ile Ala Leu Glu Lys Lys Leu Asn Ala Asn
                180                 185                 190
Ile Tyr Val Gly Met Arg Tyr Trp Tyr Pro Phe Thr Glu Glu Ala Ile
                195                 200                 205
Asp Gln Ile Lys Lys Asp Asn Ile Ser Lys Leu Val Val Leu Pro Leu
                210                 215                 220
Tyr Pro Gln Tyr Ser Ile Ser Thr Ser Gly Ser Ser Ile Arg Val Leu
225                 230                 235                 240
Gln Asn Val Val Lys Glu Asp Ser Tyr Phe Ser Gly Leu Pro Ile Ser
                245                 250                 255
Ile Ile Glu Ser Trp Tyr Gln Arg Asp Gly Tyr Val Lys Ser Met Ala
                260                 265                 270
Asp Leu Ile Glu Lys Glu Leu Ser Ala Phe Ser Asn Pro Glu Glu Val
                275                 280                 285
Met Ile Phe Phe Ser Ala His Gly Val Pro Leu Thr Tyr Val Gln Asp
                290                 295                 300
Ala Gly Asp Pro Tyr Arg Asp Gln Met Glu Asp Cys Ile Ser Leu Ile
305                 310                 315                 320
Met Gly Glu Leu Arg Ser Arg Gly Ile Leu Asn Gly His Thr Leu Ala
                325                 330                 335
Tyr Gln Ser Arg Val Gly Pro Val Gln Trp Leu Lys Pro Tyr Thr Asp
                340                 345                 350
Glu Val Leu Val Glu Leu Gly Gln Asn Gly Val Lys Ser Leu Leu Ala
                355                 360                 365
Val Pro Val Ser Phe Val Ser Glu His Ile Glu Thr Leu Glu Glu Ile
                370                 375                 380
Asp Met Glu Tyr Lys Glu Leu Ala Leu Glu Ser Gly Ile Glu Asn Trp
385                 390                 395                 400
Gly Arg Val Pro Ala Leu Gly Cys Thr Ser Thr Phe Ile Ser Asp Leu
                405                 410                 415
Ala Asp Ala Val Val Glu Ala Leu Pro Ser Ala Ser Ala Leu Gly Thr
                420                 425                 430
Arg Lys Pro Glu Asp Thr Asp Ser Ser Met Asp Leu Met His Tyr Leu
                435                 440                 445
```

Thr Lys Met Phe Phe Gly Ser Ile Leu Ala Phe Ile Leu Leu Leu Ser
     450                 455                 460

Pro Arg Leu Val Ser Ala Phe Arg Asn Thr Met Leu
465                 470                 475

<210> SEQ ID NO 9
<211> LENGTH: 1760
<212> TYPE: DNA
<213> ORGANISM: Zea mays

<400> SEQUENCE: 9

| | | |
|---|---|---|
| ccgatcgacc gttcacctcg cccgacggcc caagcagccc atgtcttcgt cgggcccctc | 60 |
| cccggcgacg ggaatccacg cgtcgccgcc gttgggcctt ttgccggcga cgggaaccca | 120 |
| tcacaccagg tcatggggca aaacaacctc acaagttttt actggttcta ccaccaaaca | 180 |
| tgagcagagc ttgcatggaa atgttaagcc gttgcaattg gcggcaaatg aatcctctcg | 240 |
| tttggcttac agaagtccag cacttaaaaa ccagtggaat cttcctgcta gttcttcctc | 300 |
| cactaatgtg gttaccacct tgatgataa cgaacacgtg tcttccagtg ttattgaaga | 360 |
| aaaagttgga gtactgttat aaaccttgg tggtccagag acacttgacg atgttcaacc | 420 |
| atttttattc aacctatttg ctgatccaga tatcattcga ctccctaggc tcttcaggtt | 480 |
| tcttcaaaga ccactggcca aacttatttc tacttttaga gctcctaaga gtaaagaagg | 540 |
| gtatgcttca attggtggtg ggtcgccgtt aaggaaaatt actgatgaac aggcgaatgc | 600 |
| tttgaagatt gccctggaaa agaaaaaatt gaacgcaaac atatatgttg ggatgcggta | 660 |
| ttggtacccct ttcacagaag aggccattga tcaaattaaa aaggataaga ttaccaagct | 720 |
| cgttgttctt ccccttacc ctcagtactc catatcaaca agtgggtcaa gcattcgtgt | 780 |
| tctccaagac attgtcaagg aagattcata ttttctggt ttgccaattt ccattattga | 840 |
| atcatggtac caacgagatg gctatgtgaa atcaatgtct gacctaattg aaaaggagct | 900 |
| ctccgccttc tccaatcctg aagaggttat gatattcttc agtgcacatg gtgtgccact | 960 |
| tacctatgtt gaggatgctg gagatcctta cagagatcag atggaggatt gtattgcttt | 1020 |
| gatcatgggg gagttaagat caagaggaat cttaaatagt cacactttgg cgtaccagag | 1080 |
| tcgggtgggg ccagttcaat ggctgaagcc atatactgat gaagttttag tagaacttgg | 1140 |
| tcaaaagggt gtgaagagcc tcctggctgt tccagtaagc tttgtgagtg agcacatcga | 1200 |
| gacattggaa gaaattgaca tggagtacaa ggagttggct ctggaatcag gcatcaagaa | 1260 |
| ctggggtcgg gttcctgctc ttggatgcac ttcaacattc atctccgacc ttgcagatgc | 1320 |
| tgtcgtcgaa gccctgccct ctgcttcagc gctcgcgacc agaaagcctg acgacatcga | 1380 |
| ttccagcatg gacctgacgc attacctcac caagatgctg tttggctcaa tcttggcatt | 1440 |
| tgtcctgctg ctatcaccaa ggctagtttc cgccttccgg agcaccatgc tttaagtttt | 1500 |
| tctccaaagc actaaatttg agattgagaa tgagatattt cattttggac ctttttttcc | 1560 |
| tccttaatag aatgatgtgc agttcttctg ctcgttccag agaaaaaaat aactgctagg | 1620 |
| aactcacaag gtagtagggg attgcaaaag ggatgtgaac agctgttttg atcgaagttg | 1680 |
| tctataaata ccgtgctcac ggactctgta ttttaaaaaa aaaaaaaaaa aaaaaaaaa | 1740 |
| aaaaaaaaaa aaaaaaaaaa | 1760 |

<210> SEQ ID NO 10
<211> LENGTH: 484
<212> TYPE: PRT

<213> ORGANISM: Zea mays

<400> SEQUENCE: 10

Met Ser Ser Ser Gly Pro Ser Pro Ala Thr Gly Ile His Ala Ser Pro
1               5                   10                  15

Pro Leu Gly Leu Leu Pro Ala Thr Gly Thr His His Thr Arg Ser Trp
            20                  25                  30

Gly Lys Thr Thr Ser Thr Ser Phe Thr Gly Ser Thr Thr Lys His Glu
        35                  40                  45

Gln Ser Leu His Gly Asn Val Lys Pro Leu Gln Leu Ala Ala Asn Glu
    50                  55                  60

Ser Ser Arg Leu Ala Tyr Arg Ser Pro Ala Leu Lys Asn Gln Trp Asn
65                  70                  75                  80

Leu Pro Ala Ser Ser Ser Thr Asn Val Val Thr Thr Phe Asp Asp
                85                  90                  95

Asn Glu His Val Ser Ser Ser Val Ile Glu Glu Lys Val Gly Val Leu
                100                 105                 110

Leu Leu Asn Leu Gly Gly Pro Glu Thr Leu Asp Asp Val Gln Pro Phe
            115                 120                 125

Leu Phe Asn Leu Phe Ala Asp Pro Asp Ile Ile Arg Leu Pro Arg Leu
130                 135                 140

Phe Arg Phe Leu Gln Arg Pro Leu Ala Lys Leu Ile Ser Thr Phe Arg
145                 150                 155                 160

Ala Pro Lys Ser Lys Glu Gly Tyr Ala Ser Ile Gly Gly Gly Ser Pro
                165                 170                 175

Leu Arg Lys Ile Thr Asp Glu Gln Ala Asn Ala Leu Lys Ile Ala Leu
            180                 185                 190

Glu Lys Lys Lys Leu Asn Ala Asn Ile Tyr Val Gly Met Arg Tyr Trp
        195                 200                 205

Tyr Pro Phe Thr Glu Glu Ala Ile Asp Gln Ile Lys Lys Asp Lys Ile
    210                 215                 220

Thr Lys Leu Val Val Leu Pro Leu Tyr Pro Gln Tyr Ser Ile Ser Thr
225                 230                 235                 240

Ser Gly Ser Ser Ile Arg Val Leu Gln Asp Ile Val Lys Glu Asp Ser
                245                 250                 255

Tyr Phe Ser Gly Leu Pro Ile Ser Ile Glu Ser Trp Tyr Gln Arg
            260                 265                 270

Asp Gly Tyr Val Lys Ser Met Ser Asp Leu Ile Glu Lys Glu Leu Ser
        275                 280                 285

Ala Phe Ser Asn Pro Glu Glu Val Met Ile Phe Ser Ala His Gly
    290                 295                 300

Val Pro Leu Thr Tyr Val Glu Asp Ala Gly Asp Pro Tyr Arg Asp Gln
305                 310                 315                 320

Met Glu Asp Cys Ile Ala Leu Ile Met Gly Glu Leu Arg Ser Arg Gly
                325                 330                 335

Ile Leu Asn Ser His Thr Leu Ala Tyr Gln Ser Arg Val Gly Pro Val
            340                 345                 350

Gln Trp Leu Lys Pro Tyr Thr Asp Glu Val Leu Val Glu Leu Gly Gln
        355                 360                 365

Lys Gly Val Lys Ser Leu Leu Ala Val Pro Val Ser Phe Val Ser Glu
    370                 375                 380

His Ile Glu Thr Leu Glu Glu Ile Asp Met Glu Tyr Lys Glu Leu Ala
385                 390                 395                 400

Leu Glu Ser Gly Ile Lys Asn Trp Gly Arg Val Pro Ala Leu Gly Cys
405                 410                 415

Thr Ser Thr Phe Ile Ser Asp Leu Ala Asp Ala Val Val Glu Ala Leu
        420                 425                 430

Pro Ser Ala Ser Ala Leu Ala Thr Arg Lys Pro Asp Asp Ile Asp Ser
        435                 440                 445

Ser Met Asp Leu Thr His Tyr Leu Thr Lys Met Leu Phe Gly Ser Ile
    450                 455                 460

Leu Ala Phe Val Leu Leu Leu Ser Pro Arg Leu Val Ser Ala Phe Arg
465                 470                 475                 480

Ser Thr Met Leu

<210> SEQ ID NO 11
<211> LENGTH: 1971
<212> TYPE: DNA
<213> ORGANISM: Oryza sativa

<400> SEQUENCE: 11
cttacagggc aacgaatgcg aacctacttc tcctagtata ctgcttttac tttagccatc      60
gccaccaccg ccattcctgg aaccccttc cctcttcctc cctcggatct ctcctcgctc     120
gcgcgttcgc gccgccgcct tccccttcc cccgttgatt gattgggagg aggatcaatg     180
gagtgcgtcc gctccggctc cggggttctt gatcccaggt gctctccgcg gttcctgggg     240
aagaagggtg gttcgctcac gtcatgtggt aaagccactt ctacaaatct tgccatttgt     300
accaaacacg agcaaaactt gcatgggaat gttaaaccct cacagttagc agcaagtgga     360
tcctcttatt ctgttcacag aagtccagtg cttaagcaga acagaatct ttctgctagg     420 tctacctctg cagatgtata tactactttt gatgaaaatg tcagagctgt atcttcacat     480
gctgctgaag aaaaggttgg agtactctta ttaaaccttg gtggcccaga gacactggat     540
gatgttcagc catttctatt caacctgttt gctgacccag atatcatccg tttgccaagg     600
ctgttcaggt ttcttcaaag accattggcc aagcttatct ccacttttag agctccaaag     660
agtaaggagg ggtacgcttc aatcggtgga ggatcacctt tgcggaaaat tactgatgag     720
caggcaaatg ctttgaaggt ggcactgaaa aagaagaatt tgaatgctaa tatatatgtt     780
ggaatgcgat actggtaccc ttttacagaa gaagccattg atcagattaa gaaggataag     840
attacaaagc ttgtcgttct tccactgtac cctcaatact ccatatcgac aagtggatca     900
agcatccgtg ttctccaaaa cattgtcaag gaggattcat attttgctgg attgccaatt     960
tccattatcg aatcatggta ccaacgtgac ggttatgtga atcaatggc tgacttaatt    1020 gaaaaggaac tgtcaatttt ttccaatcct gaagaggtta tgatattctt cagtgcacat    1080
ggagtaccac ttacctatgt tacgatgct ggagatcctt acagagatca gatggaggac    1140
tgcattgctt tgatcatggg agagttaaaa tccagaggaa tcttaaacag ccatactctg    1200
gcttaccaga gtcgagtggg gccagttcag tggctgaaac catatactga tgaagttcta    1260
gttgaactag gtcaacaggg tgtaaagagc ctcctggctg ttccagtaag ctttgtgagc    1320
gagcacatcg agaccttgga gaaaatcgac atggagtaca aggagctggc tctagaatcg    1380
ggcatcgaga ctggggaag ggttccagct cttggatgca cctcatcctt catctccgac    1440
cttgctgatg cagtggtcga agccctgccc tccgcttccg ctctcgtgac gaagaaggtg    1500
gacgagagcg attccgacat ggacctgatg cactacctga gcaagatgtt cttcggctcc    1560
atcttggcgt tcgtcctcct attgtcgcca aggctgattt ccgctttccg gaacaccctg    1620

-continued

```
ttgtaggtga tggtggcttc ttttgtttgg ttttttgcac taggggtttg gcttgagtaa    1680
gtagaaaggc aggctcgtgg gatgatagtg aatagtgatg gttaaagttc ccctttttta    1740
cagaagtaat atgcatgaag tcattgcaag gtagcttaag tggtggtttt aagcaaggag    1800
cctctagggg taaattgcca gtctgtacca gttttcttgt gctggtacaa ggcaagccta    1860 tcctttttt tcttttttt tcttttgtt acatgagcac attgataaaa catcattgat       1920
atattactaa tgcataaaca ccaaaaaaaa aaaaaaaaa aaaaaaaaa a               1971
```

```
<210> SEQ ID NO 12
<211> LENGTH: 482
<212> TYPE: PRT
<213> ORGANISM: Oryza sativa

<400> SEQUENCE: 12

Met Glu Cys Val Arg Ser Gly Ser Gly Val Leu Asp Pro Arg Cys Ser
1               5                   10                  15

Pro Arg Phe Leu Gly Lys Lys Gly Ser Leu Thr Ser Cys Gly Lys
            20                  25                  30

Ala Thr Ser Thr Asn Leu Ala Ile Cys Thr Lys His Glu Gln Asn Leu
        35                  40                  45

His Gly Asn Val Lys Pro Ser Gln Leu Ala Ala Ser Gly Ser Ser Tyr
    50                  55                  60

Ser Val His Arg Ser Pro Val Leu Lys Gln Arg Gln Asn Leu Ser Ala
65                  70                  75                  80

Arg Ser Thr Ser Ala Asp Val Tyr Thr Thr Phe Asp Glu Asn Val Arg
                85                  90                  95

Ala Val Ser Ser His Ala Ala Glu Glu Lys Val Gly Val Leu Leu Leu
            100                 105                 110

Asn Leu Gly Gly Pro Glu Thr Leu Asp Asp Val Gln Pro Phe Leu Phe
        115                 120                 125

Asn Leu Phe Ala Asp Pro Asp Ile Ile Arg Leu Pro Arg Leu Phe Arg
    130                 135                 140

Phe Leu Gln Arg Pro Leu Ala Lys Leu Ile Ser Thr Phe Arg Ala Pro
145                 150                 155                 160

Lys Ser Lys Glu Gly Tyr Ala Ser Ile Gly Gly Ser Pro Leu Arg
                165                 170                 175

Lys Ile Thr Asp Glu Gln Ala Asn Ala Leu Lys Val Ala Leu Lys Lys
            180                 185                 190

Lys Asn Leu Asn Ala Asn Ile Tyr Val Gly Met Arg Tyr Trp Tyr Pro
        195                 200                 205

Phe Thr Glu Glu Ala Ile Asp Gln Ile Lys Lys Asp Lys Ile Thr Lys
    210                 215                 220

Leu Val Val Leu Pro Leu Tyr Pro Gln Tyr Ser Ile Ser Thr Ser Gly
225                 230                 235                 240

Ser Ser Ile Arg Val Leu Gln Asn Ile Val Lys Glu Asp Ser Tyr Phe
                245                 250                 255

Ala Gly Leu Pro Ile Ser Ile Glu Ser Trp Tyr Gln Arg Asp Gly
            260                 265                 270

Tyr Val Lys Ser Met Ala Asp Leu Ile Glu Lys Glu Leu Ser Ile Phe
        275                 280                 285

Ser Asn Pro Glu Glu Val Met Ile Phe Phe Ser Ala His Gly Val Pro
    290                 295                 300

Leu Thr Tyr Val Thr Asp Ala Gly Asp Pro Tyr Arg Asp Gln Met Glu
305                 310                 315                 320
```

Asp Cys Ile Ala Leu Ile Met Gly Glu Leu Lys Ser Arg Gly Ile Leu
            325                 330                 335

Asn Ser His Thr Leu Ala Tyr Gln Ser Arg Val Gly Pro Val Gln Trp
            340                 345                 350

Leu Lys Pro Tyr Thr Asp Glu Val Leu Val Glu Leu Gly Gln Gln Gly
        355                 360                 365

Val Lys Ser Leu Leu Ala Val Pro Val Ser Phe Val Ser Glu His Ile
    370                 375                 380

Glu Thr Leu Glu Glu Ile Asp Met Glu Tyr Lys Glu Leu Ala Leu Glu
385                 390                 395                 400

Ser Gly Ile Glu Asn Trp Gly Arg Val Pro Ala Leu Gly Cys Thr Ser
            405                 410                 415

Ser Phe Ile Ser Asp Leu Ala Asp Ala Val Val Glu Ala Leu Pro Ser
            420                 425                 430

Ala Ser Ala Leu Val Thr Lys Lys Val Asp Glu Ser Asp Ser Asp Met
            435                 440                 445

Asp Leu Met His Tyr Leu Ser Lys Met Phe Phe Gly Ser Ile Leu Ala
        450                 455                 460

Phe Val Leu Leu Leu Ser Pro Arg Leu Ile Ser Ala Phe Arg Asn Thr
465                 470                 475                 480

Leu Leu

<210> SEQ ID NO 13
<211> LENGTH: 1756
<212> TYPE: DNA
<213> ORGANISM: Glycine max

<400> SEQUENCE: 13
cttttctttg ccaacactcc ttcgattagg ggtttcgatc ccaaattaca aattggtcgc      60
catgaacgca acctcatact ctgctcttcc ttctacgttc cgcagtctcc atcatcggaa     120
tttctcagcg ttttgttctg atatccaaaa tcctggctat gttgattgcc attcaaattg     180
taataagtct acatctcaag cgtctttgtt tttgtgttcc gactccaaca gtagaagaaa     240
tggtgttttt ggtagaccac tttgtgtgaa cccctctggc aggagaaacc tagttggtcc     300
agctttttat tctctggaga ctagtgctta tgacgtggct gctttagaat ctccttcccg     360
tgttgcagaa gaaaaagttg gtgtgctgct tctcaatcta ggaggaccag agacattgag     420
tgacgtgcaa ccttttctgt ttaatctttt tgcagatcct gatatcattc gtcttccaag     480
gttgtttcgg tttctccagc gaccattggc aaaattgatt tctgtacttc gggctcctaa     540
atccaaggaa gggtatgctg ctattggtgg tggctctcct ttacgaaaaa ttacagatga     600
ccaggcactt gcaattaaaa tggctttgga agcaaaggc atctcttcaa atgtctacgt     660
tgggatgcga tactggtacc catttactga agaagcaatt cagcaaatta gagggacag     720 aataacaagg cttgtggtac tacccctta tccccagttt tctatatcca caactggatc     780
aagcatccgt gttcttgagc atatattcag ggaagatgcc tacttgtcta agctccctgt     840
ttccattata aactcttggt atcaacgaga aggttatatt aagtcaatgg ctaacttaat     900
tcagaaagag ctccagagtt tttctgaacc aaaagaggta atgatatttt tcagtgccca     960
tggtgtacct gtcagttacg ttgaggaagc tggggatcca taccgagacc aaatggagga    1020
gtgcatcttc ttgatcatgc aagagttgaa agctagagga attagtaatg agcacactct    1080
tgcttatcag agtcgagtgg gtcctgtaca gtggctgaaa ccatatactg atgaagttct    1140

```
cgttgagctt ggccaaaaag gtgtgaagag tcttttagct gttccagtga gttttgtgag    1200
tgagcatatt gaaacccttg aagaaattga catggagtac aaggaattgg ctcttgaatc    1260
tggcatcaag aattgggcac gtgtacctgc ccttggtgtt accccttcct tcattacaga    1320
tttagcagat gcagtaatag aagctctccc atcagcaaca gcaatatatg caccgaccag    1380
aacctctgaa gatgttgatc atgacccagt tagatatttt atcaagatgt tctttggttc    1440
aatcttggca ttcatcttgt tcttgtcacc caaaatgatc acggcattca ggaatcatgt    1500
catttagaag aattaaatcc tgcttgctga attcaatctg caagcatata gatgaagcct    1560
attgatagca acaaagtata ctttgatttt ttgtctttgt tttacttatt caacctcta    1620 ctgtatacag cacagagcta taaggaagca attttcgca cttgattata atgagaactt    1680
gcacctcggc ttaaagagga ttcaaagaat aataattgta gaccaggatc tattcaggaa    1740
aaaaaaaaaa aaaaaa                                                    1756
```

<210> SEQ ID NO 14
<211> LENGTH: 481
<212> TYPE: PRT
<213> ORGANISM: Glycine max

<400> SEQUENCE: 14

```
Met Asn Ala Thr Ser Tyr Ser Ala Leu Pro Ser Thr Phe Arg Ser Leu
1               5                   10                  15

His His Arg Asn Phe Ser Ala Phe Cys Ser Asp Ile Gln Asn Pro Gly
                20                  25                  30

Tyr Val Asp Cys His Ser Asn Cys Asn Lys Ser Thr Ser Gln Ala Ser
            35                  40                  45

Leu Phe Leu Cys Ser Asp Ser Asn Ser Arg Arg Asn Gly Val Phe Gly
        50                  55                  60

Arg Pro Leu Cys Val Asn Pro Ser Gly Arg Arg Asn Leu Val Gly Pro
65                  70                  75                  80

Ala Phe Tyr Ser Leu Glu Thr Ser Ala Tyr Asp Val Ala Ala Leu Glu
                85                  90                  95

Ser Pro Ser Arg Val Ala Glu Glu Lys Val Gly Val Leu Leu Leu Asn
            100                 105                 110

Leu Gly Gly Pro Glu Thr Leu Ser Asp Val Gln Pro Phe Leu Phe Asn
        115                 120                 125

Leu Phe Ala Asp Pro Asp Ile Ile Arg Leu Pro Arg Leu Phe Arg Phe
    130                 135                 140

Leu Gln Arg Pro Leu Ala Lys Leu Ile Ser Val Leu Arg Ala Pro Lys
145                 150                 155                 160

Ser Lys Glu Gly Tyr Ala Ala Ile Gly Gly Gly Ser Pro Leu Arg Lys
                165                 170                 175

Ile Thr Asp Asp Gln Ala Leu Ala Ile Lys Met Ala Leu Glu Ala Lys
            180                 185                 190

Gly Ile Ser Ser Asn Val Tyr Val Gly Met Arg Tyr Trp Tyr Pro Phe
        195                 200                 205

Thr Glu Glu Ala Ile Gln Gln Ile Lys Arg Asp Arg Ile Thr Arg Leu
    210                 215                 220

Val Val Leu Pro Leu Tyr Pro Gln Phe Ser Ile Ser Thr Thr Gly Ser
225                 230                 235                 240

Ser Ile Arg Val Leu Glu His Ile Phe Arg Glu Asp Ala Tyr Leu Ser
                245                 250                 255

Lys Leu Pro Val Ser Ile Ile Asn Ser Trp Tyr Gln Arg Glu Gly Tyr
```

```
             260                 265                 270
Ile Lys Ser Met Ala Asn Leu Ile Gln Lys Glu Leu Gln Ser Phe Ser
            275                 280                 285
Glu Pro Lys Glu Val Met Ile Phe Phe Ser Ala His Gly Val Pro Val
        290                 295                 300
Ser Tyr Val Glu Glu Ala Gly Asp Pro Tyr Arg Asp Gln Met Glu Glu
305                 310                 315                 320
Cys Ile Phe Leu Ile Met Gln Glu Leu Lys Ala Arg Gly Ile Ser Asn
                325                 330                 335
Glu His Thr Leu Ala Tyr Gln Ser Arg Val Gly Pro Val Gln Trp Leu
                340                 345                 350
Lys Pro Tyr Thr Asp Glu Val Leu Val Glu Leu Gly Gln Lys Gly Val
            355                 360                 365
Lys Ser Leu Leu Ala Val Pro Val Ser Phe Val Ser Glu His Ile Glu
        370                 375                 380
Thr Leu Glu Glu Ile Asp Met Glu Tyr Lys Glu Leu Ala Leu Glu Ser
385                 390                 395                 400
Gly Ile Lys Asn Trp Ala Arg Val Pro Ala Leu Gly Val Thr Pro Ser
                405                 410                 415
Phe Ile Thr Asp Leu Ala Asp Ala Val Ile Glu Ala Leu Pro Ser Ala
                420                 425                 430
Thr Ala Ile Tyr Ala Pro Thr Arg Thr Ser Glu Asp Val Asp His Asp
            435                 440                 445
Pro Val Arg Tyr Phe Ile Lys Met Phe Phe Gly Ser Ile Leu Ala Phe
        450                 455                 460
Ile Leu Phe Leu Ser Pro Lys Met Ile Thr Ala Phe Arg Asn His Val
465                 470                 475                 480
Ile

<210> SEQ ID NO 15
<211> LENGTH: 1651
<212> TYPE: DNA
<213> ORGANISM: Tulip

<400> SEQUENCE: 15
gaaaagtcca gcgaagcctt ttccccgttt gaccgcgctc ctccaccccc gacgtggctc      60
ccaaatcccc cacattcccc cttcctctcc gatctcaaaa ccctaaccct agctccgcaa     120
ttccccaacc tcctccgcca tggaagccct cacctccggc gcctcccagc tcagcctcgc     180
cgcccaccgc cgccgccgca ccgccgccca cctctccagg ccgaggggg tcgtctcctg      240
tgcggcggcg ccggcccgat cggcgccggg gctggtgagt cggagggatg cgaggggcgc     300
ggtggcttgc ggttccaagg cgtgcacgta tgacgaggcg atcgccgggt ttggggaaag     360
cgtggcggag gagaaggtcg gggtgttgtt gctgaatctc gggggccgg atacgctcca      420
ggatgtccag ccgtttctct ttaatctctt cgctgatccg gatattattc ggcttccaag     480
gctgttccgg tttcttcaac gaccactagc acaactaata tcagttgtca gagcccccaa     540
aagccaagaa ggatatgctg ctattggtgg tggatcacct ttgcggagaa taacaaatga     600
acaggcgcag gcacttaaaa tggcactgga agaagaaac ctggatgtca atgtttatgt       660
tgcaatgaga tattggcatc cattcactga ggaagctgta catcagataa agaaggataa     720
cgttacaaag cttgtcattc taccacttta tcctcagtac tccatatcca caagtgggtc     780
aagcattcgt cttcttcaga atatcttcag ggaagactcc tattttgcag gaattccagt     840
```

```
ttctgttatt gaatattggt atcaacgtga gggttatgtc aaatcaatgt cagatttgat     900
tgaaaaggag ctatcgtgtt tctcgaatcc tgaagaggtt atgatatttt ttagcgcaca     960
tggggttcca gtgagctata ttgaggcagg agatccttat agagatcaga tggaggactg    1020
tattagtttg atcatggatg agttgaagtc aagggagtc tccaatcagc acactcttgc     1080
ttatcagagt cgagttgggc ctgttcagtg gttgaagcct acacggatg aagttatagt     1140 tgagcttggt cagaaaggtg taaagagtct tctggcggtt ccagtaagct ttgtgagtga    1200
acacatcgag actttggaag aaattgatat ggagtaccgg gagttggctc ttgaatctgg    1260
tatagagaat ggggcaggg taccagctct agggtgcaag tcttccttca ttaccgatct     1320
ggcggatgct gtaattgaat ccctcccttc tgcttctgtt atgtcaactg ccaaaagcac    1380
ctccaatgac ggcaatacag accttgtgca gtatgtagtg aacttgtttt ttgggtcgat    1440
tttcgccttc gtgttgctgt tttcacctag attgatttcc ggtatcagaa attttctta    1500 acttattcat agtgctgcag atctttgtat aagtggtaac aataaaacaa tacctcatag    1560
attttacgtg gaacatacaa ctgaagggtg taagcctttt tccccctcaa tagaatcaca    1620
aagtagtatt aataaaaaaa aaaaaaaaa a                                    1651
```

<210> SEQ ID NO 16
<211> LENGTH: 453
<212> TYPE: PRT
<213> ORGANISM: Tulip

<400> SEQUENCE: 16

```
Met Glu Ala Leu Thr Ser Gly Ala Ser Gln Leu Ser Leu Ala Ala His
1               5                   10                  15

Arg Arg Arg Arg Thr Ala Ala His Leu Ser Arg Pro Arg Gly Phe Val
            20                  25                  30

Ser Cys Ala Ala Pro Ala Arg Ser Ala Pro Gly Leu Val Ser Arg
        35                  40                  45

Arg Asp Ala Arg Gly Ala Val Ala Cys Gly Ser Lys Ala Cys Thr Tyr
    50                  55                  60

Asp Glu Ala Ile Ala Gly Phe Gly Glu Ser Val Ala Glu Glu Lys Val
65                  70                  75                  80

Gly Val Leu Leu Leu Asn Leu Gly Gly Pro Asp Thr Leu Gln Asp Val
                85                  90                  95

Gln Pro Phe Leu Phe Asn Leu Phe Ala Asp Pro Asp Ile Ile Arg Leu
            100                 105                 110

Pro Arg Leu Phe Arg Phe Leu Gln Arg Pro Leu Ala Gln Leu Ile Ser
        115                 120                 125

Val Val Arg Ala Pro Lys Ser Gln Glu Gly Tyr Ala Ala Ile Gly Gly
    130                 135                 140

Gly Ser Pro Leu Arg Arg Ile Thr Asn Glu Gln Ala Gln Ala Leu Lys
145                 150                 155                 160

Met Ala Leu Glu Lys Lys Asn Leu Asp Val Asn Val Tyr Val Ala Met
                165                 170                 175

Arg Tyr Trp His Pro Phe Thr Glu Glu Ala Val His Gln Ile Lys Lys
            180                 185                 190

Asp Asn Val Thr Lys Leu Val Ile Leu Pro Leu Tyr Pro Gln Tyr Ser
        195                 200                 205

Ile Ser Thr Ser Gly Ser Ser Ile Arg Leu Leu Gln Asn Ile Phe Arg
    210                 215                 220

Glu Asp Ser Tyr Phe Ala Gly Ile Pro Val Ser Val Ile Glu Tyr Trp
```

```
                225                 230                 235                 240
            Tyr Gln Arg Glu Gly Tyr Val Lys Ser Met Ser Asp Leu Ile Glu Lys
                            245                 250                 255

Glu Leu Ser Cys Phe Ser Asn Pro Glu Glu Val Met Ile Phe Phe Ser
                        260                 265                 270

Ala His Gly Val Pro Val Ser Tyr Ile Glu Ala Gly Asp Pro Tyr Arg
                    275                 280                 285

Asp Gln Met Glu Asp Cys Ile Ser Leu Ile Met Asp Glu Leu Lys Ser
                290                 295                 300

Arg Gly Val Ser Asn Gln His Thr Leu Ala Tyr Gln Ser Arg Val Gly
            305                 310                 315                 320

Pro Val Gln Trp Leu Lys Pro Tyr Thr Asp Glu Val Ile Val Glu Leu
                            325                 330                 335

Gly Gln Lys Gly Val Lys Ser Leu Leu Ala Val Pro Ser Phe Val
                        340                 345                 350

Ser Glu His Ile Glu Thr Leu Glu Glu Ile Asp Met Glu Tyr Arg Glu
                    355                 360                 365

Leu Ala Leu Glu Ser Gly Ile Glu Asn Trp Gly Arg Val Pro Ala Leu
                370                 375                 380

Gly Cys Lys Ser Ser Phe Ile Thr Asp Leu Ala Asp Ala Val Ile Glu
            385                 390                 395                 400

Ser Leu Pro Ser Ala Ser Val Met Ser Thr Ala Lys Ser Thr Ser Asn
                            405                 410                 415

Asp Gly Asn Thr Asp Leu Val Gln Tyr Val Val Asn Leu Phe Phe Gly
                        420                 425                 430

Ser Ile Phe Ala Phe Val Leu Leu Phe Ser Pro Arg Leu Ile Ser Gly
                    435                 440                 445

Ile Arg Asn Phe Leu
                450

<210> SEQ ID NO 17
<211> LENGTH: 1748
<212> TYPE: DNA
<213> ORGANISM: Triticum aestivum

<400> SEQUENCE: 17
gctttgattc cagaaaggga gaggagagag gggaagaaga cgccagagtc gcaacccgcc      60
gcagatctcc tccgtcctcc gcgcccagcc ccgctctgtc ctccatggag tgcgtccgct     120
ccggagctct tgatctgggg cgctccggga atttcttggg gaagagcggc tccacgacgt     180
catgtggtaa agtcagatgt tctacaaacc ttgctggttc taccaaatgc gagcaaaact     240
tgcatgggaa ggttaaaccc ttgctgttgt cagcaagtgg aaaagcaagg ggaacctctg     300
gtttggttca cagaagtgca gtacttaaac atcagcacca tctttctgtg agatccacct     360
ctaccgatgt atgtactact tttgatgaag atgtcaaagg tgtatcttca catgctgttg     420
aggaaaagat tggagtgctg ttactaaatc ttggtggtcc agagaccctc aatgatgttc     480
aaccattttt gttcaaccct tttgctgatc cagatatcat ccgactccct aggctgttca     540
ggtttcttca aagaccactg gccaaactta tttctacttt tagagctcct aagagtaaag     600
aggggtatgc ctcaattggt ggtggatcac ctctgcggaa aattaccgac gagcaggcaa     660
atgctttgaa ggttgcacta aaaagtaaga acttggaagc agatatatat gttggaatgc     720
gttattggta cccattcacc gaagaagcca tcgatcagat taagaaggat aaaattacga     780
agcttgtggt tcttccacta taccctcaat actccatatc aacaagcggg tctagtatcc     840
```

-continued

```
gcgttctcca aaacattgtc aaggaagatc aatactttgc tggcttgcca atttccatta    900
ttgaatcttg gtaccagcgc gagggctatg tgaaatcaat ggctgactta attgagaagg    960
aactatcagt ttttacgaat cctgaagagg ttatgatatt cttcagtgca catggagtac   1020
cacttaccta tgttaaggat gctggagatc catacagaga tcagatggaa gactgcattg   1080
ctttgatcat ggaggagttg aaatccagag gaaccttgaa tgaccatact ctggcttacc   1140
agagtcgcgt gggaccagtt caatggctta agccatatac tgatgaagtt ttagttgaac   1200
ttggtcaaaa gggtgtaaag agtctcctgg ctgtcccagt aagcttcgtt agcgagcata   1260
ttgagacact ggaggaaatc gacatggagt acagggagtt ggctctagag tcgggcattg   1320
agaactgggg cagggttcca gctcttggat gcacttcatc cttcatctcg gatcttgctg   1380
atgctgtcgt cgaagccctt ccatctgcct ctgcgatgac gaccagaaag gtcaaggata   1440
ctgactctga catggatatg atgcattacc tgaccaagat gttcttcggc tcggtcctgg   1500
ccttcttcct gctgttatca ccgaggctag tttccgcttt ccggaatact cttcattgag   1560
ctgcttattt ttatcgatgc tccgtggtta accattttgg cgattgtaac tagaaaccgt   1620
atacaggata atatctgggc gagaaagaaa ggaagagttt gtttcactta tgtcttgccc   1680
ataacatatc gacatgcccg ttgtatgaag gagtcatgta ccaccagcat gtataatggc   1740
agatgctt                                                           1748
```

<210> SEQ ID NO 18
<211> LENGTH: 484
<212> TYPE: PRT
<213> ORGANISM: Triticum aestivum

<400> SEQUENCE: 18

```
Met Glu Cys Val Arg Ser Gly Ala Leu Asp Leu Gly Arg Ser Gly Asn
1               5                   10                  15

Phe Leu Gly Lys Ser Gly Ser Thr Thr Ser Cys Gly Lys Val Arg Cys
            20                  25                  30

Ser Thr Asn Leu Ala Gly Ser Thr Lys Cys Glu Gln Asn Leu His Gly
        35                  40                  45

Lys Val Lys Pro Leu Leu Leu Ser Ala Ser Gly Lys Ala Arg Gly Thr
    50                  55                  60

Ser Gly Leu Val His Arg Ser Ala Val Leu Lys His Gln His Leu
65                  70                  75                  80

Ser Val Arg Ser Thr Ser Thr Asp Val Cys Thr Thr Phe Asp Glu Asp
                85                  90                  95

Val Lys Gly Val Ser Ser His Ala Val Glu Glu Lys Ile Gly Val Leu
            100                 105                 110

Leu Leu Asn Leu Gly Gly Pro Glu Thr Leu Asn Asp Val Gln Pro Phe
        115                 120                 125

Leu Phe Asn Leu Phe Ala Asp Pro Asp Ile Ile Arg Leu Pro Arg Leu
    130                 135                 140

Phe Arg Phe Leu Gln Arg Pro Leu Ala Lys Leu Ile Ser Thr Phe Arg
145                 150                 155                 160

Ala Pro Lys Ser Lys Glu Gly Tyr Ala Ser Ile Gly Gly Gly Ser Pro
                165                 170                 175

Leu Arg Lys Ile Thr Asp Glu Gln Ala Asn Ala Leu Lys Val Ala Leu
            180                 185                 190

Lys Ser Lys Asn Leu Glu Ala Asp Ile Tyr Val Gly Met Arg Tyr Trp
        195                 200                 205
```

```
Tyr Pro Phe Thr Glu Glu Ala Ile Asp Gln Ile Lys Lys Asp Lys Ile
    210                 215                 220
Thr Lys Leu Val Val Leu Pro Leu Tyr Pro Gln Tyr Ser Ile Ser Thr
225                 230                 235                 240
Ser Gly Ser Ser Ile Arg Val Leu Gln Asn Ile Val Lys Glu Asp Gln
                245                 250                 255
Tyr Phe Ala Gly Leu Pro Ile Ser Ile Glu Ser Trp Tyr Gln Arg
                260                 265                 270
Glu Gly Tyr Val Lys Ser Met Ala Asp Leu Ile Glu Lys Glu Leu Ser
                275                 280                 285
Val Phe Thr Asn Pro Glu Glu Val Met Ile Phe Ser Ala His Gly
    290                 295                 300
Val Pro Leu Thr Tyr Val Lys Asp Ala Gly Asp Pro Tyr Arg Asp Gln
305                 310                 315                 320
Met Glu Asp Cys Ile Ala Leu Ile Met Glu Glu Leu Lys Ser Arg Gly
                325                 330                 335
Thr Leu Asn Asp His Thr Leu Ala Tyr Gln Ser Arg Val Gly Pro Val
                340                 345                 350
Gln Trp Leu Lys Pro Tyr Thr Asp Glu Val Leu Val Glu Leu Gly Gln
                355                 360                 365
Lys Gly Val Lys Ser Leu Leu Ala Val Pro Val Ser Phe Val Ser Glu
    370                 375                 380
His Ile Glu Thr Leu Glu Glu Ile Asp Met Glu Tyr Arg Glu Leu Ala
385                 390                 395                 400
Leu Glu Ser Gly Ile Glu Asn Trp Gly Arg Val Pro Ala Leu Gly Cys
                405                 410                 415
Thr Ser Ser Phe Ile Ser Asp Leu Ala Asp Ala Val Val Glu Ala Leu
                420                 425                 430
Pro Ser Ala Ser Ala Met Thr Thr Arg Lys Val Lys Asp Thr Asp Ser
    435                 440                 445
Asp Met Asp Met Met His Tyr Leu Thr Lys Met Phe Phe Gly Ser Val
    450                 455                 460
Leu Ala Phe Phe Leu Leu Leu Ser Pro Arg Leu Val Ser Ala Phe Arg
465                 470                 475                 480
Asn Thr Leu His
```

<210> SEQ ID NO 19
<211> LENGTH: 1859
<212> TYPE: DNA
<213> ORGANISM: Arabidopsis thaliana

<400> SEQUENCE: 19

| | | | | | |
|---|---|---|---|---|---|
| aaaaaataaa | acaaattcga | agaaatataa | atgagatttt | tgtagctagc | tcctccaaat | 60 |
| ccaaatcgtt | gcgttaaggt | ttcttcaagt | ttcaatcttt | tgcaatgaa | ttgcccagcc | 120 |
| atgactgctt | ctccttcttc | ttcctcttct | tcttcctact | caacgtttcg | tcctcctcct | 180 |
| ccactcttgc | acaattgag | taacgattca | caaagatctg | ttgttatgca | ctgcacaaga | 240 |
| ttacccttg | aagcatttgc | tgctacttca | tcaaaccggc | ttcttgggaa | acattcattg | 300 |
| cctttgagag | cagctttggt | tacttcgaac | cctttaaaca | tttcatcttc | ctcagttatc | 360 |
| tctgatgcca | tttcatcttc | ctctgttatc | actgatgatg | ccaaaattgg | tgtcttgtta | 420 |
| ttaaaccttg | gaggtcctga | gactttagat | gatgtacaac | cctttttgtt | taacctcttc | 480 |
| gccgacccgg | acattatacg | gttgccgccg | gtattccagt | ttcttcagaa | gccattagca | 540 |

```
cagtttatat cagtagcaag agcacccaaa agcaaggaag gatatgcatc tattggtgga    600
ggttctcctc ttcgccacat aactgatgca caggctgaag aattaagaaa atgcctttgg    660
gaaaaaaatg taccagcaaa ggtatatgtt ggtatgcggt attggcatcc attcactgag    720
gaagccattg aacagataaa aagagatgga attacaaaac tagttgttct accactttat    780
cctcaatttt ctatatcaac tagtggttca agcctaagac tcttggagag aatatttcga    840
gaggacgagt atcttgttaa catgcaacat actgttatac catcgtggta tcagcgggag    900
ggatatataa aggcaatggc aaatctaatc caaagcgagt tgggaaaatt tggttctcct    960
aatcaggttg taatattttt cagtgcacat ggcgtgcctc ttgcatatgt cgaagaagcc   1020
ggtgatcctt acaaggcaga gatggaagaa tgtgttgatc taatcatgga ggaattagac   1080
aagagaaaga taactaatgc ttacactctt gcttatcaga gcagagttgg accagttgaa   1140
tggctgaaac catacactga agaagccatt actgaacttg gtaaaaaagg tgttgaaaat   1200
cttctggctg tacccataag ttttgtgagc gagcacattg aaactctgga ggagatagat   1260
gttgagtata aagagttggc tttgaagtct ggtatcaaaa actgggggcg agtacctgct   1320
ctaggaacag aacctatgtt tatatctgac ttggcagatg ctgttgtgga aagtcttcca   1380
tacgttggtg ctatggctgt ctcaaacctt gaagctcgac agtcgttagt tccgctcggg   1440
agtgtagaag aattattagc aacgtatgat tcacagagaa gggagttacc agcaccggtg   1500
acaatgtggg aatggggatg gacaaaaagt gcagaaacat ggaacggaag agcagcaatg   1560
ttagcggtgc tagcactctt ggtgctcgaa gtcaccaccg gaaaagggtt tctgcatcag   1620
tggggcatct tgccttcatt ataataaaga taacgtatag tcttttttctc tatgaaaacc   1680 caatccaaga atccaaatgt gagctttcac atgtggaata aggccagcta tgttattatg   1740
ctctcttctt ctctgttgta gaaatgttga catttaaata cttcatactg tatcttcata   1800
aaacattaaa tgttgacatt ttaatcggca tgcttttcg caacgtgaat gtttgagtc     1859

<210> SEQ ID NO 20
<211> LENGTH: 512
<212> TYPE: PRT
<213> ORGANISM: Arabidopsis thaliana

<400> SEQUENCE: 20

Met Asn Cys Pro Ala Met Thr Ala Ser Pro Ser Ser Ser Ser Ser Ser
1               5                   10                  15

Ser Tyr Ser Thr Phe Arg Pro Pro Pro Leu Leu Pro Gln Leu Ser
            20                  25                  30

Asn Asp Ser Gln Arg Ser Val Val Met His Cys Thr Arg Leu Pro Phe
        35                  40                  45

Glu Ala Phe Ala Ala Thr Ser Ser Asn Arg Leu Leu Gly Lys His Ser
    50                  55                  60

Leu Pro Leu Arg Ala Ala Leu Val Thr Ser Asn Pro Leu Asn Ile Ser
65                  70                  75                  80

Ser Ser Ser Val Ile Ser Asp Ala Ile Ser Ser Ser Val Ile Thr
                85                  90                  95

Asp Asp Ala Lys Ile Gly Val Leu Leu Leu Asn Leu Gly Gly Pro Glu
            100                 105                 110

Thr Leu Asp Asp Val Gln Pro Phe Leu Phe Asn Leu Phe Ala Asp Pro
        115                 120                 125

Asp Ile Ile Arg Leu Pro Pro Val Phe Gln Phe Leu Gln Lys Pro Leu
    130                 135                 140
```

Ala Gln Phe Ile Ser Val Ala Arg Ala Pro Lys Ser Lys Glu Gly Tyr
145                 150                 155                 160

Ala Ser Ile Gly Gly Ser Pro Leu Arg His Ile Thr Asp Ala Gln
        165                 170                 175

Ala Glu Glu Leu Arg Lys Cys Leu Trp Glu Lys Asn Val Pro Ala Lys
        180                 185                 190

Val Tyr Val Gly Met Arg Tyr Trp His Pro Phe Thr Glu Glu Ala Ile
            195                 200                 205

Glu Gln Ile Lys Arg Asp Gly Ile Thr Lys Leu Val Val Leu Pro Leu
        210                 215                 220

Tyr Pro Gln Phe Ser Ile Ser Thr Ser Gly Ser Ser Leu Arg Leu Leu
225                 230                 235                 240

Glu Arg Ile Phe Arg Glu Asp Glu Tyr Leu Val Asn Met Gln His Thr
                245                 250                 255

Val Ile Pro Ser Trp Tyr Gln Arg Glu Gly Tyr Ile Lys Ala Met Ala
            260                 265                 270

Asn Leu Ile Gln Ser Glu Leu Gly Lys Phe Gly Ser Pro Asn Gln Val
            275                 280                 285

Val Ile Phe Phe Ser Ala His Gly Val Pro Leu Ala Tyr Val Glu Glu
            290                 295                 300

Ala Gly Asp Pro Tyr Lys Ala Glu Met Glu Glu Cys Val Asp Leu Ile
305                 310                 315                 320

Met Glu Glu Leu Asp Lys Arg Lys Ile Thr Asn Ala Tyr Thr Leu Ala
                325                 330                 335

Tyr Gln Ser Arg Val Gly Pro Val Glu Trp Leu Lys Pro Tyr Thr Glu
            340                 345                 350

Glu Ala Ile Thr Glu Leu Gly Lys Lys Gly Val Glu Asn Leu Leu Ala
            355                 360                 365

Val Pro Ile Ser Phe Val Ser Glu His Ile Glu Thr Leu Glu Glu Ile
        370                 375                 380

Asp Val Glu Tyr Lys Glu Leu Ala Leu Lys Ser Gly Ile Lys Asn Trp
385                 390                 395                 400

Gly Arg Val Pro Ala Leu Gly Thr Glu Pro Met Phe Ile Ser Asp Leu
                405                 410                 415

Ala Asp Ala Val Val Glu Ser Leu Pro Tyr Val Gly Ala Met Ala Val
            420                 425                 430

Ser Asn Leu Glu Ala Arg Gln Ser Leu Val Pro Leu Gly Ser Val Glu
        435                 440                 445

Glu Leu Leu Ala Thr Tyr Asp Ser Gln Arg Arg Glu Leu Pro Ala Pro
        450                 455                 460

Val Thr Met Trp Glu Trp Gly Trp Thr Lys Ser Ala Glu Thr Trp Asn
465                 470                 475                 480

Gly Arg Ala Ala Met Leu Ala Val Leu Ala Leu Leu Val Leu Glu Val
                485                 490                 495

Thr Thr Gly Lys Gly Phe Leu His Gln Trp Gly Ile Leu Pro Ser Leu
            500                 505                 510

<210> SEQ ID NO 21
<211> LENGTH: 1797
<212> TYPE: DNA
<213> ORGANISM: Arabidopsis thaliana

<400> SEQUENCE: 21
gtttcttcaa gtttcaatct ttttgcaatg aattgcccag ccatgactgc ttctccttct    60

```
tcttcctctt cttcttccta ctcaacgttt cgtcctcctc ctccactctt gccacaattg    120
agtaacgatt cacaaagatc tgttgttatg cactgcacaa gattaccctt tgaagcattt    180
gctgctactt catcaaaccg gcttcttggg aaacattcat tgcctttgag agcagctttg    240
gttacttcga acccttttaaa catttcatct tcctcagtta tctctgatgc catttcatct    300
tcctctgtta tcactgatga tgccaaaatt ggtgtcttgt tattaaacct tggaggccct    360
gagactttag atgatgtaca acccttttg tttaacctct tcgccgaccc ggacattata    420
cggttgccgc cggtattcca gtttcttcag aagccattag cacagtttat atcagtagca    480
agagcaccaa aagcaagaag atatgcatct attggtggag gttctcctct tcgccacata    540
actgatgcac aggctgaaga attaagaaaa tgcctttggg aaaaaaatgt accagcaaag    600
gtatatgttg gtatgcggta ttggcatcca ttcactgagg aagccattga acagataaaa    660
agagatggaa ttacaaaact agttgttcta ccactttatc ctcaatttc tatatcaact    720 agtggttcaa gcctaagact cttggagaga atatttcgag aggacgagta tcttgttaac    780
atgcaacata ctgttatacc atcgtggtat cagcgggagg gatatataaa ggcaatggca    840
aatctaatcc aaagcgagtt gggaaaattt ggttctccta atcaggttgt aatattttc    900 agtgcacatg gcgtgcctct tgcatatgtc gaagaagccg gtgatcctta caaggcagag    960
atggaagaat gtgttgatct aatcatggag gaattagaca agagaaagat aactaatgct   1020
tacactcttg cttatcagag cagagttgga ccagttgaat ggctgaaacc atacactgaa   1080
gaagccatta ctgaacttgg taaaaaaggt gttgaaaatc ttctggctgt acccataagt   1140
tttgtgagcg agcacattga aactctggag gagatagatg ttgagtataa agagttggct   1200
ttgaagtctg gtatcaaaaa ctgggggcga gtacctgctc taggaacaga acctatgttt   1260
atatctgact tggcagatgc tgttgtggaa agtcttccat acgttggtgc tatggctgtc   1320
tcaaaccttg aagctcgaca gtcgttagtt ccgctcggga gtgtagaaga actattagca   1380
acgtatgatt cacagagaag ggagttacca gcaccggtga caatgtggga atggggatgg   1440
acaaaaagtg cagaaacatg gaacggaaga gcagcaatgt tagcggtgct agcactcttg   1500
gtgctcgaag tcaccaccgg aaaagggttt ctgcatcagt ggggcatctt gccttcatta   1560
taataaagat aacgtatagt ctttttctct atgaaaaccc aatccaagaa tccaaatgtg   1620
agctttcaca tgtggaataa ggccagctat gttattatgc tctcttcttc tctgtgtaga   1680
aatgtgacat ttaaatactt catactgtat cttcataaaa cattaaatgt tgacattta    1740 aaaaaaaaaa aaaaaaaaaaa aaaaaaaaaa aaaaaaaaaa aaaaaaaaaa aaaaaaa     1797
```

<210> SEQ ID NO 22
<211> LENGTH: 511
<212> TYPE: PRT
<213> ORGANISM: Arabidopsis thaliana

<400> SEQUENCE: 22

```
Met Asn Cys Pro Ala Met Thr Ala Ser Pro Ser Ser Ser Ser Ser
1               5                   10                  15

Ser Tyr Ser Thr Phe Arg Pro Pro Pro Leu Leu Pro Gln Leu Ser
                20                  25                  30

Asn Asp Ser Gln Arg Ser Val Val Met His Cys Thr Arg Leu Pro Phe
            35                  40                  45

Glu Ala Phe Ala Ala Thr Ser Ser Asn Arg Leu Leu Gly Lys His Ser
    50                  55                  60
```

```
Leu Pro Leu Arg Ala Ala Leu Val Thr Ser Asn Pro Leu Asn Ile Ser
 65                  70                  75                  80

Ser Ser Ser Val Ile Ser Asp Ala Ile Ser Ser Ser Val Ile Thr
             85                  90                  95

Asp Asp Ala Lys Ile Gly Val Leu Leu Leu Asn Leu Gly Gly Pro Glu
                100                 105                 110

Thr Leu Asp Asp Val Gln Pro Phe Leu Phe Asn Leu Phe Ala Asp Pro
            115                 120                 125

Asp Ile Ile Arg Leu Pro Pro Val Phe Gln Phe Leu Gln Lys Pro Leu
            130                 135                 140

Ala Gln Phe Ile Ser Val Ala Arg Ala Pro Lys Ala Arg Arg Tyr Ala
145                 150                 155                 160

Ser Ile Gly Gly Gly Ser Pro Leu Arg His Ile Thr Asp Ala Gln Ala
                165                 170                 175

Glu Glu Leu Arg Lys Cys Leu Trp Glu Lys Asn Val Pro Ala Lys Val
                180                 185                 190

Tyr Val Gly Met Arg Tyr Trp His Pro Phe Thr Glu Glu Ala Ile Glu
            195                 200                 205

Gln Ile Lys Arg Asp Gly Ile Thr Lys Leu Val Val Leu Pro Leu Tyr
            210                 215                 220

Pro Gln Phe Ser Ile Ser Thr Ser Gly Ser Ser Leu Arg Leu Leu Glu
225                 230                 235                 240

Arg Ile Phe Arg Glu Asp Glu Tyr Leu Val Asn Met Gln His Thr Val
                245                 250                 255

Ile Pro Ser Trp Tyr Gln Arg Glu Gly Tyr Ile Lys Ala Met Ala Asn
            260                 265                 270

Leu Ile Gln Ser Glu Leu Gly Lys Phe Gly Ser Pro Asn Gln Val Val
            275                 280                 285

Ile Phe Phe Ser Ala His Gly Val Pro Leu Ala Tyr Val Glu Glu Ala
            290                 295                 300

Gly Asp Pro Tyr Lys Ala Glu Met Glu Glu Cys Val Asp Leu Ile Met
305                 310                 315                 320

Glu Glu Leu Asp Lys Arg Lys Ile Thr Asn Ala Tyr Thr Leu Ala Tyr
                325                 330                 335

Gln Ser Arg Val Gly Pro Val Glu Trp Leu Lys Pro Tyr Thr Glu Glu
            340                 345                 350

Ala Ile Thr Glu Leu Gly Lys Lys Gly Val Glu Asn Leu Leu Ala Val
            355                 360                 365

Pro Ile Ser Phe Val Ser Glu His Ile Glu Thr Leu Glu Glu Ile Asp
            370                 375                 380

Val Glu Tyr Lys Glu Leu Ala Leu Lys Ser Gly Ile Lys Asn Trp Gly
385                 390                 395                 400

Arg Val Pro Ala Leu Gly Thr Glu Pro Met Phe Ile Ser Asp Leu Ala
                405                 410                 415

Asp Ala Val Val Glu Ser Leu Pro Tyr Val Gly Ala Met Ala Val Ser
            420                 425                 430

Asn Leu Glu Ala Arg Gln Ser Leu Val Pro Leu Gly Ser Val Glu Glu
            435                 440                 445

Leu Leu Ala Thr Tyr Asp Ser Gln Arg Arg Glu Leu Pro Ala Pro Val
            450                 455                 460

Thr Met Trp Glu Trp Gly Trp Thr Lys Ser Ala Glu Thr Trp Asn Gly
465                 470                 475                 480

Arg Ala Ala Met Leu Ala Val Leu Ala Leu Leu Val Leu Glu Val Thr
```

485                 490                 495
Thr Gly Lys Gly Phe Leu His Gln Trp Gly Ile Leu Pro Ser Leu
            500                 505                 510

<210> SEQ ID NO 23
<211> LENGTH: 2116
<212> TYPE: DNA
<213> ORGANISM: Nepeta racemosa

<400> SEQUENCE: 23

| | | | | | |
|---|---|---|---|---|---|
| gcacaatttc | atttatttt | ttgtgaataa | tctcttctct | acattatcga | aatgaaccaa | 60 |
| tcttccatga | atatacgaat | tcaagctcct | tctccatctc | tactactgcc | acgagccaaa | 120 |
| gtatgcccat | gcataagggt | gcaactggag | agttttccca | atcctaatct | tttgaaaaca | 180 |
| tccatagttg | caagatgccc | cttggggtgg | tccaagacat | catctgtatt | tgcagagcac | 240 |
| tcgatcaagc | attcaacacg | accagaagcc | ctggttaccg | ctggctctca | agaaacgtcc | 300 |
| acacctgccc | tggttggtaa | tgataagatt | ggagtgttat | tgcttaacct | tggaggtcca | 360 |
| gagactctgg | atgacgtgca | gcctttcttg | tttaatcttt | ttgcagatcc | agatattatt | 420 |
| cgattgccaa | gattattccg | gtttcttcag | aagcccttgg | cccaattcat | atctgtagct | 480 |
| agatcctcga | agagcaaaga | aggatatgct | gcaattggtg | gtggctcgcc | actgcgtcgt | 540 |
| atcactgatg | ctcaggctga | ggagttgaga | aaggcactgt | gtgacaagaa | tgtccctgca | 600 |
| aaagtgtatg | ttggtatgcg | ctactggcat | cctttcactg | aagaagcgat | tgaacagatt | 660 |
| aaggtagatg | gaatttcaaa | acttgtcgtg | cttcctctct | acccacaatt | ctcaatctca | 720 |
| actagtggtt | caagtcttcg | gcttctggag | agtatattca | gggaggatga | atatctagtc | 780 |
| aacatgcagc | atactgtaat | tccttcatgg | taccagcggg | gaggatatat | aaaagctatg | 840 |
| gcagatttga | ttgaaaagga | gttgggaaag | tttgattgtt | ctgaggaggt | gatgattttc | 900 |
| tttagtgctc | atggggtacc | actggcctat | gttgaggaag | ctggtgatcc | atacaaagct | 960 |
| gagatggagg | agtgtgttga | cttgatcatg | aagaactag | aaaacagaaa | gataaataat | 1020 |
| gcatataccc | ttgcatatca | gagcagagtt | ggacctgtag | aatggttgaa | accctacaca | 1080 |
| gatgatacaa | tcgttgaact | tggagaaaag | ggagtgaaga | gtcttctagc | tgttccaatt | 1140 |
| agttttgtga | gcgaacatat | tgaaacattg | aagaaatgg | atgttgaata | caagaattg | 1200 |
| gctctaaagt | ctggcataga | aaagtgggga | cgagttcctg | cactaggttg | cgagcctact | 1260 |
| tttatttcag | atttggctga | tgctgttata | gaaagtcttc | catatgttgg | agctatggct | 1320 |
| gtctcaaatc | tcgaagctcg | acagtcttta | gtcccactcg | gcagtgtaga | agagctattg | 1380 |
| gccgcatatg | attcacagcg | cagagagctt | cctcccctg | tggtagtttg | ggaatggggt | 1440 |
| tggacgaaaa | gtgctgaaac | atggaatggc | agagcagcga | tgctggcggt | tcttgtcctg | 1500 |
| ctcgtgctcg | aggtgactac | tggagaaggt | tttcttcacc | agtggggtat | attgcccttg | 1560 |
| gttccgtgac | cacaatttcc | cctacttcct | tcacttcctt | catcctctct | ctaacctctg | 1620 |
| tatacataaa | ctctctgcaa | tatatatgga | ccctgcataa | gaaagatact | acaaagtttg | 1680 |
| gaggaaaatc | agaaacaaaa | aatgtcaaga | gttatctgta | caagttggat | atgcacgtct | 1740 |
| cgatcctcac | gtgtaggatc | tggttcgaat | tgagctggat | aaggagaaat | cagaaagtga | 1800 |
| gaagttccgg | aaattgagag | ctcacggttt | tgaggatcgc | ttgaggtaga | ggttactttc | 1860 |
| tagaaatgga | cgtgtgagat | tcgacttttg | aagcagagct | ttctctcagt | ctgtttagtt | 1920 |
| tttcctcttc | tttttttttt | tgatacggaa | cgaacaagat | gttgttgtat | acacctccga | 1980 |

```
cattcatatg tatgctggct tatgaattta tcaagttgta tcaatgaaaa ttatgaatgt    2040
ggtaggtgca tttttacaaa aaaaaaaaaa aaaaaaaaaa aaaaaaaaaa aaaaaaaaaa    2100
aaaaaaaaaa aaaaaa                                                   2116
```

<210> SEQ ID NO 24
<211> LENGTH: 505
<212> TYPE: PRT
<213> ORGANISM: Nepeta racemosa

<400> SEQUENCE: 24

```
Met Asn Gln Ser Ser Met Asn Ile Arg Ile Gln Ala Pro Ser Pro Ser
1               5                   10                  15

Leu Leu Leu Pro Arg Ala Lys Val Cys Pro Cys Ile Arg Val Gln Leu
            20                  25                  30

Glu Ser Phe Pro Asn Pro Asn Leu Leu Lys Thr Ser Ile Val Ala Arg
        35                  40                  45

Cys Pro Leu Gly Trp Ser Lys Thr Ser Ser Val Phe Ala Glu His Ser
    50                  55                  60

Ile Lys His Ser Thr Arg Pro Glu Ala Leu Val Thr Ala Gly Ser Gln
65                  70                  75                  80

Glu Thr Ser Thr Pro Ala Leu Val Gly Asn Asp Lys Ile Gly Val Leu
                85                  90                  95

Leu Leu Asn Leu Gly Gly Pro Glu Thr Leu Asp Asp Val Gln Pro Phe
            100                 105                 110

Leu Phe Asn Leu Phe Ala Asp Pro Asp Ile Ile Arg Leu Pro Arg Leu
        115                 120                 125

Phe Arg Phe Leu Gln Lys Pro Leu Ala Gln Phe Ile Ser Val Ala Arg
    130                 135                 140

Ser Ser Lys Ser Lys Glu Gly Tyr Ala Ala Ile Gly Gly Gly Ser Pro
145                 150                 155                 160

Leu Arg Arg Ile Thr Asp Ala Gln Ala Glu Glu Leu Arg Lys Ala Leu
                165                 170                 175

Cys Asp Lys Asn Val Pro Ala Lys Val Tyr Val Gly Met Arg Tyr Trp
            180                 185                 190

His Pro Phe Thr Glu Glu Ala Ile Glu Gln Ile Lys Val Asp Gly Ile
        195                 200                 205

Ser Lys Leu Val Val Leu Pro Leu Tyr Pro Gln Phe Ser Ile Ser Thr
    210                 215                 220

Ser Gly Ser Ser Leu Arg Leu Leu Glu Ser Ile Phe Arg Glu Asp Glu
225                 230                 235                 240

Tyr Leu Val Asn Met Gln His Thr Val Ile Pro Ser Trp Tyr Gln Arg
                245                 250                 255

Gly Gly Tyr Ile Lys Ala Met Ala Asp Leu Ile Glu Lys Glu Leu Gly
            260                 265                 270

Lys Phe Asp Cys Ser Glu Glu Val Met Ile Phe Phe Ser Ala His Gly
        275                 280                 285

Val Pro Leu Ala Tyr Val Glu Glu Ala Gly Asp Pro Tyr Lys Ala Glu
    290                 295                 300

Met Glu Glu Cys Val Asp Leu Ile Met Glu Glu Leu Glu Asn Arg Lys
305                 310                 315                 320

Ile Asn Asn Ala Tyr Thr Leu Ala Tyr Gln Ser Arg Val Gly Pro Val
                325                 330                 335

Glu Trp Leu Lys Pro Tyr Thr Asp Thr Ile Val Glu Leu Gly Glu
            340                 345                 350
```

```
Lys Gly Val Lys Ser Leu Leu Ala Val Pro Ile Ser Phe Val Ser Glu
        355                 360                 365

His Ile Glu Thr Leu Glu Glu Met Asp Val Glu Tyr Lys Glu Leu Ala
        370                 375                 380

Leu Lys Ser Gly Ile Glu Lys Trp Gly Arg Val Pro Ala Leu Gly Cys
385                 390                 395                 400

Glu Pro Thr Phe Ile Ser Asp Leu Ala Asp Ala Val Ile Glu Ser Leu
                405                 410                 415

Pro Tyr Val Gly Ala Met Ala Val Ser Asn Leu Glu Ala Arg Gln Ser
            420                 425                 430

Leu Val Pro Leu Gly Ser Val Glu Leu Leu Ala Ala Tyr Asp Ser
        435                 440                 445

Gln Arg Arg Glu Leu Pro Pro Pro Val Val Trp Glu Trp Gly Trp
    450                 455                 460

Thr Lys Ser Ala Glu Thr Trp Asn Gly Arg Ala Ala Met Leu Ala Val
465                 470                 475                 480

Leu Val Leu Leu Val Leu Glu Val Thr Thr Gly Glu Gly Phe Leu His
                485                 490                 495

Gln Trp Gly Ile Leu Pro Leu Val Pro
            500                 505

<210> SEQ ID NO 25
<211> LENGTH: 2072
<212> TYPE: DNA
<213> ORGANISM: Zea mays

<400> SEQUENCE: 25
gtcccatact cccgtcctgt ccgtcttcac ctgcgttccc cgggtcccga cacgccgctg      60
taccagtccc gcccgcctgc gcacttctcc caccccgcg ccgcctccgg cgccggcgag     120
ccctcccgac gctcctcgaa cgatccgtcc ctgtcgcggc ccttctctct gccgcttcca     180
gcccaagggg aggagaggga gaggatgtgg tcgtcgagcc aggcgagcac gagggggcgtc    240 gtggagatgg ggagggtgga ggccgggccg tcgcatttcc ctaagagacc cgcgcctcag     300
aactccgcca gggtcaatct gtcaaggaca cacacagtca aacctacctc tgctggcgac     360
cgttcaggaa tttctgttaa atgcaacttg gggtggtctt ctcaaccatc gcctgacttg     420
aggcatcact ttagaggata tcatcagca tcagaggcag ttcttacttc ccaatctgat     480
gtgagaaaac tgtttgttgg caatgaaaaa atcggtgttc tcttgctgaa tcttgggggc     540
ccagagactc ttgacgatgt gcagcctttc ttgtttaatc ttttgcaga tccggacatt      600 atccgtcttc ctaggctctt tcgctttctg cagaagccac ttgcaaaatt catatcagaa     660
gtgagagcac caaaaagtaa ggaaggttat gcatccatag gtggcggttc tcctctacga     720
caaattactg atgcacaggc tgaagcactt agggaggcat acatgggaa agatgttcct      780 gccaacgtgt atgttggaat gcggtattgg catcccttca ctgaagaagc catagaacaa     840
ataaaacggg atggaatcac gaaacttgtt gtgttgcctc tataccctca gttctccata     900
tcaactagtg gttcaagtct ccgtttattg gagagcatat tcagagagga tgagtatctc     960
gtgaatatgc aacatacagt tataccttcc tggtaccaac gtgaaggata tatcaaggct    1020
atggcaactt tgattgaaaa cgaattgaca aaatttcaag aaccccaaaa ggttatgata    1080 ttttcagtg ctcatggagt tcctctggca tatgttgaag aagctggtga tccatataaa    1140
gcagaaatgg aagagtgtat cgatcttatc atggaagaac tggaaaaaag aggaataaca    1200
```

```
aatccgtgca tacttgctta tcagagccga gttggaccag tggaatggct gaaaccgtac    1260
actgatgaga caattattga gcttgggcag aaagggtaa agagcctgct tgctgttccc    1320
attagttttg ttagcgaaca cattgaaact ttggaagaaa tcgatgtgga gtacaaagag    1380
ttggctttag aatctggcat caagcactgg ggacgggttc cagcactagg ttgcgaaccc    1440
acattcattt cggatcttgc tgatgctgtt attgaaagcc taccttatgt tggcgcaatg    1500
gcagtttcca atcttgaggc tcggcagtct ctcgtacccc tcgggagcgt ggaggagctg    1560
ctagcagcat acgactcgaa gcgcgatgag ctccctccac cggtaatcgt gtgggagtgg    1620
ggctggacaa agagcgcgga gacctggaat ggtcgtgcgg cgatgctggc cgtgctggct    1680
ctcctggtgc tggaagtgac caccggcgaa gggttcctgc atcaatgggg aatcctgcct    1740
ctgttccgct gagccgacag ttctgttcat gatggggtca taattttgct gcagccgaag    1800
gaagttttga acttctgatg ctgtatatga atcaatttgc cttaaatcgt cgatgggaaa    1860
agaggagaaa atggtaaaat atggacagaa ttcgacggta tatcatgtta tattgtacct    1920
acctacatga catgggacat gaaatagggc tcagacatgc gctatggaac ttggaataca    1980
cacaaaccta acacgccaaa aaaaaaaaaa aaaaaaaaaa aaaaaaaaaa aaaaaaaaaa    2040
aaaaaaaaaa aaaaaaaaaa aaaaaaaaaa aa                                  2072

<210> SEQ ID NO 26
<211> LENGTH: 515
<212> TYPE: PRT
<213> ORGANISM: Zea mays

<400> SEQUENCE: 26

Met Trp Ser Ser Ser Gln Ala Ser Thr Arg Gly Val Val Glu Met Gly
1               5                   10                  15

Arg Val Glu Ala Gly Pro Ser His Phe Pro Lys Arg Pro Ala Pro Gln
            20                  25                  30

Asn Ser Ala Arg Val Asn Leu Ser Arg Thr His Thr Val Lys Pro Thr
        35                  40                  45

Ser Ala Gly Asp Arg Ser Gly Ile Ser Val Lys Cys Asn Leu Gly Trp
    50                  55                  60

Ser Ser Gln Pro Ser Pro Asp Leu Arg His His Phe Arg Gly Tyr Ser
65                  70                  75                  80

Ser Ala Ser Glu Ala Val Leu Thr Ser Gln Ser Asp Val Arg Lys Leu
                85                  90                  95

Phe Val Gly Asn Glu Lys Ile Gly Val Leu Leu Leu Asn Leu Gly Gly
            100                 105                 110

Pro Glu Thr Leu Asp Asp Val Gln Pro Phe Leu Phe Asn Leu Phe Ala
        115                 120                 125

Asp Pro Asp Ile Ile Arg Leu Pro Arg Leu Phe Arg Phe Leu Gln Lys
    130                 135                 140

Pro Leu Ala Lys Phe Ile Ser Glu Val Arg Ala Pro Lys Ser Lys Glu
145                 150                 155                 160

Gly Tyr Ala Ser Ile Gly Gly Gly Ser Pro Leu Arg Gln Ile Thr Asp
                165                 170                 175

Ala Gln Ala Glu Ala Leu Arg Glu Ala Leu His Gly Lys Asp Val Pro
            180                 185                 190

Ala Asn Val Tyr Val Gly Met Arg Tyr Trp His Pro Phe Thr Glu Glu
        195                 200                 205

Ala Ile Glu Gln Ile Lys Arg Asp Gly Ile Thr Lys Leu Val Val Leu
    210                 215                 220
```

```
Pro Leu Tyr Pro Gln Phe Ser Ile Ser Thr Ser Gly Ser Ser Leu Arg
225                 230                 235                 240

Leu Leu Glu Ser Ile Phe Arg Glu Asp Glu Tyr Leu Val Asn Met Gln
            245                 250                 255

His Thr Val Ile Pro Ser Trp Tyr Gln Arg Glu Gly Tyr Ile Lys Ala
        260                 265                 270

Met Ala Thr Leu Ile Glu Asn Glu Leu Thr Lys Phe Gln Glu Pro Gln
    275                 280                 285

Lys Val Met Ile Phe Phe Ser Ala His Gly Val Pro Leu Ala Tyr Val
290                 295                 300

Glu Glu Ala Gly Asp Pro Tyr Lys Ala Glu Met Glu Glu Cys Ile Asp
305                 310                 315                 320

Leu Ile Met Glu Glu Leu Glu Lys Arg Gly Ile Thr Asn Pro Cys Ile
            325                 330                 335

Leu Ala Tyr Gln Ser Arg Val Gly Pro Val Glu Trp Leu Lys Pro Tyr
        340                 345                 350

Thr Asp Glu Thr Ile Ile Glu Leu Gly Gln Lys Gly Val Lys Ser Leu
    355                 360                 365

Leu Ala Val Pro Ile Ser Phe Val Ser Glu His Ile Glu Thr Leu Glu
370                 375                 380

Glu Ile Asp Val Glu Tyr Lys Glu Leu Ala Leu Glu Ser Gly Ile Lys
385                 390                 395                 400

His Trp Gly Arg Val Pro Ala Leu Gly Cys Glu Pro Thr Phe Ile Ser
            405                 410                 415

Asp Leu Ala Asp Ala Val Ile Glu Ser Leu Pro Tyr Val Gly Ala Met
        420                 425                 430

Ala Val Ser Asn Leu Glu Ala Arg Gln Ser Leu Val Pro Leu Gly Ser
    435                 440                 445

Val Glu Glu Leu Leu Ala Ala Tyr Asp Ser Lys Arg Asp Glu Leu Pro
450                 455                 460

Pro Pro Val Ile Val Trp Glu Trp Gly Trp Thr Lys Ser Ala Glu Thr
465                 470                 475                 480

Trp Asn Gly Arg Ala Ala Met Leu Ala Val Leu Ala Leu Leu Val Leu
            485                 490                 495

Glu Val Thr Thr Gly Glu Gly Phe Leu His Gln Trp Gly Ile Leu Pro
        500                 505                 510

Leu Phe Arg
        515

<210> SEQ ID NO 27
<211> LENGTH: 1946
<212> TYPE: DNA
<213> ORGANISM: Triticum aestivum

<400> SEQUENCE: 27
ggttctcttg tacctccgcg cttccaagga tttgatttct tcgctcgttg cggatttccc      60
tactggctga gtaccaattt cgctcggttt cacaacaaat ttggatatcc atgctccacg     120
tcaggctcgc tcctgggcct gcaccgcgta atttatctag agatgggat accagcgcat      180 acctacatag ctggtgttcc gttccttgtc aagcaggct cagtctctcg aggacatatt      240
caattaaatc ttctttgatt ggtagcgcca cgggactttg tcttgggcaa tgttgccgca     300
tcaagccttt gtcctgcaaa tgcaagctag gtaggtcttc tcagccgcca ctgactcga     360 ggcaacattt tagtgcatct tcatccgcat cagaggcggt tctcactgcg cagtctgata     420
```

```
tccggaaact ttttgttgcc aatgagaaaa tcggcgttct gctgctaaac cttggaggcc      480
cagagaccct tgatgatgtc cagccttcct tgtttaatct ctttgctgat ccggatatca      540
tccgtcttcc tagggcgttc cgctttctgc agaagccgct agcacaattc atttctgttg      600
caagagcgcc aaagagcaag gaaggttatg catccatagg tggtggttca cctcttcgac      660
aaattactga tgcgcaggga gaagcactta tggaggcact atgtggaaag gatatccctg      720
ctaaggtgta cgtgggaatg cggtattggc atcccttcac cgaggaagct atagaacaaa      780
taaaaaagga tggaatcaca aaacttgttg tactacctct ttaccccag ttctccatat       840 cgaccagtgg ttcaagtctc cgtcttctgg agagcatatt cagagaggat gagtatctgg      900
tcaatatgca acatacggtt attccttctt ggtatcagcg tgaaggatat attaaggcca      960
tggcaacttt gatcgagaag gagttgttga aatttccaaa accgcagaag gttatgatat     1020
ttttcagtgc tcatggagtt cctctggcat acgttgaaga agctggtgat ccgtataaag     1080
cagagatgga gagtgcgtg gatcttatca tggaggagct cgaaaaaga ggaatggcaa       1140 atccatctac acttgcttat cagagccgag taggaccagt ggaatggctg aaaccctaca     1200
ctgacgagac aattattgct cttgggcaga gaggggtaaa gagccttcta gcagttccca     1260
ttagttttgt cagcgaacac attgagacgt tagaagaaat tgacgtcgaa tacaaggagc     1320
tggctttgca atctggtatc aagcactggg gacgagttcc cgctttaggt tgtgagccca     1380
cattcatttc agatctggcg gatgctgtta tcgaaagcct gccttatgtt ggcgcaatgg     1440
cagtttccaa ccttgaggct cggcagtcac tggtgccact tggaagcgtg gaggagctgc     1500
tagcaaccta cgactcgaaa cgcgacatgc tgcctcctcc ggtgattgtg tgggagtggg     1560
gctggacgaa gagcgccgag acatggaatg gacgtgctgc tatgctggcc gtgttggctc     1620
tcctggtgct ggaggtaaca accggacagg ggctcttgca ccagtggggt atattgccac     1680
ctctcccttg acaagcgggg atggatggat ggatggattt caggtctccc cttgagggga     1740
tctgatcgta attttggttc atttggggaa tgccctgatg ctatatatga tggatcgatt     1800
tgccttacgc caagaaagga aaatatggac tgtattcgcc ggtgtaaata tgctagactg     1860
aagagagctt tacattatta ttattaacca ataagagctg tcgaatcgtt ggctaaaaaa     1920
aaaaaaaaaa aaaaaaaaaa aaaaaa                                         1946
```

<210> SEQ ID NO 28
<211> LENGTH: 526
<212> TYPE: PRT
<213> ORGANISM: Triticum aestivum

<400> SEQUENCE: 28

```
Met Leu His Val Arg Leu Ala Pro Gly Pro Ala Pro Arg Asn Leu Ser
1               5                   10                  15

Arg Arg Trp Asp Thr Ser Ala Tyr Leu His Ser Trp Cys Ser Val Pro
            20                  25                  30

Cys Pro Ser Arg Leu Ser Leu Ser Arg Thr Tyr Ser Ile Lys Ser Ser
        35                  40                  45

Leu Ile Gly Ser Ala Thr Gly Leu Cys Leu Gly Gln Cys Cys Arg Ile
    50                  55                  60

Lys Pro Leu Ser Cys Lys Cys Lys Leu Gly Arg Ser Ser Gln Pro Pro
65                  70                  75                  80

Pro Asp Ser Arg Gln His Phe Ser Ala Ser Ser Ala Ser Glu Ala
                85                  90                  95
```

```
Val Leu Thr Ala Gln Ser Asp Ile Arg Lys Leu Phe Val Ala Asn Glu
            100                 105                 110

Lys Ile Gly Val Leu Leu Asn Leu Gly Pro Glu Thr Leu Asp
            115                 120                 125

Asp Val Gln Pro Phe Leu Phe Asn Leu Phe Ala Asp Pro Asp Ile Ile
            130                 135                 140

Arg Leu Pro Arg Ala Phe Arg Phe Leu Gln Lys Pro Leu Ala Gln Phe
145                 150                 155                 160

Ile Ser Val Ala Arg Ala Pro Lys Ser Lys Glu Gly Tyr Ala Ser Ile
            165                 170                 175

Gly Gly Gly Ser Pro Leu Arg Gln Ile Thr Asp Ala Gln Gly Glu Ala
            180                 185                 190

Leu Met Glu Ala Leu Cys Gly Lys Asp Ile Pro Ala Lys Val Tyr Val
            195                 200                 205

Gly Met Arg Tyr Trp His Pro Phe Thr Glu Glu Ala Ile Glu Gln Ile
            210                 215                 220

Lys Lys Asp Gly Ile Thr Lys Leu Val Val Leu Pro Leu Tyr Pro Gln
225                 230                 235                 240

Phe Ser Ile Ser Thr Ser Gly Ser Ser Leu Arg Leu Leu Glu Ser Ile
            245                 250                 255

Phe Arg Glu Asp Glu Tyr Leu Val Asn Met Gln His Thr Val Ile Pro
            260                 265                 270

Ser Trp Tyr Gln Arg Glu Gly Tyr Ile Lys Ala Met Ala Thr Leu Ile
            275                 280                 285

Glu Lys Glu Leu Leu Lys Phe Pro Lys Pro Gln Lys Val Met Ile Phe
            290                 295                 300

Phe Ser Ala His Gly Val Pro Leu Ala Tyr Val Glu Glu Ala Gly Asp
305                 310                 315                 320

Pro Tyr Lys Ala Glu Met Glu Glu Cys Val Asp Leu Ile Met Glu Glu
            325                 330                 335

Leu Glu Lys Arg Gly Met Ala Asn Pro Ser Thr Leu Ala Tyr Gln Ser
            340                 345                 350

Arg Val Gly Pro Val Glu Trp Leu Lys Pro Tyr Thr Asp Glu Thr Ile
            355                 360                 365

Ile Ala Leu Gly Gln Arg Gly Val Lys Ser Leu Leu Ala Val Pro Ile
            370                 375                 380

Ser Phe Val Ser Glu His Ile Glu Thr Leu Glu Glu Ile Asp Val Glu
385                 390                 395                 400

Tyr Lys Glu Leu Ala Leu Gln Ser Gly Ile Lys His Trp Gly Arg Val
            405                 410                 415

Pro Ala Leu Gly Cys Glu Pro Thr Phe Ile Ser Asp Leu Ala Asp Ala
            420                 425                 430

Val Ile Glu Ser Leu Pro Tyr Val Gly Ala Met Ala Val Ser Asn Leu
            435                 440                 445

Glu Ala Arg Gln Ser Leu Val Pro Leu Gly Ser Val Glu Glu Leu Leu
            450                 455                 460

Ala Thr Tyr Asp Ser Lys Arg Asp Met Leu Pro Pro Val Ile Val
465                 470                 475                 480

Trp Glu Trp Gly Trp Thr Lys Ser Ala Glu Thr Trp Asn Gly Arg Ala
            485                 490                 495

Ala Met Leu Ala Val Leu Ala Leu Leu Val Leu Glu Val Thr Thr Gly
            500                 505                 510

Gln Gly Leu Leu His Gln Trp Gly Ile Leu Pro Pro Leu Pro
```

<210> SEQ ID NO 29
<211> LENGTH: 2014
<212> TYPE: DNA
<213> ORGANISM: Triticum aestivum

<400> SEQUENCE: 29

```
gctcgcttcc ttccgctgcc acttgccact tcgtccttcc gcttcttccc ccgaagcccg      60
aatcctctct ctcctcccg tcataaacag ggacctcaaa caagttctct tgtacctccg     120
cgcctcctcg gatttgattt cttcgttcgt tgcggatttc cctcccgtct gagtactaat     180
ttcgctcggt ttcccaacaa atttcgatat ccatgctcca cgtcaggctc gctcctgggc     240
ctgcaccgcg taatttatct aggagatggg attccagcgc ataccctacat agctggtgtt     300
ccgttccttg tccaagcagg ctcagtctct cgagggcata ttcaattaaa tcttcttcga     360
ttggtagcgc cacggacttt tgtcttgggc aatgttgccg catcaagcct ttgtcctgca     420
aatgcaagct aggtaggtct tctcagccgc cacctgactc gaggcaacat tttagtgcat     480
cttcatccgc atcagaggcg gttctcactg cgcagtccga tatccggaaa cttttttgttg    540
ccaatgagaa aatcggcgtt ctgctgctaa accttggagg cccagagacc cttgatgatg     600
tccagccttt cttgtttaat ctctttgctg atccggatat catccgtctt cctagggcgt     660
tccgctttct gcagaagccg ctagcacaat tcatttctgt tgcaagagcg ccaaagagca     720
aggaaggtta tgcatccata ggtggtggtt cacctcttcg acaaattact gatgcgcagg     780
gagaagcact tatggaagca ttatgtgaaa aggatatccc tgctaaggtg tacgtgggaa     840
tgcggtactg gcatcccttc accgaggaag ctatagaaca ataaaaaag gatggaatca     900
caaaacttgt tgtactacct ctttacccccc agttctccat atcgaccagt ggttcaagtc     960
tccgtcttct ggagagcata ttcagagagg atgagtatct ggtcaatatg caacatacgg    1020
ttattccttc ttggtatcag cgtgaaggat atattaaggc catgacaact ttgatcgaga    1080
aggagttgtt gaaatttcca aaaccgcaga aggttatgat attttttcagt gctcatggag    1140
ttcctctggc atacgttgaa gaagctggtg atccgtataa agcagagatg gaagagtgcg    1200
tggatcttat catggaggag ctcgaaaaaa gaggaatggc aaatccatgt acacttgctt    1260
atcagagccg agtaggacca gtggaatggc tgaaaaccta cactgacgag acaattattg    1320
ctcttgggca gaggggggta aagagtcttc tagcagttcc cattagtttt gtcagcgaac    1380
acattgagac gttagaagaa attgacgtcg aatacaagga gctggctttg caatctggta    1440
tcaagcactg gggacgagtt cccgctttag gttgtgagcc cacattcatt tcagatctgg    1500
cggatgctgt tatcgaaagc ctgccttatg ttggcgcaat ggcagtttcc aaccttgagg    1560
ctcgacagtc actggtgcca cttggaagcg tggaggagct gctagcagcc tacgactcga    1620
aacgcgacat gctgcctcct ccggtgattg tgtgggagtg gggctggacg aagagcgccg    1680
agacatggaa tggacgtgct gctatgctgg ccgtgttggc tctcctggtg ctggaggtaa    1740
caaccggaca ggggctcttg caccagtggg gtattttgcc acctttccct taacaagcgg    1800
ggatggatgg atgatggat tcaggtctc cccttgaggg gatctgatcg taattttggt    1860
tcatttgggg aatgtcctga tgctatatat gatggatcga tttgccttac gccaagaaag    1920
gaaaatatgg actcaattcg ccggtgtaaa tatgctagac tgaagagagc tttacattat    1980
tattaaccaa aaaaaaaaaa aaaaaaaaaa aaaa                                 2014
```

```
<210> SEQ ID NO 30
<211> LENGTH: 526
<212> TYPE: PRT
<213> ORGANISM: Triticum aestivum

<400> SEQUENCE: 30

Met Leu His Val Arg Leu Ala Pro Gly Pro Ala Pro Arg Asn Leu Ser
1               5                   10                  15

Arg Arg Trp Asp Ser Ser Ala Tyr Leu His Ser Trp Cys Ser Val Pro
            20                  25                  30

Cys Pro Ser Arg Leu Ser Leu Ser Arg Ala Tyr Ser Ile Lys Ser Ser
        35                  40                  45

Ser Ile Gly Ser Ala Thr Gly Leu Cys Leu Gly Gln Cys Cys Arg Ile
    50                  55                  60

Lys Pro Leu Ser Cys Lys Cys Lys Leu Gly Arg Ser Ser Gln Pro Pro
65                  70                  75                  80

Pro Asp Ser Arg Gln His Phe Ser Ala Ser Ser Ala Ser Glu Ala
                85                  90                  95

Val Leu Thr Ala Gln Ser Asp Ile Arg Lys Leu Phe Val Ala Asn Glu
            100                 105                 110

Lys Ile Gly Val Leu Leu Leu Asn Leu Gly Gly Pro Glu Thr Leu Asp
        115                 120                 125

Asp Val Gln Pro Phe Leu Phe Asn Leu Phe Ala Asp Pro Asp Ile Ile
    130                 135                 140

Arg Leu Pro Arg Ala Phe Arg Phe Leu Gln Lys Pro Leu Ala Gln Phe
145                 150                 155                 160

Ile Ser Val Ala Arg Ala Pro Lys Ser Lys Glu Gly Tyr Ala Ser Ile
                165                 170                 175

Gly Gly Gly Ser Pro Leu Arg Gln Ile Thr Asp Ala Gln Gly Glu Ala
            180                 185                 190

Leu Met Glu Ala Leu Cys Gly Lys Asp Ile Pro Ala Lys Val Tyr Val
        195                 200                 205

Gly Met Arg Tyr Trp His Pro Phe Thr Glu Glu Ala Ile Glu Gln Ile
    210                 215                 220

Lys Lys Asp Gly Ile Thr Lys Leu Val Val Leu Pro Leu Tyr Pro Gln
225                 230                 235                 240

Phe Ser Ile Ser Thr Ser Gly Ser Ser Leu Arg Leu Leu Glu Ser Ile
                245                 250                 255

Phe Arg Glu Asp Glu Tyr Leu Val Asn Met Gln His Thr Val Ile Pro
            260                 265                 270

Ser Trp Tyr Gln Arg Glu Gly Tyr Ile Lys Ala Met Thr Thr Leu Ile
        275                 280                 285

Glu Lys Glu Leu Leu Lys Phe Pro Lys Pro Gln Lys Val Met Ile Phe
    290                 295                 300

Phe Ser Ala His Gly Val Pro Leu Ala Tyr Val Glu Glu Ala Gly Asp
305                 310                 315                 320

Pro Tyr Lys Ala Glu Met Glu Glu Cys Val Asp Leu Ile Met Glu Glu
                325                 330                 335

Leu Glu Lys Arg Gly Met Ala Asn Pro Cys Thr Leu Ala Tyr Gln Ser
            340                 345                 350

Arg Val Gly Pro Val Glu Trp Leu Lys Pro Tyr Thr Asp Glu Thr Ile
        355                 360                 365

Ile Ala Leu Gly Gln Arg Gly Val Lys Ser Leu Leu Ala Val Pro Ile
    370                 375                 380
```

```
Ser Phe Val Ser Glu His Ile Glu Thr Leu Glu Glu Ile Asp Val Glu
385                 390                 395                 400

Tyr Lys Glu Leu Ala Leu Gln Ser Gly Ile Lys His Trp Gly Arg Val
                405                 410                 415

Pro Ala Leu Gly Cys Glu Pro Thr Phe Ile Ser Asp Leu Ala Asp Ala
            420                 425                 430

Val Ile Glu Ser Leu Pro Tyr Val Gly Ala Met Ala Val Ser Asn Leu
        435                 440                 445

Glu Ala Arg Gln Ser Leu Val Pro Leu Gly Ser Val Glu Glu Leu Leu
    450                 455                 460

Ala Ala Tyr Asp Ser Lys Arg Asp Met Leu Pro Pro Pro Val Ile Val
465                 470                 475                 480

Trp Glu Trp Gly Trp Thr Lys Ser Ala Glu Thr Trp Asn Gly Arg Ala
                485                 490                 495

Ala Met Leu Ala Val Leu Ala Leu Leu Val Leu Glu Val Thr Thr Gly
            500                 505                 510

Gln Gly Leu Leu His Gln Trp Gly Ile Leu Pro Pro Phe Pro
        515                 520                 525
```

<210> SEQ ID NO 31
<211> LENGTH: 18491
<212> TYPE: DNA
<213> ORGANISM: Artificial
<220> FEATURE:
<223> OTHER INFORMATION: pHSbarENDs2 activation tagging vector

<400> SEQUENCE: 31

```
catgaatcaa acaaacatac acagcgactt attcacacga gctcaaatta caacggtata     60
tatcctgccg tcgacaacca tggtctagac aggatccccg ggtaccgagc tcgaatttgc    120
aggtcgactg cgtcatccct tacgtcagtg gagatatcac atcaatccac ttgctttgaa    180
gacgtggttg gaacgtcttc tttttccacg atgctcctcg tgggtggggg tccatctttg    240
ggaccactgt cggcagaggc atcttgaacg atagcctttc ctttatcgca atgatggcat    300
ttgtaggtgc caccttcctt ttctactgtc cttttgatga agtgacagat agctgggcaa    360
tggaatccga ggaggtttcc cgatattacc ctttgttgaa aagtctcaat tgccctttgg    420
tcttctgaga ctgttgcgtc atcccttacg tcagtggaga tatcacatca atccacttgc    480
tttgaagacg tggttggaac gtcttctttt tccacgatgc tcctcgtggg tgggggtcca    540
tctttgggac cactgtcggc agaggcatct tgaacgatag cctttccttt atcgcaatga    600
tggcatttgt aggtgccacc ttccttttct actgtccttt tgatgaagtg acagatagct    660
gggcaatgga atccgaggag gtttcccgat attacccttt gttgaaaagt ctcagttaac    720
ccgcgatcct gcgtcatccc ttacgtcagt ggagatatca catcaatcca cttgctttga    780
agacgtggtt ggaacgtctt ctttttccac gatgctcctc gtgggtgggg gtccatcttt    840
gggaccactg tcggcagagg catcttgaac gatagccttt cctttatcgc aatgatggca    900
tttgtaggtg ccaccttcct tttctactgt ccttttgatg aagtgacaga tagctgggca    960
atggaatccg aggaggtttc ccgatattac cctttgttga aaagtctcaa ttgccctttg   1020
gtcttctgag actgttgcgt catcccttac gtcagtggag atatcacatc aatccacttg   1080
ctttgaagac gtggttggaa cgtcttcttt ttccacgatg ctcctcgtgg gtgggggtcc   1140
atctttggga ccactgtcgg cagaggcatc ttgaacgata gcctttcctt tatcgcaatg   1200
atggcatttg taggtgccac cttccttttc tactgtcctt ttgatgaagt gacagatagc   1260
```

```
tgggcaatgg aatccgagga ggtttcccga tattacccatt tgttgaaaag tctcagttaa    1320
cccgcaattc actggccgtc gttttacaac gtcgtgactg ggaaaaccct ggcgttaccc    1380
aacttaatcg ccttgcagca catccccctt tcgccagctg gcgtaatagc gaagaggccc    1440
gcaccgatcg cccttcccaa cagttgcgca gcctgaatgg cgaatggatc gatccgtcga    1500
tcgaccaaag cggccatcgt gcctccccac tcctgcagtt cgggggcatg gatgcgcgga    1560
tagccgctgc tggtttcctg gatgccgacg gatttgcact gccggtagaa ctccgcgagg    1620
tcgtccagcc tcaggcagca gctgaaccaa ctcgcgaggg gatcgagccc ctgctgagcc    1680
tcgacatgtt gtcgcaaaat tcgccctgga cccgcccaac gatttgtcgt cactgtcaag    1740
gtttgacctg cacttcattt ggggcccaca tacaccaaaa aaatgctgca taattctcgg    1800
ggcagcaagt cggttacccg gccgccgtgc tggaccgggt tgaatggtgc ccgtaacttt    1860
cggtagagcg gacggccaat actcaacttc aaggaatctc acccatgcgc gccggcgggg    1920
aaccggagtt cccttcagtg aacgttatta gttcgccgct cggtgtgtcg tagatactag    1980
ccccctgggc cttttgaaat ttgaataaga tttatgtaat cagtcttta ggtttgaccg    2040
gttctgccgc tttttttaaa attggatttg taataataaa acgcaattgt ttgttattgt    2100
ggcgctctat catagatgtc gctataaacc tattcagcac aatatattgt tttcatttta    2160
atattgtaca tataagtagt agggtacaat cagtaaattg aacggagaat attattcata    2220
aaaatacgat agtaacgggt gatatattca ttagaatgaa ccgaaccggg cggtaaggat    2280
ctgagctaca catgctcagg ttttttacaa cgtgcacaac agaattgaaa gcaaatatca    2340
tgcgatcata ggcgtctcgc atatctcatt aaagcagggg gtgggcgaag aactccagca    2400
tgagatcccc gcgctggagg atcatccagc cggcgtcccg gaaaacgatt ccgaagccca    2460
acctttcata gaaggcggcg gtggaatcga atctcgtga tggcaggttg ggcgtcgctt    2520
ggtcggtcat ttcgaacccc agagtcccgc tcagaagaac tcgtcaagaa ggcgatagaa    2580
ggcgatgcgc tgcgaatcgg gagcggcgat accgtaaagc acgaggaagc ggtcagccca    2640
ttcgccgcca agctcttcag caatatcacg ggtagccaac gctatgtcct gatagcggtc    2700
cgccacaccc agccggccac agtcgatgaa tccagaaaag cggccatttt ccaccatgat    2760
attcggcaag caggcatcgc catgggtcac gacgagatcc tcgccgtcgg gcatgccccc    2820
caattcactg gccgtcgttt tacaacgtcg tgactgggaa aaccctggcg ttacccaact    2880
taatcgcctt gcagcacatc cccctttcgc cagctggcgt aatagcgaag aggcccgcac    2940
cgatcgccct tcccaacagt tgcgcagcct gaatggcgaa tggcgcctga tgcggtattt    3000
tctccttacg catctgtgcg gtatttcaca ccgcatatgg tgcactctca gtacaatctg    3060
ctctgatgcc gcatagttaa gccagccccg acacccgcca cacccgctg acgcgccctg    3120
acgggcttgt ctgctcccgg catccgctta cagacaagct gtgaccgtct ccgggagctg    3180
catgtgtcag aggttttcac cgtcatcacc gaaacgcgcg agacgaaagg gcctcgtgat    3240
acgcctattt ttataggtta atgtcatgat aataatggtt tcttagacgt caggtggcac    3300
ttttcgggga aatgtgcgcg gaacccctat ttgtttattt ttctaaatac attcaaatat    3360
gtatccgctc atgagacaat aaccctgata aatgcttcaa taatattgaa aaaggaagag    3420
tatgagtatt caacatttcc gtgtcgccct tattcccttt tttgcggcat tttgccttcc    3480
tgttttgct cacccagaaa cgctggtgaa agtaaaagat gctgaagatc agttgggtgc    3540
acgagtgggt tacatcgaac tggatctcaa cagcggtaag atccttgaga gttttcgccc    3600
cgaagaacgt tttccaatga tgagcacttt taaagttctg ctatgtggcg cggtattatc    3660
```

```
ccgtattgac gccgggcaag agcaactcgg tcgccgcata cactattctc agaatgactt   3720
ggttgagtac tcaccagtca cagaaaagca tcttacggat ggcatgacag taagagaatt   3780
atgcagtgct gccataacca tgagtgataa cactgcggcc aacttacttc tgacaacgat   3840
cggaggaccg aaggagctaa ccgcttttt  gcacaacatg ggggatcatg taactcgcct   3900
tgatcgttgg gaaccggagc tgaatgaagc cataccaaac gacgagcgtg acaccacgat   3960
gcctgtagca atggcaacaa cgttgcgcaa actattaact ggcgaactac ttactctagc   4020
ttcccggcaa caattaatag actggatgga ggcggataaa gttgcaggac cacttctgcg   4080
ctcggccctt ccggctggct ggtttattgc tgataaatct ggagccggtg agcgtgggtc   4140
tcgcggtatc attgcagcac tggggccaga tggtaagccc tcccgtatcg tagttatcta   4200
cacgacgggg agtcaggcaa ctatggatga acgaaataga cagatcgctg ataggtgc    4260
ctcactgatt aagcattggt aactgtcaga ccaagtttac tcatatatac tttagattga   4320
tttaaaactt catttttaat ttaaaaggat ctaggtgaag atccttttg  ataatctcat   4380
gaccaaaatc ccttaacgtg agttttcgtt ccactgagcg tcagacccg  tagaaaagat   4440
caaaggatct tcttgagatc cttttttct  gcgcgtaatc tgctgcttgc aaacaaaaaa   4500
accaccgcta ccagcggtgg tttgtttgcc ggatcaagag ctaccaactc tttttccgaa   4560
ggtaactggc ttcagcagag cgcagatacc aaatactgtc cttctagtgt agccgtagtt   4620
aggccaccac ttcaagaact ctgtagcacc gcctacatac ctcgctctgc taatcctgtt   4680
accagtggct gctgccagtg gcgataagtc gtgtcttacc gggttggact caagacgata   4740
gttaccggat aaggcgcagc ggtcgggctg aacggggggt tcgtgcacac agcccagctt   4800
ggagcgaacg acctacaccg aactgagata cctacagcgt gagcattgag aaagcgccac   4860
gcttcccgaa gggagaaagg cggacaggta tccggtaagc ggcagggtcg gaacaggaga   4920
gcgcacgagg gagcttccag ggggaaacgc ctggtatctt tatagtcctg tcgggtttcg   4980
ccacctctga cttgagcgtc gatttttgtg atgctcgtca gggggggcgga gcctatggaa   5040
aaacgccagc aacgcggcct ttttacggtt cctggccttt tgctggcctt ttgctcacat   5100
gttctttcct gcgttatccc ctgattctgt ggataaccgt attaccgcct ttgagtgagc   5160
tgataccgct cgccgcagcc gaacgaccga gcgcagcgag tcagtgagcg aggaagcgga   5220
agagcgccca atacgcaaac cgcctctccc cgcgcgttgg ccgattcatt aatgcagctg   5280
gcacgacagg tttcccgact ggaaagcggg cagtgagcgc aacgcaatta atgtgagtta   5340
gctcactcat taggcacccc aggctttaca ctttatgctt ccggctcgta tgttgtgtgg   5400
aattgtgagc ggataacaat ttcacacagg aaacagctat gaccatgatt acgccaagct   5460
ttctaggggg ggggtaccga tctgagatcg gtaacgaaaa cgaacgggta gggatgaaaa   5520
cggtcggtaa cggtcggtaa aatacctcta ccgttttcat tttcatattt aacttgcggg   5580
acggaaacga aaacgggata taccggtaac gaaaacgaac gggataaaata cggtaatcga   5640
aaaccgatac gatccggtcg ggttaaagtc gaaatcggac gggaaccggt attttgttc   5700
ggtaaaatca cacatgaaaa catatattca aaacttaaaa acaaatataa aaattgtaa   5760
acacaagtct taatgatcac tagtggcgcg cctaggagat ctcgagtagg gataacaggg   5820
taatacatag ataaaatcca tataaatctg gagcacacat agtttaatgt agcacataag   5880
tgataagtct tgggctcttg gctaacataa gaagccatat aagtctacta gcacacatga   5940
cacaatataa agtttaaaac acatattcat aatcacttgc tcacatctgg atcacttagc   6000
```

```
atgctacagc tagtgcaata ttagacactt tccatatttt ctcaaacttt tcactcattg    6060
caacggccat tctcctaatg acaaattttt catgaacaca ccattggtca atcaaatcct    6120
ttatctcaca gaaacctttg taaaataaat ttgcagtgga atattgagta ccagatagga    6180
gttcagtgag atcaaaaaac ttcttcaaac acttaaaaag agttaatgcc atcttccact    6240
cctcggcttt aggacaaatt gcatcgtacc tacaataatt gacatttgat taattgagaa    6300
tttataatga tgacatgtac aacaattgag acaaacatac ctgcgaggat cacttgtttt    6360
aagccgtgtt agtgcaggct tataatataa ggcatccctc aacatcaaat aggttgaatt    6420
ccatctagtt gagacatcat atgagatccc tttagattta tccaagtcac attcactagc    6480
acacttcatt agttcttccc actgcaaagg agaagatttt acagcaagaa caatcgcttt    6540
gattttctca attgttcctg caattacagc caagccatcc tttgcaacca agttcagtat    6600
gtgacaagca cacctcacat gaaagaaagc accatcacaa actagatttg aatcagtgtc    6660
ctgcaaatcc tcaattatat cgtgcacagc tacttcattt gcactagcat tatccaaaga    6720
caaggcaaac aatttttttct caatgttcca cttaaccatg attgcagtga aggtttgtga    6780
taacctttgg ccagtgtggc gcccttcaac atgaaaaaag ccaacaattc ttttttggag    6840
acaccaatca tcatcaatcc aatggatggt gacacacatg tatgacttat tttgacaaga    6900
tgtccacata tccatagttg tactgaagcg agactgaaca tctttttagtt ttccatacaa    6960 cttttctttt tcttccaaat acaaatccat gatatatttt ctagcagtga cacgggactt    7020
tattggaaag tgagggcgca gagacttaac aaaactcaaca aagtactcat gttctacaat    7080
attgaaagga tattcatgca tgattattgc caaatgaagc ttctttaggc taaccacttc    7140
atcgtactta taaggctcaa tgagatttat gtctttgcca tgatccttt cacttttag    7200 acacaactga cctttaacta aactatgtga tgttctcaag tgatttcgaa atccgcttgt    7260
tccatgatga ccctcagccc tatacttagc cttgcaatta ggaaagttgc aatgtcccca    7320
tacctgaacg tatttctttc catcgacctc cacttcaatt tccttcttgg tgaaatgctg    7380
ccatacatcc gatgtgcact tctttgccct cttctgtggt gcttcttctt cgggttcagg    7440
ttgtggctgt ggttgtggtt ctggttgtgg ttgtggttgt ggttgtggtt catgaacaat    7500
agccatatca tcttgactcg gatctgtagc tgtaccatt gcattactac tgcttacact    7560
ctgaataaaa tgcctctcgg cctcagctgt tgatgatgat ggtgatgtgc ggccacatcc    7620
atgcccacgc gcacgtgcac gtacattctg aatccgacta aagaggctt cagcttttct    7680 tttcaacccct gttataaaca gattttttcgt attattctac agtcaatatg atgcttccca    7740
atctacaacc aattagtaat gctaatgcta ttgctactgt ttttctaata tatccttga    7800 gcatatgcag agaatacgga atttgttttg cgagtagaag gcgctcttgt ggtagacatc    7860
aacttggcca atcttatggc tgagcctgag ggaggattat ttccaaccgg aggcgtcatc    7920
tgaggaatgg agtcgtagcc ggctagccga agtggagagc agagccctgg acagcaggtg    7980
ttcagcaatc agcttggtgc tgtactgctg tgacttgtga gcacctggac ggctggacag    8040
caatcagcag gtgttgcaga gcccctggac agcacacaaa tgacacaaca gcttggtgca    8100
atggtgctga cgtgctgtac tgctaagtgc tgtgagcctg tgagcagccg tggagacagg    8160
gagaccgcgg atggccggat gggcgagcgc cgagcagtgg aggtctggag gaccgctgac    8220
cgcagatggc ggatggcgga tgggcggacc gcgatgggc gagcagtgga gtggaggtct    8280
gggcggatgg gcggaccgcg gcgcggatgg gcgagtcgcg agcagtggag tggagggcgg    8340
accgtggatg gcggcgtctg cgtccggcgt gccgcgtcac ggccgtcacc gcgtgtggtg    8400
```

```
cctggtgcag cccagcggcc ggccggctgg gagacaggga gagtcggaga gagcaggcga    8460
gagcgagacg cgtcgccggc gtcggcgtgc ggctggcggc gtccggactc cggcgtgggc    8520
gcgtggcggc gtgtgaatgt gtgatgctgt tactcgtgtg gtgcctggcc gcctgggaga    8580
gaggcagagc agcgttcgct aggtatttct tacatgggct gggcctcagt ggttatggat    8640
gggagttgga gctggccata ttgcagtcat cccgaattag aaaatacggt aacgaaacgg    8700
gatcatcccg attaaaaacg ggatcccggt gaaacggtcg ggaaactagc tctaccgttt    8760
ccgtttccgt ttaccgtttt gtatatcccg tttccgttcc gttttcgttt tttacctcgg    8820
gttcgaaatc gatcgggata aaactaacaa aatcggttat acgataacgg tcggtacggg    8880
attttcccat cctactttca tccctgagat tattgtcgtt tctttcgcag atcggtaccc    8940
cccccctaga gtcgacatcg atctagtaac atagatgaca ccgcgcgcga taatttatcc    9000
tagtttgcgc gctatatttt gttttctatc gcgtattaaa tgtataattg cgggactcta    9060
atcataaaaa cccatctcat aaataacgtc atgcattaca tgttaattat tacatgctta    9120
acgtaattca acagaaatta tatgataatc atcgcaagac cggcaacagg attcaatctt    9180
aagaaacttt attgccaaat gtttgaacga tctgcttcga cgcactcctt ctttaggtac    9240
ggactagatc tcggtgacgg gcaggaccgg acggggcggt accggcaggc tgaagtccag    9300
ctgccagaaa cccacgtcat gccagttccc gtgcttgaag ccggccgccc gcagcatgcc    9360 gcgggggca tatccgagcg cctcgtgcat gcgcacgctc gggtcgttgg gcagcccgat    9420
gacagcgacc acgctcttga agccctgtgc ctccagggac ttcagcaggt gggtgtagag    9480
cgtggagccc agtcccgtcc gctggtggcg gggggagacg tacacggtcg actcggccgt    9540
ccagtcgtag gcgttgcgtg ccttccaggg gcccgcgtag gcgatgccgg cgacctcgcc    9600
gtccacctcg gcgacgagcc agggatagcg ctcccgcaga cggacgaggt cgtccgtcca    9660 ctcctgcgt tcctgcggct cggtacggaa gttgaccgtg cttgtctcga tgtagtggtt    9720
gacgatggtg cagaccgccg gcatgtccgc ctcggtggca cggcggatgt cggccgggcg    9780
tcgttctggg ctcatggatc tggattgaga gtgaatatga gactctaatt ggataccgag    9840
gggaatttat ggaacgtcag tggagcattt ttgacaagaa atatttgcta gctgatagtg    9900
accttaggcg acttttgaac gcgcaataat ggtttctgac gtatgtgctt agctcattaa    9960
actccagaaa cccgcggctg agtggctcct tcaatcgttg cggttctgtc agttccaaac   10020
gtaaaacggc ttgtcccgcg tcatcggcgg gggtcataac gtgactccct taattctccg   10080
ctcatgatcc ccgggtaccg agctcgaatt gcggctgagt ggctccttca atcgttgcgg   10140
ttctgtcagt tccaaacgta aaacggcttg tcccgcgtca tcggcggggg tcataacgtg   10200
actcccttaa ttctccgctc atgatcttga tcccctgcgc catcagatcc ttggcggcaa   10260
gaaagccatc cagtttactt tgcagggctt cccaaccttac cagagggcg cccagctgg    10320 caattccggt tcgcttgctg tatcgatatg gtggatttat cacaaatggg accgccgcc    10380 gacagaggtg tgatgttagg ccaggacttt gaaaatttgc gcaactatcg tatagtggcc   10440
gacaaattga cgccgagttg acagactgcc tagcatttga gtgaattatg tgaggtaatg   10500
ggctacactg aattggtagc tcaaactgtc agtatttatg tatatgagtg tatatttcg   10560 cataatctca gaccaatctg aagatgaaat gggtatctgg gaatggcgaa atcaaggcat   10620
cgatcgtgaa gttctcatc taagccccca tttggacgtg aatgtagaca cgtcgaaata   10680
aagatttccg aattagaata atttgtttat tgctttcgcc tataaatacg acggatcgta   10740
```

-continued

```
atttgtcgtt ttatcaaaat gtactttcat tttataataa cgctgcggac atctacattt   10800
ttgaattgaa aaaaaattgg taattactct ttcttttttct ccatattgac catcatactc   10860
attgctgatc catgtagatt tcccggacat gaagccattt acaattgaat atatcctgcc   10920
gccgctgccg ctttgcaccc ggtggagctt gcatgttggt ttctacgcag aactgagccg   10980
gttaggcaga taatttccat tgagaactga gccatgtgca ccttcccccc aacacggtga   11040 gcgacgggc aacggagtga tccacatggg acttttaaac atcatccgtc ggatggcgtt   11100
gcgagagaag cagtcgatcc gtgagatcag ccgacgcacc gggcaggcgc gcaacacgat   11160
cgcaaagtat ttgaacgcag gtacaatcga gccgacgttc accgtcaccc tggatgctgt   11220
aggcataggc ttggttatgc cggtactgcc gggcctcttg cgggatatcg tccattccga   11280
cagcatcgcc agtcactatg gcgtgctgct agcgctatat gcgttgatgc aatttctatg   11340
cgcacccgtt ctcggagcac tgtccgaccg ctttggccgc cgcccagtcc tgctcgcttc   11400
gctacttgga gccactatcg actacgcgat catggcgacc acacccgtcc tgtggtccaa   11460
cccctccgct gctatagtgc agtcggcttc tgacgttcag tgcagccgtc ttctgaaaac   11520
gacatgtcgc acaagtccta agttacgcga caggctgccg ccctgccctt ttcctggcgt   11580
tttcttgtcg cgtgttttag tcgcataaag tagaatactt gcgactagaa ccggagacat   11640
tacgccatga acaagagcgc cgccgctggc ctgctgggct atgcccgcgt cagcaccgac   11700
gaccaggact tgaccaacca acgggccgaa ctgcacgcgg ccggctgcac caagctgttt   11760
tccgagaaga tcaccggcac caggcgcgac cgcccggagc tggccaggat gcttgaccac   11820
ctacgccctg gcgacgttgt gacagtgacc aggctagacc gcctggcccg cagcacccgc   11880
gacctactgg acattgccga gcgcatccag gaggccggcg cgggcctgcg tagcctggca   11940
gagccgtggg ccgacaccac cacgccgccc ggccgcatgg tgttgaccgt gttcgccggc   12000
attgccgagt tcgagcgttc cctaatcatc gaccgcaccc ggagcgggcg cgaggccgcc   12060
aaggcccgag gcgtgaagtt tggcccccgc cctaccctca ccccggcaca gatcgcgcac   12120
gcccgcgagc tgatcgacca ggaaggccgc accgtgaaag aggcggctgc actgcttggc   12180
gtgcatcgct cgaccctgta ccgcgcactt gagcgcagcg aggaagtgac gcccaccgag   12240
gccaggcggc gcggtgcctt ccgtgaggac gcattgaccg aggccgacgc cctggcggcc   12300
gccgagaatg aacgccaaga ggaacaagca tgaaaccgca ccaggacggc caggacgaac   12360 cgttttcat taccgaagag atcgaggcgg agatgatcgc ggccgggtac gtgttcgagc   12420
cgcccgcgca cgtctcaacc gtgcggctgc atgaaatcct ggccggtttg tctgatgcca   12480
agctggcggc ctggccggcc agcttggccg ctgaagaaac cgagcgccgc cgtctaaaaa   12540
ggtgatgtgt atttgagtaa aacagcttgc gtcatgcggt cgctgcgtat atgatgcgat   12600
gagtaaataa acaaatacgc aagggaacgc atgaagttat cgctgtactt aaccagaaag   12660
gcgggtcagg caagacgacc atcgcaaccc atctagcccg cgccctgcaa ctcgccgggg   12720
ccgatgttct gttagtcgat tccgatcccc agggcagtgc ccgcgattgg gcggccgtgc   12780
gggaagatca accgctaacc gttgtcggca tcgaccgccc gacgattgac cgcgacgtga   12840
aggccatcgg ccggcgcgac ttcgtagtga tcgacgagcg ccccaggcg gcggacttgg   12900 ctgtgtccgc gatcaaggca gccgacttcg tgctgattcc ggtgcagcca agcccttacg   12960
acatatgggc caccgccgac ctggtggagc tggttaagca gcgcattgag gtcacggatg   13020
gaaggctaca gcggcctttt gtcgtgtcgc gggcgatcaa aggcacgcgc atcggcgtgt   13080
aggttgccga ggcgctggcc gggtacgagc tgcccattct tgagtcccgt atcacgcagc   13140
```

-continued

```
gcgtgagcta cccaggcact gccgccgccg gcacaaccgt tcttgaatca gaacccgagg    13200
gcgacgctgc ccgcgaggtc caggcgctgg ccgctgaaat taaatcaaaa ctcatttgag    13260
ttaatgaggt aaagagaaaa tgagcaaaag cacaaacacg ctaagtgccg gccgtccgag    13320
cgcacgcagc agcaaggctg caacgttggc cagcctggca gacacgccag ccatgaagcg    13380
ggtcaacttt cagttgccgg cggaggatca caccaagctg aagatgtacg cggtacgcca    13440
aggcaagacc attaccgagc tgctatctga atacatcgcg cagctaccag agtaaatgag    13500
caaatgaata aatgagtaga tgaattttag cggctaaagg aggcggcatg gaaaatcaag    13560
aacaaccagg caccgacgcc gtggaatgcc ccatgtgtgg aggaacgggc ggttggccag    13620
gcgtaagcgg ctgggttgtc tgccggccct gcaatggcac tggaaccccc aagcccgagg    13680
aatcggcgtg agcggtcgca aaccatccgc cccggtacaa atcggcgcgg cgctgggtga    13740
tgacctggtg gagaagttga aggccgcgca ggccgcccag cggcaacgca tcgaggcaga    13800
agcacgcccc ggtgaatcgt ggcaagcggc cgctgatcga atccgcaaag aatcccggca    13860
accgccggca gccggtgcgc cgtcgattag gaagccgccc aagggcgacg agcaaccaga    13920
ttttttcgtt ccgatgctct atgacgtggg cacccgcgat agtcgcagca tcatggacgt    13980
ggccgttttc cgtctgtcga agcgtgaccg acgagctggc gaggtgatcc gctacgagct    14040
tccagacggg cacgtagagg tttccgcagg gccggccggc atggccagtg tgtgggatta    14100
cgacctggta ctgatggcgg tttcccatct aaccgaatcc atgaaccgat accgggaagg    14160
gaagggagac aagcccggcc gcgtgttccg tccacacgtt gcggacgtac tcaagttctg    14220
ccggcgagcc gatggcggaa agcagaaaga cgacctggta gaaacctgca ttcggttaaa    14280
caccacgcac gttgccatgc agcgtacgaa gaaggccaag aacggccgcc tggtgacggt    14340
atccgagggt gaagccttga ttagccgcta caagatcgta aagagcgaaa ccgggcggcc    14400
ggagtacatc gagatcgagc tagctgattg gatgtaccgc gagatcacag aaggcaagaa    14460
cccggacgtg ctgacggttc accccgatta cttttttgatc gatcccggca tcggccgttt    14520
tctctaccgc ctggcacgcc gcgccgcagg caaggcagaa gccagatggt tgttcaagac    14580
gatctacgaa cgcagtggca gcgccggaga gttcaagaag ttctgtttca ccgtgcgcaa    14640
gctgatcggg tcaaatgacc tgccggagta cgatttgaag gaggaggcgg ggcaggctgg    14700
cccgatccta gtcatgcgct accgcaacct gatcgagggc gaagcatccg ccggttccta    14760
atgtacggag cagatgctag ggcaaattgc cctagcaggg gaaaaaggtc gaaaaggtct    14820
ctttcctgtg gatagcacgt acattgggaa cccaaagccg tacattggga accggaaccc    14880
gtacattggg aacccaaagc cgtacattgg gaaccggtca cacatgtaag tgactgatat    14940
aaaagagaaa aaaggcgatt tttccgccta aaactcttta aaacttatta aaactcttaa    15000
aacccgcctg gcctgtgcat aactgtctgg ccagcgcaca gccgaagagc tgcaaaaagc    15060
gcctaccctt cggtcgctgc gctccctacg ccccgccgct tcgcgtcggc ctatcgcggc    15120
cgctggccgc tcaaaaatgg ctggcctacg gccaggcaat ctaccagggc gcggacaagc    15180
cgcgccgtcg ccactcgacc gccggcgccc acatcaaggc accctgcctc gcgcgtttcg    15240
gtgatgacgg tgaaaacctc tgacacatgc agctcccgga cggtcacag cttgtctgt    15300 aagcggatgc cgggagcaga caagcccgtc agggcgcgtc agcgggtgtt ggcgggtgtc    15360
ggggcgcagc catgacccag tcacgtagcg atagcggagt gtatactggc ttaactatgc    15420
ggcatcagag cagattgtac tgagagtgca ccatatgcgg tgtgaaatac cgcacagatg    15480
```

```
cgtaaggaga aaataccgca tcaggcgctc ttccgcttcc tcgctcactg actcgctgcg    15540
ctcggtcgtt cggctgcggc gagcggtatc agctcactca aaggcggtaa tacggttatc    15600
cacagaatca ggggataacg caggaaagaa catgtgagca aaaggccagc aaaaggccag    15660
gaaccgtaaa aaggccgcgt tgctggcgtt tttccatagg ctccgccccc ctgacgagca    15720
tcacaaaaat cgacgctcaa gtcagaggtg gcgaaacccg acaggactat aaagatacca    15780
ggcgtttccc cctggaagct ccctcgtgcg ctctcctgtt ccgaccctgc cgcttaccgg    15840
atacctgtcc gcctttctcc cttcgggaag cgtggcgctt tctcatagct cacgctgtag    15900
gtatctcagt tcggtgtagg tcgttcgctc caagctgggc tgtgtgcacg aaccccccgt    15960
tcagcccgac cgctgcgcct tatccggtaa ctatcgtctt gagtccaacc cggtaagaca    16020
cgacttatcg ccactggcag cagccactgg taacaggatt agcagagcga ggtatgtagg    16080
cggtgctaca gagttcttga agtggtggcc taactacggc tacactagaa ggacagtatt    16140
tggtatctgc gctctgctga agccagttac cttcggaaaa agagttggta gctcttgatc    16200
cggcaaacaa accaccgctg gtagcggtgg ttttttttgtt tgcaagcagc agattacgcg    16260
cagaaaaaaa ggatctcaag aagatccttt gatcttttct acggggtctg acgctcagtg    16320
gaacgaaaac tcacgttaag ggattttggt catgagatta tcaaaaagga tcttcaccta    16380
gatcctttta aattaaaaat gaagttttaa atcaatctaa agtatatatg agtaaacttg    16440
gtctgacagt taccaatgct taatcagtga ggcacctatc tcagcgatct gtctatttcg    16500
ttcatccata gttgcctgac tccccgtcgt gtagataact acgatacggg agggcttacc    16560
atctggcccc agtgctgcaa tgataccgcg agacccacgc tcaccggctc cagatttatc    16620
agcaataaac cagccagccg aagggccga gcgcagaagt ggtcctgcaa ctttatccgc    16680
ctccatccag tctattaatt gttgccggga agctagagta gtagttcgc cagttaatag    16740 tttgcgcaac gttgttgcca ttgctacagg catcgtggtg tcacgctcgt cgtttggtat    16800
ggcttcattc agctccggtt cccaacgatc aaggcgagtt acatgatccc ccatgttgtg    16860
caaaaaagcg gttagctcct tcggtcctcc gatcgttgtc agaagtaagt tggccgcagt    16920
gttatcactc atggttatgg cagcactgca taattctctt actgtcatgc catccgtaag    16980
atgcttttct gtgactggtg agtactcaac caagtcattc tgagaatagt gtatgcggcg    17040
accgagttgc tcttgcccgg cgtcaacacg ggataatacc gcgccacata gcagaacttt    17100
aaaagtgctc atcattggaa aagacctgca gggggggggg ggaaagccac gttgtgtctc    17160
aaaatctctg atgttacatt gcacaagata aaaatatatc atcatgaaca ataaaactgt    17220
ctgcttacat aaacagtaat acaagggtg ttatgagcca tattcaacgg gaaacgtctt    17280
gctcgaggcc gcgattaaat tccaacatgg atgctgattt atatgggtat aaatgggctc    17340
gcgataatgt cgggcaatca ggtgcgacaa tctatcgatt gtatgggaag cccgatgcgc    17400
cagagttgtt tctgaaacat ggcaaaggta gcgttgccaa tgatgttaca gatgagatgg    17460
tcagactaaa ctggctgacg gaatttatgc ctcttccgac catcaagcat tttatccgta    17520
ctcctgatga tgcatggtta ctcaccactg cgatccccgg aaaacagca ttccaggtat    17580 tagaagaata tcctgattca ggtgaaaata ttgttgatgc gctggcagtg ttcctgcgcc    17640
ggttgcattc gattcctgtt tgtaattgtc cttttaacag cgatcgcgta tttcgtctcg    17700
ctcaggcgca atcacgaatg aataacggtt tggttgatgc gagtgatttt gatgacgagc    17760
gtaatggctg gcctgttgaa caagtctgga agaaaatgca taagctttg ccattctcac    17820 cggattcagt cgtcactcat ggtgatttct cacttgataa ccttattttt gacgagggga    17880
```

```
aattaatagg ttgtattgat gttggacgag tcggaatcgc agaccgatac caggatcttg    17940
ccatcctatg gaactgcctc ggtgagtttt ctccttcatt acagaaacgg cttttttcaaa   18000 aatatggtat tgataatcct gatatgaata aattgcagtt tcatttgatg ctcgatgagt    18060 tttttctaatc agaattggtt aattggttgt aacactggca gagcattacg ctgacttgac   18120
gggacggcgg ctttgttgaa taaatcgaac ttttgctgag ttgaaggatc agatcacgca    18180
tcttcccgac aacgcagacc gttccgtggc aaagcaaaag ttcaaaatca ccaactggtc    18240
cacctacaac aaagctctca tcaaccgtgg ctccctcact ttctggctgg atgatggggc    18300
gattcaggcc tggtatgagt cagcaacacc ttcttcacga ggcagacctc agcgcccccc    18360 ccccccctgca ggtcaattcg gtcgatatgg ctattacgaa gaaggctcgt gcgcggagtc    18420
ccgtgaactt tcccacgcaa caagtgaacc gcaccgggtt tgccggaggc catttcgtta    18480
aaatgcgcag c                                                          18491

<210> SEQ ID NO 32
<211> LENGTH: 4291
<212> TYPE: DNA
<213> ORGANISM: Artificial
<220> FEATURE:
<223> OTHER INFORMATION: Donor vector pDONR/Zeo

<400> SEQUENCE: 32
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagtttta tggcgggcgt cctgcccgcc accctccggg ccgttgcttc     360
acaacgttca atccgctcc cggcggattt gtcctactca ggagagcgtt caccgacaaa      420
caacagataa aacgaaaggc ccagtcttcc gactgagcct ttcgttttat ttgatgcctg     480
gcagttccct actctcgcgt taacgctagc atggatgttt tcccagtcac gacgttgtaa     540
aacgacggcc agtcttaagc tcgggcccca ataatgatt ttatttgac tgatagtgac      600 ctgttcgttg caacacattg atgagcaatg ctttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt    780
agatggtatt agtgacctgt agtcgaccga cagccttcca atgttcttc gggtgatgct    840 gccaacttag tcgaccgaca gccttccaaa tgttcttctc aaacggaatc gtcgtatcca    900
gcctactcgc tattgtcctc aatgccgtat aaatcataa aagaaataa gaaaaagagg    960 tgcgagcctc ttttttgtgt gacaaaataa aacatctac ctattcatat acgctagtgt   1020
catagtcctg aaaatcatct gcatcaagaa caatttcaca actcttatac ttttctctta   1080
caagtcgttc ggcttcatct ggattttcag cctctatact tactaaacgt gataaagttt   1140
ctgtaatttc tactgtatcg acctgcagac tggctgtgta aagggagcc tgacatttat    1200 attccccaga acatcaggtt aatggcgttt ttgatgtcat tttcgcggtg gctgagatca   1260
gccacttctt ccccgataac ggagaccggc acactggcca tatcgtggt catcatgcgc    1320 cagctttcat ccccgatatg caccaccggg taaagttcac gggagacttt atctgacagc    1380
```

```
agacgtgcac tggccagggg gatcaccatc cgtcgcccgg gcgtgtcaat aatatcactc    1440
tgtacatcca caaacagacg ataacggctc tctcttttat aggtgtaaac cttaaactgc    1500
atttcaccag cccctgttct cgtcagcaaa agagccgttc atttcaataa accgggcgac    1560
ctcagccatc ccttcctgat tttccgcttt ccagcgttcg gcacgcagac gacgggcttc    1620
attctgcatg gttgtgctta ccagaccgga gatattgaca tcatatatgc cttgagcaac    1680
tgatagctgt cgctgtcaac tgtcactgta atacgctgct tcatagcata cctctttttg    1740
acatacttcg ggtatacata tcagtatata ttcttatacc gcaaaaatca gcgcgcaaat    1800
acgcatactg ttatctggct tttagtaagc cggatccacg cggcgtttac gccccgccct    1860
gccactcatc gcagtactgt tgtaattcat taagcattct gccgacatgg aagccatcac    1920
agacggcatg atgaacctga atcgccagcg gcatcagcac cttgtcgcct tgcgtataat    1980
atttgcccat ggtgaaaacg ggggcgaaga agttgtccat attggccacg tttaaatcaa    2040
aactggtgaa actcacccag ggattggctg agacgaaaaa catattctca ataaacccctt    2100 tagggaaata ggccaggttt tcaccgtaac acgccacatc ttgcgaatat atgtgtagaa    2160
actgccggaa atcgtcgtgg tattcactcc agagcgatga aaacgtttca gtttgctcat    2220
ggaaaacggt gtaacaaggg tgaacactat cccatatcac cagctcaccg tctttcattg    2280
ccatacggaa ttccggatga gcattcatca ggcgggcaag aatgtgaata aaggccggat    2340
aaaacttgtg cttattttc tttacggtct ttaaaaaggc cgtaatatcc agctgaacgg    2400
tctggttata ggtacattga gcaactgact gaaatgcctc aaaatgttct ttacgatgcc    2460
attgggatat atcaacggtg gtatatccag tgattttttt ctccatttta gcttccttag    2520
ctcctgaaaa tctcgataac tcaaaaaata cgcccggtag tgatcttatt tcattatggt    2580
gaaagttgga acctcttacg tgccgatcaa cgtctcattt tcgccaaaag ttgggcccagg    2640 gcttcccggt atcaacaggg acaccaggat ttatttattc tgcgaagtga tcttccgtca    2700
caggtattta ttcggcgcaa agtgcgtcgg gtgatgctgc caacttagtc gactacaggt    2760
cactaatacc atcaagtag ttgattcata gtgactggat atgttgtgtt ttacagtatt    2820
atgtagtctg ttttttatgc aaaatctaat ttaatatatt gatatttata tcattttacg    2880
tttctcgttc agcttttcttg tacaaagttg gcattataag aaagcattgc ttatcaattt    2940
gttgcaacga acaggtcact atcagtcaaa ataaaatcat tatttgccat ccagctgata    3000 tccccctatag tgagtcgtat tacatggtca tagctgtttc ctggcagctc tggcccgtgt    3060
ctcaaaatct ctgatgttac attgcacaag ataaaataat atcatcatga tcagtcctgc    3120
tcctcggcca cgaagtgcac gcagttgccg gccgggtcgc gcagggcgaa ctcccgcccc    3180
cacggctgct cgccgatctc ggtcatggcc ggcccgagg cgtcccggaa gttcgtggac    3240
acgacctccg accactcggc gtacagctcg tccaggccgc gcacccacac ccaggccagg    3300
gtgttgtccg gcaccacctg gtcctggacc gcgctgatga cagggtcac gtcgtcccgg    3360 accacaccgg cgaagtcgtc ctccacgaag tcccgggaga acccgagccg gtcggtccag    3420
aactcgaccg ctccggcgac gtcgcgcgcg gtgagcaccg gaacggcact ggtcaacttg    3480
gccatggttt agttcctcac cttgtcgtat tatactatgc cgatatacta tgccgatgat    3540
taattgtcaa cacgtgctga tcatgaccaa aatcccttaa cgtgagttac gcgtcgttcc    3600
actgagcgtc agacccgta gaaaagatca aaggatcttc ttgagatcct ttttttctgc    3660
gcgtaatctg ctgcttgcaa acaaaaaaac caccgctacc agcggtggtt tgtttgccgg    3720
atcaagagct accaactctt tttccgaagg taactggctt cagcagagcg cagataccaa    3780
```

-continued

```
atactgttct tctagtgtag ccgtagttag gccaccactt caagaactct gtagcaccgc    3840
ctacatacct cgctctgcta atcctgttac cagtggctgc tgccagtggc gataagtcgt    3900
gtcttaccgg gttggactca agacgatagt taccggataa ggcgcagcgg tcgggctgaa    3960
cggggggttc gtgcacacag cccagcttgg agcgaacgac ctacaccgaa ctgagatacc    4020
tacagcgtga gctatgagaa agcgccacgc ttcccgaagg gagaaaggcg gacaggtatc    4080
cggtaagcgg cagggtcgga acaggagagc gcacgaggga gcttccaggg ggaaacgcct    4140
ggtatcttta tagtcctgtc gggtttcgcc acctctgact tgagcgtcga ttttttgtgat    4200 gctcgtcagg gggggcggagc ctatggaaaa acgccagcaa cgcggccttt ttacggttcc    4260
tggccttttg ctggccttttt gctcacatgt t                                  4291
```

<210> SEQ ID NO 33
<211> LENGTH: 4762
<212> TYPE: DNA
<213> ORGANISM: Artificial
<220> FEATURE:
<223> OTHER INFORMATION: Donor vector pDONR221

<400> SEQUENCE: 33

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca atccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt tcccagtcac gacgttgtaa     540
aacgacggcc agtcttaagc tcgggcccca ataatgatt ttattttgac tgatagtgac     600
ctgttcgttg caacacattg atgagcaatg cttttttata atgccaactt tgtacaaaaa     660
agctgaacga gaaacgtaaa atgatataaa tatcaatata ttaaattaga ttttgcataa     720
aaaacagact acataatact gtaaaacaca acatatccag tcactatgaa tcaactactt     780
agatggtatt agtgacctgt agtcgaccga cagccttcca atgttcttc gggtgatgct     840 gccaacttag tcgaccgaca gccttccaaa tgttcttctc aaacggaatc gtcgtatcca     900
gcctactcgc tattgtcctc aatgccgtat aaatcataa aagaaataa gaaaagagg     960 tgcgagcctc tttttgtgt gacaaaataa aacatctac ctattcatat acgctagtgt     1020
catagtcctg aaaatcatct gcatcaagaa caatttcaca actcttatac tttctctta     1080 caagtcgttc ggcttcatct ggattttcag cctctatact tactaaacgt gataaagttt     1140 ctgtaattc tactgtatcg acctgcagac tggctgtgta agggagcc tgacatttat     1200 attccccaga acatcaggtt aatggcgttt ttgatgtcat tttcgcggtg gctgagatca     1260
gccacttctt ccccgataac ggagaccggc acactggcca tatcggtggt catcatgcgc     1320
cagctttcat ccccgatatg caccaccggg taaagttcac gggagacttt atctgacagc     1380
agacgtgcac tggccagggg gatcaccatc cgtcgcccgg gcgtgtcaat aatatcactc     1440
tgtacatcca caaacagacg ataacggctc tctcttttat aggtgtaaac cttaaactgc     1500
```

```
atttcaccag cccctgttct cgtcagcaaa agagccgttc atttcaataa accgggcgac   1560
ctcagccatc ccttcctgat tttccgcttt ccagcgttcg gcacgcagac gacgggcttc   1620
attctgcatg gttgtgctta ccagaccgga gatattgaca tcatatatgc cttgagcaac   1680
tgatagctgt cgctgtcaac tgtcactgta atacgctgct tcatagcata cctcttttg   1740 acatacttcg ggtatacata tcagtatata ttcttatacc gcaaaatca gcgcgcaaat   1800 acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct tgcgtataat   1980
atttgcccat ggtgaaaacg ggggcgaaga agttgtccat attggccacg tttaaatcaa   2040
aactggtgaa actcacccag ggattggctg agacgaaaaa catattctca ataaaccctt   2100
tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280
ccatacggaa ttccggatga gcattcatca ggcgggcaag aatgtgaata aaggccggat   2340
aaaacttgtg cttattttc tttacggtct ttaaaaaggc cgtaatatcc agctgaacgg   2400
tctggttata ggtacattga gcaactgact gaaatgcctc aaaatgttct ttacgatgcc   2460
attgggatat atcaacggtg gtatatccag tgatttttt ctccatttta gcttccttag   2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640
gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg ttttttatgc aaaatctaat ttaatatatt gatatttata tcattttacg   2880
tttctcgttc agctttcttg tacaaagttg gcattataag aaagcattgc ttatcaattt   2940
gttgcaacga acaggtcact atcagtcaaa ataaaatcat tatttgccat ccagctgata   3000
tcccctatag tgagtcgtat tacatggtca tagctgtttc ctggcagctc tggcccgtgt   3060
ctcaaaatct ctgatgttac attgcacaag ataaataat atcatcatga acaataaaac   3120
tgtctgctta cataaacagt aatacaaggg gtgttatgag ccatattcaa cgggaaacgt   3180
cgaggccgcg attaaattcc aacatggatg ctgatttata tgggtataaa tgggctcgcg   3240
ataatgtcgg gcaatcaggt gcgacaatct atcgcttgta tgggaagccc gatgcgccag   3300
agttgtttct gaaacatggc aaaggtagcg ttgccaatga tgttacagat gagatggtca   3360
gactaaactg gctgacggaa tttatgcctc ttccgaccat caagcatttt atccgtactc   3420
ctgatgatgc atggttactc accactgcga tccccggaaa aacagcattc caggtattag   3480
aagaatatcc tgattcaggt gaaaatattg ttgatgcgct ggcagtgttc ctgcgccggt   3540
tgcattcgat tcctgtttgt aattgtcctt ttaacagcga tcgcgtattt cgtctcgctc   3600
aggcgcaatc acgaatgaat aacggtttgg ttgatgcgag tgattttgat gacgagcgta   3660
atggctggcc tgttgaacaa gtctggaaag aaatgcataa acttttgcca ttctcaccgg   3720
attcagtcgt cactcatggt gatttctcac ttgataacct tattttgac gaggggaaat   3780 taataggttg tattgatgtt ggacgagtcg gaatcgcaga ccgataccag gatcttgcca   3840
tcctatggaa ctgcctcggt gagttttctc cttcattaca gaaacggctt tttcaaaaat   3900
```

```
atggtattga taatcctgat atgaataaat tgcagtttca tttgatgctc gatgagtttt    3960
tctaatcaga attggttaat tggttgtaac actggcagag cattacgctg acttgacggg    4020
acggcgcaag ctcatgacca aaatccctta acgtgagtta cgcgtcgttc cactgagcgt    4080
cagaccccgt agaaaagatc aaaggatctt cttgagatcc tttttttctg cgcgtaatct    4140
gctgcttgca aacaaaaaaa ccaccgctac cagcggtggt ttgtttgccg gatcaagagc    4200
taccaactct ttttccgaag gtaactggct tcagcagagc gcagatacca atactgttc    4260 ttctagtgta gccgtagtta ggccaccact tcaagaactc tgtagcaccg cctacatacc    4320
tcgctctgct aatcctgtta ccagtggctg ctgccagtgg cgataagtcg tgtcttaccg    4380
ggttggactc aagacgatag ttaccggata aggcgcagcg gtcgggctga acggggggtt    4440
cgtgcacaca gcccagcttg gagcgaacga cctacaccga actgagatac ctacagcgtg    4500
agctatgaga aagcgccacg cttcccgaag ggagaaaggc ggacaggtat ccggtaagcg    4560
gcagggtcgg aacaggagag cgcacgaggg agcttccagg gggaaacgcc tggtatcttt    4620
atagtcctgt cgggtttcgc cacctctgac ttgagcgtcg attttgtga tgctcgtcag    4680 gggggcggag cctatggaaa aacgccagca acgcggcctt tttacggttc ctggccttt    4740 gctggccttt tgctcacatg tt                                              4762
```

<210> SEQ ID NO 34  
<211> LENGTH: 16843  
<212> TYPE: DNA  
<213> ORGANISM: Artificial  
<220> FEATURE:  
<223> OTHER INFORMATION: Destination vector pBC-yellow

<400> SEQUENCE: 34

```
ccgggctggt tgccctcgcc gctgggctgg cggccgtcta tggccctgca aacgcgccag      60
aaacgccgtc gaagccgtgt gcgagacacc gcggccgccg gcgttgtgga tacctcgcgg     120
aaaacttggc cctcactgac agatgagggg cggacgttga cacttgaggg gccgactcac     180
ccggcgcggc gttgacagat gaggggcagg ctcgatttcg gccggcgacg tggagctggc     240
cagcctcgca aatcggcgaa aacgcctgat tttacgcgag tttcccacag atgatgtgga     300
caagcctggg gataagtgcc ctgcggtatt gacacttgag gggcgcgact actgacagat     360
gaggggcgcg atccttgaca cttgaggggc agagtgctga cagatgaggg gcgcacctat     420
tgacatttga gggctgtcc acaggcagaa aatccagcat ttgcaagggt ttccgcccgt     480
ttttcggcca ccgctaacct gtcttttaac ctgcttttaa accaatattt ataaaccttg    540
tttttaacca gggctgcgcc ctgtgcgcgt gaccgcgcac gccgaagggg ggtgcccccc   600
cttctcgaac cctcccggcc cgctaacgcg ggcctcccat cccccagggg gctgcgcccc    660
tcggccgcga acggcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcggcc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa   1020
acgagaattg gacctttaca gaattactct atgaagcgcc atatttaaaa agctaccaag   1080
acgaagagga tgaagaggat gaggaggcag attgccttga atatattgac aatactgata   1140
```

```
agataatata tcttttatat agaagatatc gccgtatgta aggatttcag ggggcaaggc    1200
ataggcagcg cgcttatcaa tatatctata gaatgggcaa agcataaaaa cttgcatgga    1260
ctaatgcttg aaacccagga caataacctt atagcttgta aattctatca taattgggta    1320
atgactccaa cttattgata gtgttttatg ttcagataat gcccgatgac tttgtcatgc    1380
agctccaccg atttgagaa cgacagcgac ttccgtccca gccgtgccag gtgctgcctc     1440
agattcaggt tatgccgctc aattcgctgc gtatatcgct tgctgattac gtgcagcttt    1500
cccttcaggc gggattcata cagcggccag ccatccgtca tccatatcac cacgtcaaag    1560
ggtgacagca ggctcataag acgccccagc gtcgccatag tgcgttcacc gaatacgtgc    1620
gcaacaaccg tcttccggag actgtcatac gcgtaaaaca gccagcgctg gcgcgattta    1680
gccccgacat agccccactg ttcgtccatt tccgcgcaga cgatgacgtc actgcccggc    1740
tgtatgcgcg aggttaccga ctgcggcctg agttttttaa gtgacgtaaa atcgtgttga    1800
ggccaacgcc cataatgcgg gctgttgccc ggcatccaac gccattcatg gccatatcaa    1860
tgattttctg gtgcgtaccg ggttgagaag cggtgtaagt gaactgcagt tgccatgttt    1920
tacggcagtg agagcagaga tagcgctgat gtccggcggt gcttttgccg ttacgcacca    1980
ccccgtcagt agctgaacag gagggacagc tgatagacac agaagccact ggagcacctc    2040
aaaaacacca tcatacacta aatcagtaag ttggcagcat cacccataat tgtggtttca    2100
aaatcggctc cgtcgatact atgttatacg ccaactttga aaacaactt gaaaagctg      2160 ttttctggta tttaaggttt tagaatgcaa ggaacagtga attggagttc gtcttgttat    2220
aattagcttc ttggggtatc tttaaatact gtagaaaaga ggaaggaaat aataaatggc    2280
taaaatgaga atatcaccgg aattgaaaaa actgatcgaa aaataccgct gcgtaaaaga    2340 tacgaagga atgtctcctg ctaaggtata taagctggtg ggagaaaatg aaaacctata     2400
tttaaaaatg acggacagcc ggtataaagg gaccacctat gatgtggaac gggaaaagga    2460
catgatgcta tggctggaag gaaagctgcc tgttccaaag gtcctgcact ttgaacggca    2520
tgatggctgg agcaatctgc tcatgagtga ggccgatggc gtcctttgct cggaagagta    2580
tgaagatgaa caaagccctg aaaagattat cgagctgtat gcggagtgca tcaggctctt    2640
tcactccatc gacatatcgg attgtcccta tacgaatagc ttagacagcc gcttagccga    2700
attggattac ttactgaata acgatctggc cgatgtggat tgcgaaaact gggaagaaga    2760
cactccattt aaagatccgc gcgagctgta tgattttta aagacggaaa agcccgaaga    2820
ggaacttgtc ttttcccacg cgacctggg agacagcaac atctttgtga agatggcaa     2880 agtaagtggc tttattgatc ttgggagaag cggcagggcg gacaagtggt atgacattgc    2940
cttctgcgtc cggtcgatca ggaggatat cggggaagaa cagtatgtcg agctattttt      3000
tgacttactg gggatcaagc ctgattggga gaaaataaaa tattatattt tactggatga    3060 attgtttag tacctagatg tggcgcaacg atgccggcga caagcaggag cgcaccgact     3120
tcttccgcat caagtgtttt ggctctcagg ccgaggccca cggcaagtat ttgggcaagg    3180
ggtcgctggt attcgtgcag ggcaagattc ggaataccaa gtacgagaag gacggccaga    3240
cggtctacgg gaccgacttc attgccgata aggtggatta tctggacacc aaggcaccag    3300
gcgggtcaaa tcaggaataa gggcacattg ccccggcgtg agtcggggca atcccgcaag    3360
gagggtgaat gaatcggacg tttgaccgga aggcatacag gcaagaactg atcgacgcgg    3420
ggttttccgc cgaggatgcc gaaaccatcg caagccgcac cgtcatgcgt gcgccccgcg    3480
aaaccttcca gtccgtcggc tcgatggtcc agcaagctac ggccaagatc gagcgcgaca    3540
```

```
gcgtgcaact ggctcccct gccctgcccg cgccatcggc cgccgtggag cgttcgcgtc    3600
gtctcgaaca ggaggcggca ggtttggcga agtcgatgac catcgacacg cgaggaacta    3660
tgacgaccaa gaagcgaaaa accgccggcg aggacctggc aaaacaggtc agcgaggcca    3720
agcaggccgc gttgctgaaa cacacgaagc agcagatcaa ggaaatgcag ctttccttgt    3780
tcgatattgc gccgtggccg gacacgatgc gagcgatgcc aaacgacacg gcccgctctg    3840
ccctgttcac cacgcgcaac aagaaaatcc cgcgcgaggc gctgcaaaac aaggtcattt    3900
tccacgtcaa caaggacgtg aagatcacct acaccggcgt cgagctgcgg gccgacgatg    3960
acgaactggt gtggcagcag gtgttggagt acgcgaagcg caccctatc ggcgagccga    4020 tcaccttcac gttctacgag cttgccagg acctgggctg gtcgatcaat ggccggtatt    4080
acacgaaggc cgaggaatgc ctgtcgcgcc tacaggcgac ggcgatgggc ttcacgtccg    4140
accgcgttgg gcacctggaa tcggtgtcgc tgctgcaccg cttccgcgtc ctggaccgtg    4200
gcaagaaaac gtcccgttgc caggtcctga tcgacgagga atcgtcgtg ctgtttgctg    4260 gcgaccacta cacgaaattc atatgggaga agtaccgcaa gctgtcgccg acggcccgac    4320
ggatgttcga ctatttcagc tcgcaccggg agccgtaccc gctcaagctg gaaaccttcc    4380
gcctcatgtg cggatcggat ccacccgcg tgaagaagtg gcgcgagcag gtcggcgaag    4440
cctgcgaaga gttgcgaggc agcggcctgg tggaacacgc ctgggtcaat gatgacctgg    4500
tgcattgcaa acgctagggc cttgtgggt cagttccggc tggggttca gcagccagcg    4560 ctttactggc atttcaggaa caagcgggca ctgctcgacg cacttgcttc gctcagtatc    4620
gctcgggacg cacggcgcgc tctacgaact gccgataaac agaggattaa aattgacaat    4680
tgtgattaag gctcagattc gacggcttgg agcggccgac gtgcaggatt ccgcgagat    4740 ccgattgtcg gccctgaaga aagctccaga gatgttcggg tccgtttacg agcacgagga    4800
gaaaaagccc atggaggcgt tcgctgaacg gttgcgagat gccgtggcat tcggcgccta    4860
catcgacggc gagatcattg gctgtcggt cttcaaacag gaggacggcc caaggacgc    4920 tcacaaggcg catctgtccg gcgttttcgt ggagcccgaa cagcgaggcc gaggggtcgc    4980
cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgttatt cggtctaccg cctgccgggc ggggtcgcgg cgacggtagg    5160
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca gcgctagatc ctgtcggcgt cgcagcgggc ctggcggggg cggtttccat    5340
ggcgttcgga accgtgctga cccgcaagtg gcaacctccc gtgcctctgc tcacctttac    5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggctttctca gccccagatc tggggtcgat cagccgggga tgcatcaggc    5640
cgacagtcgg aacttcgggt ccccgacctg taccattcgg tgagcaatgg ataggggagt    5700
tgatatcgtc aacgttcact tctaaagaaa tagcgccact cagcttcctc agcggcttta    5760
tccagcgatt tccctattatg tcggcatagt tctcaagatc gacagcctgt cacggttaag    5820
cgagaaatga ataagaaggc tgataattcg gatctctgcg agggagatga tatttgatca    5880
```

-continued

```
caggcagcaa cgctctgtca tcgttacaat caacatgcta ccctccgcga gatcatccgt    5940
gtttcaaacc cggcagctta gttgccgttc ttccgaatag catcggtaac atgagcaaag    6000
tctgccgcct tacaacggct ctcccgctga cgccgtcccg gactgatggg ctgcctgtat    6060
cgagtggtga ttttgtgccg agctgccggt cggggagctg ttggctggct ggtggcagga    6120
tatattgtgg tgtaaacaaa ttgacgctta gacaacttaa taacacattg cggacgtttt    6180
taatgtactg gggtggtttt tcttttcacc agtgagacgg gcaacagctg attgcccttc    6240
accgcctggc cctgagagag ttgcagcaag cggtccacgc tggtttgccc cagcaggcga    6300
aaatcctgtt tgatggtggt tccgaaatcg gcaaaatccc ttataaatca aaagaatagc    6360
ccgagatagg gttgagtgtt gttccagttt ggaacaagag tccactatta agaacgtgg    6420
actccaacgt caaagggcga aaaccgtct atcagggcga tggcccacta cctgtatggc    6480
cgcattcgca aaacacacct agactagatt tgttttgcta acccaattga tattaattat    6540
atatgattaa tatttatatg tatatggatt tggttaatga aatgcatctg gttcatcaaa    6600
gaattataaa gacacgtgac attcatttag gataagaaat atggatgatc tctttctctt    6660
ttattcagat aactagtaat tacacataac acacaacttt gatgcccaca ttatagtgat    6720
tagcatgtca ctatgtgtgc atcctttat ttcatacatt aattaagttg gccaatccag    6780
aagatggaca agtctaggtt aaccatgtgg tacctacgcg ttcgaatatc catgggccgc    6840
ttcaggccag ggcgctgggg aaggcgatgg cgtgctcgt cagctgccac ttctggttct    6900
tggcgtcgct ccggtcctcc cgcagcagct tgtgctggat gaagtgccac tcgggcatct    6960
tgctgggcac gctcttggcc ttgtacacgg tgtcgaactg caccggtac cggccgccgt    7020
ccttcagcag caggtacatg ctcacgtcgc ccttcaggat gccctgctta ggcacgggca    7080
tgatcttctc gcagctggcc tcccagttgg tggtcatctt cttcatcacg gggccgtcgg    7140
cggggaagtt cacgccgttg aagatgctct tgtggtagat gcagttctcc ttcacgctca    7200
cggtgatgtc cacgttacag atgcacacgg cgccgtcctc gaacaggaag ctccggcccc    7260
aggtgtagcc ggcggggcag ctgttcttga agtagtccac gatgtcctgg gggtactcgg    7320
tgaagatccg gtcgccgtac ttgaagccgg cgctcaggat gtcctcgctg aagggcaggg    7380
ggccgccctc gatcacgcac aggttgatgg tctgcttgcc cttgaagggg tagccgatgc    7440
cctcgccggt gatcacgaac ttgtggccgt tcacgcagcc ctccatgtgg tacttcatgg    7500
tcatctcctc cttcaggccg tgcttgctgt gggccatggt ggcgaccggt gaattcgagc    7560
tcggtacccg gggatcctga gtaaaacaga ggagggtctc actaagttta tagagagact    7620
gagagagata aagggacacg tatgaagcgt ctgttttcgt ggtgtgacgt caaagtcatt    7680
ttgctctcta cgcgtgtctg tgtcggcttg atcttttttt ttgcttttg gaactcatgt    7740
cggtagtata tcttttattt attttttctt ttttcccctt ttctttcaaa ctgatgtcgg    7800
tatgatattt attccatcct aaaatgtaac ttactattat tagtagtcgg tccatgtcta    7860
ttggcccatc atgtggtcat tttacgttta cgtcgtgtgg ctgtttatta taacaaacgg    7920
cacatccttc tcattcgaat tgtatttctc cttaatcgtt ctaataggta tgatctttta    7980
ttttatacgt aaaattaaaa ttgaatgatg tcaagaacga aaattaattt gtatttacaa    8040
aggagctaaa tattgtttat tcctctactg gtagaagata aagaagtag atgaaataat    8100
gatcttacta gagaatattc ctcatttaca ctagtcaaat ggaaatcttg taaacttta    8160
caataattta tcctgaaaat atgaaaaaat agaagaaaat gtttacctcc tctctcctct    8220
taattcacct acgatcggtg cgggcctctt cgctattacg ccagctggcg aaaggggat    8280
```

```
gtgctgcaag gcgattaagt tgggtaacgc cagggttttc ccagtcacga cgttgtaaaa    8340
cgacggccag tgaattcgag ctcggtaccc ggggatcctc tagagtcgac ctgcaggcat    8400
gcaagcttgt tgaaacatcc ctgaagtgtc tcattttatt ttatttattc tttgctgata    8460
aaaaaataaa ataaaagaag ctaagcacac ggtcaaccat tgctctactg ctaaaagggt    8520
tatgtgtagt gttttactgc ataaattatg cagcaaacaa gacaactcaa attaaaaaat    8580
ttcctttgct tgttttttg ttgtctctga cttgactttc ttgtggaagt tggttgtata    8640
aggattggga cacaccattg tccttcttaa tttaattta tttctttgct gataaaaaaa    8700
aaaaatttca tatagtgtta aataataatt tgttaaataa ccaaaaagtc aaatatgttt    8760
actctcgttt aaataattga gagtcgtcca gcaaggctaa acgattgtat agatttatga    8820
caatatttac ttttttatag ataaatgtta tattataata aatttatata catatattat    8880
atgttattta ttatttatta ttattttaaa tccttcaata ttttatcaaa ccaactcata    8940
attttttttt tatctgtaag aagcaataaa attaaataga cccactttaa ggatgatcca    9000 accttttatac agagtaagag agttcaaata gtacccttc atatacatat caactaaaat    9060
attagaaata tcatggatca aaccttataa agacattaaa taagtggata agtataaat    9120 ataaatgggt agtatataat atataaatgg atacaaactt ctctctttat aattgttatg    9180
tctccttaac atcctaatat aatacataag tgggtaatat ataatatata aatggagaca    9240
aacttcttcc attataattg ttatgtcttc ttaacactta tgtctcgttc acaatgctaa    9300
agttagaatt gtttagaaag tcttatagta cacatttgtt ttgtactat ttgaagcatt    9360 ccataagccg tcacgattca gatgatttat aataataaga ggaaatttat catagaacaa    9420
taaggtgcat agatagagtg ttaatatatc ataacatcct ttgtttattc atagaagaag    9480
tgagatggag ctcagttatt atactgttac atggtcggat acaatattcc atgctctcca    9540
tgagctctta cacctacatg catttagtt catacttcat gcacgtggcc atcacagcta    9600
gctgcagcta catatttaca ttttacaaca ccaggagaac tgccctgtta gtgcataaca    9660
atcagaagat ggccgtggct actcgagtta tcgaaccact ttgtacaaga aagctgaacg    9720
agaaacgtaa aatgatataa atatcaatat attaaattag attttgcata aaaaacagac    9780
tacataatac tgtaaaacac aacatatcca gtcactatgg tcgacctgca gactggctgt    9840
gtataaggga gcctgacatt tatattcccc agaacatcag gttaatgcg tttttgatgt    9900 cattttcgcg gtggctgaga tcagccactt cttccccgat aacggagacc ggcacactgg    9960
ccatatcggt ggtcatcatg cgccagcttt catccccgat atgcaccacc gggtaaagtt   10020
cacgggagac tttatctgac agcagacgtg cactggccag ggggatcacc atccgtcgcc   10080
cgggcgtgtc aataatatca ctctgtacat ccacaaacag acgataacgg ctctctcttt   10140
tataggtgta aaccttaaac tgcatttcac cagtccctgt tctcgtcagc aaaagagccg   10200
ttcatttcaa taaccgggc gacctcagcc atcccttcct gatttccgc tttccagcgt    10260 tcggcacgca gacgacgggc ttcattctgc atggttgtgc ttaccagacc ggagatattg   10320
acatcatata tgccttgagc aactgatagc tgtcgctgtc aactgtcact gtaatacgct   10380
gcttcatagc acacctcttt ttgacatact tcgggtatac atatcagtat atattcttat   10440
accgcaaaaa tcagcgcgca aatacgcata ctgttatctg gcttttagta agccggatcc   10500
tctagattac gccccgccct gccactcatc gcagtactgt tgtaattcat taagcattct   10560
gccgacatgg aagccatcac agacggcatg atgaacctga atcgccagcg gcatcagcac   10620
```

```
cttgtcgcct tgcgtataat atttgcccat ggtgaaaacg ggggcgaaga agttgtccat   10680
attggccacg tttaaatcaa aactggtgaa actcacccag ggattggctg agacgaaaaa   10740
catattctca ataaacccti tagggaaata ggccaggttt tcaccgtaac acgccacatc   10800
ttgcgaatat atgtgtagaa actgccgaaa atcgtcgtgg tattcactcc agagcgatga   10860
aaacgtttca gtttgctcat ggaaaacggt gtaacaaggg tgaacactat cccatatcac   10920
cagctcaccg tctttcattg ccatacgaaa ttccggatga gcattcatca ggcgggcaag   10980
aatgtgaata aaggccggat aaaacttgtg cttattttc tttacggtct ttaaaaaggc   11040
cgtaatatcc agctgaacgg tctggttata ggtacattga gcaactgact gaaatgcctc   11100
aaaatgttct ttacgatgcc attgggatat atcaacggtg gtatatccag tgatttttt   11160
ctccatttta gcttccttag ctcctgaaaa tctcgccgga tcctaactca aaatccacac   11220
attatacgag ccggaagcat aaagtgtaaa gcctggggtg cctaatgcgg ccgccatagt   11280
gactggatat gttgtgtttt acagtattat gtagtctgtt ttttatgcaa aatctaattt   11340
aatatattga tatttatatc atttttacgtt tctcgttcag cttttttgta caaacttgtt   11400
tgataaccgg tactagtgtg cacgtcgagc gtgtcctctc caaatgaaat gaacttcctt   11460
atatagagga agggtcttgc gaaggatagt gggattgtgc gtcatcccti acgtcagtgg   11520
agatgtcaca tcaatccact tgctttgaag acgtggttgg aacgtcttct ttttccacga   11580
tgctcctcgt gggtggggggt ccatcttigg gaccactgtc ggcagaggca tcttgaatga   11640
tagcctttcc tttatcgcaa tgatggcatt tgtaggagcc accttccttt tctactgtcc   11700
tttcgatgaa gtgacagata gctgggcaat ggaatccgag gaggtttccc gaaattatcc   11760
tttgttgaaa agtctcaata gcccttiggt cttctgagac tgtatcttg acattttgg   11820
agtagaccag agtgtcgtgc tccaccatgt tgacgaagat tttcttcttg tcattgagtc   11880
gtaaaagact ctgtatgaac tgttcgccag tcttcacggc gagttctgtt agatcctcga   11940
tttgaatctt agactccatg catggcctta gattcagtag gaactacctt tttagagact   12000
ccaatctcta ttacttgcct tggtttatga agcaagcctt gaatcgtcca tactggaata   12060
gtacttctga tcttgagaaa tatgtctttc tctgtgttct tgatgcaatt agtcctgaat   12120
cttttgactg catctttaac cttcttggga aggtatttga tctcctggag attgttactc   12180
gggtagatcg tcttgatgag acctgctgcg taggcctctc taaccatctg tgggtcagca   12240
ttctttctga aattgaagag gctaaccttc tcattatcag tggtgaacat agtgtcgtca   12300
ccttcacctt cgaacttcct tcctagatcg taaagataga ggaaatcgtc cattgtaatc   12360
tccggggcaa aggagatctc ttttgggget ggatcactgc tgggccttit ggttcctagc   12420
gtgagccagt gggcttttg ctttggtggg cttgttaggg ccttagcaaa gctcttgggc   12480
ttgagttgag cttctccttt ggggatgaag ttcaacctgt ctgtttgctg acttgttgtg   12540
tacgcgtcag ctgctgctct tgcctctgta atagtggcaa atttcttgtg tgcaactccg   12600
ggaacgccgt ttgttgccgc cttttgtacaa ccccagtcat cgtatatacc ggcatgtgga   12660
ccgttataca caacgtagta gttgatatga gggtgttgaa tacccgattc tgctctgaga   12720
ggagcaactg tgctgttaag ctcagatttt tgtgggattg gaattggatc ctctagagca   12780
aagcttggcg taatcatggt catagctgtt tcctgtgtga aattgttatc cgctcacaat   12840
tccacacaac atacgagccg gaagcataaa gtgtaaagcc tggggtgcct aatgagtgag   12900
ctaactcaca ttaattgcgt tgcgctcact gcccgctttc cagtcgggaa acctgtcgtg   12960
ccagctgcat taatgaatcg gccaacgcgc ggggagaggc ggtttgcgta ttgggccaaa   13020
```

```
gacaaaaggg cgacattcaa ccgattgagg gagggaaggt aaatattgac ggaaattatt   13080
cattaaaggt gaattatcac cgtcaccgac ttgagccatt tgggaattag agccagcaaa   13140
atcaccagta gcaccattac cattagcaag gccggaaacg tcaccaatga aaccatcatc   13200
tagtaacata gatgacaccg cgcgcgataa tttatcctag tttgcgcgct atattttgtt   13260
ttctatcgcg tattaaatgt ataattgcgg gactctaatc ataaaaaccc atctcataaa   13320
taacgtcatg cattacatgt taattattac atgcttaacg taattcaaca gaaattatat   13380
gataatcatc gcaagaccgg caacaggatt caatcttaag aaactttatt gccaaatgtt   13440
tgaacgatct gcttcgacgc actccttctt taggtacgga ctagatctcg gtgacgggca   13500
ggaccggacg gggcggtacc ggcaggctga agtccagctg ccagaaaccc acgtcatgcc   13560
agttcccgtg cttgaagccg gccgcccgca gcatgccgcg ggggcatat ccgagcgcct   13620 cgtgcatgcg cacgctcggg tcgttgggca gcccgatgac agcgaccacg ctcttgaagc   13680
cctgtgcctc cagggacttc agcaggtggg tgtagagcgt ggagcccagt cccgtccgct   13740
ggtggcgggg ggagacgtac acggtcgact cggccgtcca gtcgtaggcg ttgcgtgcct   13800
tccaggggcc cgcgtaggcg atgccggcga cctcgccgtc cacctcggcg acgagccagg   13860
gatagcgctc ccgcagacgg acgaggtcgt ccgtccactc ctgcggttcc tgcggctcgg   13920
tacggaagtt gaccgtgctt gtctcgatgt agtggttgac gatggtgcag accgccggca   13980
tgtccgcctc ggtggcacgg cggatgtcgg ccgggcgtcg ttctgggctc atggatctgg   14040
attgagagtg aatatgagac tctaattgga taccgagggg aatttatgga acgtcagtgg   14100 agcattttg acaagaaata tttgctagct gatagtgacc ttaggcgact tttgaacgcg   14160
caataatggt ttctgacgta tgtgcttagc tcattaaact ccagaaaccc gcggctgagt   14220
ggctccttca acgttgcggt tctgtcagtt ccaaacgtaa aacggcttgt cccgcgtcat   14280
cggcgggggt cataacgtga ctcccttaat tctccgctca tgatcagatt gtcgtttccc   14340
gccttcagtt taaactatca gtgtttgaca ggatatattg gcgggtaaac ctaagagaaa   14400
agagcgttta ttagaataat cggatattta aaagggcgtg aaaaggttta tccgttcgtc   14460
catttgtatg tgcatgccaa ccacagggtt ccccagatct ggcgccggcc agcgagacga   14520
gcaagattgg ccgccgcccg aaacgatccg acagcgcgcc cagcacaggt gcgcaggcaa   14580
attgcaccaa cgcatacagc gccagcagaa tgccatagtg ggcggtgacg tcgttcgagt   14640
gaaccagatc gcgcaggagg cccggcagca ccggcataat caggccgatg ccgacagcgt   14700
cgagcgcgac agtgctcaga attacgatca ggggtatgtt gggtttcacg tctggcctcc   14760
ggaccagcct ccgctggtcc gattgaacgc gcggattctt tatcactgat aagttggtgg   14820
acatattatg tttatcagtg ataaagtgtc aagcatgaca aagttgcagc cgaatacagt   14880
gatccgtgcc gccctggacc tgttgaacga ggtcggcgta gacggtctga cgacacgcaa   14940
actggcggaa cggttggggg ttcagcagcc ggcgctttac tggcacttca ggaacaagcg   15000
ggcgctgctc gacgcactgg ccgaagccat gctggcggag aatcatacgc attcggtgcc   15060
gagagccgac gacgactggc gctcatttct gatcgggaat gcccgcagct tcaggcaggc   15120
gctgctcgcc taccgcgatg gcgcgcgcat ccatgccggc acgcgaccgg gcgcaccgca   15180
gatggaaacg gccgacgcgc agcttcgctt cctctgcgag gcgggttttt cggccgggga   15240
cgccgtcaat gcgctgatga caatcagcta cttcactgtt ggggccgtgc ttgaggagca   15300
ggccggcgac agcgatgccg gcgagcgcgg cggcaccgtt gaacaggctc cgctctcgcc   15360
```

```
gctgttgcgg gccgcgatag acgccttcga cgaagccggt ccggacgcag cgttcgagca   15420
gggactcgcg gtgattgtcg atggattggc gaaaaggagg ctcgttgtca ggaacgttga   15480
aggaccgaga aagggtgacg attgatcagg accgctgccg gagcgcaacc cactcactac   15540
agcagagcca tgtagacaac atcccctccc cctttccacc gcgtcagacg cccgtagcag   15600
cccgctacgg gcttttttcat gccctgccct agcgtccaag cctcacggcc gcgctcggcc   15660
tctctggcgg ccttctggcg ctcttccgct tcctcgctca ctgactcgct gcgctcggtc   15720
gttcggctgc ggcgagcggt atcagctcac tcaaaggcgg taatacggtt atccacagaa   15780 tcagggata acgcaggaaa gaacatgtga gcaaaaggcc agcaaaaggc caggaaccgt   15840
aaaaaggccg cgttgctggc gttttccat aggctccgcc cccctgacga gcatcacaaa   15900
aatcgacgct caagtcagag gtggcgaaac ccgacaggac tataaagata ccaggcgttt   15960 cccccctggaa gctccctcgt gcgctctcct gttccgaccc tgccgcttac cggatacctg   16020
tccgcctttc tcccttcggg aagcgtggcg cttttccgct gcataaccct gcttcggggt   16080
cattatagcg atttttcgg tatatccatc cttttcgca cgatatacag gattttgcca   16140
aagggttcgt gtagactttc cttggtgtat ccaacggcgt cagccgggca ggataggtga   16200
agtaggccca cccgcgagcg gtgttcctt cttcactgtc ccttattcgc acctggcggt   16260
gctcaacggg aatcctgctc tgcgaggctg gccggctacc gccggcgtaa cagatgaggg   16320
caagcggatg gctgatgaaa ccaagccaac caggaagggc agcccaccta tcaaggtgta   16380
ctgccttcca gacgaacgaa gagcgattga ggaaaaggcg gcggcggccg gcatgagcct   16440
gtcggcctac ctgctggccg tcggccaggg ctacaaaatc acgggcgtcg tggactatga   16500
gcacgtccgc gagctggccc gcatcaatgg cgacctgggc cgcctgggcg gcctgctgaa   16560
actctggctc accgacgacc cgcgcacggc gcggttcggt gatgccacga tcctcgccct   16620
gctggcgaag atcgaagaga agcaggacga gcttggcaag gtcatgatgg gcgtggtccg   16680
cccgagggca gagccatgac ttttttagcc gctaaaacgg ccgggggggtg cgcgtgattg   16740 ccaagcacgt ccccatgcgc tccatcaaga agagcgactt cgcggagctg gtgaagtaca   16800
tcaccgacga gcaaggcaag accgagcgcc tttgcgacgc tca                     16843

<210> SEQ ID NO 35
<211> LENGTH: 9142
<212> TYPE: DNA
<213> ORGANISM: Artificial
<220> FEATURE:
<223> OTHER INFORMATION: Destination vector PHP27840

<400> SEQUENCE: 35
ctagttatct gaataaaaga gaaagagatc atccatattt cttatcctaa atgaatgtca    60
cgtgtcttta taattctttg atgaaccaga tgcatttcat taaccaaatc catatacata   120
taaatattaa tcatatataa ttaatatcaa ttgggttagc aaaacaaatc tagtctaggt   180
gtgttttgcg aattcgatat caagcttgat gggtaccggc gcgcccgatc atccggatat   240
agttcctcct ttcagcaaaa aaccccctcaa gacccgttta gaggccccaa ggggttatgc   300
tagttattgc tcagcggtgg cagcagccaa ctcagcttcc tttcgggctt tgttagcagc   360
cggatcgatc caagctgtac ctcactattc ctttgccctc ggacgagtgc tggggcgtcg   420
gtttccacta tcggcgagta cttctacaca gccatcggtc cagacggccg cgcttctgcg   480
ggcgatttgt gtacgcccga cagtcccggc tccggatcgg acgattgcgt cgcatcgacc   540
ctgcgcccaa gctgcatcat cgaaattgcc gtcaaccaag ctctgataga gttggtcaag   600
```

```
accaatgcgg agcatatacg cccggagccg cggcgatcct gcaagctccg gatgcctccg    660
ctcgaagtag cgcgtctgct gctccataca agccaaccac ggcctccaga agaagatgtt    720
ggcgacctcg tatttgggaat ccccgaacat cgcctcgctc cagtcaatga ccgctgttat   780
gcggccattg tccgtcagga cattgttgga gccgaaatcc gcgtgcacga ggtgccggac    840
ttcggggcag tcctcggccc aaagcatcag ctcatcgaga gcctgcgcga cggacgcact    900
gacggtgtcg tccatcacag tttgccagtg atacacatgg ggatcagcaa tcgcgcatat    960
gaaatcacgc catgtagtgt attgaccgat tccttgcggt ccgaatgggc cgaacccgct   1020
cgtctggcta agatcggccg cagcgatcgc atccatagcc tccgcgaccg gctgcagaac   1080
agcgggcagt tcggtttcag gcaggtcttg caacgtgaca ccctgtgcac ggcgggagat   1140
gcaataggtc aggctctcgc tgaattcccc aatgtcaagc acttccggaa tcgggagcgc   1200
ggccgatgca aagtgccgat aaacataacg atctttgtag aaaccatcgg cgcagctatt   1260
tacccgcagg acatatccac gccctcctac atcgaagctg aaagcacgag attcttcgcc   1320
ctccgagagc tgcatcaggt cggagacgct gtcgaacttt tcgatcagaa acttctcgac   1380
agacgtcgcg gtgagttcag gcttttccat gggtatatct ccttcttaaa gttaaacaaa   1440
attatttcta gagggaaacc gttgtggtct ccctatagtg agtcgtatta atttcgcggg   1500
atcgagatct gatcaacctg cattaatgaa tcggccaacg cgcggggaga ggcggtttgc   1560
gtattgggcg ctcttccgct tcctcgctca ctgactcgct gcgctcggtc gttcggctgc   1620
ggcgagcggt atcagctcac tcaaaggcgg taatacggtt atccacagaa tcagggggata   1680
acgcaggaaa gaacatgtga gcaaaaggcc agcaaaaggc caggaaccgt aaaaaggccg   1740
cgttgctggc gtttttccat aggctccgcc cccctgacga gcatcacaaa aatcgacgct   1800
caagtcagag gtggcgaaac ccgacaggac tataaagata ccaggcgttt ccccctggaa   1860
gctccctcgt gcgctctcct gttccgaccc tgccgcttac cggatacctg tccgcctttc   1920
tcccttcggg aagcgtggcg ctttctcaat gctcacgctg taggtatctc agttcggtgt   1980
aggtcgttcg ctccaagctg ggctgtgtgc acgaaccccc cgttcagccc gaccgctgcg   2040
ccttatccgg taactatcgt cttgagtcca acccggtaag acacgactta tcgccactgg   2100
cagcagccac tggtaacagg attagcagag cgaggtatgt aggcggtgct acagagttct   2160
tgaagtggtg gcctaactac ggctacacta gaaggacagt atttggtatc tgcgctctgc   2220
tgaagccagt taccttcgga aaaagagttg gtagctcttg atccggcaaa caaaccaccg   2280
ctggtagcgg tggtttttttt gtttgcaagc agcagattac gcgcagaaaa aaggatctc    2340
aagaagatcc tttgatcttt tctacggggt ctgacgctca gtggaacgaa aactcacgtt   2400
aagggatttt ggtcatgaca ttaacctata aaaataggcg tatcacgagg ccctttcgtc   2460
tcgcgcgttt cggtgatgac ggtgaaaacc tctgacacat gcagctcccg gagacggtca   2520
cagcttgtct gtaagcggat gccgggagca gacaagcccg tcaggcgcg tcagcgggtg    2580
ttggcgggtg tcgggctgg cttaactatg cggcatcaga gcagattgta ctgagagtgc    2640
accatatgga catattgtcg ttagaacgcg gctacaatta atacataacc ttatgtatca   2700
tacacatacg atttaggtga cactatagaa cggcgcgcca agctgggtct agaactagaa   2760
acgtgatgcc acttgttatt gaagtcgatt acagcatcta ttctgtttta ctatttataa   2820
cttttgccatt tctgactttt gaaaactatc tctggatttc ggtatcgctt tgtgaagatc   2880
gagcaaaaga gacgttttgt ggacgcaatg gtccaaatcc gttctacatg aacaaattgg   2940
```

```
tcacaatttc cactaaaagt aaataaatgg caagttaaaa aaggaatatg cattttactg    3000
attgcctagg tgagctccaa gagaagttga atctacacgt ctaccaaccg ctaaaaaaag    3060
aaaaacattg aatatgtaac ctgattccat tagcttttga cttcttcaac agattctcta    3120
cttagatttc taacagaaat attattacta gcacatcatt ttcagtctca ctacagcaaa    3180
aaatccaacg gcacaataca gacaacagga gatatcagac tacagagata gatagatgct    3240
actgcatgta gtaagttaaa taaaaggaaa ataaaatgtc ttgctaccaa aactactaca    3300
gactatgatg ctcaccacag gccaaatcct gcaactagga cagcattatc ttatatatat    3360
tgtacaaaac aagcatcaag gaacatttgg tctaggcaat cagtacctcg ttctaccatc    3420
accctcagtt atcacatcct tgaaggatcc attactggga atcatcggca acacatgctc    3480
ctgatggggc acaatgacat caagaaggta ggggccaggg gtgtccaaca ttctctgaat    3540
tgccgctcta agctcttcct tcttcgtcac tcgcgctgcc ggtatccact aagcatcagc    3600
aaacttgagc atgtttggga atatctcgct ctcgctagac ggatctccaa gataggtgtg    3660
agctctattg gacttgtaga acctatcctc caactgaacc accatatccca aatgctgatt    3720 gttcaacaac aatatcttaa ctgggagatt ctccactctt atagtggcca actcctgaac    3780
attcatgatg aaactaccat ccccatcaat gtcaaccaca acagcccag ggttagcaac     3840 agcagcacca atagccgcag gcaatccaaa acccatggct ccaagacccc ctgaggtcaa    3900
ccactgcctc ggtctcttgt acttgtaaaa ctgcgcagcc cacatttgat gctgcccaac    3960
cccagtacta acaatagcat ctccattagt caactcatca agaacctcga tagcatgctg    4020
cggagaaatc gcgtcctgga atgtcttgta acccaatgga aacttgtgtt ctgcacatt    4080 aatctcttct ctccaacctc caagatcaaa cttaccctcc actcctttct cctccaaaat    4140
catattaatt cccttcaagg ccaacttcaa atccgcgcaa accgacacgt gcgcctgctt    4200
gttcttccca atctcggcag aatcaatatc aatgtgaaca atcttagccc tactagcaaa    4260
agcctcaagc ttcccagtaa cacggtcatc aaaccttacc ccaaaggcaa gcaacaaatc    4320
actattgtca acagcatagt tagcataaac agtaccatgc atacccagca tctgaaggga    4380
atattcatca ccaataggaa aagttccaag acccattaaa gtgctagcaa cgggaatacc    4440
agtgagttca acaaagcgcc tcaattcagc actggaattc aaactgccac cgccgacgta    4500
gagaacgggt ttttgggcct ccatgatgag tctgacaatg tgttccaatt gggcctcggc    4560
ggggggcctg gcagcctggc gaggtaacc ggggaggtta acgggctcgt cccaattagg     4620
cacggcgagt gctgctgaa cgtctttggg aatgtcgatg aggaccggac cggggcggcc     4680
ggaggtggcg acgaagaaag cctcggcgac gacgcggggg atgtcgtcga cgtcgaggat    4740
gaggtagttg tgcttcgtga tggatctgct cacctccacg atcggggttt cttggaaggc    4800
gtcggtgccg atcatccggc gggcgacctg gccggtgatg gcgacgactg ggacgctgtc    4860
cattaaagcg tcggcgaggc cgctcacgag gttggtggcg ccggggccgg aggtggcaat    4920
gcagacgccg gggaggccgg aggaacgcgc gtagccttcg gcggcgaaga cgccgccctg    4980
ctcgtggcgc gggagcacgt tgcggatggc ggcggagcgc gtgagcgcct ggtggatctc    5040
catcgacgca ccgccgggt acgcgaacac cgtcgtcacg ccctgcctct ccagcgcctc    5100
cacaaggatg tccgcgccct tgcgaggttc gccggaggcg aaccgtgaca cgaagggctc    5160
cgtggtcggc gcttccttgg tgaagggcgc cgccgtgggg ggtttggaga tggaacattt    5220
gattttgaga gcgtggttgg gtttggtgag ggtttgatga gagagaggga gggtggatct    5280
agtaatgcgt ttggggaagg tggggtgtga agaggaagaa gagaatcggg tggttctgga    5340
```

```
agcggtggcc gccattgtgt tgtgtggcat ggttatactt caaaaactgc acaacaagcc    5400
tagagttagt acctaaacag taaatttaca acagagagca aagacacatg caaaaatttc    5460
agccataaaa aaagttataa tagaatttaa agcaaaagtt tcatttttta aacatatata    5520
caaacaaact ggatttgaag gaagggatta attcccctgc tcaaagtttg aattcctatt    5580
gtgacctata ctcgaataaa attgaagcct aaggaatgta tgagaaacaa gaaaacaaaa    5640
caaaactaca gacaaacaag tacaattaca aaattcgcta aaattctgta atcaccaaac    5700
cccatctcag tcagcacaag gcccaaggtt tattttgaaa taaaaaaaaa gtgattttat    5760
ttctcataag ctaaagaaa gaaaggcaat tatgaaatga tttcgactag atctgaaagt    5820
caaacgcgta ttccgcagat attaaagaaa gagtagagtt tcacatggat cctagatgga    5880
cccagttgag gaaaaagcaa ggcaaagcaa accagaagtg caagatccga aattgaacca    5940
cggaatctag gatttggtag agggagaaga aaagtacctt gagaggtaga agagaagaga    6000
agagcagaga gatatatgaa cgagtgtgtc ttggtctcaa ctctgaagcg atacgagttt    6060
agaggggagc attgagttcc aatttatagg gaaaccgggt ggcagggtg agttaatgac    6120 ggaaaagccc ctaagtaacg agattggatt gtgggttaga ttcaaccgtt tgcatccgcg    6180
gcttagattg gggaagtcag agtgaatctc aaccgttgac tgagttgaaa attgaatgta    6240
gcaaccaatt gagccaaccc cagcctttgc cctttgattt tgatttgttt gttgcatact    6300
ttttatttgt cttctggttc tgactctctt tctctcgttt caatgccagg ttgcctactc    6360
ccacaccact cacaagaaga ttctactgtt agtattaaat atttttaat gtattaaatg    6420 atgaatgctt ttgtaaacag aacaagacta tgtctaataa gtgtcttgca acatttttta    6480
agaaattaaa aaaatatat ttattatcaa aatcaaatgt atgaaaatc atgaataata    6540 taatttata catttttta aaaatctttt taattctta attaatatct taaaataat    6600 gattaatatt taacccaaaa taattagtat gattggtaag gaagatatcc atgttatgtt    6660
tggatgtgag tttgatctag agcaaagctt actagagtcg acctgcagcc cctccaccgc    6720
ggtggcggcc gctctagaga tccgtcaaca tggtggagca cgacactctc gtctactcca    6780
agaatatcaa agatacagtc tcagaagacc aaagggctat tgagactttt caacaaaggg    6840
taatatcggg aaacctcctc ggattccatt gcccagctat ctgtcacttc atcaaaagga    6900
cagtagaaaa ggaaggtggc acctacaaat gccatcattg cgataaagga aaggctatcg    6960
ttcaagatgc ctctgccgac agtggtccca agatggaccc ccacccacg aggagcatcg    7020 tggaaaaaga agacgttcca accacgtctt caaagcaagt ggattgatgt gatgatccta    7080
tgcgtatggt atgacgtgtg ttcaagatga tgacttcaaa cctacctatg acgtatggta    7140
tgacgtgtgt cgactgatga cttagatcca ctcgagcggc tataaatacg tacctacgca    7200
ccctgcgcta ccatccctag agctgcagct tattttaca acaattacca acaacaacaa    7260
acaacaaaca acattacaat tactatttac aattacagtc gacccatcaa caagtttgta    7320
caaaaaagct gaacgagaaa cgtaaaatga tataaatatc aatatattaa attagatttt    7380
gcataaaaaa cagactacat aatactgtaa aacacaacat atccagtcat attggcggcc    7440
gcattaggca ccccaggctt tacactttat gcttccggct cgtataatgt gtggattttg    7500
agttaggatc cgtcgagatt ttcaggagct aaggaagcta aaatggagaa aaaaatcact    7560
ggatatacca ccgttgatat atcccaatgg catcgtaaag aacattttga ggcatttcag    7620
tcagttgctc aatgtaccta taaccagacc gttcagctgg atattacggc ctttttaaag    7680
```

```
accgtaaaga aaataagca caagttttat ccggcccttta ttcacattct tgcccgcctg     7740
atgaatgctc atccggaatt ccgtatggca atgaaagacg gtgagctggt gatatgggat     7800
agtgttcacc cttgttacac cgttttccat gagcaaactg aaacgttttc atcgctctgg    7860
agtgaatacc acgacgattt ccggcagttt ctacacatat attcgcaaga gtgccgtgt    7920
tacggtgaaa acctggccta tttccctaaa gggtttattg agaatatgtt tttcgtctca    7980
gccaatccct gggtgagttt caccagtttt gatttaaacg tggccaatat ggacaacttc    8040
ttcgcccccg tttcaccat ggcaaatat tatacgcaag gcgacaaggt gctgatgccg     8100
ctggcgattc aggttcatca tgccgtttgt gatggcttcc atgtcggcag aatgcttaat    8160
gaattacaac agtactgcga tgagtggcag ggcggggcgt aaagatctgg atccggctta    8220
ctaaaagcca gataacagta tgcgtatttg cgcgctgatt tttgcggtat aagaatatat    8280
actgatatgt atcccgaag tatgtcaaaa agaggtatgc tatgaagcag cgtattacag    8340
tgacagttga cagcgacagc tatcagttgc tcaaggcata tatgatgtca atatctccgg    8400
tctggtaagc acaaccatgc agaatgaagc ccgtcgtctg cgtgccgaac gctggaaagc    8460
ggaaaatcag gaagggatgg ctgaggtcgc ccggtttatt gaaatgaacg gctctttgc    8520
tgacgagaac aggggctggt gaaatgcagt ttaaggttta cctataaa agagagagcc    8580
gttatcgtct gtttgtggat gtacagagtg atattattga cacgcccggg cgacggatgg    8640
tgatccccct ggccagtgca cgtctgctgt cagataaagt ctcccgtgaa ctttacccgg    8700
tggtgcatat cggggatgaa agctggcgca tgatgaccac cgatatggcc agtgtgccgg    8760
tctccgttat cggggaagaa gtggctgatc tcagccaccg cgaaaatgac atcaaaaacg    8820
ccattaacct gatgttctgg ggaatataaa tgtcaggctc ccttatacac agccagtctg    8880
caggtcgacc atagtgactg gatatgttgt gttttacagt attatgtagt ctgtttttta    8940
tgcaaaatct aatttaatat attgatattt atatcatttt acgtttctcg ttcagctttc    9000
ttgtacaaag tggttgataa cctagacttg tccatcttct ggattggcca acttaattaa    9060
tgtatgaaat aaaaggatgc acacatagtg acatgctaat cactataatg tgggcatcaa    9120
agttgtgtgt tatgtgtaat ta                                             9142
```

<210> SEQ ID NO 36
<211> LENGTH: 49911
<212> TYPE: DNA
<213> ORGANISM: Artificial
<220> FEATURE:
<223> OTHER INFORMATION: Destination vector PHP23236

<400> SEQUENCE: 36

```
gtgcagcgtg acccggtcgt gcccctctct agagataatg agcattgcat gtctaagtta      60
taaaaaatta ccacatattt ttttgtcac acttgtttga agtgcagttt atctatcttt     120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg ttttttataga ctaattttt tagtacatct attttattct attttagcct    420
ctaaattaag aaaactaaaa ctctatttta gttttttat ttaataattt agatataaaa    480
tagaataaaa taaagtgact aaaaattaaa caaatacct taagaaatt aaaaaaacta     540
aggaaacatt tttcttgttt cgagtagata atgccagcct gttaaacgcc gtcgacgagt    600
```

```
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcacggca gctacggggg attcctttcc caccgctcct    840
tcgctttccc ttcctcgccc gccgtaataa atagacaccc cctccacacc ctctttcccc    900
aacctcgtgt tgttcggagc gcacacacac acaaccagat ctcccccaaa tccacccgtc    960
ggcacctccg cttcaaggta cgccgctcgt cctccccccc cccccctctc taccttctct   1020
agatcggcgt tccggtccat ggttagggcc cggtagttct acttctgttc atgtttgtgt   1080
tagatccgtg tttgtgttag atccgtgctg ctagcgttcg tacacggatg cgacctgtac   1140
gtcagacacg ttctgattgc taacttgcca gtgtttctct ttggggaatc ctgggatggc   1200
tctagccgtt ccgcagacgg gatcgatttc atgatttttt ttgtttcgtt gcatagggtt   1260
tggtttgccc ttttccttta tttcaatata tgccgtgcac ttgtttgtcg ggtcatcttt   1320
tcatgctttt ttttgtcttg gttgtgatga tgtggtctgg ttgggcggtc gttctagatc   1380
ggagtagaat tctgtttcaa actacctggt ggatttatta attttggatc tgtatgtgtg   1440
tgccatacat attcatagtt acgaattgaa gatgatggat ggaaatatcg atctaggata   1500
ggtatacatg ttgatgcggg ttttactgat gcatatacag agatgctttt tgttcgcttg   1560
gttgtgatga tgtggtgtgg ttgggcggtc gttcattcgt tctagatcgg agtagaatac   1620
tgtttcaaac tacctggtgt atttattaat tttggaactg tatgtgtgtg tcatacatct   1680
tcatagttac gagtttaaga tggatggaaa tatcgatcta ggataggtat acatgttgat   1740
gtgggtttta ctgatgcata tacatgatgg catatgcagc atctattcat atgctctaac   1800
cttgagtacc tatctattat aataaacaag tatgttttat aattattttg atcttgatat   1860
acttggatga tggcatatgc agcagctata tgtggatttt tttagccctg ccttcatacg   1920
ctatttattt gcttggtact gtttcttttg tcgatgctca ccctgttgtt tggtgttact   1980
tctgcaggtc gactctagag gatccacaag tttgtacaaa aaagctgaac gagaaacgta   2040
aaatgatata aatatcaata tattaaatta gattttgcat aaaaaacaga ctacataata   2100
ctgtaaaaca caacatatcc agtcactatg gcggccgcat taggcacccc aggctttaca   2160
ctttatgctt ccggctcgta taatgtgtgg attttgagtt aggatttaaa tacgcgttga   2220
tccggcttac taaaagccag ataacagtat gcgtatttgc gcgctgattt ttgcggtata   2280
agaatatata ctgatatgta tacccgaagt atgtcaaaaa gaggtatgct atgaagcagc   2340
gtattacagt gacagttgac agcgacagct atcagttgct caaggcatat atgatgtcaa   2400
tatctccggt ctggtaagca caaccatgca gaatgaagcc cgtcgtctgc gtgccgaacg   2460
ctggaaagcg gaaaatcagg aagggatggc tgaggtcgcc cggtttattg aaatgaacgg   2520
ctcttttgct gacgagaaca ggggctggtg aaatgcagtt taaggtttac acctataaaa   2580
gagagagccg ttatcgtctg tttgtggatg tacagagtga tatcattgac acgcccggtc   2640
gacggatggt gatcccccctg gccagtgcac gtctgctgtc agataaagtc tcccgtgaac   2700
tttacccggt ggtgcatatc ggggatgaaa gctggcgcat gatgaccacc gatatggcca   2760
gtgtgccggt ctccgttatc ggggaagaag tggctgatct cagccaccgc gaaaatgaca   2820
tcaaaaacgc cattaacctg atgttctggg aatataaat gtcaggctcc cttatacaca   2880
gccagtctgc aggtcgacca tagtgactgg atatgttgtg ttttacagta ttatgtagtc   2940
```

```
tgtttttat   gcaaaatcta   atttaatata   ttgatattta   tatcatttta   cgtttctcgt   3000
tcagctttct   tgtacaaagt   ggtgttaacc   tagacttgtc   catcttctgg   attggccaac   3060
ttaattaatg   tatgaaataa   aaggatgcac   acatagtgac   atgctaatca   ctataatgtg   3120
ggcatcaaag   ttgtgtgtta   tgtgtaatta   ctagttatct   gaataaaaga   gaaagagatc   3180
atccatattt   cttatcctaa   atgaatgtca   cgtgtcttta   taattctttg   atgaaccaga   3240
tgcatttcat   taaccaaatc   catatacata   taaatattaa   tcatatataa   ttaatatcaa   3300
ttgggttagc   aaaacaaatc   tagtctaggt   gtgttttgcg   aattgcggcc   gccaccgcgg   3360
tggagctcga   attccggtcc   gggtcacctt   tgtccaccaa   gatggaactg   cggccgctca   3420
ttaattaagt   caggcgcgcc   tctagttgaa   gacacgttca   tgtcttcatc   gtaagaagac   3480
actcagtagt   cttcggccag   aatggccatc   tggattcagc   aggcctagaa   ggccatttaa   3540
atcctgagga   tctggtcttc   ctaaggaccc   gggatatcgg   accgattaaa   ctttaattcg   3600
gtccgaagct   tgcatgcctg   cagtgcagcg   tgacccggtc   gtgcccctct   ctagagataa   3660
tgagcattgc   atgtctaagt   tataaaaaat   taccacatat   ttttttttgtc   acacttgttt   3720 gaagtgcagt   ttatctatct   ttatacatat   atttaaactt   tactctacga   ataatataat   3780
ctatagtact   acaataatat   cagtgtttta   gagaatcata   taaatgaaca   gttagacatg   3840
gtctaaagga   caattgagta   ttttgacaac   aggactctac   agttttatct   ttttagtgtg   3900
catgtgttct   ccttttttttt   tgcaaatagc   ttcacctata   taatacttca   tccattttat   3960
tagtacatcc   atttagggtt   tagggttaat   ggttttata   gactaattt   tttagtacat   4020 ctattttatt   ctattttagc   ctctaaatta   agaaaactaa   aactctattt   tagttttttt   4080
atttaataat   ttagatataa   aatagaataa   aataaagtga   ctaaaaatta   aacaaatacc   4140
ctttaagaaa   ttaaaaaaac   taaggaaaca   ttttcttgt   ttcgagtaga   taatgccagc   4200
ctgttaaacg   ccgtcgacga   gtctaacgga   caccaaccag   cgaaccagca   gcgtcgcgtc   4260
gggccaagcg   aagcagacgg   cacggcatct   ctgtcgctgc   ctctggaccc   ctctcgagag   4320
ttccgctcca   ccgttggact   tgctccgctg   tcggcatcca   gaaattgcgt   ggcggagcgg   4380
cagacgtgag   ccggcacggc   aggcggcctc   ctcctcctct   cacggcaccg   gcagctacgg   4440
gggattcctt   tcccaccgct   ccttcgcttt   ccttcctcg   cccgccgtaa   taaatagaca   4500 cccctccac   accctctttc   cccaacctcg   tgttgttcgg   agcgcacaca   cacacaacca   4560
gatctccccc   aaatccaccc   gtcggcacct   ccgcttcaag   gtacgccgct   cgtcctcccc   4620 ccccccctc   tctaccttct   ctagatcggc   gttccggtcc   atgcatggtt   agggcccggt   4680
agttctactt   ctgttcatgt   ttgtgttaga   tccgtgtttg   tgttagatcc   gtgctgctag   4740
cgttcgtaca   cggatgcgac   ctgtacgtca   gacacgttct   gattgctaac   ttgccagtgt   4800
ttctctttgg   ggaatcctgg   gatggctcta   gccgttccgc   agacgggatc   gatttcatga   4860
ttttttttgt   ttcgttgcat   agggtttggt   ttgccctttt   cctttatttc   aatatatgcc   4920
gtgcacttgt   ttgtcgggtc   atcttttcat   gcttttttttt   gtcttggttg   tgatgatgtg   4980
gtctggttgg   gcggtcgttc   tagatcggag   tagaattctg   tttcaaacta   cctggtggat   5040
ttattaattt   tggatctgta   tgtgtgtgcc   atacatattc   atagttacga   attgaagatg   5100
atggatggaa   atatcgatct   aggataggta   tacatgttga   tgcgggtttt   actgatgcat   5160
atacagagat   gcttttttgtt   cgcttggttg   tgatgatgtg   gtgtggttgg   gcggtcgttc   5220
attcgttcta   gatcggagta   gaatactgtt   tcaaactacc   tggtgtattt   attaattttg   5280
gaactgtatg   tgtgtgtcat   acatcttcat   agttacgagt   ttaagatgga   tggaaatatc   5340
```

```
gatctaggat aggtatacat gttgatgtgg gttttactga tgcatataca tgatggcata      5400
tgcagcatct attcatatgc tctaaccttg agtacctatc tattataata aacaagtatg      5460
ttttataatt attttgatct tgatatactt ggatgatggc atatgcagca gctatatgtg      5520
gattttttta gccctgcctt catacgctat ttatttgctt ggtactgttt cttttgtcga      5580
tgctcaccct gttgtttggt gttacttctg caggtcgact ttaacttagc ctaggatcca      5640
cacgacacca tgtcccccga gcgccgcccc gtcgagatcc gcccggccac cgccgccgac      5700
atggccgccg tgtgcgacat cgtgaaccac tacatcgaga cctccaccgt gaacttccgc      5760
accgagccgc agaccccgca ggagtggatc gacgacctgg agcgcctcca ggaccgctac      5820
ccgtggctcg tggccgaggt ggagggcgtg gtggccggca tcgcctacgc cggcccgtgg      5880
aaggcccgca acgcctacga ctggaccgtg gagtccaccg tgtacgtgtc ccaccgccac      5940
cagcgcctcg gcctcggctc caccctctac acccacctcc tcaagagcat ggaggcccag      6000
ggcttcaagt ccgtggtggc cgtgatcggc ctcccgaacg acccgtccgt gcgcctccac      6060
gaggccctcg gctacaccgc ccgcggcacc ctccgcgccg ccggctacaa gcacggcggc      6120
tggcacgacg tcggcttctg gcagcgcgac ttcgagctgc cggccccgcc gcgcccggtg      6180
cgcccggtga cgcagatctg agtcgaaacc tagacttgtc catcttctgg attggccaac      6240
ttaattaatg tatgaaataa aaggatgcac acatagtgac atgctaatca ctataatgtg      6300
ggcatcaaag ttgtgtgtta tgtgtaatta ctagttatct gaataaaaga gaaagagatc      6360
atccatattt cttatcctaa atgaatgtca cgtgtcttta taattctttg atgaaccaga      6420
tgcatttcat taaccaaatc catatacata taaatattaa tcatatataa ttaatatcaa      6480
ttgggttagc aaaacaaatc tagtctaggt gtgttttgcg aattgcggcc gccaccgcgg      6540
tggagctcga attcattccg attaatcgtg gcctcttgct cttcaggatg aagagctatg      6600
tttaaacgtg caagcgctac tagacaattc agtacattaa aaacgtccgc aatgtgttat      6660
taagttgtct aagcgtcaat ttggtttaca ccacaatata tcctgccacc agccagccaa      6720
cagctccccg accggcagct cggcacaaaa tcaccactcg atacaggcag cccatcagtc      6780
cgggacggcg tcagcgggag agccgttgta aggcggcaga ctttgctcat gttaccgatg      6840
ctattcggaa gaacggcaac taagctgccg ggtttgaaac acggatgatc tcgcggaggg      6900
tagcatgttg attgtaacga tgacagagcg ttgctgcctg tgatcaaata tcatctcct       6960 cgcagagatc cgaattatca gccttcttat tcatttctcg cttaaccgtg acaggctgtc      7020
gatcttgaga actatgccga cataatagga aatcgctgga taaagccgct gaggaagctg      7080
agtggcgcta tttctttaga agtgaacgtt gacgatcgtc gaccgtaccc cgatgaatta      7140
attcggacgt acgttctgaa cacagctgga tacttacttg ggcgattgtc atacatgaca      7200
tcaacaatgt acccgtttgt gtaaccgtct cttggaggtt cgtatgacac tagtggttcc      7260
cctcagcttg cgactagatg ttgaggccta acatttatt agagagcagg ctagttgctt       7320
agatacatga tcttcaggcc gttatctgtc agggcaagcg aaaattggcc atttatgacg      7380
accaatgccc cgcagaagct cccatctttg ccgccataga cgccgcgccc ccttttggg       7440 gtgtagaaca tccttttgcc agatgtggaa aagaagttcg ttgtcccatt gttggcaatg      7500
acgtagtagc cggcgaaagt gcgagaccca tttgcgctat atataagcct acgatttccg      7560
ttgcgactat tgtcgtaatt ggatgaacta ttatcgtagt tgctctcaga gttgtcgtaa      7620
tttgatggac tattgtcgta attgcttatg gagttgtcgt agttgcttgg agaaatgtcg      7680
```

```
tagttggatg gggagtagtc atagggaaga cgagcttcat ccactaaaac aattggcagg    7740
tcagcaagtg cctgccccga tgccatcgca agtacgaggc ttagaaccac cttcaacaga    7800
tcgcgcatag tcttccccag ctctctaacg cttgagttaa gccgcgccgc gaagcggcgt    7860
cggcttgaac gaattgttag acattatttg ccgactacct tggtgatctc gcctttcacg    7920
tagtgaacaa attcttccaa ctgatctgcg cgcgaggcca agcgatcttc ttgtccaaga    7980
taagcctgcc tagcttcaag tatgacgggc tgatactggg ccggcaggcg ctccattgcc    8040
cagtcggcag cgacatcctt cggcgcgatt ttgccggtta ctgcgctgta ccaaatgcgg    8100
gacaacgtaa gcactacatt tcgctcatcg ccagcccagt cgggcggcga gttccatagc    8160
gttaaggttt catttagcgc ctcaaataga tcctgttcag gaaccggatc aaagagttcc    8220
tccgccgctg gacctaccaa ggcaacgcta tgttctcttg cttttgtcag caagatagcc    8280
agatcaatgt cgatcgtggc tggctcgaag atacctgcaa gaatgtcatt gcgctgccat    8340
tctccaaatt gcagttcgcg cttagctgga taacgccacg gaatgatgtc gtcgtgcaca    8400
acaatggtga cttctacagc gcggagaatc tcgctctctc caggggaagc cgaagtttcc    8460
aaaaggtcgt tgatcaaagc tcgccgcgtt gtttcatcaa gccttacagt caccgtaacc    8520
agcaaatcaa tatcactgtg tggcttcagg ccgcccatcc atgcggagcc gtacaaatgt    8580
acggccagca acgtcggttc gagatggcgc tcgatgacgc caactacctc tgatagttga    8640
gtcgatactt cggcgatcac cgcttccctc atgatgttta actcctgaat taagccgcgc    8700
cgcgaagcgg tgtcggcttg aatgaattgt taggcgtcat cctgtgctcc cgagaaccag    8760
taccagtaca tcgctgtttc gttcgagact tgaggtctag ttttatacgt gaacaggtca    8820
atgccgccga gagtaaagcc acattttgcg tacaaattgc aggcaggtac attgttcgtt    8880
tgtgtctcta atcgtatgcc aaggagctgt ctgcttagtg cccactttt cgcaaattcg    8940
atgagactgt gcgcgactcc tttgcctcgg tgcgtgtgcg acacaacaat gtgttcgata    9000
gaggctagat cgttccatgt tgagttgagt tcaatcttcc cgacaagctc ttggtcgatg    9060
aatgcgccat agcaagcaga gtcttcatca gagtcatcat ccgagatgta atccttccgg    9120
taggggctca cacttctggt agatagttca aagccttggt cggataggtg cacatcgaac    9180
acttcacgaa caatgaaatg gttctcagca tccaatgttt ccgccacctg ctcagggatc    9240
accgaaatct tcatatgacg cctaacgcct ggcacagcgg atcgcaaacc tggcgcggct    9300
tttggcacaa aaggcgtgac aggtttgcga atccgttgct gccacttgtt aaccctttg    9360
ccagatttgg taactataat ttatgttaga ggcgaagtct tgggtaaaaa ctggcctaaa    9420
attgctgggg atttcaggaa agtaaacatc accttccggc tcgatgtcta ttgtagatat    9480
atgtagtgta tctacttgat cgggggatct gctgcctcgc gcgtttcggt gatgacggtg    9540
aaaacctctg acacatgcag ctcccggaga cggtcacagc ttgtctgtaa gcggatgccg    9600
ggagcagaca agcccgtcag ggcgcgtcag cgggtgttgg cgggtgtcgg ggcgcagcca    9660
tgacccagtc acgtagcgat agcggagtgt atactggctt aactatgcgg catcagagca    9720
gattgtactg agagtgcacc atatgcggtg tgaaataccg cacagatgcg taaggagaaa    9780
ataccgcatc aggcgctctt ccgcttcctc gctcactgac tcgctgcgct cggtcgttcg    9840
gctgcggcga gcggtatcag ctcactcaaa ggcggtaata cggttatcca cagaatcagg    9900
ggataacgca ggaaagaaca tgtgagcaaa aggccagcaa aaggccagga accgtaaaaa    9960
ggccgcgttg ctggcgtttt tccataggct ccgcccccct gacgagcatc acaaaaatcg   10020
acgctcaagt cagaggtggc gaaacccgac aggactataa agataccagg cgtttccccc   10080
```

```
tggaagctcc ctcgtgcgct ctcctgttcc gaccctgccg cttaccggat acctgtccgc   10140
ctttctccct tcgggaagcg tggcgctttc tcatagctca cgctgtaggt atctcagttc   10200
ggtgtaggtc gttcgctcca agctgggctg tgtgcacgaa ccccccgttc agcccgaccg   10260
ctgcgcctta tccggtaact atcgtcttga gtccaacccg gtaagacacg acttatcgcc   10320
actggcagca gccactggta acaggattag cagagcgagg tatgtaggcg gtgctacaga   10380
gttcttgaag tggtggccta actacggcta cactagaagg acagtatttg gtatctgcgc   10440
tctgctgaag ccagttacct tcggaaaaag agttggtagc tcttgatccg gcaaacaaac   10500
caccgctggt agcggtggtt tttttgtttg caagcagcag attacgcgca gaaaaaaagg   10560
atctcaagaa gatcctttga tcttttctac ggggtctgac gctcagtgga acgaaaactc   10620
acgttaaggg attttggtca tgagattatc aaaaaggatc ttcacctaga tccttttaaa   10680
ttaaaaatga agttttaaat caatctaaag tatatatgag taaacttggt ctgacagtta   10740
ccaatgctta atcagtgagg cacctatctc agcgatctgt ctatttcgtt catccatagt   10800
tgcctgactc cccgtcgtgt agataactac gatacgggag ggcttaccat ctggccccag   10860
tgctgcaatg ataccgcgag acccacgctc accggctcca gatttatcag caataaacca   10920
gccagccgga agggccgagc gcagaagtgg tcctgcaact ttatccgcct ccatccagtc   10980
tattaattgt tgccgggaag ctagagtaag tagttcgcca gttaatagtt tgcgcaacgt   11040
tgttgccatt gctgcagggg ggggggggg ggggacttc cattgttcat tccacggaca   11100
aaaacagaga aaggaaacga cagaggccaa aaagcctcgc tttcagcacc tgtcgtttcc   11160
tttcttttca gagggtattt taaataaaaa cattaagtta tgacgaagaa gaacggaaac   11220
gccttaaacc ggaaaatttt cataaatagc gaaaacccgc gaggtcgccg cccgtaacc   11280 tacctgtcgg atcaccggaa aggacccgta aagtgataat gattatcatc tacatatcac   11340
aacgtgcgtg gaggccatca aaccacgtca ataatcaat tatgacgcag gtatcgtatt   11400
aattgatctg catcaactta acgtaaaaac aacttcagac aatacaaatc agcgacactg   11460 aatacgggc aacctcatgt ccccccccc ccccccctg caggcatcgt ggtgtcacgc   11520
tcgtcgtttg gtatggcttc attcagctcc ggttcccaac gatcaaggcg agttacatga   11580 tccccatgt tgtgcaaaaa agcggttagc tccttcggtc ctccgatcgt tgtcagaagt   11640
aagttggccg cagtgttatc actcatggtt atggcagcac tgcataattc tcttactgtc   11700
atgccatccg taagatgctt ttctgtgact ggtgagtact caaccaagtc attctgagaa   11760
tagtgtatgc ggcgaccgag ttgctcttgc ccggcgtcaa cacgggataa taccgcgcca   11820
catagcagaa ctttaaaagt gctcatcatt ggaaaacgtt cttcggggcg aaaactctca   11880
aggatcttac cgctgttgag atccagttcg atgtaaccca ctcgtgcacc caactgatct   11940
tcagcatctt ttactttcac cagcgtttct gggtgagcaa aaacaggaag gcaaaatgcc   12000
gcaaaaaagg aataagggc gacacggaaa tgttgaatac tcatactctt ccttttcaa   12060 tattattgaa gcatttatca gggttattgt ctcatgagcg gatacatatt tgaatgtatt   12120
tagaaaaata aacaaatagg ggttccgcgc acatttcccc gaaaagtgcc acctgacgtc   12180
taagaaacca ttattatcat gacattaacc tataaaaata ggcgtatcac gaggcccttt   12240
cgtcttcaag aattcggagc ttttgccatt ctcaccggat tcagtcgtca ctcatggtga   12300
tttctcactt gataacctta ttttttgacga ggggaaatta ataggttgta ttgatgttgg   12360
acgagtcgga atcgcagacc gataccagga tcttgccatc ctatggaact gcctcggtga   12420
```

```
gttttctcct tcattacaga aacggctttt tcaaaaatat ggtattgata atcctgatat   12480
gaataaattg cagtttcatt tgatgctcga tgagtttttc taatcagaat tggttaattg   12540
gttgtaacac tggcagagca ttacgctgac ttgacgggac ggcggctttg ttgaataaat   12600
cgaacttttg ctgagttgaa ggatcagatc acgcatcttc ccgacaacgc agaccgttcc   12660
gtggcaaagc aaaagttcaa aatcaccaac tggtccacct acaacaaagc tctcatcaac   12720
cgtggctccc tcactttctg gctggatgat ggggcgattc aggcctggta tgagtcagca   12780
acaccttctt cacgaggcag acctcagcgc cagaaggccg ccagagaggc cgagcgcggc   12840
cgtgaggctt ggacgctagg gcagggcatg aaaaagcccg tagcgggctg ctacgggcgt   12900
ctgacgcggt ggaaaggggg aggggatgtt gtctacatgg ctctgctgta gtgagtgggt   12960
tgcgctccgg cagcggtcct gatcaatcgt caccctttct cggtccttca acgttcctga   13020
caacgagcct ccttttcgcc aatccatcga caatcaccgc gagtccctgc tcgaacgctg   13080
cgtccggacc ggcttcgtcg aaggcgtcta tcgcggcccg caacagcggc gagagcggag   13140
cctgttcaac ggtgccgccg cgctcgccgg catcgctgtc gccggcctgc tcctcaagca   13200
cggccccaac agtgaagtag ctgattgtca tcagcgcatt gacggcgtcc ccggccgaaa   13260
aacccgcctc gcagaggaag cgaagctgcg cgtcggccgt ttccatctgc ggtgcgcccg   13320
gtcgcgtgcc ggcatggatg cgcgcgccat cgcggtaggc gagcagcgcc tgcctgaagc   13380
tgcgggcatt cccgatcaga atgagcgcc agtcgtcgtc ggctctcggc accgaatgcg   13440
tatgattctc cgccagcatg gcttcggcca gtgcgtcgag cagcgcccgc ttgttcctga   13500
agtgccagta aagcgccggc tgctgaaccc ccaaccgttc cgccagtttg cgtgtcgtca   13560
gaccgtctac gccgacctcg ttcaacaggt ccagggcggc acggatcact gtattcggct   13620
gcaactttgt catgcttgac actttatcac tgataaacat aatatgtcca ccaacttatc   13680
agtgataaag aatccgcgcg ttcaatcgga ccagcggagg ctggtccgga ggccagacgt   13740
gaaacccaac atacccctga tcgtaattct gagcactgtc gcgctcgacg ctgtcggcat   13800
cggcctgatt atgccggtgc tgccgggcct cctgcgcgat ctggttcact cgaacgacgt   13860
caccgcccac tatggcattc tgctggcgct gtatgcgttg gtgcaatttg cctgcgcacc   13920
tgtgctgggc gcgctgtcgg atcgtttcgg gcggcggcca atcttgctcg tctcgctggc   13980
cggcgccact gtcgactacg ccatcatggc gacagcgcct ttcctttggg ttctctatat   14040
cgggcggatc gtggccggca tcaccggggc gactggggcg gtagccggcg cttatattgc   14100
cgatatcact gatggcgatg agcgcgcgcg gcacttcggc ttcatgagcg cctgtttcgg   14160
gttcgggatg gtcgcgggac ctgtgctcgg tgggctgatg ggcggtttct cccccacgc   14220 tccgttcttc gccgcggcag ccttgaacgg cctcaatttc ctgacgggct gtttcctttt   14280
gccggagtcg cacaaaggcg aacgccggcc gttacgccgg gaggctctca cccgctcgc   14340 ttcgttccgg tgggcccggg gcatgaccgt cgtcgccgcc ctgatggcgg tcttcttcat   14400
catgcaactt gtcggacagg tgccggccgc gctttgggtc attttcggcg aggatcgctt   14460
tcactgggac gcgaccacga tcggcatttc gcttgccgca tttggcattc tgcattcact   14520
cgcccaggca atgatcaccg gcctgtagc cgcccggctc ggcgaaaggc gggcactcat   14580
gctcggaatg attgccgacg gcacaggcta catcctgctt gccttcgcga cacggggatg   14640
gatggcgttc ccgatcatgg tcctgcttgc ttcgggtggc atcggaatgc cggcgctgca   14700
agcaatgttg tccaggcagg tggatgagga acgtcagggg cagctgcaag gctcactggc   14760
ggcgctcacc agcctgacct cgatcgtcgg acccctcctc ttcacggcga tctatgcggc   14820
```

```
ttctataaca acgtggaacg ggtgggcatg gattgcaggc gctgccctct acttgctctg    14880
cctgccggcg ctgcgtcgcg ggctttggag cggcgcaggg caacgagccg atcgctgatc    14940
gtggaaacga taggcctatg ccatgcgggt caaggcgact tccggcaagc tatacgcgcc    15000
ctaggagtgc ggttggaacg ttggcccagc cagatactcc cgatcacgag caggacgccg    15060
atgatttgaa gcgcactcag cgtctgatcc aagaacaacc atcctagcaa cacggcggtc    15120
cccgggctga gaaagcccag taaggaaaca actgtaggtt cgagtcgcga gatccccgg    15180 aaccaaagga agtaggttaa acccgctccg atcaggccga ccacgccag gccgagaaca    15240 ttggttcctg taggcatcgg gattggcgga tcaaacacta aagctactgg aacgagcaga    15300
agtcctccgg ccgccagttg ccaggcggta aaggtgagca gaggcacggg aggttgccac    15360
ttgcgggtca gcacggttcc gaacgccatg gaaaccgccc ccgccaggcc cgctgcgacg    15420
ccgacaggat ctagcgctgc gtttggtgtc aacaccaaca gcgccacgcc cgcagttccg    15480
caaatagccc ccaggaccgc catcaatcgt atcgggctac ctagcagagc ggcagagatg    15540
aacacgacca tcagcggctg cacagcgcct accgtcgccg cgaccccgcc cggcaggcgg    15600
tagaccgaaa taacaacaa gctccagaat agcgaaatat taagtgcgcc gaggatgaag    15660
atgcgcatcc accagattcc cgttggaatc tgtcggacga tcatcacgag caataaaccc    15720
gccggcaacg cccgcagcag cataccggcg acccctcggc ctcgctgttc gggctccacg    15780
aaaacgccgg acagatgcgc cttgtgagcg tccttggggc cgtcctcctg tttgaagacc    15840
gacagcccaa tgatctcgcc gtcgatgtag gcgccgaatg ccacggcatc tcgcaaccgt    15900
tcagcgaacg cctccatggg cttttttctcc tcgtgctcgt aaacggaccc gaacatctct    15960
ggagctttct tcagggccga caatcggatc tcgcggaaat cctgcacgtc ggccgctcca    16020
agccgtcgaa tctgagcctt aatcacaatt gtcaattta atcctctgtt tatcggcagt    16080
tcgtagagcg cgccgtgcgt cccgagcgat actgagcgaa gcaagtgcgt cgagcagtgc    16140
ccgcttgttc ctgaaatgcc agtaaagcgc tggctgctga accccagcc ggaactgacc    16200 ccacaaggcc ctagcgtttg caatgcacca ggtcatcatt gacccaggcg tgttccacca    16260
ggccgctgcc tcgcaactct tcgcaggctt cgccgacctg ctcgcgccac ttcttcacgc    16320
gggtggaatc cgatccgcac atgaggcgga aggtttccag cttgagcggg tacggctccc    16380
ggtgcgagct gaaatagtcg aacatccgtc gggccgtcgg cgacagcttg cggtacttct    16440
cccatatgaa tttcgtgtag tggtcgccag caaacagcac gacgatttcc tcgtcgatca    16500
ggacctggca acgggacgtt ttcttgccac ggtccaggac gcggaagcgg tgcagcagcg    16560
acaccgattc caggtgccca acgcggtcgg acgtgaagcc catcgccgtc gcctgtaggc    16620
gcgacaggca ttcctcggcc ttcgtgtaat accggccatt gatcgaccag cccaggtcct    16680
ggcaaagctc gtagaacgtg aaggtgatcg gctcgccgat aggggtgcgc ttcgcgtact    16740
ccaacacctg ctgccacacc agttcgtcat cgtcggcccg cagctcgacg ccggtgtagg    16800
tgatcttcac gtccttgttg acgtggaaaa tgaccttgtt ttgcagcgcc tcgcgcggga    16860
ttttcttgtt gcgcgtggtg aacagggcag agcgggccgt gtcgtttggc atcgctcgca    16920
tcgtgtccgg ccacggcgca atatcgaaca aggaaagctg catttccttg atctgctgct    16980
tcgtgtgttt cagcaacgcg gcctgcttgg cctcgctgac ctgttttgcc aggtcctcgc    17040
cggcggtttt tcgcttcttg gtcgtcatag ttcctcgcgt gtcgatggtc atcgacttcg    17100
ccaaacctgc cgcctcctgt tcgagacgac gcgaacgctc cacggcggcc gatggcgcgg    17160
```

```
gcagggcagg gggagccagt tgcacgctgt cgcgctcgat cttggccgta gcttgctgga   17220
ccatcgagcc gacggactgg aaggtttcgc ggggcgcacg catgacggtg cggcttgcga   17280
tggtttcggc atcctcggcg gaaaacccCg cgtcgatcag ttcttgcctg tatgccttcc   17340
ggtcaaacgt ccgattcatt caccctcctt gcgggattgc cccgactcac gccggggcaa   17400
tgtgccctta ttcctgattt gacccgcctg gtgccttggt gtccagataa tccaccttat   17460
cggcaatgaa gtcggtcccg tagaccgtct ggccgtcctt ctcgtacttg gtattccgaa   17520
tcttgccctg cacgaatacc agcgacccct tgcccaaata cttgccgtgg gcctcggcct   17580
gagagccaaa acacttgatg cggaagaagt cggtgcgctc ctgcttgtcg ccggcatcgt   17640
tgcgccactc ttcattaacc gctatatcga aaattgcttg cggcttgtta gaattgccat   17700
gacgtacctc ggtgtcacgg gtaagattac cgataaactg gaactgatta tggctcatat   17760
cgaaagtctc cttgagaaag gagactctag tttagctaaa cattggttcc gctgtcaaga   17820
actttagcgg ctaaaatttt gcgggccgcg accaaaggtg cgaggggcgg cttccgctgt   17880
gtacaaccag atattttTca ccaacatcct tcgtctgctc gatgagcggg gcatgacgaa   17940
acatgagctg tcggagaggg caggggtttc aatttcgttt ttatcagact taaccaacgg   18000
taaggccaac ccctcgttga aggtgatgga ggccattgcc gacgccctgg aaactcccct   18060
acctcttctc ctggagtcca ccgaccttga ccgcgaggca ctcgcggaga ttgcgggtca   18120
tcctttcaag agcagcgtgc cgcccggata cgaacgcatc agtgtggttt tgccgtcaca   18180
taaggcgttt atcgtaaaga aatggggcga cgacacccga aaaaagctgc gtggaaggct   18240
ctgacgccaa gggttagggc ttgcacttcc ttctttagcc gctaaaacgg ccccttctct   18300
gcgggccgtc ggctcgcgca tcatatcgac atcctcaacg gaagccgtgc cgcgaatggc   18360
atcgggcggg tgcgctttga cagttgtttt ctatcagaac ccctacgtcg tgcggttcga   18420
ttagctgttt gtcttgcagg ctaaacactt tcggtatatc gtttgcctgt gcgataatgt   18480
tgctaatgat ttgttgcgta ggggttactg aaaagtgagc gggaagaag agtttcagac    18540 catcaaggag cgggccaagc gcaagctgga acgcgacatg ggtgcggacc tgttggccgc   18600
gctcaacgac ccgaaaaccg ttgaagtcat gctcaacgcg gacggcaagg tgtggcacga   18660
acgccttggc gagccgatgc ggtacatctg cgacatgcgg cccagccagt cgcaggcgat   18720
tatagaaacg gtgccggat tccacggcaa agaggtcacg cggcattcgc ccatcctgga    18780
aggcgagttc cccttggatg gcagccgctt tgccggccaa ttgccgccgg tcgtggccgc   18840
gccaaccttt gcgatccgca agcgcgcggt cgccatcttc acgctggaac agtacgtcga   18900
ggcgggcatc atgacccgcg agcaatacga ggtcattaaa agcgccgtcg cggcgcatcg   18960
aaacatcctc gtcattggcg gtactggctc gggcaagacc acgctcgtca acgcgatcat   19020
caatgaaatg gtcgccttca acccgtctga gcgcgtcgtc atcatcgagg acaccggcga   19080
aatccagtgc gccgcagaga acgccgtcca ataccacacc agcatcgacg tctcgatgac   19140
gctgctgctc aagacaacgc tgcgtatgcg ccccgaccgc atcctggtcg gtgaggtacg   19200
tggccccgaa gcccttgatc tgttgatggc ctggaacacc gggcatgaag gaggtgccgc   19260
caccctgcac gcaaacaacc ccaaagcggg cctgagccgg ctcgccatgc ttatcagcat   19320
gcacccggat tcaccgaaac ccattgagcc gctgattggc gaggcggttc atgtggtcgt   19380
ccatatcgcc aggaccccta gcggccgtcg agtgcaagaa attctcgaag ttcttggtta   19440
cgagaacggc cagtacatca ccaaaaccct gtaaggagta tttccaatga caacggctgt   19500
tccgttccgt ctgaccatga atcgcggcat tttgttctac cttgccgtgt tcttcgttct   19560
```

```
cgctctcgcg ttatccgcgc atccggcgat ggcctcggaa ggcaccggcg gcagcttgcc   19620
atatgagagc tggctgacga acctgcgcaa ctccgtaacc ggcccggtgg ccttcgcgct   19680
gtccatcatc ggcatcgtcg tcgccggcgg cgtgctgatc ttcggcggcg aactcaacgc   19740
cttcttccga accctgatct tcctggttct ggtgatggcg ctgctggtcg gcgcgcagaa   19800
cgtgatgagc accttcttcg gtcgtggtgc cgaaatcgcg gccctcggca cggggcgct   19860 gcaccaggtg caagtcgcgg cggcggatgc cgtgcgtgcg gtagcggctg gacggctcgc   19920
ctaatcatgg ctctgcgcac gatccccatc cgtcgcgcag gcaaccgaga aaacctgttc   19980
atgggtggta atcgtgaact ggtgatgttc tcgggcctga tggcgtttgc gctgattttc   20040
agcgcccaag agctgcgggc accgtggtc ggtctgatcc tgtggttcgg ggcgctctat   20100
gcgttccgaa tcatggcgaa ggccgatccg aagatgcggt tcgtgtacct gcgtcaccgc   20160
cggtacaagc cgtattaccc ggcccgctcg accccgttcc gcgagaacac caatagccaa   20220
gggaagcaat accgatgatc caagcaattg cgattgcaat cgcgggcctc ggcgcgcttc   20280
tgttgttcat cctctttgcc cgcatccgcg cggtcgatgc cgaactgaaa ctgaaaaagc   20340
atcgttccaa ggacgccggc ctggccgatc tgctcaacta cgccgctgtc gtcgatgacg   20400
gcgtaatcgt gggcaagaac ggcagcttta tggctgcctg gctgtacaag ggcgatgaca   20460
acgcaagcag caccgaccag cagcgcgaag tagtgtccgc ccgcatcaac caggccctcg   20520
cgggcctggg aagtgggtgg atgatccatg tggacgccgt gcggcgtcct gctccgaact   20580
acgcggagcg gggcctgtcg gcgttccctg accgtctgac ggcagcgatt gaagaagagc   20640
gctcggtctt gccttgctcg tcggtgatgt acttcaccag ctccgcgaag tcgctcttct   20700
tgatggagcg catggggacg tgcttggcaa tcacgcgcac cccccggccg ttttagcggc   20760
taaaaaagtc atggctctgc cctcgggcgg accacgccca tcatgacctt gccaagctcg   20820
tcctgcttct cttcgatctt cgccagcagg gcgaggatcg tggcatcacc gaaccgcgcc   20880
gtgcgcgggt cgtcggtgag ccagagtttc agcaggccgc ccaggcggcc caggtcgcca   20940
ttgatgcggg ccagctcgcg gacgtgctca tagtccacga cgcccgtgat tttttagccc   21000
tggccgacgg ccagcaggta ggccgacagg ctcatgccgg ccgccgccgc ctttttcctca  21060 atcgctcttc gttcgtctgg aaggcagtac accttgatag gtgggctgcc cttcctggtt   21120
ggcttggttt catcagccat ccgcttgccc tcatctgtta cgccggcggt agccggccag   21180
cctcgcagag caggattccc gttgagcacc gccaggtgcg aataagggac agtgaagaag   21240 gaacaccgc tcgcgggtgg gcctacttca cctatcctgc ccggctgacg ccgttggata   21300
caccaaggaa agtctacacg aacccttggg caaaatcctg tatatcgtgc gaaaaaggat   21360
ggatataccg aaaaaatcgc tataatgacc ccgaagcagg ttatgcagc ggaaaagcgc   21420 tgcttccctg ctgttttgtg gaatatctac cgactggaaa caggcaaatg caggaaatta   21480
ctgaactgag gggacaggcg agagacgatg ccaaagagct acaccgacga gctggccgag   21540
tgggttgaat cccgcgcggc caagaagcgc cggcgtgatg aggctgcggt tgcgttcctg   21600
gcggtgaggg cggatgtcga ggcggcgtta gcgtccggct atgcgctcgt caccatttgg   21660
gagcacatgc gggaaacggg gaaggtcaag ttctcctacg agacgttccg ctcgcacgcc   21720
aggcggcaca tcaaggccaa gcccgccgat gtgcccgcac cgcaggccaa ggctgcggaa   21780
cccgcgccgg cacccaagac gccggagcca cggcggccga agcagggggg caaggctgaa   21840
aagccggccc ccgctgcggc cccgaccggc ttcaccttca acccaacacc ggacaaaaag   21900
```

```
gatctactgt aatggcgaaa attcacatgg ttttgcaggg caagggcggg gtcggcaagt    21960
cggccatcgc cgcgatcatt gcgcagtaca agatggacaa ggggcagaca cccttgtgca    22020
tcgacaccga cccggtgaac gcgacgttcg agggctacaa ggccctgaac gtccgccggc    22080
tgaacatcat ggccggcgac gaaattaact cgcgcaactt cgacaccctg gtcgagctga    22140
ttgcgccgac caaggatgac gtggtgatcg acaacggtgc cagctcgttc gtgcctctgt    22200
cgcattacct catcagcaac caggtgccgg ctctgctgca agaaatgggg catgagctgg    22260
tcatccatac cgtcgtcacc ggcggccagg ctctcctgga cacggtgagc ggcttcgccc    22320
agctcgccag ccagttcccg gccgaagcgc ttttcgtggt ctggctgaac ccgtattggg    22380
ggcctatcga gcatgagggc aagagctttg agcagatgaa ggcgtacacg gccaacaagg    22440
cccgcgtgtc gtccatcatc cagattccgg ccctcaagga agaaacctac ggccgcgatt    22500
tcagcgacat gctgcaagag cggctgacgt tcgaccaggc gctggccgat gaatcgctca    22560
cgatcatgac gcggcaacgc ctcaagatcg tgcggcgcgg cctgtttgaa cagctcgacg    22620
cggcggccgt gctatgagcg accagattga agagctgatc cgggagattg cggccaagca    22680
cggcatcgcc gtcggccgcg acgacccggt gctgatcctg cataccatca acgcccggct    22740
catggccgac agtgcggcca agcaagagga aatccttgcc gcgttcaagg aagagctgga    22800
agggatcgcc catcgttggg gcgaggacgc caaggccaaa gcggagcgga tgctgaacgc    22860
ggccctggcg gccagcaagg acgcaatggc gaaggtaatg aaggacagcg ccgcgcaggc    22920
ggccgaagcg atccgcaggg aaatcgacga cggccttggc cgccagctcg cggccaaggt    22980
cgcggacgcg cggcgcgtgg cgatgatgaa catgatcgcc ggcggcatgg tgttgttcgc    23040
ggccgccctg gtggtgtggg cctcgttatg aatcgcagag gcgcagatga aaaagcccgg    23100
cgttgccggg ctttgttttt gcgttagctg ggcttgtttg acaggcccaa gctctgactg    23160
cgcccgcgct cgcgctcctg ggcctgtttc ttctcctgct cctgcttgcg catcagggcc    23220
tggtgccgtc gggctgcttc acgcatcgaa tcccagtcgc cggccagctc gggatgctcc    23280
gcgcgcatct tgcgcgtcgc cagttcctcg atcttgggcg cgtgaatgcc catgccttcc    23340
ttgatttcgc gcaccatgtc cagccgcgtg tgcagggtct gcaagcgggc ttgctgttgg    23400
gcctgctgct gctgccaggc ggccttttgta cgcggcaggg acagcaagcc gggggcattg    23460
gactgtagct gctgcaaacg cgcctgctga cggtctacga gctgttctag gcggtcctcg    23520
atgcgctcca cctggtcatg ctttgcctgc acgtagagcg caagggtctg ctggtaggtc    23580
tgctcgatgg gcgcggattc taagagggcc tgctgttccg tctcggcctc ctgggccgcc    23640
tgtagcaaat cctcgccgct gttgccgctg gactgcttta ctgccgggga ctgctgttgc    23700
cctgctcgcg ccgtcgtcgc agttcggctt gcccccactc gattgactgc ttcatttcga    23760
gccgcagcga tgcgatctcg gattgcgtca acggacgggg cagcgcggag gtgtccggct    23820
tctccttggg tgagtcggtc gatgccatag ccaaaggttt ccttccaaaa tgcgtccatt    23880
gctggaccgt gtttctcatt gatgcccgca agcatcttcg gcttgaccgc caggtcaagc    23940
gcgccttcat gggcggtcat gacggacgcc gccatgacct tgccgccgtt gttctcgatg    24000
tagccgcgta atgaggcaat ggtgccgccc atcgtcagcg tgtcatcgac aacgatgtac    24060
ttctggccgg ggatcaccct cccctcgaaa gtcgggttga acgccaggcg atgatctgaa    24120
ccggctccgg ttcgggcgac cttctcccgc tgcacaatgt ccgtttcgac ctcaaggcca    24180
aggcggtcgc ccagaacgac cgccatcatg gccggaatct tgttgttccc cgccgcctcg    24240
acggcgagga ctggaacgat gcggggcttg tcgtcgccga tcagcgtctt gagctgggca    24300
```

```
acagtgtcgt ccgaaatcag gcgctcgacc aaattaagcg ccgcttccgc gtcgccctgc    24360
ttcgcagcct ggtattcagg ctcgttggtc aaagaaccaa ggtcgccgtt gcgaaccacc    24420
ttcgggaagt ctccccacgg tgcgcgctcg gctctgctgt agctgctcaa gacgcctccc    24480
tttttagccg ctaaaactct aacgagtgcg cccgcgactc aacttgacgc tttcggcact    24540
tacctgtgcc ttgccacttg cgtcataggt gatgcttttc gcactcccga tttcaggtac    24600
tttatcgaaa tctgaccggg cgtgcattac aaagttcttc cccacctgtt ggtaaatgct    24660
gccgctatct gcgtggacga tgctgccgtc gtggcgctgc gacttatcgg ccttttgggc    24720
catatagatg ttgtaaatgc caggtttcag ggccccggct ttatctacct tctggttcgt    24780
ccatgcgcct tggttctcgg tctggacaat tctttgccca ttcatgacca ggaggcggtg    24840
tttcattggg tgactcctga cggttgcctc tggtgttaaa cgtgtcctgg tcgcttgccg    24900
gctaaaaaaa agccgacctc ggcagttcga ggccggcttt ccctagagcc gggcgcgtca    24960
aggttgttcc atctatttta gtgaactgcg ttcgatttat cagttacttt cctcccgctt    25020
tgtgtttcct cccactcgtt tccgcgtcta gccgacccct caacatagcg gcctcttctt    25080
gggctgcctt tgcctcttgc cgcgcttcgt cacgctcggc ttgcaccgtc gtaaagcgct    25140
cggcctgcct ggccgcctct tgcgccgcca acttcctttg ctcctggtgg gcctcggcgt    25200
cggcctgcgc cttcgctttc accgctgcca actccgtgcg caaactctcc gcttcgcgcc    25260
tggtggcgtc gcgctcgccg cgaagcgcct gcatttcctg gttggccgcg tccagggtct    25320
tgcggctctc ttctttgaat gcgcgggcgt cctggtgagc gtagtccagc tcggcgcgca    25380
gctcctgcgc tcgacgctcc acctcgtcgg cccgctgcgt cgccagcgcg gccgctgct    25440
cggctcctgc cagggcggtg cgtgcttcgg ccagggcttg ccgctggcgt gcggccagct    25500
cggccgcctc ggcggcctgc tgctctagca atgtaacgcg cgcctgggct tcttccagct    25560
cgcgggcctg cgcctcgaag gcgtcggcca gctccccgcg cacggcttcc aactcgttgc    25620
gctcacgatc ccagccggct tgcgctgcct gcaacgattc attggcaagg gcctgggcgg    25680
cttgccagag ggcggccacg gcctggttgc cggcctgctg caccgcgtcc ggcacctgga    25740
ctgccagcgg ggcggcctgc gccgtgcgct ggcgtcgcca ttcgcgcatg ccggcgctgg    25800
cgtcgttcat gttgacgcgg gcggccttac gcactgcatc cacggtcggg aagttctccc    25860
ggtcgccttg ctcgaacagc tcgtccgcag ccgcaaaaat gcggtcgcgc gtctctttgt    25920
tcagttccat gttggctccg gtaattggta agaataataa tactcttacc taccttatca    25980
gcgcaagagt ttagctgaac agttctcgac ttaacggcag gttttttagc ggctgaaggg    26040
caggcaaaaa aagccccgca cggtcggcgg gggcaaaggg tcagcgggaa ggggattagc    26100
gggcgtcggg cttcttcatg cgtcgggccc gcgcttcttg ggatggagca cgacgaagcg    26160
cgcacgcgca tcgtcctcgg ccctatcggc ccgcgtcgcg gtcaggaact tgtcgcgcgc    26220
taggtcctcc ctggtgggca ccaggggcat gaactcggcc tgctcgatgt aggtccactc    26280
catgaccgca tcgcagtcga ggccgcgttc cttcaccgtc tcttgcaggt cgcggtacgc    26340
ccgctcgttg agcggctggt aacgggccaa ttggtcgtaa atggctgtcg gccatgagcg    26400
gccttttcctt ttgagccagc agccgacgac gaagccggca atgcaggccc ctggcacaac    26460
caggccgacg ccgggggcag gggatggcag cagctcgcca accaggaacc ccgccgcgat    26520
gatgccgatg ccggtcaacc agcccttgaa actatccggc cccgaaacac ccctgcgcat    26580
tgcctggatg ctgcgccgga tagcttgcaa catcaggagc cgtttctttt gttcgtcagt    26640
```

```
catggtccgc cctcaccagt tgttcgtatc ggtgtcggac gaactgaaat cgcaagagct   26700
gccggtatcg gtccagccgc tgtccgtgtc gctgctgccg aagcacggcg aggggtccgc   26760
gaacgccgca gacggcgtat ccggccgcag cgcatcgccc agcatggccc cggtcagcga   26820
gccgccggcc aggtagccca gcatggtgct gttggtcgcc ccggccacca gggccgacgt   26880
gacgaaatcg ccgtcattcc ctctggattg ttcgctgctc ggcggggcag tgcgccgcgc   26940
cggcggcgtc gtggatggct cgggttggct ggcctgcgac ggccggcgaa aggtgcgcag   27000
cagctcgtta tcgaccggct gcggcgtcgg ggccgccgcc ttgcgctgcg gtcggtgttc   27060
cttcttcggc tcgcgcagct tgaacagcat gatcgcggaa accagcagca acgccgcgcc   27120
tacgcctccc gcgatgtaga acagcatcgg attcattctt cggtcctcct tgtagcggaa   27180
ccgttgtctg tgcggcgcgg gtggcccgcg ccgctgtctt tggggatcag ccctcgatga   27240
gcgcgaccag tttcacgtcg gcaaggttcg cctcgaactc ctggccgtcg tcctcgtact   27300
tcaaccaggc atagccttcc gccggcggcc gacggttgag gataaggcgg gcagggcgct   27360
cgtcgtgctc gacctggacg atggccttt tcagcttgtc cgggtccggc tccttcgcgc    27420
ccttttcctt ggcgtcctta cgtcctggt cgccgtcctc gccgtcctgg ccgtcgccgg    27480
cctccgcgtc acgtcggca tcagtctggc cgttgaaggc atcgacggtg ttgggatcgc    27540
ggcccttctc gtccaggaac tcgcgcagca gcttgaccgt gccgcgcgtg atttcctggg    27600
tgtcgtcgtc aagccacgcc tcgacttcct ccgggcgctt cttgaaggcc gtcaccagct    27660
cgttcaccac ggtcacgtcg cgcacgcggc cggtgttgaa cgcatcggcg atcttctccg    27720
gcaggtccag cagcgtgacg tgctgggtga tgaacgccgg cgacttgccg atttccttgg    27780
cgatatcgcc tttcttcttg cccttcgcca gctcgcggcc aatgaagtcg gcaatttcgc    27840
gcggggtcag ctcgttgcgt tgcaggttct cgataacctg gtcggcttcg ttgtagtcgt    27900
tgtcgatgaa cgccgggatg gacttcttgc cggcccactt cgagccacgg tagcggcggg    27960
cgccgtgatt gatgatatag cggcccggct gctcctggtt ctcgcgcacc gaaatgggtg    28020
acttcacccc gcgctctttg atcgtggcac cgatttccgc gatgctctcc ggggaaaagc    28080
cggggttgtc ggccgtccgc ggctgatgcg gatcttcgtc gatcaggtcc aggtccagct    28140
cgatagggcc ggaaccgccc tgagacgccg caggagcgtc caggaggctc gacaggtcgc    28200
cgatgctatc caaccccagg ccggacggct gcgccgcgcc tgcggcttcc tgagcggccg    28260
cagcggtgtt tttcttggtg gtcttggctt gagccgcagt cattgggaaa tctccatctt    28320
cgtgaacacg taatcagcca gggcgcgaac ctctttcgat gccttgcgcg cggccgtttt    28380
cttgatcttc cagaccggca caccggatgc gagggcatcg gcgatgctgc tgcgcaggcc    28440
aacggtggcc ggaatcatca tcttggggta cgcggccagc agctcggctt ggtggcgcgc    28500
gtggcgcgga ttccgcgcat cgaccttgct gggcaccatg ccaaggaatt gcagcttggc    28560
gttcttctgg cgcacgttcg caatggtcgt gaccatcttc ttgatgccct ggatgctgta    28620
cgcctcaagc tcgatggggg acagcacata gtcggccgcg aagagggcgg ccgccaggcc    28680
gacgccaagg gtcggggccg tgtcgatcag gcacacgtcg aagccttggt tcgccagggc    28740
cttgatgttc gccccgaaca gctcgcgggc gtcgtccagc gacagccgtt cggcgttcgc    28800
cagtaccggg ttggactcga tgagggcgag gcgcgcggcc tggccgtcgc cggctgcggg    28860
tgcggtttcg gtccagccgc cggcaggac agcgccgaac agcttgcttg catgcaggcc    28920
ggtagcaaag tccttgagcg tgtaggacgc attgccctgg gggtccaggt cgatcacggc    28980
aacccgcaag ccgcgctcga aaaagtcgaa ggcaagatgc acaagggtcg aagtcttgcc    29040
```

```
gacgccgcct ttctggttgg ccgtgaccaa agttttcatc gtttggtttc ctgtttttc    29100
ttggcgtccg cttcccactt ccggacgatg tacgcctgat gttccggcag aaccgccgtt   29160
acccgcgcgt accccctcggg caagttcttg tcctcgaacg cggcccacac gcgatgcacc  29220
gcttgcgaca ctgcgcccct ggtcagtccc agcgacgttg cgaacgtcgc ctgtggcttc   29280
ccatcgacta agacgccccg cgctatctcg atggtctgct ccccacttc cagcccctgg    29340
atcgcctcct ggaactggct ttcggtaagc cgtttcttca tggataacac ccataatttg   29400
ctccgcgcct tggttgaaca tagcggtgac agccgccagc acatgagaga agtttagcta   29460
aacatttctc gcacgtcaac acctttagcc gctaaaactc gtccttggcg taacaaaaca   29520
aaagcccgga aaccgggctt tcgtctcttg ccgcttatgg ctctgcaccc ggctccatca   29580
ccaacaggtc gcgcacgcgc ttcactcggt tgcggatcga cactgccagc caacaaagc    29640
cggttgccgc cgccgccagg atcgcgccga tgatgccggc cacaccggcc atcgcccacc   29700
aggtcgccgc cttccggttc cattcctgct ggtactgctt cgcaatgctg acctcggct    29760
caccataggc tgaccgctcg atggcgtatg ccgcttctcc ccttggcgta aacccagcg    29820
ccgcaggcgg cattgccatg ctgcccgccg ctttcccgac cacgacgcgc gcaccaggct   29880
tgcggtccag accttcggcc acggcgagct gcgcaaggac ataatcagcc gccgacttgg   29940
ctccacgcgc ctcgatcagc tcttgcactc gcgcgaaatc cttggcctcc acggccgcca   30000
tgaatcgcgc acgcggcgaa ggctccgcag ggccggcgtc gtgatcgccg ccgagaatgc   30060
ccttcaccaa gttcgacgac acgaaaatca tgctgacggc tatcaccatc atgcagacgt   30120
atcgcacgaa cccgctgaat tgaacacgag cacggcaccc gcgaccacta tgccaagaat   30180
gcccaaggta aaaattgccg gccccgccat gaagtccgtg aatgcccga cggccgaagt    30240
gaagggcagg ccgccaccca ggccgccgcc ctcactgccc ggcacctggt cgctgaatgt   30300
cgatgccagc acctgcggca cgtcaatgct tccgggcgtc gcgctcgggc tgatcgccca   30360
tcccgttact gccccgatcc cggcaatggc aaggactgcc agcgctgcca ttttgggt    30420
gaggccgttc gcggccgagg ggcgcagccc ctgggggat gggaggcccg cgttagcggg    30480
ccgggagggt tcgagaaggg ggggcacccc ccttcggcgt gcgcggtcac gcgcacaggg   30540
cgcagccctg gttaaaaaca aggtttataa atattggttt aaaagcaggt taaaagacag   30600
gttagcggtg gccgaaaaac gggcggaaac ccttgcaaat gctggatttt ctgcctgtgg   30660
acagcccctc aaatgtcaat aggtgcgccc ctcatctgtc agcactctgc ccctcaagtg   30720
tcaaggatcg cgcccctcat ctgtcagtag tcgcgcccct caagtgtcaa taccgcaggg   30780
cacttatccc caggcttgtc cacatcatct gtgggaaact cgcgtaaaat caggcgtttt   30840
cgccgatttg cgaggctggc cagctccacg tcgccggccg aaatcgagcc tgcccctcat   30900
ctgtcaacgc cgcgccgggt gagtcggccc ctcaagtgtc aacgtccgcc cctcatctgt   30960
cagtgagggc caagttttcc gcgaggtatc cacaacgccg gcggccgcgg tgtctcgcac   31020
acggcttcga cggcgtttct ggcgcgtttg cagggccata gacggccgcc agcccagcgg   31080
cgagggcaac cagcccggtg agcgtcggaa aggcgctgga agcccgtag cgacgcggag    31140
aggggcgaga caagccaagg gcgcaggctc gatgcgcagc acgacatagc cggttctcgc   31200
aaggacgaga atttccctgc ggtgcccctc aagtgtcaat gaaagtttcc aacgcgagcc   31260
attcgcgaga gccttgagtc cacgctagat gagagctttg ttgtaggtgg accagttggt   31320
gattttgaac ttttgctttg ccacggaacg gtctgcgttg tcgggaagat gcgtgatctg   31380
```

```
atccttcaac tcagcaaaag ttcgatttat tcaacaaagc cacgttgtgt ctcaaaatct   31440
ctgatgttac attgcacaag ataaaaatat atcatcatga acaataaaac tgtctgctta   31500
cataaacagt aatacaaggg gtgttatgag ccatattcaa cgggaaacgt cttgctcgac   31560
tctagagctc gttcctcgag gaacggtacc tgcggggaag cttacaataa tgtgtgttgt   31620
taagtcttgt tgcctgtcat cgtctgactg actttcgtca taaatcccgg cctccgtaac   31680
ccagctttgg gcaagctcac ggatttgatc cggcggaacg ggaatatcga gatgccgggc   31740
tgaacgctgc agttccagct ttcccttttcg ggacaggtac tccagctgat tgattatctg   31800
ctgaagggtc ttggttccac ctcctggcac aatgcgaatg attacttgag cgcgatcggg   31860
catccaattt tctcccgtca ggtgcgtggt caagtgctac aaggcacctt tcagtaacga   31920
gcgaccgtcg atccgtcgcc gggatacgga caaaatggag cgcagtagtc catcgagggc   31980
ggcgaaagcc tcgccaaaag caatacgttc atctcgcaca gcctccagat ccgatcgagg   32040
gtcttcggcg taggcagata gaagcatgga tacattgctt gagagtattc cgatggactg   32100
aagtatggct tccatctttt ctcgtgtgtc tgcatctatt tcgagaaagc ccccgatgcg   32160
gcgcaccgca acgcgaattg ccatactatc cgaaagtccc agcaggcgcg cttgatagga   32220
aaaggtttca tactcggccg atcgcagacg ggcactcacg accttgaacc cttcaacttt   32280
cagggatcga tgctggttga tggtagtctc actcgacgtg gctctggtgt gttttgacat   32340
agcttcctcc aaagaaagcg gaaggtctgg atactccagc acgaaatgtg cccggggtaga   32400 cggatggaag tctagccctg ctcaatatga aatcaacagt acatttacag tcaatactga   32460
atatacttgc tacatttgca attgtcttat aacgaatgtg aaataaaaat agtgtaacaa   32520
cgcttttact catcgataat cacaaaaaca tttatacgaa caaaaataca aatgcactcc   32580
ggtttcacag gataggcggg atcagaatat gcaacttttg acgttttgtt cttttcaaagg   32640 gggtgctggc aaaaccaccg cactcatggg cctttgcgct gctttggcaa atgacggtaa   32700
acgagtggcc ctctttgatg ccgacgaaaa ccggcctctg acgcgatgga gagaaaacgc   32760
cttacaaagc agtactggga tcctcgctgt gaagtctatt ccgccgacga aatgcccctt   32820
cttgaagcag cctatgaaaa tgccgagctc gaaggatttg attatgcgtt ggccgatacg   32880
cgtggcggct cgagcgagct caacaacaca atcatcgcta gctcaaacct gcttctgatc   32940
cccaccatgc taacgccgct cgacatcgat gaggcactat ctacctaccg ctacgtcatc   33000
gagctgctgt tgagtgaaaa tttggcaatt cctacagctg ttttgcgcca acgcgtcccg   33060
gtcggccgat tgacaacatc gcaacgcagg atgtcagaga cgctagagag ccttccagtt   33120
gtaccgtctc ccatgcatga aagagatgca tttgccgcga tgaaagaacg cggcatgttg   33180
catcttacat tactaaacac gggaactgat ccgacgatgc gcctcataga gaggaatctt   33240
cggattgcga tggaggaagt cgtggtcatt tcgaaactga tcagcaaaat cttggaggct   33300
tgaagatggc aattcgcaag cccgcattgt cggtcggcga agcacggcgg cttgctggtg   33360
ctcgacccga gatccaccat cccaacccga cacttgttcc ccagaagctg gacctccagc   33420
acttgcctga aaaagccgac gagaaagacc agcaacgtga gcctctcgtc gccgatcaca   33480
tttacagtcc cgatcgacaa cttaagctaa ctgtggatgc ccttagtcca cctccgtccc   33540
cgaaaaagct ccaggttttt cttcagcgc gaccgcccgc gcctcaagtg tcgaaaacat   33600
atgacaacct cgttcggcaa tacagtccct cgaagtcgct acaaatgatt ttaaggcgcg   33660
cgttggacga tttcgaaagc atgctggcag atggatcatt tcgcgtggcc ccgaaaagtt   33720
atccgatccc ttcaactaca gaaaaatccg ttctcgttca gacctcacgc atgttcccgg   33780
```

```
ttgcgttgct cgaggtcgct cgaagtcatt ttgatccgtt ggggttggag accgctcgag    33840
ctttcggcca aagctggct accgccgcgc tcgcgtcatt ctttgctgga gagaagccat     33900
cgagcaattg gtgaagaggg acctatcgga accctcacc aaatattgag tgtaggtttg     33960
aggccgctgg ccgcgtcctc agtcaccttt tgagccagat aattaagagc caatgcaat    34020 tggctcaggc tgccatcgtc ccccgtgcg aaacctgcac gtccgcgtca agaaataac     34080 cggcacctct tgctgttttt atcagttgag ggcttgacgg atccgcctca agtttgcggc    34140
gcagccgcaa aatgagaaca tctatactcc tgtcgtaaac ctcctcgtcg cgtactcgac    34200
tggcaatgag aagttgctcg cgcgatgaaa cgtcgcgggg tttctctaaa aacgcgagga    34260
gaagattgaa ctcacctgcc gtaagtttca cctcaccgcc agcttcggac atcaagcgac    34320
gttgcctgag attaagtgtc cagtcagtaa aacaaaaaga ccgtcggtct ttggagcgga    34380
caacgttggg gcgcacgcgc aaggcaaccc gaatgcgtgc aagaaactct ctcgtactaa    34440
acggcttagc gataaaatca cttgctccta gctcgagtgc aacaacttta tccgtctcct    34500
caaggcggtc gccactgata attatgattg gaatatcaga cttttgccgcc agatttcgaa    34560 cgatctcaag cccatcttca cgacctaaat ttagatcaac aaccacgaca tcgaccgtcg    34620
cggaagagag tactctagtg aactgggtgc tgtcggctac cgcggtcact ttgaaggcgt    34680
ggatcgtaag gtattcgata ataagatgcc gcatagcgac atcgtcatcg ataagaagaa    34740 cgtgttttcaa cggctcacct ttcaatctaa aatctgaacc cttgttcaca gcgcttgaga    34800
aattttcacg tgaaggatgt acaatcatct ccagctaaat gggcagttcg tcagaattgc    34860
ggctgaccgc ggatgacgaa aatgcgaacc aagtatttca attttatgac aaaagttctc    34920
aatcgttgtt acaagtgaaa cgcttcgagg ttacagctac tattgattaa ggagatcgcc    34980
tatggtctcg ccccggcgtc gtgcgtccgc cgcgagccag atctcgccta cttcataaac    35040
gtcctcatag gcacggaatg gaatgatgac atcgatcgcc gtagagagca tgtcaatcag    35100
tgtgcgatct tccaagctag caccttgggc gctacttttg acaagggaaa acagtttctt    35160
gaatccttgg attggattcg cgccgtgtat tgttgaaatc gatcccggat gtcccgagac    35220
gacttcactc agataagccc atgctgcatc gtcgcgcatc tcgccaagca atatccggtc    35280
cggccgcata cgcagacttg cttggagcaa gtgctcggcg ctcacagcac ccagcccagc    35340
accgttcttg gagtagagta gtctaacatg attatcgtgt ggaatgacga gttcgagcgt    35400
atcttctatg gtgattagcc tttcctgggg ggggatggcg ctgatcaagg tcttgctcat    35460
tgttgtcttg ccgcttccgg tagggccaca tagcaacatc gtcagtcggc tgacgacgca    35520
tgcgtgcaga aacgcttcca aatccccgtt gtcaaaatgc tgaaggatag cttcatcatc    35580
ctgattttgg cgtttccttc gtgtctgcca ctggttccac ctcgaagcat cataacggga    35640
ggagacttct ttaagaccag aaacacgcga gcttggccgt cgaatggtca agctgacggt    35700
gcccgaggga acggtcggcg gcagacagat ttgtagtcgt tcaccaccag gaagttcagt    35760
ggcgcagagg gggttacgtg gtccgacatc ctgctttctc agcgcgcccg ctaaaatagc    35820
gatatcttca agatcatcat aagagacggg caaaggcatc ttggtaaaaa tgccggcttg    35880
gcgcacaaat gcctctccag gtcgattgat cgcaatttct tcagtcttcg ggtcatcgag    35940
ccattccaaa atcggcttca gaagaaagcg tagttgcgga tccacttcca tttacaatgt    36000
atcctatctc taagcggaaa tttgaattca ttaagagcgg cggttcctcc ccgcgtggc     36060 gccgccagtc aggcggagct ggtaaacacc aaagaaatcg aggtcccgtg ctacgaaaat    36120
```

```
ggaaacggtg tcaccctgat tcttcttcag ggttggcggt atgttgatgg ttgccttaag   36180
ggctgtctca gttgtctgct caccgttatt ttgaaagctg ttgaagctca tcccgccacc   36240
cgagctgccg gcgtaggtgc tagctgcctg aaggcgcct  tgaacaacac tcaagagcat   36300
agctccgcta aaacgctgcc agaagtggct gtcgaccgag cccggcaatc ctgagcgacc   36360
gagttcgtcc gcgcttggcg atgttaacga gatcatcgca tggtcaggtg tctcggcgcg   36420
atcccacaac acaaaaacgc gcccatctcc ctgttgcaag ccacgctgta tttcgccaac   36480
aacggtggtg ccacgatcaa gaagcacgat attgttcgtt gttccacgaa tatcctgagg   36540
caagacacac tttacatagc ctgccaaatt tgtgtcgatt gcggtttgca agatgcacgg   36600
aattattgtc ccttgcgtta ccataaaatc ggggtgcggc aagagcgtgg cgctgctggg   36660
ctgcagctcg gtgggtttca tacgtatcga caaatcgttc tcgccggaca cttcgccatt   36720
cggcaaggag ttgtcgtcac gcttgccttc ttgtcttcgg cccgtgtcgc cctgaatggc   36780
gcgtttgctg acccccttgat cgccgctgct atatgcaaaa atcggtgttt cttccggccg   36840
tggctcatgc cgctccggtt cgcccctcgg cggtagagga gcagcaggct gaacagcctc   36900
ttgaaccgct ggaggatccg gcggcacctc aatcggagct ggatgaaatg gcttggtgtt   36960
tgttgcgatc aaagttgacg gcgatgcgtt ctcattcacc ttcttttggc gcccacctag   37020
ccaaatgagg cttaatgata acgcgagaac gacacctccg acgatcaatt tctgagaccc   37080
cgaaagacgc cggcgatgtt tgtcggagac cagggatcca gatgcatcaa cctcatgtgc   37140
cgcttgctga ctatcgttat tcatcccttc gccccttca  ggacgcgttt cacatcgggc   37200
ctcaccgtgc ccgtttgcgg cctttggcca acgggatcgt aagcggtgtt ccagatacat   37260
agtactgtgt ggccatccct cagacgccaa cctcgggaaa ccgaagaaat ctcgacatcg   37320
ctccctttaa ctgaatagtt ggcaacagct tccttgccat caggattgat ggtgtagatg   37380
gagggtatgc gtacattgcc cggaaagtgg aataccgtcg taaatccatt gtcgaagact   37440
tcgagtggca acagcgaacg atcgccttgg gcgacgtagt gccaattact gtccgccgca   37500
ccaagggctg tgacaggctg atccaataaa ttctcagctt tccgttgata ttgtgcttcc   37560
gcgtgtagtc tgtccacaac agccttctgt tgtgcctccc ttcgccgagc cgccgcatcg   37620
tcggcggggt aggcgaattg gacgctgtaa tagagatcgg gctgctcttt atcgaggtgg   37680
gacagagtct tggaacttat actgaaaaca taacggcgca tcccggagtc gcttgcggtt   37740
agcacgatta ctggctgagg cgtgaggacc tggcttgcct tgaaaaatag ataatttccc   37800
cgcggtaggg ctgctagatc tttgctattt gaaacggcaa ccgctgtcac cgtttcgttc   37860
gtggcgaatg ttacgaccaa agtagctcca accgccgtcg agaggcgcac cacttgatcg   37920
ggattgtaag ccaaataacg catgcgcgga tctagcttgc ccgccattgg agtgtcttca   37980
gcctccgcac cagtcgcagc ggcaaataaa catgctaaaa tgaaagtgc  ttttctgatc   38040 atggttcgct gtggcctacg tttgaaacgg tatcttccga tgtctgatag gaggtgacaa   38100
ccagacctgc cgggttggtt agtctcaatc tgccgggcaa gctggtcacc ttttcgtagc   38160
gaactgtcgc ggtccacgta ctcaccacag gcattttgcc gtcaacgacg agggtccttt   38220
tatagcgaat ttgctgcgtg cttggagtta catcatttga agcgatgtgc tcgacctcca   38280
ccctgccgcg tttgccaaga atgacttgag gcgaactggg attgggatag ttgaagaatt   38340
gctggtaatc ctggcgcact gttggggcac tgaagttcga taccaggtcg taggcgtact   38400
gagcggtgtc ggcatcataa ctctcgcgca ggcgaacgta ctcccacaat gaggcgttaa   38460
cgacggcctc ctcttgagtt gcaggcaatc gcgagacaga cacctcgctg tcaacggtgc   38520
```

```
cgtccggccg tatccataga tatacgggca caagcctgct caacggcacc attgtggcta   38580
tagcgaacgc ttgagcaaca tttcccaaaa tcgcgatagc tgcgacagct gcaatgagtt   38640
tggagagacg tcgcgccgat ttcgctcgcg cggtttgaaa ggcttctact tccttatagt   38700
gctcggcaag gctttcgcgc gccactagca tggcatattc aggccccgtc atagcgtcca   38760
cccgaattgc cgagctgaag atctgacgga gtaggctgcc atcgcccac attcagcggg    38820 aagatcgggc ctttgcagct cgctaatgtg tcgtttgtct ggcagccgct caaagcgaca   38880
actaggcaca gcaggcaata cttcatagaa ttctccattg aggcgaattt ttgcgcgacc   38940
tagcctcgct caacctgagc gaagcgacgg tacaagctgc tggcagattg ggttgcgccg   39000
ctccagtaac tgcctccaat gttgccggcg atcgccggca aagcgacaat gagcgcatcc   39060
cctgtcagaa aaacatatc gagttcgtaa agaccaatga tcttggccgc ggtcgtaccg    39120
gcgaaggtga ttacaccaag cataagggtg agcgcagtcg cttcggttag gatgacgatc   39180
gttgccacga ggtttaagag gagaagcaag agaccgtagg tgataagttg cccgatccac   39240
ttagctgcga tgtcccgcgt gcgatcaaaa atatatccga cgaggatcag aggcccgatc   39300
gcgagaagca ctttcgtgag aattccaacg gcgtcgtaaa ctccgaaggc agaccagagc   39360
gtgccgtaaa ggacccactg tgcccctttgg aaagcaagga tgtcctggtc gttcatcgga  39420
ccgatttcgg atgcgatttt ctgaaaaacg gcctgggtca cggcgaacat tgtatccaac   39480
tgtgccggaa cagtctgcag aggcaagccg gttacactaa actgctgaac aaagtttggg   39540
accgtctttt cgaagatgga aaccacatag tcttggtagt tagcctgccc aacaattaga   39600
gcaacaacga tggtgaccgt gatcacccga gtgataccgc tacgggtatc gacttcgccg   39660
cgtatgacta aaatacctg aacaataatc caaagagtga cacaggcgat caatggcgca   39720
ctcaccgcct cctggatagt ctcaagcatc gagtccaagc ctgtcgtgaa ggctacatcg   39780
aagatcgtat gaatggccgt aaacggcgcc ggaatcgtga aattcatcga ttggacctga   39840
acttgactgg tttgtcgcat aatgttggat aaaatgagct cgcattcggc gaggatgcgg   39900
gcggatgaac aaatcgccca gccttagggg agggcaccaa agatgacagc ggtcttttga   39960
tgctccttgc gttgagcggc cgcctcttcc gcctcgtgaa ggccggcctg cgcggtagtc   40020
atcgttaata ggcttgtcgc ctgtacattt tgaatcattg cgtcatggat ctgcttgaga   40080
agcaaaccat tggtcacggt tgcctgcatg atattgcgag atcgggaaag ctgagcgac   40140 gtatcagcat tcgccgtcaa gcgtttgtcc atcgtttcca gattgtcagc cgcaatgcca   40200
gcgctgtttg cggaaccggt gatctgcgat cgcaacaggt ccgcttcagc atcactaccc   40260
acgactgcac gatctgtatc gctggtgatc gcacgtgccg tggtcgacat tggcattcgc   40320
ggcgaaaaca tttcattgtc taggtccttc gtcgaaggat actgattttt ctggttgagc   40380
gaagtcagta gtccagtaac gccgtaggcc gacgtcaaca tcgtaaccat cgctatagtc   40440
tgagtgagat tctccgcagt cgcgagcgca gtcgcgagcg tctcagcctc cgttgccggg   40500
tcgctaacaa caaactgcgc ccgcgcgggc tgaatatata gaaagctgca ggtcaaaact   40560
gttgcaataa gttgcgtcgt cttcatcgtt tcctacctta tcaatcttct gcctcgtggt   40620
gacgggccat gaattcgctg agccagccag atgagttgcc ttcttgtgcc tcgcgtagtc   40680
gagttgcaaa gcgcaccgtg ttggcacgcc ccgaaagcac ggcgacatat tcacgcatat   40740
cccgcagatc aaattcgcag atgacgcttc cactttctcg tttaagaaga aacttacggc   40800
tgccgaccgt catgtcttca cggatcgcct gaaattcctt ttcggtacat ttcagtccat   40860
```

```
cgacataagc cgatcgatct gcggttggtg atggatagaa aatcttcgtc atacattgcg    40920
caaccaagct ggctcctagc ggcgattcca gaacatgctc tggttgctgc gttgccagta    40980
ttagcatccc gttgtttttt cgaacggtca ggaggaattt gtcgacgaca gtcgaaaatt    41040
tagggtttaa caaataggcg cgaaactcat cgcagctcat cacaaaacgg cggccgtcga    41100
tcatggctcc aatccgatgc aggagatatg ctgcagcggg agcgcatact tcctcgtatt    41160
cgagaagatg cgtcatgtcg aagccggtaa tcgacggatc taactttact tcgtcaactt    41220
cgccgtcaaa tgcccagcca agcgcatggc cccggcacca gcgttggagc gcgctcctg    41280 cgccttcggc gggcccatgc aacaaaaatt cacgtaaccc cgcgattgaa cgcatttgtg    41340
gatcaaacga gagctgacga tggataccac ggaccagacg gcggttctct tccggagaaa    41400
tcccaccccg accatcactc tcgatgagag ccacgatcca ttcgcgcaga aaatcgtgtg    41460
aggctgctgt gttttctagg ccacgcaacg gcgccaaccc gctgggtgtg cctctgtgaa    41520
gtgccaaata tgttcctcct gtggcgcgaa ccagcaattc gccacccgg tccttgtcaa    41580 agaacacgac cgtacctgca cggtcgacca tgctctgttc gagcatggct agaacaaaca    41640
tcatgagcgt cgtcttaccc ctcccgatag gcccgaatat tgccgtcatg ccaacatcgt    41700
gctcatgcgg gatatagtcg aaaggcgttc cgccattggt acgaaatcgg gcaatcgcgt    41760
tgccccagtg gcctgagctg gcgccctctg gaaagttttc gaaagagaca aaccctgcga    41820
aattgcgtga agtgattgcg ccagggcgtg tgcgccactt aaaattcccc ggcaattggg    41880
accaataggc cgcttccata ccaatacctt cttggacaac cacggcacct gcatccgcca    41940
ttcgtgtccg agcccgcgcg cccctgtccc caagactatt gagatcgtct gcatagacgc    42000
aaaggctcaa atgatgtgag cccataacga attcgttgct cgcaagtgcg tcctcagcct    42060
cggataattt gccgatttga gtcacggctt tatcgccgga actcagcatc tggctcgatt    42120
tgaggctaag tttcgcgtgc gcttgcgggc gagtcaggaa cgaaaaactc tgcgtgagaa    42180
caagtggaaa atcgagggat agcagcgcgt tgagcatgcc cggccgtgtt tttgcaggt    42240 attcgcgaaa cgaatagatg gatccaacgt aactgtcttt tggcgttctg atctcgagtc    42300
ctcgcttgcc gcaaatgact ctgtcggtat aaatcgaagc gccgagtgag ccgctgacga    42360
ccggaaccgg tgtgaaccga ccagtcatga tcaaccgtag cgcttcgcca atttcggtga    42420
agagcacacc ctgcttctcg cggatgccaa gacgatgcag gccatacgct taagagagc    42480 cagcgacaac atgccaaaga tcttccatgt tcctgatctg gcccgtgaga tcgttttccc    42540 ttttccgct tagcttggtg aacctcctct ttaccttccc taaagccgcc tgtgggtaga    42600
caatcaacgt aaggaagtgt tcattgcgga ggagttggcc ggagagcacg cgctgttcaa    42660
aagcttcgtt caggctagcg gcgaaaacac tacggaagtg tcgcggcgcc gatgatggca    42720
cgtcggcatg acgtacgagg tgagcatata ttgacacatg atcatcagcg atattgcgca    42780
acagcgtgtt gaacgcacga caacgcgcat tgcgcatttc agtttcctca agctcgaatg    42840
caacgccatc aattctcgca atggtcatga tcgatccgtc ttcaagaagg acgatatggt    42900
cgctgaggtg gccaatataa gggagataga tctcaccgga tctttcggtc gttccactcg    42960
cgccgagcat cacaccattc ctctccctcg tgggggaacc ctaattggat ttgggctaac    43020
agtagcgccc cccaaactg cactatcaat gcttcttccc gcggtccgca aaaatagcag    43080
gacgacgctc gccgcattgt agtctcgctc cacgatgagc cgggctgcaa accataacgg    43140
cacgagaacg acttcgtaga gcgggttctg aacgataacg atgacaaagc cggcgaacat    43200
catgaataac cctgccaatg tcagtggcac cccaagaaac aatgcgggcc gtgtggctgc    43260
```

```
gaggtaaagg gtcgattctt ccaaacgatc agccatcaac taccgccagt gagcgtttgg    43320
ccgaggaagc tcgccccaaa catgataaca atgccgccga cgacgccggc aaccagccca    43380
agcgaagccc gcccgaacat ccaggagatc ccgatagcga caatgccgag aacagcgagt    43440
gactggccga acgaccaag gataaacgtg catatattgt taaccattgt ggcggggtca     43500
gtgccgccac ccgcagattg cgctgcggcg ggtccggatg aggaaatgct ccatgcaatt    43560
gcaccgcaca agcttggggc gcagctcgat atcacgcgca tcatcgcatt cgagagcgag    43620
aggcgattta gatgtaaacg gtatctctca aagcatcgca tcaatgcgca cctccttagt    43680
ataagtcgaa taagacttga ttgtcgtctg cggatttgcc gttgtcctgg tgtggcggtg    43740
gcggagcgat taaccgcca gcgccatcct cctgcgagcg gcgctgatat gaccccaaa     43800 catcccacgt ctcttcggat tttagcgcct cgtgatcgtc ttttggaggc tcgattaacg    43860
cgggcaccag cgattgagca gctgtttcaa cttttcgcac gtagccgttt gcaaaaccgc    43920
cgatgaaatt accggtgttg taagcggaga tcgcccgacg aagcgcaaat tgcttctcgt    43980
caatcgtttc gccgcctgca taacgacttt tcagcatgtt tgcagcggca gataatgatg    44040
tgcacgcctg gagcgcaccg tcaggtgtca gaccgagcat agaaaaattt cgagagttta    44100
tttgcatgag gccaacatcc agcgaatgcc gtgcatcgag acggtgcctg acgacttggg    44160
ttgcttggct gtgatcttgc cagtgaagcg tttcgccggt cgtgttgtca tgaatcgcta    44220
aaggatcaaa gcgactctcc accttagcta tcgccgcaag cgtagatgtc gcaactgatg    44280
gggcacactt gcgagcaaca tggtcaaact cagcagatga gagtggcgtg gcaaggctcg    44340
acgaacagaa ggagaccatc aaggcaagag aaagcgaccc cgatctctta agcatacctt    44400
atctccttag ctcgcaacta acaccgcctc tcccgttgga agaagtgcgt tgttttatgt    44460
tgaagattat cgggagggtc ggttactcga aaattttcaa ttgcttcttt atgatttcaa    44520
ttgaagcgag aaacctcgcc cggcgtcttg gaacgcaaca tggaccgaga accgcgcatc    44580
catgactaag caaccggatc gacctattca ggccgcagtt ggtcaggtca ggctcagaac    44640
gaaaatgctc ggcgaggtta cgctgtctgt aaacccattc gatgaacggg aagcttcctt    44700
ccgattgctc ttggcaggaa tattggccca tgcctgcttg cgctttgcaa atgctcttat    44760
cgcgttggta tcatatgcct tgtccgccag cagaaacgca ctctaagcga ttatttgtaa    44820
aaatgtttcg gtcatgcggc ggtcatgggc ttgacccgct gtcagcgcaa gacggatcgg    44880
tcaaccgtcg gcatcgacaa cagcgtgaat cttggtggtc aaaccgccac gggaacgtcc    44940
catacagcca tcgtcttgat cccgctgttt cccgtcgccg catgttggtg gacgcggaca    45000
caggaactgt caatcatgac gacattctat cgaaagcctt ggaaatcaca ctcagaatat    45060
gatcccagac gtctgcctca cgccatcgta caaagcgatt gtagcaggtt gtacaggaac    45120
cgtatcgatc aggaacgtct gcccagggcg ggcccgtccg gaagcgccac aagatgacat    45180
tgatcacccg cgtcaacgcg cggcacgcga cgcggcttat ttgggaacaa aggactgaac    45240
aacagtccat tcgaaatcgg tgacatcaaa gcggggacgg gttatcagtg gcctccaagt    45300
caagcctcaa tgaatcaaaa tcagaccgat ttgcaaacct gatttatgag tgtgcggcct    45360
aaatgatgaa atcgtccttc tagatcgcct ccgtggtgta gcaacacctc gcagtatcgc    45420
cgtgctgacc ttggccaggg aattgactgg caagggtgct ttcacatgac cgctcttttg    45480
gccgcgatag atgatttcgt tgctgctttg ggcacgtaga aggagagaag tcatatcgga    45540
gaaattcctc ctggcgcgag agcctgctct atcgcgacgg catcccactg tcgggaacag    45600
```

```
accggatcat tcacgaggcg aaagtcgtca acacatgcgt tataggcatc ttcccttgaa   45660
ggatgatctt gttgctgcca atctggaggt gcggcagccg caggcagatg cgatctcagc   45720
gcaacttgcg gcaaaacatc tcactcacct gaaaaccact agcgagtctc gcgatcagac   45780
gaaggccttt tacttaacga cacaatatcc gatgtctgca tcacaggcgt cgctatccca   45840
gtcaatacta aagcggtgca ggaactaaag attactgatg acttaggcgt gccacgaggc   45900
ctgagacgac gcgcgtagac agttttttga aatcattatc aaagtgatgg cctccgctga   45960
agcctatcac ctctgcgccg gtctgtcgga gagatgggca agcattatta cggtcttcgc   46020
gcccgtacat gcattggacg attgcagggt caatggatct gagatcatcc agaggattgc   46080
cgcccttacc ttccgtttcg agttggagcc agcccctaaa tgagacgaca tagtcgactt   46140
gatgtgacaa tgccaagaga gagatttgct taacccgatt tttttgctca agcgtaagcc   46200
tattgaagct tgccggcatg acgtccgcgc cgaaagaata tcctacaagt aaaacattct   46260
gcacaccgaa atgcttggtg tagacatcga ttatgtgacc aagatcctta gcagtttcgc   46320
ttggggaccg ctccgaccag aaataccgaa gtgaactgac gccaatgaca ggaatccctt   46380
ccgtctgcag ataggtacca tcgatagatc tgctgcctcg cgcgtttcgg tgatgacggt   46440
gaaaacctct gacacatgca gctcccggag acggtcacag cttgtctgta agcggatgcc   46500
gggagcagac aagcccgtca gggcgcgtca gcgggtgttg gcgggtgtcg gggcgcagcc   46560
atgacccagt cacgtagcga tagcggagtg tatactggct taactatgcg gcatcagagc   46620
agattgtact gagagtgcac catatgcggt gtgaaatacc gcacagatgc gtaaggagaa   46680
aataccgcat caggcgctct tccgcttcct cgctcactga ctcgctgcgc tcggtcgttc   46740
ggctgcggcg agcggtatca gctcactcaa aggcggtaat acggttatcc acagaatcag   46800
gggataacgc aggaaagaac atgtgagcaa aaggccagca aaaggccagg aaccgtaaaa   46860
aggccgcgtt gctggcgttt ttccataggc tccgcccccc tgacgagcat cacaaaaatc   46920
gacgctcaag tcagaggtgg cgaaacccga caggactata aagataccag gcgtttcccc   46980
ctggaagctc cctcgtgcgc tctcctgttc cgaccctgcc gcttaccgga tacctgtccg   47040
cctttctccc ttcgggaagc gtggcgcttt ctcatagctc acgctgtagg tatctcagtt   47100
cggtgtaggt cgttcgctcc aagctgggct gtgtgcacga acccccccgtt cagcccgacc   47160 gctgcgcctt atccggtaac tatcgtcttg agtccaaccc ggtaagacac gacttatcgc   47220
cactggcagc agccactggt aacaggatta gcagagcgag gtatgtaggc ggtgctacag   47280
agttcttgaa gtggtggcct aactacggct acactagaag gacagtattt ggtatctgcg   47340
ctctgctgaa gccagttacc ttcggaaaaa gagttggtag ctcttgatcc ggcaaacaaa   47400
ccaccgctgg tagcggtggt ttttttgttt gcaagcagca gattacgcgc agaaaaaaag   47460
gatctcaaga agatcctttg atcttttcta cggggtctga cgctcagtgg aacgaaaact   47520
cacgttaagg gattttggtc atgagattat caaaaaggat cttcacctag atccttttaa   47580
attaaaaatg aagttttaaa tcaatctaaa gtatatatga gtaaacttgg tctgacagtt   47640
accaatgctt aatcagtgag gcacctatct cagcgatctg tctatttcgt tcatccatag   47700
ttgcctgact ccccgtcgtg tagataacta cgatacggga gggcttacca tctggcccca   47760
gtgctgcaat gataccgcga gacccacgct caccggctcc agatttatca gcaataaacc   47820
agccagccgg aagggccgag cgcagaagtg gtcctgcaac tttatccgcc tccatccagt   47880
ctattaattg ttgccgggaa gctagagtaa gtagttcgcc agttaatagt ttgcgcaacg   47940
ttgttgccat tgctgcaggg gggggggggg gggggactt ccattgttca ttccacggac   48000
```

```
aaaaacagag aaaggaaacg acagaggcca aaaagcctcg ctttcagcac ctgtcgtttc   48060
ctttcttttc agagggtatt ttaaataaaa acattaagtt atgacgaaga agaacggaaa   48120
cgccttaaac cggaaaattt tcataaatag cgaaaacccg cgaggtcgcc gccccgtagt   48180
cggatcaccg gaaaggaccc gtaaagtgat aatgattatc atctacatat cacaacgtgc   48240
gtggaggcca tcaaaccacg tcaaataatc aattatgacg caggtatcgt attaattgat   48300
ctgcatcaac ttaacgtaaa aacaacttca gacaatacaa atcagcgaca ctgaatacgg   48360
ggcaacctca tgtcccccccc cccccccccc ctgcaggcat cgtggtgtca cgctcgtcgt   48420
ttggtatggc ttcattcagc tccggttccc aacgatcaag gcgagttaca tgatccccca   48480
tgttgtgcaa aaaagcggtt agctccttcg gtcctccgat cgttgtcaga agtaagttgg   48540
ccgcagtgtt atcactcatg gttatggcag cactgcataa ttctcttact gtcatgccat   48600
ccgtaagatg cttttctgtg actggtgagt actcaaccaa gtcattctga aatagtgta   48660
tgcggcgacc gagttgctct tgcccggcgt caacacggga taataccgcg ccacatagca   48720
gaactttaaa agtgctcatc attggaaaac gttcttcggg gcgaaaactc tcaaggatct   48780
taccgctgtt gagatccagt tcgatgtaac ccactcgtgc acccaactga tcttcagcat   48840
cttttacttt caccagcgtt tctgggtgag caaaaacagg aaggcaaaat gccgcaaaaa   48900
agggaataag ggcgacacgg aaatgttgaa tactcatact cttcctttt caatattatt   48960
gaagcattta tcagggttat tgtctcatga gcggatacat atttgaatgt atttagaaaa   49020
ataaacaaat aggggttccg cgcacatttc cccgaaaagt gccacctgac gtctaagaaa   49080
ccattattat catgacatta acctataaaa ataggcgtat cacgaggccc tttcgtcttc   49140
aagaattggt cgacgatctt gctgcgttcg gatattttcg tggagttccc gccacagacc   49200
cggattgaag gcgagatcca gcaactcgcg ccagatcatc ctgtgacgga actttggcgc   49260
gtgatgactg gccaggacgt cggccgaaag agcgacaagc agatcacgct tttcgacagc   49320
gtcggatttg cgatcgagga ttttttcggcg ctgcgctacg tccgcgaccg cgttgaggga   49380
tcaagccaca gcagcccact cgaccttcta gccgacccag acgagccaag ggatcttttt   49440
ggaatgctgc tccgtcgtca ggcttttccga cgtttgggtg gttgaacaga agtcattatc   49500
gtacggaatg ccaagcactc ccgagggggaa ccctgtggtt ggcatgcaca tacaaatgga   49560
cgaacggata aaccttttca cgccttttta aatatccgtt attctaataa acgctctttt   49620
ctcttaggtt tacccgccaa tatatcctgt caaacactga tagtttaaac tgaaggcggg   49680
aaacgacaat ctgatcatga gcggagaatt aagggagtca cgttatgacc cccgccgatg   49740
acgcgggaca agccgttta cgtttggaac tgacagaacc gcaacgttga aggagccact   49800
cagcaagctg gtacgattgt aatacgactc actatagggc gaattgagcg ctgtttaaac   49860
gctcttcaac tggaagagcg gttacccgga ccgaagcttg catgcctgca g            49911
```

<210> SEQ ID NO 37
<211> LENGTH: 36909
<212> TYPE: DNA
<213> ORGANISM: Artificial
<220> FEATURE:
<223> OTHER INFORMATION: Vector PHP10523

<400> SEQUENCE: 37

```
tctagagctc gttcctcgag gcctcgaggc ctcgaggaac ggtacctgcg gggaagctta     60
caataatgtg tgttgttaag tcttgttgcc tgtcatcgtc tgactgactt tcgtcataaa    120
```

-continued

| | |
|---|---|
| tcccggcctc cgtaacccag cttgggcaa gctcacggat tgatccggc ggaacgggaa | 180 |
| tatcgagatg ccgggctgaa cgctgcagtt ccagctttcc ctttcgggac aggtactcca | 240 |
| gctgattgat tatctgctga agggtcttgg ttccacctcc tggcacaatg cgaatgatta | 300 |
| cttgagcgcg atcgggcatc caattttctc ccgtcaggtg cgtggtcaag tgctacaagg | 360 |
| cacctttcag taacgagcga ccgtcgatcc gtcgccggga tacggacaaa atggagcgca | 420 |
| gtagtccatc gagggcggcg aaagcctcgc caaaagcaat acgttcatct cgcacagcct | 480 |
| ccagatccga tcgagggtct tcggcgtagg cagatagaag catggataca ttgcttgaga | 540 |
| gtattccgat ggactgaagt atggcttcca tcttttctcg tgtgtctgca tctatttcga | 600 |
| gaaagccccc gatgcggcgc accgcaacgc gaattgccat actatccgaa agtcccagca | 660 |
| ggcgcgcttg ataggaaaag gtttcatact cggccgatcg cagacgggca ctcacgacct | 720 |
| tgaacccttc aactttcagg gatcgatgct ggttgatggt agtctcactc gacgtggctc | 780 |
| tggtgtgttt tgacatagct tcctccaaag aaagcggaag gtctggatac tccagcacga | 840 |
| aatgtgcccg ggtagacgga tggaagtcta gccctgctca atatgaaatc aacagtacat | 900 |
| ttacagtcaa tactgaatat acttgctaca tttgcaattg tcttataacg aatgtgaaat | 960 |
| aaaaatagtg taacaacgct tttactcatc gataatcaca aaaacattta tacgaacaaa | 1020 |
| aatacaaatg cactccggtt tcacaggata ggcgggatca gaatatgcaa cttttgacgt | 1080 |
| tttgttcttt caaggggggt gctggcaaaa ccaccgcact catgggcctt tgcgctgctt | 1140 |
| tggcaaatga cggtaaacga gtggccctct ttgatgccga cgaaaaccgg cctctgacgc | 1200 |
| gatggagaga aaacgcctta caaagcagta ctgggatcct cgctgtgaag tctattccgc | 1260 |
| cgacgaaatg cccccttctg aagcagccta tgaaaatgcc gagctcgaag gatttgatta | 1320 |
| tgcgttggcc gatacgcgtg gcggctcgag cgagctcaac aacacaatca tcgctagctc | 1380 |
| aaacctgctt ctgatcccca ccatgctaac gccgctcgac atcgatgagg cactatctac | 1440 |
| ctaccgctac gtcatcgagc tgctgttgag tgaaaatttg gcaattccta cagctgtttt | 1500 |
| gcgccaacgc gtcccggtcg gccgattgac aacatcgcaa cgcaggatgt cagagacgct | 1560 |
| agagagcctt ccagttgtac cgtctcccat gcatgaaaga gatgcatttg ccgcgatgaa | 1620 |
| agaacgcggc atgttgcatc ttacattact aaacacggga actgatccga cgatgcgcct | 1680 |
| catagagagg aatcttcgga ttgcgatgga ggaagtcgtg gtcatttcga aactgatcag | 1740 |
| caaaatcttg gaggcttgaa gatggcaatt cgcaagcccg cattgtcggt cggcgaagca | 1800 |
| cggcggcttg ctggtgctcg acccgagatc caccatccca acccgacact tgttccccag | 1860 |
| aagctggacc tccagcactt gcctgaaaaa gccgacgaga aagaccagca acgtgagcct | 1920 |
| ctcgtcgccg atcacattta cagtcccgat cgacaactta agctaactgt ggatgccctt | 1980 |
| agtccacctc cgtccccgaa aaagctccag gtttttcttt cagcgcgacc gcccgcgcct | 2040 |
| caagtgtcga aaacatatga caacctcgtt cggcaataca gtccctcgaa gtcgctacaa | 2100 |
| atgattttaa ggcgcgcgtt ggacgatttc gaaagcatgc tggcagatgg atcatttcgc | 2160 |
| gtggccccga aaagttatcc gatcccttca actacagaaa aatccgttct cgttcagacc | 2220 |
| tcacgcatgt tccggttgc gttgctcgag gtcgctcgaa gtcatttga tccgttgggg | 2280 |
| ttggagaccg ctcgagcttt cggccacaag ctggctaccg ccgcgctcgc gtcattcttt | 2340 |
| gctggagaga agccatcgag caattggtga agagggacct atcggaaccc ctcaccaaat | 2400 |
| attgagtgta ggtttgaggc cgctggccgc gtcctcagtc acctttgag ccagataatt | 2460 |
| aagagccaaa tgcaattggc tcaggctgcc atcgtccccc cgtgcgaaac ctgcacgtcc | 2520 |

```
gcgtcaaaga ataaccggc acctcttgct gtttttatca gttgagggct tgacggatcc   2580
gcctcaagtt tgcggcgcag ccgcaaaatg agaacatcta tactcctgtc gtaaacctcc   2640
tcgtcgcgta ctcgactggc aatgagaagt tgctcgcgcg atagaacgtc gcggggtttc   2700
tctaaaaacg cgaggagaag attgaactca cctgccgtaa gtttcacctc accgccagct   2760
tcggacatca agcgacgttg cctgagatta agtgtccagt cagtaaaaca aaaagaccgt   2820
cggtctttgg agcggacaac gttggggcgc acgcgcaagg caacccgaat gcgtgcaaga   2880
aactctctcg tactaaacgg cttagcgata aaatcacttg ctcctagctc gagtgcaaca   2940
actttatccg tctcctcaag gcggtcgcca ctgataatta tgattggaat atcagacttt   3000
gccgccagat ttcgaacgat ctcaagccca tcttcacgac ctaaatttag atcaacaacc   3060
acgacatcga ccgtcgcgga agagagtact ctagtgaact gggtgctgtc ggctaccgcg   3120
gtcactttga aggcgtggat cgtaaggtat tcgataataa gatgccgcat agcgacatcg   3180
tcatcgataa aagaacgtg tttcaacggc tcacctttca atctaaaatc tgaacccttg   3240
ttcacagcgc ttgagaaatt ttcacgtgaa ggatgtacaa tcatctccag ctaaatgggc   3300
agttcgtcag aattgcggct gaccgcggat gacgaaaatg cgaaccaagt atttcaattt   3360
tatgacaaaa gttctcaatc gttgttacaa gtgaaacgct tcgaggttac agctactatt   3420
gattaaggag atcgcctatg gtctcgcccc ggcgtcgtgc gtccgccgcg agccagatct   3480
cgcctacttc ataaacgtcc tcataggcac ggaatggaat gatgacatcg atcgccgtag   3540
agagcatgtc aatcagtgtg cgatcttcca agctagcacc ttgggcgcta cttttgacaa   3600
gggaaaacag tttcttgaat ccttggattg gattcgcgcc gtgtattgtt gaaatcgatc   3660
ccggatgtcc cgagacgact tcactcgagat aagcccatgc tgcatcgtcg cgcatctcgc   3720
caagcaatat ccggtccggc cgcatacgca gacttgcttg gagcaagtgc tcggcgctca   3780
cagcacccag cccagcaccg ttcttggagt agagtagtct aacatgatta tcgtgtggaa   3840
tgacgagttc gagcgtatct tctatggtga ttagcctttc ctgggggggg atggcgctga   3900
tcaaggtctt gctcattgtt gtcttgccgc ttccggtagg gccacatagc aacatcgtca   3960
gtcggctgac gacgcatgcg tgcagaaacg cttccaaatc cccgttgtca aaatgctgaa   4020
ggatagcttc atcatcctga ttttggcgtt tccttcgtgt ctgccactgg ttccacctcg   4080
aagcatcata acgggaggag acttctttaa gaccagaaac acgcgagctt ggccgtcgaa   4140
tggtcaagct gacggtgccc gagggaacgg tcggcggcag acagatttgt agtcgttcac   4200
caccaggaag ttcagtggcg cagaggggt tacgtggtcc gacatcctgc tttctcagcg   4260
cgcccgctaa aatagcgata tcttcaagat catcataaga gacgggcaaa ggcatcttgg   4320
taaaaatgcc ggcttggcgc acaaatgcct ctccaggtcg attgatcgca atttcttcag   4380
tcttcgggtc atcgagccat tccaaaatcg gcttcagaag aaagcgtagt tgcggatcca   4440
cttccatttta caatgtatcc tatctctaag cggaaatttg aattcattaa gagcggcggt   4500
tcctcccccg cgtggcgccg ccagtcaggc ggagctggta acaccaaag aaatcgaggt   4560
cccgtgctac gaaaatggaa acggtgtcac cctgattctt cttcagggtt ggcggtatgt   4620
tgatggttgc cttaagggct gtctcagttg tctgctcacc gttattttga aagctgttga   4680
agctcatccc gccacccgag ctgccggcgt aggtgctagc tgcctggaag gcgccttgaa   4740
caacactcaa gagcatagct ccgctaaaac gctgccagaa gtggctgtcg accgagcccg   4800
gcaatcctga gcgaccgagt tcgtccgcgc ttggcgatgt taacgagatc atcgcatggt   4860
```

```
caggtgtctc ggcgcgatcc cacaacacaa aaacgcgccc atctccctgt tgcaagccac    4920
gctgtatttc gccaacaacg gtggtgccac gatcaagaag cacgatattg ttcgttgttc    4980
cacgaatatc ctgaggcaag acacacttta catagcctgc caaatttgtg tcgattgcgg    5040
tttgcaagat gcacggaatt attgtccctt gcgttaccat aaaatcgggg tgcggcaaga    5100
gcgtggcgct gctgggctgc agctcggtgg gtttcatacg tatcgacaaa tcgttctcgc    5160
cggacacttc gccattcggc aaggagttgt cgtcacgctt gccttcttgt cttcggcccg    5220
tgtcgccctg aatggcgcgt tgctgaccc cttgatcgcc gctgctatat gcaaaaatcg    5280
gtgtttcttc cggccgtggc tcatgccgct ccggttcgcc cctcggcggt agaggagcag    5340
caggctgaac agcctcttga accgctggag gatccggcgg cacctcaatc ggagctggat    5400
gaaatggctt ggtgtttgtt gcgatcaaag ttgacggcga tgcgttctca ttcaccttct    5460
tttggcgccc acctagccaa atgaggctta atgataacgc gagaacgaca cctccgacga    5520
tcaatttctg agaccccgaa agacgccggc gatgtttgtc ggagaccagg gatccagatg    5580
catcaacctc atgtgccgct tgctgactat cgttattcat cccttcgccc ccttcaggac    5640
gcgtttcaca tcgggcctca ccgtgcccgt ttgcggcctt tggccaacgg gatcgtaagc    5700
ggtgttccag atacatagta ctgtgtggcc atccctcaga cgccaacctc gggaaaccga    5760
agaaatctcg acatcgctcc ctttaactga atagttggca acagcttcct tgccatcagg    5820
attgatggtg tagatggagg gtatgcgtac attgcccgga aagtggaata ccgtcgtaaa    5880
tccattgtcg aagacttcga gtggcaacag cgaacgatcg ccttgggcga cgtagtgcca    5940
attactgtcc gccgcaccaa gggctgtgac aggctgatcc aataaattct cagctttccg    6000
ttgatattgt gcttccgcgt gtagtctgtc cacaacagcc ttctgttgtg cctcccttcg    6060
ccgagccgcc gcatcgtcgg cggggtaggc gaattggacg ctgtaataga gatcgggctg    6120
ctctttatcg aggtgggaca gagtcttgga acttatactg aaaacataac ggcgcatccc    6180
ggagtcgctt gcgttagca cgattactgg ctgaggcgtg aggacctggc ttgccttgaa    6240
aaatagataa tttccccgcg gtagggctgc tagatctttg ctatttgaaa cggcaaccgc    6300
tgtcaccgtt tcgttcgtgg cgaatgttac gaccaaagta gctccaaccg ccgtcgagag    6360
gcgcaccact tgatcgggat tgtaagccaa ataacgcatg cgcggatcta gcttgcccgc    6420
cattggagtg tcttcagcct ccgcaccagt cgcagcggca aataaacatg ctaaaatgaa    6480
aagtgctttt ctgatcatgg ttcgctgtgg cctacgtttg aaacggtatc ttccgatgtc    6540
tgataggagg tgacaaccag acctgccggg ttggttagtc tcaatctgcc gggcaagctg    6600 gtcaccttt cgtagcgaac tgtcgcggtc cacgtactca ccacaggcat tttgccgtca    6660
acgacgaggg tccttttata gcgaatttgc tgcgtgcttg gagttacatc atttgaagcg    6720
atgtgctcga cctccaccct gccgcgtttg ccaagaatga cttgaggcga actgggattg    6780
ggatagttga agaattgctg gtaatcctgg cgcactgttg gggcactgaa gttcgatacc    6840
aggtcgtagg cgtactgagc ggtgtcggca tcataactct cgcgcaggcg aacgtactcc    6900
cacaatgagg cgttaacgac ggcctcctct tgagttgcag gcaatcgcga gacagacacc    6960
tcgctgtcaa cggtgccgtc cggccgtatc catagatata cgggcacaag cctgctcaac    7020
ggcaccattg tggctatagc gaacgcttga gcaacatttc ccaaaatcgc gatagctgcg    7080
acagctgcaa tgagtttgga gagacgtcgc gccgatttcg ctcgcgcggt ttgaaaggct    7140
tctacttcct tatagtgctc ggcaaggctt tcgcgcgcca ctagcatggc atattccaggc   7200 cccgtcatag cgtccacccg aattgccgag ctgaagatct gacggagtag gctgccatcg    7260
```

```
cccacattc agcgggaaga tcgggccttt gcagctcgct aatgtgtcgt ttgtctggca   7320
gccgctcaaa gcgacaacta ggcacagcag gcaatacttc atagaattct ccattgaggc   7380
gaattttgc gcgacctagc ctcgctcaac ctgagcgaag cgacggtaca agctgctggc    7440
agattgggtt gcgccgctcc agtaactgcc tccaatgttg ccggcgatcg ccggcaaagc   7500
gacaatgagc gcatcccctg tcagaaaaaa catatcgagt tcgtaaagac caatgatctt   7560
ggccgcggtc gtaccggcga aggtgattac accaagcata agggtgagcg cagtcgcttc   7620
ggttaggatg acgatcgttg ccacgaggtt taagaggaga agcaagagac cgtaggtgat   7680
aagttgcccg atccacttag ctgcgatgtc ccgcgtgcga tcaaaaatat atccgacgag   7740
gatcagaggc ccgatcgcga gaagcacttt cgtgagaatt ccaacggcgt cgtaaactcc   7800
gaaggcagac cagagcgtgc cgtaaaggac ccactgtgcc ccttggaaag caaggatgtc   7860
ctggtcgttc atcggaccga tttcggatgc gattttctga aaaacggcct gggtcacggc   7920
gaacattgta tccaactgtg ccggaacagt ctgcagaggc aagccggtta cactaaactg   7980
ctgaacaaag tttgggaccg tcttttcgaa gatggaaacc acatagtctt ggtagttagc   8040
ctgcccaaca attagagcaa caacgatggt gaccgtgatc acccgagtga taccgctacg   8100
ggtatcgact tcgccgcgta tgactaaaat accctgaaca ataatccaaa gagtgacaca   8160
ggcgatcaat ggcgcactca ccgcctcctg gatagtctca agcatcgagt ccaagcctgt   8220
cgtgaaggct acatcgaaga tcgtatgaat ggccgtaaac ggcgccggaa tcgtgaaatt   8280
catcgattgg acctgaactt gactggtttg tcgcataatg ttggataaaa tgagctcgca   8340
ttcggcgagg atgcgggcgg atgaacaaat cgcccagcct taggggaggg caccaaagat   8400
gacagcggtc tttgatgct ccttgcgttg agcggccgcc tcttccgcct cgtgaaggcc    8460
ggcctgcgcg gtagtcatcg ttaataggct tgtcgcctgt acattttgaa tcattgcgtc   8520
atggatctgc ttgagaagca aaccattggt cacggttgcc tgcatgatat tgcgagatcg   8580
ggaaagctga gcagacgtat cagcattcgc cgtcaagcgt ttgtccatcg tttccagatt   8640
gtcagccgca atgccagcgc tgtttgcgga accggtgatc tgcgatcgca acaggtccgc   8700
ttcagcatca ctacccacga ctgcacgatc tgtatcgctg gtgatcgcac gtgccgtggt   8760
cgacattggc attcgcggcg aaaacatttc attgtctagg tccttcgtcg aaggatactg   8820
atttttctgg ttgagcgaag tcagtagtcc agtaacgccg taggccgacg tcaacatcgt   8880
aaccatcgct atagtctgag tgagattctc cgcagtcgcg agcgcagtcg cgagcgtctc   8940
agcctccgtt gccgggtcgc taacaacaaa ctgcgcccgc gcgggctgaa tatatagaaa   9000
gctgcaggtc aaaactgttg caataagttg cgtcgtcttc atcgtttcct accttatcaa   9060
tcttctgcct cgtggtgacg ggccatgaat tcgctgagcc agccagatga gttgccttct   9120
tgtgcctcgc gtagtcgagt tgcaaagcgc accgtgttgg cacgccccga agcacggcg    9180
acatattcac gcatatcccg cagatcaaat tcgcagatga cgcttccact ttctcgttta   9240
agaagaaact tacggctgcc gaccgtcatg tcttcacgga tcgcctgaaa ttccttttcg   9300
gtacatttca gtccatcgac ataagccgat cgatctgcgg ttggtgatgg atagaaaatc   9360
ttcgtcatac attgcgcaac caagctgct cctagcggcg attccagaac atgctctggt    9420
tgctgcgttg ccagtattag catcccgttg ttttttcgaa cggtcaggag gaatttgtcg   9480
acgacagtcg aaaatttagg gtttaacaaa taggcgcgaa actcatcgca gctcatcaca   9540
aaacggcggc cgtcgatcat ggctccaatc cgatgcagga gatatgctgc agcgggagcg   9600
```

```
catacttcct cgtattcgag aagatgcgtc atgtcgaagc cggtaatcga cggatctaac    9660
tttacttcgt caacttcgcc gtcaaatgcc cagccaagcg catggcccg gcaccagcgt     9720
tggagccgcg ctcctgcgcc ttcggcgggc ccatgcaaca aaaattcacg taaccccgcg   9780
attgaacgca tttgtggatc aaacgagagc tgacgatgga taccacggac cagacggcgg   9840
ttctcttccg gagaaatccc accccgacca tcactctcga tgagagccac gatccattcg   9900
cgcagaaaat cgtgtgaggc tgctgtgttt tctaggccac gcaacggcgc caacccgctg   9960
ggtgtgcctc tgtgaagtgc caaatatgtt cctcctgtgg cgcgaaccag caattcgcca  10020
ccccggtcct tgtcaaagaa cacgaccgta cctgcacggt cgaccatgct ctgttcgagc  10080
atggctagaa caaacatcat gagcgtcgtc ttacccctcc cgataggccc gaatattgcc  10140
gtcatgccaa catcgtgctc atgcgggata tagtcgaaag gcgttccgcc attggtacga  10200
aatcgggcaa tcgcgttgcc ccagtggcct gagctggcgc cctctggaaa gttttcgaaa  10260
gagacaaacc ctgcgaaatt gcgtgaagtg attgcgccag ggcgtgtgcg ccacttaaaa  10320
ttccccggca attgggacca ataggccgct tccataccaa taccttcttg gacaaccacg  10380
gcacctgcat ccgccattcg tgtccgagcc cgcgcgcccc tgtccccaag actattgaga  10440
tcgtctgcat agacgcaaag gctcaaatga tgtgagccca taacgaattc gttgctcgca  10500
agtgcgtcct cagcctcgga taatttgccg atttgagtca cggctttatc gccggaactc  10560
agcatctggc tcgatttgag gctaagtttc gcgtgcgctt gcgggcgagt caggaacgaa  10620
aaactctgcg tgagaacaag tggaaaatcg agggatagca gcgcgttgag catgcccggc  10680
cgtgttttttg cagggtattc gcgaaacgaa tagatggatc caacgtaact gtcttttggc  10740
gttctgatct cgagtcctcg cttgccgcaa atgactctgt cggtataaat cgaagcgccg  10800
agtgagccgc tgacgaccgg aaccggtgtg aaccgaccag tcatgatcaa ccgtagcgct  10860
tcgccaattt cggtgaagag cacaccctgc ttctcgcgga tgccaagacg atgcaggcca  10920
tacgctttaa gagagccagc gacaacatgc caaagatctt ccatgttcct gatctggccc  10980
gtgagatcgt tttccctttt tccgcttagc ttggtgaacc tcctctttac cttccctaaa  11040
gccgcctgtg ggtagacaat caacgtaagg aagtgttcat tgcggaggag ttggccgag   11100
agcacgcgct gttcaaaagc ttcgttcagg ctagcggcga aaacactacg gaagtgtcgc  11160
ggcgccgatg atggcacgtc ggcatgacgt acgaggtgag catatattga cacatgatca  11220
tcagcgatat tgcgcaacag cgtgttgaac gcacgacaac gcgcattgcg catttcagtt  11280
tcctcaagct cgaatgcaac gccatcaatt ctcgcaatgg tcatgatcga tccgtcttca  11340
agaaggacga tatggtcgct gaggtggcca atataaggga gatagatctc accggatctt  11400
tcggtcgttc cactcgcgcc gagcatcaca ccattcctct ccctcgtggg ggaaccctaa  11460
ttggatttgg gctaacagta gcgccccccc aaactgcact atcaatgctt cttcccgcgg  11520
tccgcaaaaa tagcaggacg acgctcgccg cattgtagtc tcgctccacg atgagccggg  11580
ctgcaaacca taacggcacg agaacgactt cgtagagcgg gttctgaacg ataacgatga  11640
caaagccggc gaacatcatg aataaccctg ccaatgtcag tggcaccca agaaacaatg  11700
cgggccgtgt ggctgcgagg taaagggtcg attcttccaa acgatcagcc atcaactacc  11760
gccagtgagc gtttggccga ggaagctcgc cccaaacatg ataacaatgc cgccgacgac  11820
gccggcaacc agcccaagcg aagcccgccc gaacatccag gagatcccga tagcgacaat  11880
gccgagaaca gcgagtgact ggccgaacgg accaaggata aacgtgcata tattgttaac  11940
cattgtggcg gggtcagtgc cgccacccgc agattgcgct gcggcgggtc cggatgagga  12000
```

```
aatgctccat gcaattgcac cgcacaagct tggggcgcag ctcgatatca cgcgcatcat    12060
cgcattcgag agcgagaggc gatttagatg taaacggtat ctctcaaagc atcgcatcaa    12120
tgcgcacctc cttagtataa gtcgaataag acttgattgt cgtctgcgga tttgccgttg    12180
tcctggtgtg gcggtggcgg agcgattaaa ccgccagcgc catcctcctg cgagcggcgc    12240
tgatatgacc cccaaacatc ccacgtctct tcggatttta gcgcctcgtg atcgtctttt    12300
ggaggctcga ttaacgcggg caccagcgat tgagcagctg tttcaacttt tcgcacgtag    12360
ccgtttgcaa aaccgccgat gaaattaccg gtgttgtaag cggagatcgc ccgacgaagc    12420
gcaaattgct tctcgtcaat cgtttcgccg cctgcataac gacttttcag catgtttgca    12480
gcggcagata atgatgtgca cgcctggagc gcaccgtcag gtgtcagacc gagcatagaa    12540
aaatttcgag agtttatttg catgaggcca acatccagcg aatgccgtgc atcgagacgg    12600
tgcctgacga cttgggttgc ttggctgtga tcttgccagt gaagcgtttc gccggtcgtg    12660
ttgtcatgaa tcgctaaagg atcaaagcga ctctccacct tagctatcgc cgcaagcgta    12720
gatgtcgcaa ctgatggggc acacttgcga gcaacatggt caaactcagc agatgagagt    12780
ggcgtggcaa ggctcgacga acagaaggag accatcaagg caagagaaag cgaccccgat    12840
ctcttaagca taccttatct ccttagctcg caactaacac cgcctctccc gttggaagaa    12900
gtgcgttgtt ttatgttgaa gattatcggg agggtcggtt actcgaaaat tttcaattgc    12960
ttctttatga tttcaattga agcgagaaac ctcgcccggc gtcttggaac gcaacatgga    13020
ccgagaaccg cgcatccatg actaagcaac cggatcgacc tattcaggcc gcagttggtc    13080
aggtcaggct cagaacgaaa atgctcggcg aggttacgct gtctgtaaac ccattcgatg    13140
aacgggaagc ttccttccga ttgctcttgg caggaatatt ggcccatgcc tgcttgcgct    13200
ttgcaaatgc tcttatcgcg ttggtatcat atgccttgtc cgccagcaga aacgcactct    13260
aagcgattat ttgtaaaaat gtttcggtca tgcggcggtc atgggcttga cccgctgtca    13320
gcgcaagacg gatcggtcaa ccgtcggcat cgacaacagc gtgaatcttg gtggtcaaac    13380
cgccacggga acgtcccata cagccatcgt cttgatcccg ctgtttcccg tcgccgcatg    13440
ttggtggacg cggacacagg aactgtcaat catgacgaca ttctatcgaa agccttggaa    13500
atcacactca gaatatgatc ccagacgtct gcctcacgcc atcgtacaaa gcgattgtag    13560
caggttgtac aggaaccgta tcgatcagga acgtctgccc agggcgggcc cgtccggaag    13620
cgccacaaga tgacattgat cacccgcgtc aacgcgcggc acgcgacgcg gcttatttgg    13680
gaacaaagga ctgaacaaca gtccattcga aatcggtgac atcaaagcgg ggacgggtta    13740
tcagtggcct ccaagtcaag cctcaatgaa tcaaaatcag accgatttgc aaacctgatt    13800
tatgagtgtg cggcctaaat gatgaaatcg tccttctaga tcgcctccgt ggtgtagcaa    13860
cacctcgcag tatcgccgtg ctgaccttgg ccagggaatt gactggcaag ggtgctttca    13920
catgaccgct cttttggccg cgatagatga tttcgttgct gctttgggca cgtagaagga    13980
gagaagtcat atcggagaaa ttcctcctgg cgcgagagcc tgctctatcg cgacggcatc    14040
ccactgtcgg gaacagaccg gatcattcac gaggcgaaag tcgtcaacac atgcgttata    14100
ggcatcttcc cttgaaggat gatcttgttg ctgccaatct ggaggtgcgg cagccgcagg    14160
cagatgcgat ctcagcgcaa cttgcggcaa acatctcac tcacctgaaa accactagcg    14220
agtctcgcga tcgacgaag gccttttact taacgacaca atatccgatg tctgcatcac    14280
aggcgtcgct atcccagtca atactaaagc ggtgcaggaa ctaaagatta ctgatgactt    14340
```

```
aggcgtgcca cgaggcctga gacgacgcgc gtagacagtt ttttgaaatc attatcaaag   14400
tgatggcctc cgctgaagcc tatcacctct gcgccggtct gtcggagaga tgggcaagca   14460
ttattacggt cttcgcgccc gtacatgcat tggacgattg cagggtcaat ggatctgaga   14520
tcatccagag gattgccgcc cttaccttcc gtttcgagtt ggagccagcc cctaaatgag   14580
acgacatagt cgacttgatg tgacaatgcc aagagagaga tttgcttaac ccgattttt    14640
tgctcaagcg taagcctatt gaagcttgcc ggcatgacgt ccgcgccgaa agaatatcct   14700
acaagtaaaa cattctgcac accgaaatgc ttggtgtaga catcgattat gtgaccaaga   14760
tccttagcag tttcgcttgg ggaccgctcc gaccagaaat accgaagtga actgacgcca   14820
atgacaggaa tcccttccgt ctgcagatag gtaccatcga tagatctgct gcctcgcgcg   14880
tttcggtgat gacggtgaaa acctctgaca catgcagctc ccggagacgg tcacagcttg   14940
tctgtaagcg gatgccggga gcagacaagc ccgtcagggc gcgtcagcgg gtgttggcgg   15000
gtgtcgggc gcagccatga cccagtcacg tagcgatagc ggagtgtata ctggcttaac    15060
tatgcggcat cagagcagat tgtactgaga gtgcaccata tgcggtgtga aataccgcac   15120
agatgcgtaa ggagaaaata ccgcatcagg cgctcttccg cttcctcgct cactgactcg   15180
ctgcgctcgg tcgttcggct gcggcgagcg gtatcagctc actcaaaggc ggtaatacgg   15240
ttatccacag aatcagggga taacgcagga agaacatgt gagcaaaagg ccagcaaaag    15300
gccaggaacc gtaaaaaggc cgcgttgctg gcgttttcc ataggctccg cccccctgac    15360
gagcatcaca aaaatcgacg ctcaagtcag aggtggcgaa acccgacagg actataaaga   15420
taccaggcgt ttccccctgg aagctccctc gtgcgctctc ctgttccgac cctgccgctt   15480
accggatacc tgtccgcctt tctcccttcg ggaagcgtgg cgctttctca tagctcacgc   15540
tgtaggtatc tcagttcggt gtaggtcgtt cgctccaagc tgggctgtgt gcacgaaccc   15600
cccgttcagc ccgaccgctg cgccttatcc ggtaactatc gtcttgagtc aacccggta    15660
agacacgact tatcgccact ggcagcagcc actggtaaca ggattagcag agcgaggtat   15720
gtaggcggtg ctacagagtt cttgaagtgg tggcctaact acggctacac tagaaggaca   15780
gtatttggta tctgcgctct gctgaagcca gttaccttcg gaaaaagagt tggtagctct   15840
tgatccggca acaaaccac cgctggtagc ggtggttttt ttgtttgcaa gcagcagatt     15900
acgcgcagaa aaaaggatc tcaagaagat cctttgatct tttctacggg gtctgacgct   15960
cagtggaacg aaaactcacg ttaagggatt ttggtcatga gattatcaaa aaggatcttc   16020
acctagatcc ttttaaatta aaaatgaagt tttaaatcaa tctaaagtat atatgagtaa   16080
acttggtctg acagttacca atgcttaatc agtgaggcac ctatctcagc gatctgtcta   16140
tttcgttcat ccatagttgc ctgactcccc gtcgtgtaga taactacgat acgggagggc   16200
ttaccatctg gccccagtgc tgcaatgata ccgcgagacc cacgctcacc ggctccagat   16260
ttatcagcaa taaccagcc agccggaagg gccgagcgca gaagtggtcc tgcaacttta   16320
tccgcctcca tccagtctat taattgttgc cgggaagcta gagtaagtag ttcgccagtt   16380
aatagtttgc gcaacgttgt tgccattgct gcagggggg ggggggggg gttccattgt     16440
tcattccacg gacaaaaaca gagaaaggaa acgacagagg ccaaaaagct cgctttcagc   16500
acctgtcgtt tccttttctt tcagagggta ttttaaataa aaacattaag ttatgacgaa   16560
gaagaacgga aacgccttaa accggaaaat tttcataaat agcgaaaacc cgcgaggtcg   16620
ccgccccgta acctgtcgga tcaccggaaa ggacccgtaa agtgataatg attatcatct   16680
acatatcaca acgtgcgtgg aggccatcaa accacgtcaa ataatcaatt atgacgcagg   16740
```

```
tatcgtatta attgatctgc atcaacttaa cgtaaaaaca acttcagaca atacaaatca    16800
gcgacactga atacggggca acctcatgtc cccccccccc cccccctgc aggcatcgtg     16860
gtgtcacgct cgtcgtttgg tatggcttca ttcagctccg gttcccaacg atcaaggcga    16920
gttacatgat cccccatgtt gtgcaaaaaa gcggttagct ccttcggtcc tccgatcgtt    16980
gtcagaagta agttggccgc agtgttatca ctcatggtta tggcagcact gcataattct    17040
cttactgtca tgccatccgt aagatgcttt tctgtgactg gtgagtactc aaccaagtca    17100
ttctgagaat agtgtatgcg gcgaccgagt tgctcttgcc cggcgtcaac acgggataat    17160
accgcgccac atagcagaac tttaaaagtg ctcatcattg gaaaacgttc ttcggggcga    17220
aaactctcaa ggatcttacc gctgttgaga tccagttcga tgtaacccac tcgtgcaccc    17280
aactgatctt cagcatcttt tactttcacc agcgttctg ggtgagcaaa acaggaagg     17340
caaaatgccg caaaaagggg aataagggcg acacggaaat gttgaatact catactcttc    17400
cttttcaat attattgaag catttatcag ggttattgtc tcatgagcgg atacatattt     17460
gaatgtattt agaaaaataa acaaataggg gttccgcgca catttccccg aaaagtgcca    17520
cctgacgtct aagaaaccat tattatcatg acattaacct ataaaaatag gcgtatcacg    17580
aggcccttc gtcttcaaga attcggagct tttgccattc tcaccggatt cagtcgtcac     17640
tcatggtgat ttctcacttg ataaccttat ttttgacgag gggaaattaa taggttgtat    17700
tgatgttgga cgagtcggaa tcgcagaccg ataccaggat cttgccatcc tatggaactg    17760
cctcggtgag ttttctcctt cattacagaa acggcttttt caaaaatatg gtattgataa    17820
tcctgatatg aataaattgc agtttcattt gatgctcgat gagtttttct aatcagaatt    17880
ggttaattgg ttgtaacact ggcagagcat tacgctgact tgacgggacg gcggctttgt    17940
tgaataaatc gaacttttgc tgagttgaag gatcagatca cgcatcttcc cgacaacgca    18000
gaccgttccg tggcaaagca aaagttcaaa atcaccaact ggtccaccta caacaaagct    18060
ctcatcaacc gtggctccct cactttctgg ctggatgatg gggcgattca ggcctggtat    18120
gagtcagcaa caccttcttc acgaggcaga cctcagcgcc agaaggccgc cagagaggcc    18180
gagcgcggcc gtgaggcttg gacgctaggg caggcatga aaaagcccgt agcgggctgc     18240
tacgggcgtc tgacgcggtg gaaaggggga ggggatgttg tctacatggc tctgctgtag    18300
tgagtgggtt gcgctccggc agcggtcctg atcaatcgtc accctttctc ggtccttcaa    18360
cgttcctgac aacgagcctc cttttcgcca atccatcgac aatcaccgcg agtccctgct    18420
cgaacgctgc gtccggaccg gcttcgtcga aggcgtctat cgcggcccgc aacagcggcg    18480
agagcggagc ctgttcaacg gtgccgccgc gctcgccggc atcgctgtcg ccggcctgct    18540
cctcaagcac ggccccaaca gtgaagtagc tgattgtcat cagcgcattg acggcgtccc    18600
cggccgaaaa accgcctcg cagaggaagc gaagctgcgc gtcggccgtt ccatctgcg     18660
gtgcgcccgg tcgcgtgccg gcatggatgc gcgcgccatc gcgtaggcg agcagcgcct     18720
gcctgaagct gcgggcattc ccgatcagaa atgagcgcca gtcgtcgtcg gctctcggca    18780
ccgaatgcgt atgattctcc gccagcatgg cttcggccag tgcgtcgagc agcgcccgct    18840
tgttcctgaa gtgccagtaa agcgccggct gctgaacccc caaccgttcc gccagtttgc    18900
gtgtcgtcag accgtctacg ccgacctcgt tcaacaggtc cagggcggca cggatcactg    18960
tattcggctg caactttgtc atgcttgaca ctttatcact gataaacata atatgtccac    19020
caacttatca gtgataaaga atccgcgcgt tcaatcggac cagcggaggc tggtccggag    19080
```

```
gccagacgtg aaacccaaca taccoctgat cgtaattctg agcactgtcg cgctcgacgc   19140
tgtcggcatc ggcctgatta tgccggtgct gccgggcctc ctgcgcgatc tggttcactc   19200
gaacgacgtc accgcccact atggcattct gctggcgctg tatgcgttgg tgcaatttgc   19260
ctgcgcacct gtgctgggcg cgctgtcgga tcgtttcggg cggcggccaa tcttgctcgt   19320
ctcgctggcc ggcgccactg tcgactacgc catcatggcg acagcgcctt cctttgggt   19380 tctctatatc gggcggatcg tggccggcat caccggggcg actggggcgg tagccggcgc   19440
ttatattgcc gatatcactg atggcgatga gcgcgcgcgg cacttcggct tcatgagcgc   19500
ctgtttcggg ttcgggatgg tcgcgggacc tgtgctcggt gggctgatgg gcggtttctc   19560
cccccacgct ccgttcttcg ccgcggcagc cttgaacggc ctcaatttcc tgacgggctg   19620
tttccttttg ccggagtcgc acaaaggcga acgccggccg ttacgccggg aggctctcaa   19680
cccgctcgct tcgttccggt gggcccgggg catgaccgtc gtcgccgccc tgatggcggt   19740
cttcttcatc atgcaacttg tcggacaggt gccggccgcg cttgtgggtca ttttcggcga   19800 ggatcgcttt cactgggacg cgaccacgat cggcatttcg cttgccgcat ttggcattct   19860
gcattcactc gcccaggcaa tgatcaccgg ccctgtagcc gccggctcg gcgaaaggcg   19920 ggcactcatg ctcggaatga ttgccgacgg cacaggctac atcctgcttg ccttcgcgac   19980
acggggatgg atggcgttcc cgatcatggt cctgcttgct tcgggtggca tcggaatgcc   20040
ggcgctgcaa gcaatgttgt ccaggcaggt ggatgaggaa cgtcagggggc agctgcaagg   20100 ctcactggcg gcgctcacca gcctgacctc gatcgtcgga cccctcctct tcacggcgat   20160
ctatgcggct tctataacaa cgtggaacgg gtgggcatgg attgcaggcg ctgcccctcta   20220 cttgctctgc ctgccggcgc tgcgtcgcgg gctttggagc ggcgcagggc aacgagccga   20280
tcgctgatcg tggaaacgat aggcctatgc catgcgggtc aaggcgactt ccggcaagct   20340
atacgcgccc taggagtgcg gttggaacgt tggcccagcc agatactccc gatcacgagc   20400
aggacgccga tgatttgaag cgcactcagc gtctgatcca agaacaacca tcctagcaac   20460
acggcggtcc ccgggctgag aaagcccagt aaggaaacaa ctgtaggttc gagtcgcgag   20520
atcccccgga accaaaggaa gtaggttaaa cccgctccga tcaggccgag ccacgccagg   20580
ccgagaacat tggttcctgt aggcatcggg attggcggat caaacactaa agctactgga   20640
acgagcagaa gtcctccggc cgccagttgc caggcggtaa aggtgagcag aggcacggga   20700
ggttgccact tgcgggtcag cacggttccg aacgccatgg aaaccgcccc cgccaggccc   20760
gctgcgacgc cgacaggatc tagcgctgcg tttggtgtca acaccaacag cgccacgccc   20820
gcagttccgc aaatagcccc caggaccgcc atcaatcgta tcgggctacc tagcagagcg   20880
gcagagatga acacgaccat cagcggctgc acagcgccta ccgtcgccgc gaccccgccc   20940
ggcaggcggt agaccgaaat aaacaacaag ctccagaata gcgaaatatt aagtgcgccg   21000
aggatgaaga tgcgcatcca ccagattccc gttggaatct gtcggacgat catcacgagc   21060
aataaacccg ccggcaacgc ccgcagcagc ataccggcga cccctcggcc tcgctgttcg   21120
ggctccacga aaacgccgga cagatgcgcc ttgtgagcgt ccttgggggcc gtcctcctgt   21180 ttgaagaccg acagcccaat gatctcgccg tcgatgtagg cgccgaatgc cacggcatct   21240
cgcaaccgtt cagcgaacgc ctccatgggc tttttctcct cgtgctcgta aacggacccg   21300
aacatctctg gagctttctt cagggccgac aatcggatct cgcggaaatc ctgcacgtcg   21360
gccgctccaa gccgtcgaat ctgagcctta atcacaattg tcaattttaa tcctctgttt   21420
atcggcagtt cgtagagcgc gccgtgcgtc ccgagcgata ctgagcgaag caagtgcgtc   21480
```

```
gagcagtgcc cgcttgttcc tgaaatgcca gtaaagcgct ggctgctgaa cccccagccg   21540
gaactgaccc cacaaggccc tagcgtttgc aatgcaccag gtcatcattg acccaggcgt   21600
gttccaccag gccgctgcct cgcaactctt cgcaggcttc gccgacctgc tcgcgccact   21660
tcttcacgcg gtggaatcc gatccgcaca tgaggcggaa ggtttccagc ttgagcgggt    21720
acggctcccg gtgcgagctg aaatagtcga acatccgtcg ggccgtcggc gacagcttgc   21780
ggtacttctc ccatatgaat ttcgtgtagt ggtcgccagc aaacagcacg acgatttcct   21840
cgtcgatcag gacctggcaa cgggacgttt tcttgccacg gtccaggacg cggaagcgt    21900 gcagcagcga caccgattcc aggtgcccaa cgcggtcgga cgtgaagccc atcgccgtcg   21960
cctgtaggcg cgacaggcat tcctcggcct tcgtgtaata ccggccattg atcgaccagc   22020
ccaggtcctg gcaaagctcg tagaacgtga aggtgatcgg ctcgccgata ggggtgcgct   22080
tcgcgtactc caacacctgc tgccacacca gttcgtcatc gtcggcccgc agctcgacgc   22140
cggtgtaggt gatcttcacg tccttgttga cgtggaaaat gaccttgttt tgcagcgcct   22200
cgcgcgggat tttcttgttg cgcgtggtga acagggcaga gcgggccgtg tcgtttggca   22260
tcgctcgcat cgtgtccggc cacggcgcaa tatcgaacaa ggaaagctgc atttccttga   22320
tctgctgctt cgtgtgtttc agcaacgcgg cctgcttggc ctcgctgacc tgttttgcca   22380
ggtcctcgcc ggcggttttt cgcttcttgg tcgtcatagt tcctcgcgtg tcatggtca    22440 tcgacttcgc caaacctgcc gcctcctgtt cgagacgacg cgaacgctcc acggcggccg   22500
atggcgcggg cagggcaggg ggagccagtt gcacgctgtc gcgctcgatc ttggccgtag   22560
cttgctggac catcgagccg acggactgga aggtttcgcg gggcgcacgc atgacggtgc   22620
ggcttgcgat ggtttcggca tcctcggcgg aaaaccccgc gtcgatcagt tcttgcctgt   22680
atgccttccg gtcaaacgtc cgattcattc accctccttg cgggattgcc ccgactcacg   22740
ccggggcaat gtgcccttat tcctgatttg acccgcctgg tgccttggtg tccagataat   22800
ccaccttatc ggcaatgaag tcggtcccgt agaccgtctg gccgtccttc tcgtacttgg   22860
tattccgaat cttgccctgc acgaatacca gcgaccccct tgcccaaatac ttgccgtggg   22920 cctcggcctg agagccaaaa cacttgatgc ggaagaagtc ggtgcgctcc tgcttgtcgc   22980
cggcatcgtt gcgccactct tcattaaccg ctatatcgaa aattgcttgc ggcttgttag   23040
aattgccatg acgtacctcg gtgtcacggg taagattacc gataaactgg aactgattat   23100
ggctcatatc gaaagtctcc ttgagaaagg agactctagt ttagctaaac attggttccg   23160
ctgtcaagaa ctttagcggc taaaattttg cgggccgcga ccaaaggtgc gaggggcggc   23220
ttccgctgtg tacaaccaga tattttttcac caacatcctt cgtctgctcg atgagcgggg   23280
catgacgaaa catgagctgt cggagagggc aggggtttca atttcgtttt tatcagactt   23340
aaccaacggt aaggccaacc cctcgttgaa ggtgatggag gccattgccg acgccctgga   23400
aactccccta cctcttctcc tggagtccac cgaccttgac cgcgaggcac tcgcggagat   23460
tgcgggtcat cctttcaaga gcagcgtgcc gcccggatac gaacgcatca gtgtggtttt   23520
gccgtcacat aaggcgttta tcgtaaagaa atggggcgac gacacccgaa aaaagctgcg   23580
tggaaggctc tgacgccaag ggttagggct tgcacttcct tctttagccg ctaaaacggc   23640
cccttctctg cgggccgtcg gctcgcgcat catatcgaca tcctcaacgg aagccgtgcc   23700
gcgaatggca tcgggcgggt gcgctttgac agttgttttc tatcagaacc cctacgtcgt   23760
gcggttcgat tagctgtttg tcttgcaggc taaacacttt cggtatatcg tttgcctgtg   23820
```

```
cgataatgtt gctaatgatt tgttgcgtag gggttactga aaagtgagcg ggaaagaaga    23880
gtttcagacc atcaaggagc gggccaagcg caagctggaa cgcgacatgg gtgcggacct    23940
gttggccgcg ctcaacgacc cgaaaaccgt tgaagtcatg ctcaacgcgg acggcaaggt    24000
gtggcacgaa cgccttggcg agccgatgcg gtacatctgc gacatgcggc ccagccagtc    24060
gcaggcgatt atagaaacgg tggccggatt ccacggcaaa gaggtcacgc ggcattcgcc    24120
catcctggaa ggcgagttcc ccttggatgg cagccgcttt gccggccaat tgccgccggt    24180
cgtggccgcg ccaacctttg cgatccgcaa gcgcgcggtc gccatcttca cgctggaaca    24240
gtacgtcgag gcgggcatca tgacccgcga gcaatacgag gtcattaaaa gcgccgtcgc    24300
ggcgcatcga aacatcctcg tcattggcgg tactggctcg ggcaagacca cgctcgtcaa    24360
cgcgatcatc aatgaaatgg tcgccttcaa cccgtctgag cgcgtcgtca tcatcgagga    24420
caccggcgaa atccagtgcg ccgcagagaa cgccgtccaa taccacacca gcatcgacgt    24480
ctcgatgacg ctgctgctca agacaacgct gcgtatgcgc cccgaccgca tcctggtcgg    24540
tgaggtacgt ggccccgaag cccttgatct gttgatggcc tggaacaccg gcatgaaggg    24600
aggtgccgcc accctgcacg caaacaaccc caaagcgggc ctgagccggc tcgccatgct    24660
tatcagcatg cacccggatt caccgaaacc cattgagccg ctgattggcg aggcggttca    24720
tgtggtcgtc catatcgcca ggaccccctag cggccgtcga gtgcaagaaa ttctcgaagt    24780
tcttggttac gagaacggcc agtacatcac caaaaccctg taaggagtat ttccaatgac    24840
aacggctgtt ccgttccgtc tgaccatgaa tcgcggcatt tgttctacc ttgccgtgtt    24900 cttcgttctc gctctcgcgt tatccgcgca tccggcgatg gcctcggaag caccggcgg    24960 cagcttgcca tatgagagct ggctgacgaa cctgcgcaac tccgtaaccg gcccggtggc    25020
cttcgcgctg tccatcatcg gcatcgtcgt cgccggcggc gtgctgatct tcggcggcga    25080
actcaacgcc ttcttccgaa ccctgatctt cctggttctg gtgatggcgc tgctggtcgg    25140
cgcgcagaac gtgatgagca ccttcttcgg tcgtggtgcc gaaatcgcgg ccctcggcaa    25200
cggggcgctg caccaggtgc aagtcgcggc ggcggatgcc gtgcgtgcgg tagcggctgg    25260
acggctcgcc taatcatggc tctgcgcacg atccccatcc gtcgcgcagg caaccgagaa    25320
aacctgttca tgggtggtga tcgtgaactg gtgatgttct cgggcctgat ggcgtttgcg    25380
ctgattttca gcgcccaaga gctgcgggcc accgtggtcg gtctgatcct gtggttcggg    25440
gcgctctatg cgttccgaat catggcgaag gccgatccga agatgcggtt cgtgtacctg    25500
cgtcaccgcc ggtacaagcc gtattacccg gcccgctcga ccccgttccg cgagaacacc    25560
aatagccaag ggaagcaata ccgatgatcc aagcaattgc gattgcaatc gcgggcctcg    25620
gcgcgcttct gttgttcatc ctctttgccc gcatccgcgc ggtcgatgcc gaactgaaac    25680
tgaaaaagca tcgttccaag gacgccggcc tggccgatct gctcaactac gccgctgtcg    25740
tcgatgacgg cgtaatcgtg ggcaagaacg gcagctttat ggctgcctgg ctgtacaagg    25800
gcgatgacaa cgcaagcagc accgaccagc agcgcgaagt agtgtccgcc cgcatcaacc    25860
aggccctcgc gggcctggga agtgggtgga tgatccatgt ggacgccgtg cggcgtcctg    25920
ctccgaacta cgcggagcgg ggcctgtcgg cgttccctga ccgtctgacg gcagcgattg    25980
aagaagagcg ctcggtcttg ccttgctcgt cggtgatgta cttcaccagc tccgcgaagt    26040
cgctcttctt gatggagcgc atggggacgt gcttggcaat cacgcgcacc ccccggccgt    26100
tttagcggct aaaaaagtca tggctctgcc ctcgggcgga ccacgccat catgaccttg    26160 ccaagctcgt cctgcttctc ttcgatcttc gccagcaggg cgaggatcgt ggcatcaccg    26220
```

```
aaccgcgccg tgcgcgggtc gtcggtgagc cagagtttca gcaggccgcc caggcggccc   26280
aggtcgccat tgatgcgggc cagctcgcgg acgtgctcat agtccacgac gcccgtgatt   26340
ttgtagccct ggccgacggc cagcaggtag gccgacaggc tcatgccggc cgccgccgcc   26400
ttttcctcaa tcgctcttcg ttcgtctgga aggcagtaca ccttgatagg tgggctgccc   26460
ttcctggttg gcttggtttc atcagccatc cgcttgccct catctgttac gccggcggta   26520
gccggccagc ctcgcagagc aggattcccg ttgagcaccg ccaggtgcga ataagggaca   26580
gtgaagaagg aacacccgct cgcgggtggg cctacttcac ctatcctgcc cggctgacgc   26640
cgttggatac accaaggaaa gtctacacga acccttggc aaaatcctgt atatcgtgcg   26700
aaaaaggatg gatataccga aaaaatcgct ataatgaccc cgaagcaggg ttatgcagcg   26760
gaaaagcgct gcttccctgc tgttttgtgg aatatctacc gactggaaac aggcaaatgc   26820
aggaaattac tgaactgagg ggacaggcga gagacgatgc caaagagcta caccgacgag   26880
ctggccgagt gggttgaatc ccgcgcggcc aagaagcgcc ggcgtgatga ggctgcggtt   26940
gcgttcctgg cggtgagggc ggatgtcgag gcggcgttag cgtccggcta tgcgctcgtc   27000
accatttggg agcacatgcg ggaaacgggg aaggtcaagt tctcctacga gacgttccgc   27060
tcgcacgcca ggcggcacat caaggccaag cccgccgatg tgcccgcacc gcaggccaag   27120
gctgcggaac ccgcgccggc acccaagacg ccggagccac ggcggccgaa gcaggggggc   27180
aaggctgaaa agccggcccc cgctgcggcc ccgaccggct tcaccttcaa cccaacaccg   27240
gacaaaaagg atctactgta atggcgaaaa ttcacatggt tttgcagggc aagggcgggg   27300
tcggcaagtc ggccatcgcc gcgatcattg cgcagtacaa gatggacaag gggcagacac   27360
ccttgtgcat cgacaccgac ccggtgaacg cgacgttcga gggctacaag gccctgaacg   27420
tccgccggct gaacatcatg gccggcgacg aaattaactc gcgcaacttc gacaccctgg   27480
tcgagctgat tgcgccgacc aaggatgacg tggtgatcga caacggtgcc agctcgttcg   27540
tgcctctgtc gcattacctc atcagcaacc aggtgccggc tctgctgcaa gaaatggggc   27600
atgagctggt catccatacc gtcgtcaccg gcggccaggc tctcctggac acggtgagcg   27660
gcttcgccca gctcgccagc cagttcccgg ccgaagcgct tttcgtggtc tggctgaacc   27720
cgtattgggg gcctatcgag catgagggca agagctttga gcagatgaag gcgtacacgg   27780
ccaacaaggc ccgcgtgtcg tccatcatcc agattccggc cctcaaggaa gaaacctacg   27840
gccgcgattt cagcgacatg ctgcaagagc ggctgacgtt cgaccaggcg ctggccgatg   27900
aatcgctcac gatcatgacg cggcaacgcc tcaagatcgt gcggcgcggc ctgtttgaac   27960
agctcgacgc ggcggccgtg ctatgagcga ccagattgaa gagctgatcc gggagattgc   28020
ggccaagcac ggcatcgccg tcggccgcga cgacccggtg ctgatcctgc ataccatcaa   28080
cgcccggctc atggccgaca gtgcggccaa gcaagaggaa atccttgccg cgttcaagga   28140
agagctggaa gggatcgccc atcgttgggg cgaggacgcc aaggccaaag cggagcggat   28200
gctgaacgcg gccctggcgg ccagcaagga cgcaatggcg aaggtaatga aggacagcgc   28260
cgcgcaggcg gccgaagcga tccgcaggga aatcgacgac ggccttggcc gccagctcgc   28320
ggccaaggtc gcggacgcgc ggcgcgtggc gatgatgaac atgatcgccg gcggcatggt   28380
gttgttcgcg gccgccctgg tggtgtgggc ctcgttatga atcgcagagg cgcagatgaa   28440
aaagcccggc gttgccgggc tttgtttttg cgttagctgg gcttgtttga caggcccaag   28500
ctctgactgc gcccgcgctc gcgctcctgg gcctgtttct tctcctgctc ctgcttgcgc   28560
```

```
atcagggcct ggtgccgtcg ggctgcttca cgcatcgaat cccagtcgcc ggccagctcg   28620
ggatgctccg cgcgcatctt gcgcgtcgcc agttcctcga tcttgggcgc gtgaatgccc   28680
atgccttcct tgatttcgcg caccatgtcc agccgcgtgt gcagggtctg caagcgggct   28740
tgctgttggg cctgctgctg ctgccaggcg gcctttgtac gcggcaggga cagcaagccg   28800
ggggcattgg actgtagctg ctgcaaacgc gcctgctgac ggtctacgag ctgttctagg   28860
cggtcctcga tgcgctccac ctggtcatgc tttgcctgca cgtagagcgc aagggtctgc   28920
tggtaggtct gctcgatggg cgcggattct aagagggcct gctgttccgt ctcggcctcc   28980
tgggccgcct gtagcaaatc ctcgccgctg ttgccgctgg actgctttac tgccggggac   29040
tgctgttgcc ctgctcgcgc cgtcgtcgca gttcggcttg cccccactcg attgactgct   29100
tcatttcgag ccgcagcgat gcgatctcgg attgcgtcaa cggacggggc agcgcggagg   29160
tgtccggctt ctccttgggt gagtcggtcg atgccatagc caaaggtttc cttccaaaat   29220
gcgtccattg ctggaccgtg tttctcattg atgcccgcaa gcatcttcgg cttgaccgcc   29280
aggtcaagcg cgccttcatg ggcggtcatg acggacgccg ccatgacctt gccgccgttg   29340
ttctcgatgt agccgcgtaa tgaggcaatg gtgccgccca tcgtcagcgt gtcatcgaca   29400
acgatgtact tctggccggg gatcacctcc ccctcgaaag tcgggttgaa cgccaggcga   29460
tgatctgaac cggctccggt tcgggcgacc ttctcccgct gcacaatgtc cgtttcgacc   29520
tcaaggccaa ggcggtcggc cagaacgacc gccatcatgg ccggaatctt gttgttcccc   29580
gccgcctcga cggcgaggac tggaacgatg cggggcttgt cgtcgccgat cagcgtcttg   29640
agctgggcaa cagtgtcgtc cgaaatcagg cgctcgacca aattaagcgc cgcttccgcg   29700
tcgccctgct tcgcagcctg gtattcaggc tcgttggtca agaaccaag gtcgccgttg   29760
cgaaccacct tcgggaagtc tccccacggt gcgcgctcgg ctctgctgta gctgctcaag   29820
acgcctccct ttttagccgc taaaactcta acgagtgcgc ccgcgactca acttgacgct   29880
ttcggcactt acctgtgcct tgccacttgc gtcataggtg atgcttttcg cactcccgat   29940
ttcaggtact ttatcgaaat ctgaccgggc gtgcattaca aagttcttcc ccacctgttg   30000
gtaaatgctg ccgctatctg cgtggacgat gctgccgtcg tggcgctgcg acttatcggc   30060
cttttgggcc atatagatgt tgtaaatgcc aggtttcagg gccccggctt tatctacctt   30120
ctggttcgtc catgcgcctt ggttctcggt ctggacaatt cttttgcccat tcatgaccag   30180
gaggcggtgt tcattgggt gactcctgac ggttgcctct ggtgttaaac gtgtcctggt   30240
cgcttgccgg ctaaaaaaaa gccgacctcg gcagttcgag gccggctttc cctagagccg   30300
ggcgcgtcaa ggttgttcca tctatttag tgaactgcgt tcgatttatc agttactttc   30360
ctcccgcttt gtgtttcctc ccactcgttt ccgcgtctag ccgacccctc aacatagcgg   30420
cctcttcttg ggctgccttt gcctcttgcc gcgcttcgtc acgctcggct tgcaccgtcg   30480
taaagcgctc ggcctgcctg gccgcctctt gcgccgccaa cttcctttgc tcctggtggg   30540
cctcggcgtc ggcctgcgcc ttcgctttca ccgctgccaa ctccgtgcgc aaactctccg   30600
cttcgcgcct ggtggcgtcg cgctcgccgc gaagcgcctg catttcctgg ttggccgcgt   30660
ccagggtctt gcgctctct tctttgaatg cgcgggcgtc ctggtgagcg tagtccagct   30720
cggcgcgcag ctcctgcgct cgacgctcca cctcgtcggc ccgctgcgtc gccagcgcgg   30780
cccgctgctc ggctcctgcc agggcggtgc gtgcttcggc cagggcttgc cgctggcgtg   30840
cggccagctc ggccgcctcg gcggcctgct gctctagcaa tgtaacgcgc gcctgggctt   30900
cttccagctc gcgggcctgc gcctcgaagg cgtcggccag ctccccgcgc acggcttcca   30960
```

```
actcgttgcg ctcacgatcc cagccggctt gcgctgcctg caacgattca ttggcaaggg    31020
cctgggcggc ttgccagagg gcggccacgg cctggttgcc ggcctgctgc accgcgtccg    31080
gcacctggac tgccagcggg gcggcctgcg ccgtgcgctg gcgtcgccat tcgcgcatgc    31140
cggcgctggc gtcgttcatg ttgacgcggg cggccttacg cactgcatcc acggtcggga    31200
agttctcccg gtcgccttgc tcgaacagct cgtccgcagc cgcaaaaatg cggtcgcgcg    31260
tctctttgtt cagttccatg ttggctccgg taattggtaa gaataataat actcttacct    31320
accttatcag cgcaagagtt tagctgaaca gttctcgact taacggcagg ttttttagcg    31380
gctgaagggc aggcaaaaaa agccccgcac ggtcggcggg ggcaaagggt cagcgggaag    31440
gggattagcg ggcgtcgggc ttcttcatgc gtcggggccg cgcttcttgg gatggagcac    31500
gacgaagcgc gcacgcgcat cgtcctcggc cctatcggcc cgcgtcgcgg tcaggaactt    31560
gtcgcgcgct aggtcctccc tggtgggcac caggggcatg aactcggcct gctcgatgta    31620
ggtccactcc atgaccgcat cgcagtcgag gccgcgttcc ttcaccgtct cttgcaggtc    31680
gcggtacgcc cgctcgttga gcggctggta acgggccaat tggtcgtaaa tggctgtcgg    31740
ccatgagcgg cctttcctgt tgagccagca gccgacgacg aagccggcaa tgcaggcccc    31800
tggcacaacc aggccgacgc cgggggcagg ggatggcagc agctcgccaa ccaggaaccc    31860
cgccgcgatg atgccgatgc cggtcaacca gcccttgaaa ctatccggcc ccgaaacacc    31920
cctgcgcatt gcctggatgc tgcgccggat agcttgcaac atcaggagcc gtttcttttg    31980
ttcgtcagtc atggtccgcc ctcaccagtt gttcgtatcg gtgtcggacg aactgaaatc    32040
gcaagagctg ccggtatcgg tccagccgct gtccgtgtcg ctgctgccga agcacggcga    32100
ggggtccgcg aacgccgcag acggcgtatc cggccgcagc gcatcgccca gcatggcccc    32160
ggtcagcgag ccgccggcca ggtagcccag catggtgctg ttggtcgccc cggccaccag    32220
ggccgacgtg acgaaatcgc cgtcattccc tctggattgt tcgctgctcg gcggggcagt    32280
gcgccgcgcc ggcggcgtcg tggatggctc gggttggctg gcctgcgacg gccggcgaaa    32340
ggtgcgcagc agctcgttat cgaccggctg cggcgtcggg gccgccgcct tgcgctgcgg    32400
tcggtgttcc ttcttcggct cgcgcagctt gaacagcatg atcgcggaaa ccagcagcaa    32460
cgccgcgcct acgcctcccg cgatgtagaa cagcatcgga ttcattcttc ggtcctcctt    32520
gtagcggaac cgttgtctgt gcggcgcggg tggcccgcgc cgctgtcttt ggggatcagc    32580
cctcgatgag cgcgaccagt ttcacgtcgg caaggttcgc ctcgaactcc tggccgtcgt    32640
cctcgtactt caaccaggca tagccttccg ccggcggccg acggttgagg ataaggcggg    32700
cagggcgctc gtcgtgctcg acctggacga tggccttttt cagcttgtcc gggtccggct    32760
ccttcgcgcc cttttccttg gcgtccttac cgtcctggtc gccgtcctcg ccgtcctggc    32820
cgtcgccggc ctccgcgtca cgctcggcat cagtctggcc gttgaaggca tcgacggtgt    32880
tgggatcgcg gcccttctcg tccaggaact cgcgcagcag cttgaccgtg ccgcgcgtga    32940
tttcctgggt gtcgtcgtca agccacgcct cgacttcctc cgggcgcttc ttgaaggccg    33000
tcaccagctc gttcaccacg gtcacgtcgc gcacgcggcc ggtgttgaac gcatcggcga    33060
tcttctccgg caggtccagc agcgtgacgt gctgggtgat gaacgccggc gacttgccga    33120
tttccttggc gatatcgcct ttcttcttgc ccttcgccag ctcgcggcca atgaagtcgg    33180
caatttcgcg cggggtcagc tcgttgcgtt gcaggttctc gataacctgg tcggcttcgt    33240
tgtagtcgtt gtcgatgaac gccgggatgg acttcttgcc ggcccacttc gagccacggt    33300
```

```
agcggcgggc gccgtgattg atgatatagc ggcccggctg ctcctggttc tcgcgcaccg   33360
aaatgggtga cttcaccccg cgctctttga tcgtggcacc gatttccgcg atgctctccg   33420
gggaaaagcc ggggttgtcg gccgtccgcg gctgatgcgg atcttcgtcg atcaggtcca   33480
ggtccagctc gatagggccg gaaccgccct gagacgccgc aggagcgtcc aggaggctcc   33540
acaggtcgcc gatgctatcc aaccccaggc cggacggctg cgccgcgcct gcggcttcct   33600
gagcggccgc agcggtgttt ttcttggtgg tcttggcttg agccgcagtc attgggaaat   33660
ctccatcttc gtgaacacgt aatcagccag ggcgcgaacc tctttcgatg ccttgcgcgc   33720
ggccgttttc ttgatcttcc agaccggcac accggatgcg agggcatcgg cgatgctgct   33780
gcgcaggcca acggtggccg gaatcatcat cttggggtac gcggccagca gctcggcttg   33840
gtggcgcgcg tggcgcggat tccgcgcatc gaccttgctg gcaccatgc caaggaattg    33900
cagcttggcg ttcttctggc gcacgttcgc aatggtcgtg accatcttct tgatgccctg   33960
gatgctgtac gcctcaagct cgatggggga cagcacatag tcggccgcga agagggcggc   34020
cgccaggccg acgccaaggg tcggggccgt gtcgatcagg cacacgtcga agccttggtt   34080
cgccagggcc ttgatgttcg ccccgaacag ctcgcgggcg tcgtccagcg acagccgttc   34140
ggcgttcgcc agtaccgggt tggactcgat gagggcgagg cgcgcggcct ggccgtcgcc   34200
ggctgcgggt gcggtttcgg tccagccgcc ggcagggaca cgccgaaca gcttgcttgc    34260
atgcaggccg gtagcaaagt ccttgagcgt gtaggacgca ttgccctggg ggtccaggtc    34320
gatcacggca acccgcaagc cgcgctcgaa aaagtcgaag gcaagatgca caagggtcga   34380
agtcttgccg acgccgcctt tctggttggc cgtgaccaaa gttttcatcg tttggtttcc   34440
tgttttttct tggcgtccgc ttcccacttc cggacgatgt acgcctgatg ttccggcaga    34500
accgccgtta cccgcgcgta cccctcgggc aagttcttgt cctcgaacgc ggcccacacg   34560
cgatgcaccg cttgcgacac tgcgcccctg gtcagtccca gcgacgttgc gaacgtcgcc   34620
tgtggcttcc catcgactaa gacgccccgc gctatctcga tggtctgctg ccccacttcc   34680
agcccctgga tcgcctcctg gaactggctt tcggtaagcc gtttcttcat ggataacacc   34740
cataatttgc tccgcgcctt ggttgaacat agcggtgaca gccgccagca catgagagaa   34800
gtttagctaa acatttctcg cacgtcaaca cctttagccg ctaaaactcg tccttggcgt   34860
aacaaaacaa aagcccggaa accgggcttt cgtctcttgc cgcttatggc tctgcacccg   34920
gctccatcac caacaggtcg cgcacgcgct tcactcggtt gcggatcgac actgccagcc   34980
caacaaagcc ggttgccgcc gccgccagga tcgcgccgat gatgccggcc acaccggcca   35040
tcgcccacca ggtcgccgcc ttccggttcc attcctgctg gtactgcttc gcaatgctgg   35100
acctcggctc accataggct gaccgctcga tggcgtatgc cgcttctccc cttggcgtaa   35160
aacccagcgc cgcaggcggc attgccatgc tgcccgccgc tttcccgacc acgacgcgcg   35220
caccaggctt gcggtccaga ccttcggcca cggcgagctg cgcaaggaca taatcagccg   35280
ccgacttggc tccacgcgcc tcgatcagct cttgcactcg cgcgaaatcc ttggcctcca   35340
cggccgccat gaatcgcgca cgcggcgaag ctccgcagg gccggcgtcg tgatcgccgc    35400
cgagaatgcc cttcaccaag ttcgacgaca cgaaaatcat gctgacggct atcaccatca   35460
tgcagacgga tcgcacgaac ccgctgaatt gaacacgagc acggcacccg cgaccactat   35520
gccaagaatg cccaaggtaa aaattgccgg cccccgccat gaagtccgtga atgcccccgac   35580
ggccgaagtg aagggcaggc cgccacccag gccgccgccc tcactgcccg gcacctggtc   35640
gctgaatgtc gatgccagca cctgcggcac gtcaatgctt ccgggcgtcg cgctcgggct   35700
```

```
gatcgcccat cccgttactg ccccgatccc ggcaatggca aggactgcca gcgctgccat    35760 tttttggggtg aggccgttcg cggccgaggg gcgcagcccc tggggggatg ggaggcccgc    35820
gttagcgggc cggagggatt cgagaagggg gggcacccc cttcggcgtg cgcggtcacg      35880
cgcacagggc gcagcctgg ttaaaaacaa ggtttataaa tattggttta aaagcaggtt      35940
aaaagacagg ttagcggtgg ccgaaaaacg ggcggaaacc cttgcaaatg ctggattttc    36000
tgcctgtgga cagcccctca aatgtcaata ggtgcgcccc tcatctgtca gcactctgcc    36060
cctcaagtgt caaggatcgc gccctcatc tgtcagtagt cgcgcccctc aagtgtcaat     36120
accgcagggc acttatcccc aggcttgtcc acatcatctg tgggaaactc gcgtaaaatc    36180
aggcgttttc gccgatttgc gaggctggcc agctccacgt cgccggccga atcgagcct     36240 gcccctcatc tgtcaacgcc gcgcggtg agtcggcccc tcaagtgtca acgtccgccc     36300
ctcatctgtc agtgagggcc aagttttccg cgaggtatcc acaacgccgg cggccgcggt    36360
gtctcgcaca cggcttcgac ggcgtttctg gcgcgtttgc agggccatag acggccgcca    36420
gcccagcggc gagggcaacc agcccggtga gcgtcggaaa ggcgctggaa gccccgtagc    36480
gacgcggaga ggggcgagac aagccaaggg cgcaggctcg atgcgcagca cgacatagcc    36540
ggttctcgca aggacgagaa tttccctgcg gtgcccctca agtgtcaatg aaagtttcca    36600
acgcgagcca ttcgcgagag ccttgagtcc acgctagatg agagctttgt tgtaggtgga    36660
ccagttggtg attttgaact tttgctttgc cacggaacgg tctgcgttgt cgggaagatg    36720
cgtgatctga tccttcaact cagcaaaagt tcgatttatt caacaaagcc acgttgtgtc    36780
tcaaaatctc tgatgttaca ttgcacaaga taaaaatata tcatcatgaa caataaaact    36840
gtctgcttac ataaacagta atacaagggg tgttatgagc catattcaac gggaaacgtc    36900
ttgctcgac                                                             36909
```

<210> SEQ ID NO 38
<211> LENGTH: 13019
<212> TYPE: DNA
<213> ORGANISM: Artificial
<220> FEATURE:
<223> OTHER INFORMATION: Destination vector PHP23235

<400> SEQUENCE: 38

```
gttacccgga ccgaagctta gcccgggcat gcctgcagtg cagcgtgacc cggtcgtgcc      60
cctctctaga gataatgagc attgcatgtc taagttataa aaaattacca catatttttt    120
ttgtcacact tgtttgaagt gcagtttatc tatcttatta catatattta aactttactc    180
tacgaataat ataatctata gtactacaat aatatcagtg ttttagagaa tcatataaat    240
gaacagttag acatggtcta aaggacaatt gagtattttg acaacaggac tctacagttt    300
tatcttttta gtgtgcatgt gttctccttt tttttgcaa atagcttcac ctatataata    360
cttcatccat tttattagta catccattta gggtttaggg ttaatggttt ttatagacta    420 attttttag tacatctatt ttattctatt ttagcctcta aattaagaaa actaaaactc      480
tattttagtt tttttattta ataatttaga tataaatag aataaaataa agtgactaaa    540
aattaaacaa ataccctta agaaattaaa aaaactaagg aaacatttt cttgtttcga    600 gtagataatg ccagcctgtt aaacgccgtc gacgagtcta acggacacca accagcgaac    660
cagcagcgtc gcgtcgggcc aagcgaagca gacggcacgg catctctgtc gctgcctctg    720 gaccccctc gagagttccg ctccaccgtt ggacttgctc cgctgtcggc atccagaaat    780
```

```
tgcgtggcgg agcggcagac gtgagccggc acggcaggcg gcctcctcct cctctcacgg    840
cacggcagct acgggggatt cctttcccac cgctccttcg cttttcccttc ctcgcccgcc    900 gtaataaata gacaccccct ccacaccctc tttccccaac ctcgtgttgt tcggagcgca    960
cacacacaca accagatctc ccccaaatcc acccgtcggc acctccgctt caaggtacgc   1020
cgctcgtcct cccccccccc ccctctctac cttctctaga tcggcgttcc ggtccatggt   1080
tagggcccgg tagttctact tctgttcatg tttgtgttag atccgtgttt gtgttagatc   1140
cgtgctgcta gcgttcgtac acggatgcga cctgtacgtc agacacgttc tgattgctaa   1200
cttgccagtg tttctctttg gggaatcctg ggatggctct agccgttccg cagacgggat   1260
cgatttcatg attttttttg tttcgttgca tagggtttgg tttgcccttt tcctttattt   1320
caatatatgc cgtgcacttg tttgtcgggt catcttttca tgcttttttt tgtcttggtt   1380
gtgatgatgt ggtctggttg ggcggtcgtt ctagatcgga gtagaattct gtttcaaact   1440
acctggtgga tttattaatt ttggatctgt atgtgtgtgc catacatatt catagttacg   1500
aattgaagat gatggatgga aatatcgatc taggataggt atacatgttg atgcgggttt   1560
tactgatgca tatacagaga tgcttttttgt tcgcttggtt gtgatgatgt ggtgtggttg   1620
ggcggtcgtt cattcgttct agatcggagt agaaatactgt ttcaaactac ctggtgtatt   1680
tattaatttt ggaactgtat gtgtgtgtca tacatcttca tagttacgag tttaagatgg   1740
atggaaatat cgatctagga taggtataca tgttgatgtg ggttttactg atgcatatac   1800
atgatggcat atgcagcatc tattcatatg ctctaacctt gagtacctat ctattataat   1860
aaacaagtat gttttataat tattttgatc ttgatatact tggatgatgg catatgcagc   1920
agctatatgt ggatttttttt agccctgcct tcatacgcta tttatttgct tggtactgtt   1980
tcttttgtcg atgctcaccc tgttgtttgg tgttacttct gcaggtcgac tctagaggat   2040
ccacaagttt gtacaaaaaa gctgaacgag aaacgtaaaa tgatataaat atcaatatat   2100
taaattagat tttgcataaa aaacagacta cataatactg taaaacacaa catatccagt   2160
cactatggcg gccgcattag gcaccccagg ctttacactt tatgcttccg gctcgtataa   2220
tgtgtggatt ttgagttagg atttaaatac gcgttgatcc ggcttactaa aagccagata   2280
acagtatgcg tatttgcgcg ctgattttgt cggtataaga atatatactg atatgtatac   2340
ccgaagtatg tcaaaagag gtatgctatg aagcagcgta ttacagtgac agttgacagc   2400
gacagctatc agttgctcaa ggcatatatg atgtcaatat ctccggtctg gtaagcacaa   2460
ccatgcagaa tgaagcccgt cgtctgcgtg ccgaacgctg gaaagcggaa atcaggaag    2520 ggatggctga ggtcgcccgg tttattgaaa tgaacggctc ttttgctgac gagaacaggg   2580
gctggtgaaa tgcagtttaa ggtttacacc tataaaagag agagccgtta tcgtctgttt   2640
gtggatgtac agagtgatat cattgacacg cccggtcgac ggatggtgat cccctggcc   2700 agtgcacgtc tgctgtcaga taaagtctcc cgtgaacttt acccggtggt gcatatcggg   2760
gatgaaagct ggcgcatgat gaccaccgat atggccagtg tgccggtctc cgttatcggg   2820
gaagaagtgg ctgatctcag ccaccgcgaa aatgacatca aaacgccat taacctgatg   2880 ttctggggaa tataaatgtc aggctcccct atacacagcc agtctgcagg tcgaccatag   2940
tgactggata tgttgtgttt tacagtatta tgtagtctgt ttttttatgca aaatctaatt   3000 taatatattg atatttatat cattttacgt ttctcgttca gctttcttgt acaaagtggt   3060
gttaacctag acttgtccat cttctggatt ggccaactta ttaatgtat gaaataaaag    3120 gatgcacaca tagtgacatg ctaatcacta taatgtgggc atcaaagttg tgtgttatgt   3180
```

```
gtaattacta gttatctgaa taaaagagaa agagatcatc catatttctt atcctaaatg    3240
aatgtcacgt gtctttataa ttctttgatg aaccagatgc atttcattaa ccaaatccat    3300
atacatataa atattaatca tatataatta atatcaattg ggttagcaaa acaaatctag    3360
tctaggtgtg ttttgcgaat tgcggccgcc accgcggtgg agctcgaatt ccggtccggg    3420
tcacctttgt ccaccaagat ggaactgcgg ccgctcatta attaagtcag gcgcgcctct    3480
agttgaagac acgttcatgt cttcatcgta agaagacact cagtagtctt cggccagaat    3540
ggccatctgg attcagcagg cctagaaggc catttaaatc ctgaggatct ggtcttccta    3600
aggacccggg atatcggacc gattaaactt taattcggtc cgaagcttgc atgcctgcag    3660
tgcagcgtga cccggtcgtg cccctctcta gagataatga gcattgcatg tctaagttat    3720
aaaaaattac cacatatttt ttttgtcaca cttgtttgaa gtgcagttta tctatcttta    3780
tacatatatt taaactttac tctacgaata atataatcta tagtactaca ataatatcag    3840
tgttttagag aatcatataa atgaacagtt agacatggtc taaaggacaa ttgagtattt    3900
tgacaacagg actctacagt tttatctttt tagtgtgcat gtgttctcct ttttttttgc    3960
aaatagcttc acctatataa tacttcatcc attttattag tacatccatt tagggtttag    4020
ggttaatggt ttttatagac taattttttt agtacatcta ttttattcta ttttagcctc    4080
taaattaaga aaactaaaac tctattttag tttttttatt taataattta gatataaaat    4140
agaataaaat aaagtgacta aaaattaaac aaatacccct taagaaatta aaaaaactaa    4200
ggaaacattt ttcttgtttc gagtagataa tgccagcctg ttaaacgccg tcgacgagtc    4260
taacggacac caaccagcga accagcagcg tcgcgtcggg ccaagcgaag cagacggcac    4320
ggcatctctg tcgctgcctc tggaccccct cgagagttc cgctccaccg ttggacttgc    4380
tccgctgtcg gcatccagaa attgcgtggc ggagcggcag acgtgagccg cacggcagg    4440 cggcctcctc ctcctctcac ggcaccggca gctacggggg attcctttcc caccgctcct    4500
tcgctttccc ttcctcgccc gccgtaataa atagacaccc cctccacacc ctctttcccc    4560
aacctcgtgt tgttcggagc gcacacacac acaaccagat ctcccccaaa tccacccgtc    4620
ggcacctccg cttcaaggta cgccgctcgt cctccccccc cccctctct accttctcta    4680 gatcggcgtt ccgtccatg catggttagg gcccggtagt tctacttctg ttcatgtttg    4740
tgttagatcc gtgtttgtgt tagatccgtg ctgctagcgt tcgtacacgg atgcgacctg    4800
tacgtcagac acgttctgat tgctaacttg ccagtgtttc tctttgggga atcctgggat    4860
ggctctagcc gttccgcaga cgggatcgat ttcatgattt tttttgtttc gttgcatagg    4920
gtttggtttg ccctttttcct ttatttcaat atatgccgtg cacttgtttg tcgggtcatc    4980
ttttcatgct ttttttttgtc ttggttgtga tgatgtggtc tggttgggcg gtcgttctag    5040
atcggagtag aattctgttt caaactacct ggtggattta ttaattttgg atctgtatgt    5100
gtgtgccata catattcata gttacgaatt gaagatgatg gatggaaata tcgatctagg    5160
ataggtatac atgttgatgc gggttttact gatgcatata cagagatgct ttttgttcgc    5220
ttggttgtga tgatgtggtg tggttgggcg gtcgttcatt cgttctagat cggagtagaa    5280
tactgtttca aactacctgg tgtatttatt aattttggaa ctgtatgtgt gtgtcataca    5340
tcttcatagt tacgagtttta agatggatgg aaatatcgat ctaggatagg tatacatgtt    5400 gatgtggggtt ttactgatgc atatacatga tggcatatgc agcatctatt catatgctct    5460
aaccttgagt acctatctat tataataaac aagtatgttt tataattatt ttgatcttga    5520
```

```
tatacttgga tgatggcata tgcagcagct atatgtggat ttttttagcc ctgccttcat   5580
acgctattta tttgcttggt actgtttctt ttgtcgatgc tcaccctgtt gtttggtgtt   5640
acttctgcag gtcgacttta acttagccta ggatccacac gacaccatgt cccccgagcg   5700
ccgccccgtc gagatccgcc cggccaccgc cgccgacatg gccgccgtgt gcgacatcgt   5760
gaaccactac atcgagacct ccaccgtgaa cttccgcacc gagccgcaga ccccgcagga   5820
gtggatcgac gacctggagc gcctccagga ccgctacccg tggctcgtgg ccgaggtgga   5880
gggcgtggtg gccggcatcg cctacgccgg cccgtggaag gcccgcaacg cctacgactg   5940
gaccgtggag tccaccgtgt acgtgtccca ccgccaccag cgcctcggcc tcggctccac   6000
cctctacacc cacctcctca agagcatgga ggcccagggc ttcaagtccg tggtggccgt   6060
gatcggcctc ccgaacgacc cgtccgtgcg cctccacgag gccctcggct acaccgcccg   6120
cggcacccctc cgcgccgccg gctacaagca cggcggctgg cacgacgtcg gcttctggca   6180
gcgcgacttc gagctgccgg ccccgccgcg cccggtgcgc ccggtgacgc agatctgagt   6240
cgaaacctag acttgtccat cttctggatt ggccaactta attaatgtat gaaataaaag   6300
gatgcacaca tagtgacatg ctaatcacta taatgtgggc atcaaagttg tgtgttatgt   6360
gtaattacta gttatctgaa taaagagaa agagatcatc catatttctt atcctaaatg   6420
aatgtcacgt gtctttataa ttctttgatg aaccagatgc atttcattaa ccaaatccat   6480
atacatataa atattaatca tatataatta atatcaattg ggttagcaaa acaaatctag   6540
tctaggtgtg ttttgcgaat tgcggccgcc accgcggtgg agctcgaatt cattccgatt   6600
aatcgtggcc tcttgctctt caggatgaag agctatgttt aaacgtgcaa gcgctactag   6660
acaattcagt acattaaaaa cgtccgcaat gtgttattaa gttgtctaag cgtcaatttg   6720
tttacaccac aatatatcct gccaccagcc agccaacagc tccccgaccg gcagctcggc   6780
acaaaatcac cactcgatac aggcagccca tcagtccggg acggcgtcag cgggagagcc   6840
gttgtaaggc ggcagacttt gctcatgtta ccgatgctat tcggaagaac ggcaactaag   6900
ctgccgggtt tgaaacacgg atgatctcgc ggagggtagc atgttgattg taacgatgac   6960
agagcgttgc tgcctgtgat caaatatcat ctccctcgca gagatccgaa ttatcagcct   7020
tcttattcat ttctcgctta accgtgacag gctgtcgatc ttgagaacta tgccgacata   7080
ataggaaatc gctggataaa gccgctgagg aagctgagtg gcgctatttc tttagaagtg   7140
aacgttgacg atcgtcgacc gtaccccgat gaattaattc ggacgtacgt tctgaacaca   7200
gctggatact tacttgggcg attgtcatac atgacatcaa caatgtaccc gtttgtgtaa   7260
ccgtctcttg gaggttcgta tgacactagt ggttcccctc agcttgcgac tagatgttga   7320
ggcctaacat tttattagag agcaggctag ttgcttagat acatgatctt caggccgtta   7380
tctgtcaggg caagcgaaaa ttggccattt atgacgacca atgccccgca gaagctccca   7440
tctttgccgc catagacgcc gcgcccccct tttggggtgt agaacatcct tttgccagat   7500
gtggaaaaga agttcgttgt cccattgttg gcaatgacgt agtagccggc gaaagtgcga   7560
gacccatttg cgctatatat aagcctacga tttccgttgc gactattgtc gtaattggat   7620
gaactattat cgtagttgct ctcagagttg tcgtaatttg atggactatt gtcgtaattg   7680
cttatggagt tgtcgtagtt gcttggagaa atgtcgtagt tggatgggga gtagtcatag   7740
ggaagacgag cttcatccac taaaacaatt ggcaggtcag caagtgcctg ccccgatgcc   7800
atcgcaagta cgaggcttag aaccaccttc aacagatcgc gcatagtctt ccccagctct   7860
ctaacgcttg agttaagccg cgccgcgaag cggcgtcggc ttgaacgaat tgttagacat   7920
```

```
tatttgccga ctaccttggt gatctcgcct ttcacgtagt gaacaaattc ttccaactga   7980
tctgcgcgcg aggccaagcg atcttcttgt ccaagataag cctgcctagc ttcaagtatg   8040
acgggctgat actgggccgg caggcgctcc attgcccagt cggcagcgac atccttcggc   8100
gcgattttgc cggttactgc gctgtaccaa atgcgggaca acgtaagcac tacatttcgc   8160
tcatcgccag cccagtcggg cggcgagttc catagcgtta aggtttcatt tagcgcctca   8220
aatagatcct gttcaggaac cggatcaaag agttcctccg ccgctggacc taccaaggca   8280
acgctatgtt ctcttgcttt tgtcagcaag atagccagat caatgtcgat cgtggctggc   8340
tcgaagatac ctgcaagaat gtcattgcgc tgccattctc caaattgcag ttcgcgctta   8400
gctggataac gccacggaat gatgtcgtcg tgcacaacaa tggtgacttc tacagcgcgg   8460
agaatctcgc tctctccagg ggaagccgaa gtttccaaaa ggtcgttgat caaagctcgc   8520
cgcgttgttt catcaagcct tacagtcacc gtaaccagca aatcaatatc actgtgtggc   8580
ttcaggccgc catccactgc ggagccgtac aaatgtacgg ccagcaacgt cggttcgaga   8640
tggcgctcga tgacgccaac tacctctgat agttgagtcg atacttcggc gatcaccgct   8700
tccctcatga tgtttaactc ctgaattaag ccgcgccgcg aagcggtgtc ggcttgaatg   8760
aattgttagg cgtcatcctg tgctcccgag aaccagtacc agtacatcgc tgtttcgttc   8820
gagacttgag gtctagtttt atacgtgaac aggtcaatgc cgccgagagt aaagccacat   8880
tttgcgtaca aattgcaggc aggtacattg ttcgtttgtg tctctaatcg tatgccaagg   8940
agctgtctgc ttagtgccca cttttttcgca aattcgatga gactgtgcgc gactcctttg   9000
cctcggtgcg tgtgcgacac aacaatgtgt tcgatagagg ctagatcgtt ccatgttgag   9060
ttgagttcaa tcttcccgac aagctcttgg tcgatgaatg cgccatagca agcagagtct   9120
tcatcagagt catcatccga gatgtaatcc ttccggtagg ggctcacact tctggtagat   9180
agttcaaagc cttggtcgga taggtgcaca tcgaacactt cacgaacaat gaaatggttc   9240
tcagcatcca atgtttccgc cacctgctca gggatcaccg aaatcttcat atgacgccta   9300
acgcctggca cagcggatcg caaacctggc gcggcttttg gcacaaaagg cgtgacaggt   9360
ttgcgaatcc gttgctgcca cttgttaacc cttttgccag atttggtaac tataatttat   9420
gttagaggcg aagtcttggg taaaaactgg cctaaaattg ctggggatttt caggaaagta   9480 aacatcacct tccggctcga tgtctattgt agatatatgt agtgtatcta cttgatcggg   9540
ggatctgctg cctcgcgcgt ttcggtgatg acggtgaaaa cctctgacac atgcagctcc   9600
cggagacggt cacagcttgt ctgtaagcgg atgccgggag cagacaagcc cgtcagggcg   9660
cgtcagcggg tgttggcggg tgtcggggcg cagccatgac ccagtcacgt agcgatagcg   9720
gagtgtatac tggcttaact atgcggcatc agagcagatt gtactgagag tgcaccatat   9780
gcggtgtgaa ataccgcaca gatgcgtaag gagaaaatac cgcatcaggc gctcttccgc   9840
ttcctcgctc actgactcgc tgcgctcggt cgttcggctg cggcgagcgg tatcagctca   9900
ctcaaaggcg gtaatacggt tatccacaga atcagggggat aacgcaggaa agaacatgtg   9960
agcaaaaggc cagcaaaagg ccaggaaccg taaaaaggcc gcgttgctgg cgttttccca  10020
taggctccgc cccctgacg agcatcacaa aaatcgacgc tcaagtcaga ggtggcgaaa  10080
cccgacagga ctataaagat accaggcgtt tcccctgga agctccctcg tgcgctctcc  10140
tgttccgacc ctgccgctta ccggatacct gtccgccttt ctcccttcgg gaagcgtggc  10200
gctttctcat agctcacgct gtaggtatct cagttcggtg taggtcgttc gctccaagct  10260
```

```
gggctgtgtg cacgaacccc ccgttcagcc cgaccgctgc gccttatccg gtaactatcg    10320
tcttgagtcc aacccggtaa gacacgactt atcgccactg gcagcagcca ctggtaacag    10380
gattagcaga gcgaggtatg taggcggtgc tacagagttc ttgaagtggt ggcctaacta    10440
cggctacact agaaggacag tatttggtat ctgcgctctg ctgaagccag ttaccttcgg    10500
aaaaagagtt ggtagctctt gatccggcaa acaaaccacc gctggtagcg gtggtttttt    10560
tgtttgcaag cagcagatta cgcgcagaaa aaaggatct caagaagatc ctttgatctt    10620
ttctacgggg tctgacgctc agtggaacga aaactcacgt taagggattt tggtcatgag    10680
attatcaaaa aggatcttca cctagatcct tttaaattaa aaatgaagtt ttaaatcaat    10740
ctaaagtata tatgagtaaa cttggtctga cagttaccaa tgcttaatca gtgaggcacc    10800
tatctcagcg atctgtctat ttcgttcatc catagttgcc tgactccccg tcgtgtagat    10860
aactacgata cgggagggct taccatctgg ccccagtgct gcaatgatac cgcgagaccc    10920
acgctcaccg gctccagatt tatcagcaat aaaccagcca gccggaaggg ccgagcgcag    10980
aagtggtcct gcaactttat ccgcctccat ccagtctatt aattgttgcc gggaagctag    11040
agtaagtagt tcgccagtta atagtttgcg caacgttgtt gccattgctg caggggggg    11100 gggggggggg gacttccatt gttcattcca cggacaaaaa cagagaaagg aaacgacaga    11160
ggccaaaaag cctcgctttc agcacctgtc gtttcctttc ttttcagagg gtatttaaa    11220 taaaaacatt aagttatgac gaagaagaac ggaaacgcct taaaccggaa aattttcata    11280
aatagcgaaa acccgcgagg tcgccgcccc gtaacctgtc ggatcaccgg aaaggacccg    11340
taaagtgata atgattatca tctacatatc acaacgtgcg tggaggccat caaaccacgt    11400
caaataatca attatgacgc aggtatcgta ttaattgatc tgcatcaact aacgtaaaa    11460 acaacttcag acaatacaaa tcagcgacac tgaatacggg gcaacctcat gtccccccc    11520 ccccccccccc tgcaggcatc gtggtgtcac gctcgtcgtt tggtatggct tcattcagct    11580
ccggttccca acgatcaagg cgagttacat gatcccccat gttgtgcaaa aaagcggtta    11640
gctccttcgg tcctccgatc gttgtcagaa gtaagttggc cgcagtgtta tcactcatgg    11700
ttatggcagc actgcataat tctcttactg tcatgccatc cgtaagatgc ttttctgtga    11760
ctggtgagta ctcaaccaag tcattctgag aatagtgtat gcggcgaccg agttgctctt    11820
gcccggcgtc aacacgggat aataccgcgc cacatagcag aactttaaaa gtgctcatca    11880
ttggaaaacg ttcttcgggg cgaaaactct caaggatctt accgctgttg agatccagtt    11940
cgatgtaacc cactcgtgca cccaactgat cttcagcatc ttttactttc accagcgttt    12000
ctgggtgagc aaaaacagga aggcaaaatg ccgcaaaaaa gggaataagg gcgacacgga    12060
aatgttgaat actcatactc ttcctttttc aatattattg aagcatttat cagggttatt    12120
gtctcatgag cggatacata tttgaatgta tttagaaaaa taaacaaata ggggttccgc    12180
gcacatttcc ccgaaaagtg ccacctgacg tctaagaaac cattattatc atgacattaa    12240
cctataaaaa taggcgtatc acgaggccct ttcgtcttca agaattggtc gacgatcttg    12300
ctgcgttcgg atattttcgt ggagttcccg ccacagaccc ggattgaagg cgagatccag    12360
caactcgcgc cagatcatcc tgtgacgaa cttggcgcg tgatgactgg ccaggacgtc    12420
ggccgaaaga gcgacaagca gatcacgctt ttcgacagcg tcggatttgc gatcgaggat    12480
ttttcggcgc tgcgctacgt ccgcgaccgc gttgagggat caagccacag cagcccactc    12540
gaccttctag ccgacccaga cgagccaagg gatcttttg gaatgctgct ccgtcgtcag    12600
gctttccgac gtttgggtgg ttgaacagaa gtcattatcg tacggaatgc caagcactcc    12660
```

```
cgaggggaac cctgtggttg gcatgcacat acaaatggac gaacggataa accttttcac   12720 gccctttta  atatccgtta ttctaataaa cgctcttttc tcttaggttt acccgccaat   12780
atatcctgtc aaacactgat agtttaaact gaaggcggga aacgacaatc tgatcatgag   12840
cggagaatta agggagtcac gttatgaccc ccgccgatga cgcgggacaa gccgttttac   12900
gtttggaact gacagaaccg caacgttgaa ggagccactc agcaagctgg tacgattgta   12960
atacgactca ctatagggcg aattgagcgc tgtttaaacg ctcttcaact ggaagagcg    13019
```

<210> SEQ ID NO 39
<211> LENGTH: 15663
<212> TYPE: DNA
<213> ORGANISM: Artificial
<220> FEATURE:
<223> OTHER INFORMATION: Destination vector PHP28647

<400> SEQUENCE: 39

```
gtttacccgc caatatatcc tgtcaaacac tgatagttta aactgaaggc gggaaacgac     60
aatctgatca tgagcggaga attaagggag tcacgttatg accccgccg  atgacgcggg    120 acaagccgtt ttacgtttgg aactgacaga accgcaacgt tgaaggagcc actcagcaag    180
ctggtacgat tgtaatacga ctcactatag gcgaattga  gcgctgttta aacgctcttc    240
aactggaaga gcggttaccc ggaccgaagc ttgcatgcct gcagtgcagc gtgacccggt    300 cgtgccctc  tctagagata tgagcattg  catgtctaag ttataaaaaa ttaccacata    360
ttttttttgt cacacttgtt tgaagtgcag tttatctatc tttatacata tatttaaact    420
ttactctacg aataatataa tctatagtac tacaataata tcagtgtttt agagaatcat    480
ataaatgaac agttagacat ggtctaaagg acaattgagt attttgacaa caggactcta    540
cagttttatc ttttagtgt  gcatgtgttc tcctttttt  ttgcaaatag cttcacctat    600
ataatacttc atccatttta ttagtacatc catttagggt ttaggttaa  tggtttttat    660 agactaattt ttttagtaca tctattttat tctatttag  cctctaaatt aagaaaacta    720
aaactctatt ttagttttt  tatttaataa tttagatata aaatagaata aaataaagtg    780
actaaaaatt aaacaaatac cctttaagaa attaaaaaaa ctaaggaaac attttttcttg    840 tttcgagtag ataatgccag cctgttaaac gccgtcgacg agtctaacgg acaccaacca    900
gcgaaccagc agcgtcgcgt cgggccaagc gaagcagacg gcacggcatc tctgtcgctg    960
cctctggacc cctctcgaga gttccgctcc accgttggac ttgctccgct gtcggcatcc   1020
agaaattgcg tggcggagcg gcagacgtga gccggcacgg caggcggcct cctcctcctc   1080
tcacggcacg gcagctacgg gggattcctt tcccaccgct ccttcgcttt cccttcctcg   1140
cccgccgtaa taaatagaca cccctcca   ccctctttc cccaacctcg tgttgttcgg    1200
agcgcacaca cacacaacca gatctccccc aaatccaccc gtcggcacct ccgcttcaag   1260
gtacgccgct cgtcctccccc cccccccct  ctctaccttc tctagatcgg cgttccggtc   1320
catggttagg gcccggtagt tctacttctg ttcatgtttg tgttagatcc gtgtttgtgt   1380
tagatccgtg ctgctagcgt tcgtacacga atgcgacctg tacgtcagac acgttctgat   1440
tgctaacttg ccagtgtttc tctttgggga atcctgggat ggctctagcc gttccgcaga   1500
cgggatcgat ttcatgattt ttttgtttc  gttgcatagg gtttggttg  cccttttcct   1560 ttattcaat  atatgccgtg cacttgttg  tcgggtcatc ttttcatgct tttttttgtc   1620
ttggttgtga tgatgtggtc tggttgggcg gtcgttctag atcggagtag aattctgttt   1680
```

```
caaactacct ggtggattta ttaattttgg atctgtatgt gtgtgccata catattcata    1740
gttacgaatt gaagatgatg gatggaaata tcgatctagg ataggtatac atgttgatgc    1800 gggtttttact gatgcatata cagagatgct ttttgttcgc ttggttgtga tgatgtggtg   1860
tggttgggcg gtcgttcatt cgttctagat cggagtagaa tactgtttca aactacctgg    1920
tgtatttatt aattttggaa ctgtatgtgt gtgtcataca tcttcatagt tacgagttta    1980
agatggatgg aaatatcgat ctaggatagg tatacatgtt gatgtgggtt ttactgatgc    2040
atatacatga tggcatatgc agcatctatt catatgctct aaccttgagt acctatctat    2100
tataataaac aagtatgttt tataattatt ttgatcttga tatacttgga tgatggcata    2160
tgcagcagct atatgtggat ttttttagcc ctgccttcat acgctattta tttgcttggt    2220
actgtttctt ttgtcgatgc tcaccctgtt gtttggtgtt acttctgcag gtcgactcta    2280
gaggatctac aagtttgtac aaaaaagctg aacgagaaac gtaaaatgat ataaatatca    2340
atatattaaa ttagattttg cataaaaaac agactacata atactgtaaa acacaacata    2400
tccagtcact atggcggccg cattaggcac cccaggcttt acactttatg cttccggctc    2460
gtataatgtg tggattttga gttaggatcc ggcgagattt tcaggagcta aggaagctaa    2520
aatggagaaa aaaatcactg gatataccac cgttgatata tcccaatggc atcgtaaaga    2580 acatttgag gcatttcagt cagttgctca atgtacctat aaccagaccg ttcagctgga    2640
tattacggcc ttttaaaga ccgtaaagaa aaataagcac aagttttatc cggcctttat    2700
tcacattctt gcccgcctga tgaatgctca tccggaattc cgtatggcaa tgaaagacgg    2760
tgagctggta tatgggata gtgttcaccc ttgttacacc gttttccatg agcaaactga    2820
aacgttttca tcgctctgga gtgaatacca cgacgatttc cggcagtttc tacacatata    2880
ttcgcaagat gtggcgtgtt acggtgaaaa cctggcctat ttccctaaag ggtttattga    2940
gaatatgttt ttcgtctcag ccaatccctg ggtgagtttc accagttttg atttaaacgt    3000
ggccaatatg gacaacttct tcgcccccgt tttcaccatg gcaaatatt atacgcaagg    3060 cgacaaggtg ctgatgccgc tggcgattca ggttcatcat gccgtctgtg atggcttcca    3120
tgtcggcaga atgcttaatg aattacaaca gtactgcgat gagtggcagg cggggcgta    3180 aacgcgtgga tccggcttac taaaagccag ataacagtat gcgtatttgc gcgctgattt    3240
ttgcggtata agaatatata ctgatatgta tacccgaagt atgtcaaaaa gaggtatgct    3300
atgaagcagc gtattacagt gacagttgac agcgacagct atcagttgct caaggcatat    3360
atgatgtcaa tatctccggt ctggtaagca caaccatgca gaatgaagcc cgtcgtctgc    3420
gtgccgaacg ctggaaagcg gaaaatcagg aagggatggc tgaggtcgcc cggtttattg    3480
aaatgaacgg ctcttttgct gacgagaaca ggggctggtg aaatgcagtt taaggtttac    3540
acctataaaa gagagagccg ttatcgtctg tttgtggatg tacagagtga tattattgac    3600
acgcccgggc gacggatggt gatccccctg gccagtgcac gtctgctgtc agataaagtc    3660
tcccgtgaac tttacccggt ggtgcatatc ggggatgaaa gctggcgcat gatgaccacc    3720
gatatggcca gtgtgccggt ctccgttatc ggggaagaag tggctgatct cagccaccgc    3780
gaaaatgaca tcaaaaacgc cattaacctg atgttctggg aatataaat gtcaggctcc    3840 cttatacaca gccagtctgc aggtcgacca tagtgactgg atatgttgtg ttttacagta    3900
ttatgtagtc tgttttttat gcaaaatcta atttaatata ttgatattta tcattttta    3960 cgtttctcgt tcagctttct tgtacaaagt ggtgttaacc tagacttgtc catcttctgg    4020
attggccaac ttaattaatg tatgaaataa aaggatgcac acatagtgac atgctaatca    4080
```

```
ctataatgtg ggcatcaaag ttgtgtgtta tgtgtaatta ctagttatct gaataaaaga   4140
gaaagagatc atccatattt cttatcctaa atgaatgtca cgtgtctttta taattctttg   4200
atgaaccaga tgcatttcat taaccaaatc catatacata taaatattaa tcatatataa   4260
ttaatatcaa ttgggttagc aaaacaaatc tagtctaggt gtgttttgcg aattgcggcc   4320
gccaccgcgg tggagctcga attccggtcc gggtcacctt tgtccaccaa gatggaactg   4380
cggccgctca ttaattaagt caggcgcgcc tctagttgaa gacacgttca tgtcttcatc   4440
gtaagaagac actcagtagt cttcggccag aatggccatc tggattcagc aggcctagaa   4500
ggccatttaa atcctgagga tctggtcttc ctaaggaccc gggatatcgg accgaagctg   4560
gccgctctag aactagtgga tctcgatgtg tagtctacga aagggttaa ccgtctcttc   4620
gtgagaataa ccgtggccta aaaataagcc gatgaggata aataaaatgt ggtggtacag   4680
tacttcaaga ggtttactca tcaagaggat gcttttccga tgagctctag tagtacatcg   4740
gacctcacat acctccattg tggtgaaata ttttgtgctc atttagtgat gggtaaattt   4800
tgtttatgtc actctaggtt ttgacatttc agttttgcca ctcttaggtt ttgacaaata   4860
atttccattc cgcggcaaaa gcaaacaat tttattttac ttttaccact cttagctttc   4920
acaatgtatc acaaatgcca ctctagaaat tctgtttatg ccacagaatg tgaaaaaaaa   4980
cactcactta tttgaagcca aggtgttcat ggcatgaaaa tgtgacataa agtaacgttc   5040
gtgtataaga aaaaattgta ctcctcgtaa caagagacgg aaacatcatg agacaatcgc   5100
gtttggaagg ctttgcatca cctttggatg atgcgcatga atggagtcgt ctgcttgcta   5160
gccttcgcct accgcccact gagtccgggc ggcaactacc atcggcgaac gacccagctg   5220
acctctaccg accggacttg aatgcgctac cttcgtcagc gacgatggcc gcgtacgctg   5280
gcgacgtgcc cccgcatgca tggcggcaca tggcgagctc agaccgtgcg tggctggcta   5340
caaatacgta ccccgtgagt gccctagcta gaaacttaca cctgcaactg cgagagcgag   5400
cgtgtgagtg tagccgagta gatccccgg gctgcaggtc gactctagag gatccaccgg   5460
tcgccaccat ggcctcctcc gagaacgtca tcaccgagtt catgcgcttc aaggtgcgca   5520
tggagggcac cgtgaacggc cacgagttcg agatcgaggg cgagggcgag ggccgcccct   5580
acgagggcca acaccgtg aagctgaagg tgacgaaggg cggccccctg cccttcgcct   5640
gggacatcct gtcccccag ttccagtacg gctccaaggt gtacgtgaag caccccgccg   5700
acatccccga ctacaagaag ctgtccttcc ccgagggctt caagtgggag cgcgtgatga   5760
acttcgagga cggcggcgtg gcgaccgtga cccaggacte ctccctgcag gacggctgct   5820
tcatctacaa ggtgaagttc atcggcgtga acttcccctc cgacggcccc gtgatgcaga   5880
agaagaccat gggctgggag gcctccaccg agcgcctgta ccccgcgac ggcgtgctga   5940
agggcgagac ccacaaggcc ctgaagctga aggacggcgg ccactacctg gtggagttca   6000
agtccatcta catggccaag aagcccgtgc agctgcccgg ctactactac gtggacgcca   6060
agctggacat cacctcccac aacgaggact acaccatcgt ggagcagtac gagcgcaccg   6120
agggccgcca ccacctgttc ctgtagcggc ccatggatat tcgaacgcgt aggtaccaca   6180
tggttaacct agacttgtcc atcttctgga ttggccaact taattaatgt atgaaataaa   6240
aggatgcaca catagtgaca tgctaatcac tataatgtgg gcatcaaagt tgtgtgttat   6300
gtgtaattac tagttatctg aataaaagag aaagagatca tccatatttc ttatcctaaa   6360
tgaatgtcac gtgtctttat aattctttga tgaaccagat gcatttcatt aaccaaatcc   6420
```

```
atatacatat aaatattaat catatataat taatatcaat tgggttagca aaacaaatct    6480
agtctaggtg tgttttgcga atgcggccgc caccgcggtg gagctcgaat tccggtccga    6540
agcttgcatg cctgcagtgc agcgtgaccc ggtcgtgccc ctctctagag ataatgagca    6600
ttgcatgtct aagttataaa aaattaccac atatttttt tgtcacactt gtttgaagtg     6660
cagtttatct atctttatac atatatttaa actttactct acgaataata taatctatag    6720
tactacaata atatcagtgt tttagagaat catataaatg aacagttaga catggtctaa    6780
aggacaattg agtattttga caacaggact ctacagtttt atcttttag tgtgcatgtg     6840 ttctcctttt tttttgcaaa tagcttcacc tatataatac ttcatccatt ttattagtac    6900
atccatttag ggtttagggt taatggtttt tatagactaa ttttttagt acatctattt     6960 tattctattt tagcctctaa attaagaaaa ctaaaactct attttagttt ttttatttaa    7020
taatttagat ataaaataga ataaaataaa gtgactaaaa attaaacaaa tacccttaa     7080 gaaattaaaa aaactaagga aacattttc ttgtttcgag tagataatgc cagcctgtta    7140
aacgccgtcg acgagtctaa cggacaccaa ccagcgaacc agcagcgtcg cgtcgggcca    7200
agcgaagcag acggcacggc atctctgtcg ctgcctctgg acccctctcg agagttccgc    7260
tccaccgttg gacttgctcc gctgtcggca tccagaaatt gcgtggcgga gcggcagacg    7320
tgagccggca cggcaggcgg cctcctcctc ctctcacggc accggcagct acggggggatt   7380 cctttcccac cgctccttcg ctttcccttc ctcgcccgcc gtaataaata gacaccccct    7440
ccacaccctc tttccccaac ctcgtgttgt tcggagcgca cacacacaca accagatctc    7500
ccccaaatcc acccgtcggc acctccgctt caaggtacgc cgctcgtcct ccccccccc    7560 cctctctacc ttctctagat cggcgttccg gtccatgcat ggttagggcc cggtagttct    7620
acttctgttc atgtttgtgt tagatccgtg tttgtgttag atccgtgctg ctagcgttcg    7680
tacacggatg cgacctgtac gtcagacacg ttctgattgc taacttgcca gtgtttctct    7740
ttggggaatc ctgggatggc tctagccgtt ccgcagacgg gatcgatttc atgatttttt    7800
ttgtttcgtt gcatagggtt tggtttgccc ttttccttta tttcaatata tgccgtgcac    7860
ttgtttgtcg ggtcatcttt tcatgctttt ttttgtcttg gttgtgatga tgtggtctgg    7920
ttgggcggtc gttctagatc ggagtagaat tctgtttcaa actacctggt ggatttatta    7980
attttggatc tgtatgtgtg tgccatacat attcatagtt acgaattgaa gatgatggat    8040
ggaaatatcg atctaggata ggtatacatg ttgatgcggg ttttactgat gcatatacag    8100
agatgctttt tgttcgcttg gttgtgatga tgtggtgtgg ttgggcggtc gttcattcgt    8160
tctagatcgg agtagaatac tgtttcaaac tacctggtgt atttattaat tttggaactg    8220
tatgtgtgtg tcatacatct tcatagttac gagtttaaga tggatggaaa tatcgatcta    8280
ggataggtat acatgttgat gtgggtttta ctgatgcata tacatgatgg catatgcagc    8340
atctattcat atgctctaac cttgagtacc tatctattat aataaacaag tatgttttat    8400
aattattttg atcttgatat acttggatga tggcatatgc agcagctata tgtggatttt    8460
tttagccctg ccttcatacg ctatttattt gcttggtact gtttcttttg tcgatgctca    8520
ccctgttgtt tggtgttact tctgcaggtc gactttaact tagcctagga tccacacgac    8580
accatgtccc ccgagcgccg ccccgtcgag atccgcccgg ccaccgccgc cgacatggcc    8640
gccgtgtgcg acatcgtgaa ccactacatc gagacctcca ccgtgaactt ccgcaccgag    8700
ccgcagaccc gcaggagtg gatcgacgac ctggagcgcc tccaggaccg ctaccctgtgg    8760 ctcgtggccg aggtggaggg cgtggtggcc ggcatcgcct acgccggccc gtggaaggcc    8820
```

```
cgcaacgcct acgactggac cgtggagtcc accgtgtacg tgtcccaccg ccaccagcgc   8880
ctcggcctcg gctccaccct ctacacccac ctcctcaaga gcatggaggc cagggcttc    8940 aagtccgtgg tggccgtgat cggcctcccg aacgacccgt ccgtgcgcct ccacgaggcc   9000
ctcggctaca ccgcccgcgg caccctccgc gccgccggct acaagcacgg cggctggcac   9060
gacgtcggct tctggcagcg cgacttcgag ctgccggccc cgccgcgccc ggtgcgcccg   9120
gtgacgcaga tctgagtcga aacctagact tgtccatctt ctggattggc aacttaatt    9180 aatgtatgaa ataaaaggat gcacacatag tgacatgcta atcactataa tgtgggcatc   9240
aaagttgtgt gttatgtgta attactagtt atctgaataa aagagaaaga gatcatccat   9300
atttcttatc ctaaatgaat gtcacgtgtc tttataattc tttgatgaac cagatgcatt   9360
tcattaacca aatccatata catataaata ttaatcatat ataattaata tcaattgggt   9420
tagcaaaaca aatctagtct aggtgtgttt tgcgaattgc ggccgccacc gcggtggagc   9480
tcgaattcat tccgattaat cgtggcctct tgctcttcag gatgaagagc tatgtttaaa   9540
cgtgcaagcg ctactagaca attcagtaca ttaaaaacgt ccgcaatgtg ttattaagtt   9600
gtctaagcgt caatttgttt acaccacaat atatcctgcc accagccagc caacagctcc   9660
ccgaccggca gctcggcaca aaatcaccac tcgatacagg cagcccatca gtccgggacg   9720
gcgtcagcgg gagagccgtt gtaaggcggc agactttgct catgttaccg atgctattcg   9780
gaagaacggc aactaagctg ccgggtttga acacggatg atctcgcgga gggtagcatg    9840
ttgattgtaa cgatgacaga gcgttgctgc ctgtgatcaa atatcatctc cctcgcagag   9900
atccgaatta tcagccttct tattcatttc tcgcttaacc gtgacaggct gtcgatcttg   9960
agaactatgc cgacataata ggaaatcgct ggataaagcc gctgaggaag ctgagtggcg  10020
ctatttcttt agaagtgaac gttgacgatc gtcgaccgta ccccgatgaa ttaattcgga  10080
cgtacgttct gaacacagct ggatacttac tgggcgatt gtcatacatg acatcaacaa   10140
tgtacccgtt tgtgtaaccg tctcttggag gttcgtatga cactagtggt tcccctcagc  10200
ttgcgactag atgttgaggc ctaacatttt attagagagc aggctagttg cttagataca  10260
tgatcttcag gccgttatct gtcagggcaa gcgaaaattg gccatttatg acgaccaatg  10320
ccccgcagaa gctcccatct ttgccgccat agacgccgcg ccccccttttt ggggtgtaga  10380 acatcctttt gccagatgtg gaaaagaagt tcgttgtccc attgttggca atgacgtagt   10440
agccggcgaa agtgcgagac ccatttgcgc tatatataag cctacgattt ccgttgcgac   10500
tattgtcgta attggatgaa ctattatcgt agttgctctc agagttgtcg taatttgatg   10560
gactattgtc gtaattgctt atggagttgt cgtagttgct tggagaaatg tcgtagttgg   10620
atggggagta gtcataggga agacgagctt catccactaa aacaattggc aggtcagcaa   10680
gtgcctgccc cgatgccatc gcaagtacga ggcttagaac caccttcaac agatcgcgca   10740
tagtcttccc cagctctcta acgcttgagt taagccgcgc cgcgaagcgg cgtcggcttg   10800
aacgaattgt tagacattat ttgccgacta ccttggtgat ctcgcctttc acgtagtgaa   10860
caaattcttc caactgatct gcgcgcgagg ccaagcgatc ttcttgtcca agataagcct   10920
gcctagcttc aagtatgacg ggctgatact gggccggcag gcgctccatt gcccagtcgg   10980
cagcgacatc cttcggcgcg attttgccgg ttactgcgct gtaccaaatg cgggacaacg   11040
taagcactac atttcgctca tcgccagccc agtcgggcgg cgagttccat agcgttaagg   11100
tttcatttag cgcctcaaat agatcctgtt caggaaccgg atcaaagagt tcctccgccg   11160
```

```
ctggacctac caaggcaacg ctatgttctc ttgcttttgt cagcaagata gccagatcaa    11220
tgtcgatcgt ggctggctcg aagatacctg caagaatgtc attgcgctgc cattctccaa    11280
attgcagttc gcgcttagct ggataacgcc acggaatgat gtcgtcgtgc acaacaatgg    11340
tgacttctac agcgcggaga atctcgctct ctccagggga agccgaagtt tccaaaaggt    11400
cgttgatcaa agctcgccgc gttgtttcat caagccttac agtcaccgta accagcaaat    11460
caatatcact gtgtggcttc aggccgccat ccactgcgga gccgtacaaa tgtacggcca    11520
gcaacgtcgg ttcgagatgg cgctcgatga cgccaactac ctctgatagt tgagtcgata    11580
cttcggcgat caccgcttcc ctcatgatgt ttaactcctg aattaagccg cgccgcgaag    11640
cggtgtcggc ttgaatgaat tgttaggcgt catcctgtgc tcccgagaac cagtaccagt    11700
acatcgctgt ttcgttcgag acttgaggtc tagttttata cgtgaacagg tcaatgccgc    11760
cgagagtaaa gccacatttt gcgtacaaat tgcaggcagg tacattgttc gtttgtgtct    11820
ctaatcgtat gccaaggagc tgtctgctta gtgcccactt tttcgcaaat tcgatgagac    11880
tgtgcgcgac tcctttgcct cggtgcgtgt gcgacacaac aatgtgttcg atagaggcta    11940
gatcgttcca tgttgagttg agttcaatct tcccgacaag ctcttggtcg atgaatgcgc    12000
catagcaagc agagtcttca tcagagtcat catccgagat gtaatccttc cggtaggggc    12060
tcacacttct ggtagatagt tcaaagcctt ggtcggatag gtgcacatcg aacacttcac    12120
gaacaatgaa atggttctca gcatccaatg tttccgccac ctgctcaggg atcaccgaaa    12180
tcttcatatg acgcctaacg cctggcacag cggatcgcaa acctggcgcg gcttttggca    12240
caaaaggcgt gacaggtttg cgaatccgtt gctgccactt gttaacccct ttgccagatt    12300
tggtaactat aatttatgtt agaggcgaag tcttgggtaa aaactggcct aaaattgctg    12360
gggatttcag gaaagtaaac atcaccttcc ggctcgatgt ctattgtaga tatatgtagt    12420
gtatctactt gatcggggga tctgctgcct cgcgcgtttc ggtgatgacg gtgaaaacct    12480
ctgacacatg cagctcccgg agacggtcac agcttgtctg taagcggatg ccgggagcag    12540
acaagcccgt cagggcgcgt cagcgggtgt tggcgggtgt cggggcgcag ccatgaccca    12600
gtcacgtagc gatagcggag tgtatactgg cttaactatg cggcatcaga gcagattgta    12660
ctgagagtgc accatatgcg gtgtgaaata ccgcacagat gcgtaaggag aaaataccgc    12720
atcaggcgct cttccgcttc ctcgctcact gactcgctgc gctcggtcgt tcggctgcgg    12780
cgagcggtat cagctcactc aaaggcggta atacggttat ccacagaatc aggggataac    12840
gcaggaaaga acatgtgagc aaaaggccag caaaaggcca ggaaccgtaa aaaggccgcg    12900
ttgctggcgt ttttccatag gctccgcccc cctgacgagc atcacaaaaa tcgacgctca    12960
agtcagaggt ggcgaaaccc gacaggacta taaagatacc aggcgtttcc ccctggaagc    13020
tccctcgtgc gctctcctgt tccgaccctg ccgcttaccg gatacctgtc cgcctttctc    13080
ccttcgggaa gcgtggcgct ttctcatagc tcacgctgta ggtatctcag ttcggtgtag    13140
gtcgttcgct ccaagctggg ctgtgtgcac gaaccccccg ttcagcccga ccgctgcgcc    13200
ttatccggta actatcgtct tgagtccaac ccggtaagac acgacttatc gccactggca    13260
gcagccactg gtaacaggat tagcagagcg aggtatgtag gcggtgctac agagttcttg    13320
aagtggtggc ctaactacgg ctacactaga aggacagtat ttggtatctg cgctctgctg    13380
aagccagtta ccttcggaaa aagagttggt agctcttgat ccggcaaaca aaccaccgct    13440
ggtagcggtg gtttttttgt ttgcaagcag cagattacgc gcagaaaaaa aggatctcaa    13500
gaagatcctt tgatcttttc tacggggtct gacgctcagt ggaacgaaaa ctcacgttaa    13560
```

```
gggattttgg tcatgagatt atcaaaaagg atcttcacct agatccttt  aaattaaaaa   13620
tgaagtttta aatcaatcta aagtatatat gagtaaactt ggtctgacag ttaccaatgc   13680
ttaatcagtg aggcacctat ctcagcgatc tgtctatttc gttcatccat agttgcctga   13740
ctccccgtcg tgtagataac tacgatacgg agggcttac  catctggccc cagtgctgca   13800
atgataccgc gagacccacg ctcaccggct ccagatttat cagcaataaa ccagccagcc   13860
ggaagggccg agcgcagaag tggtcctgca actttatccg cctccatcca gtctattaat   13920
tgttgccggg aagctagagt aagtagttcg ccagttaata gtttgcgcaa cgttgttgcc   13980
attgctgcag gggggggggg ggggggggac ttccattgtt cattccacgg acaaaaacag   14040
agaaaggaaa cgacagaggc caaaaagcct cgctttcagc acctgtcgtt tcctttcttt   14100
tcagagggta ttttaaataa aaacattaag ttatgacgaa gaagaacgga aacgccttaa   14160
accggaaaat tttcataaat agcgaaaacc cgcgaggtcg ccgccccgta acctgtcgga   14220
tcaccggaaa ggaccccgtaa agtgataatg attatcatct acatatcaca acgtgcgtgg   14280
aggccatcaa accacgtcaa ataatcaatt atgacgcagg tatcgtatta attgatctgc   14340
atcaacttaa cgtaaaaaca acttcagaca atacaaatca gcgacactga atacggggca   14400
acctcatgtc cccccccccc ccccccctgc aggcatcgtg gtgtcacgct cgtcgtttgg   14460
tatggcttca ttcagctccg gttcccaacg atcaaggcga gttacatgat cccccatgtt   14520
gtgcaaaaaa gcggttagct ccttcggtcc tccgatcgtt gtcagaagta agttggccgc   14580
agtgttatca ctcatggtta tggcagcact gcataattct cttactgtca tgccatccgt   14640
aagatgcttt tctgtgactg gtgagtactc aaccaagtca ttctgagaat agtgtatgcg   14700
gcgaccgagt tgctcttgcc cggcgtcaac acgggataat accgcgccac atagcagaac   14760
tttaaaagtg ctcatcattg gaaaacgttc ttcggggcga aaactctcaa ggatcttacc   14820
gctgttgaga tccagttcga tgtaacccac tcgtgcaccc aactgatctt cagcatcttt   14880
tactttcacc agcgtttctg ggtgagcaaa aacaggaagg caaaatgccg caaaaaaggg   14940
aataagggcg acacggaaat gttgaatact catactcttc cttttcaat  attattgaag   15000
catttatcag ggttattgtc tcatgagcgg atacatattt gaatgtattt agaaaaataa   15060
acaaataggg gttccgcgca catttccccg aaaagtgcca cctgacgtct aagaaaccat   15120
tattatcatg acattaacct ataaaaatag gcgtatcacg aggcccttc  gtcttcaaga   15180
attggtcgac gatcttgctg cgttcggata ttttcgtgga gttcccgcca cagacccgga   15240
ttgaaggcga gatccagcaa ctcgcgccag atcatcctgt gacggaactt tggcgcgtga   15300
tgactggcca ggacgtcggc cgaaagagcg acaagcagat cacgcttttc gacagcgtcg   15360
gatttgcgat cgaggatttt tcggcgctgc gctacgtccg cgaccgcgtt gagggatcaa   15420
gccacagcag cccactcgac cttctagccg acccagacga gccaagggat cttttggaa   15480
tgctgctccg tcgtcaggct ttccgacgtt gggtggttg  aacagaagtc attatcgtac   15540
ggaatgccaa gcactcccga ggggaaccct gtggttggca tgcacataca aatggacgaa   15600
cggataaacc ttttcacgcc cttttaaata tccgttattc taataaacgc tcttttctct   15660
tag                                                                15663
```

<210> SEQ ID NO 40  
<211> LENGTH: 25  
<212> TYPE: DNA  
<213> ORGANISM: Artificial  
<220> FEATURE:

<223> OTHER INFORMATION: attB1 site

<400> SEQUENCE: 40
acaagtttgt acaaaaaagc aggct                                    25

<210> SEQ ID NO 41
<211> LENGTH: 25
<212> TYPE: DNA
<213> ORGANISM: Artificial
<220> FEATURE:
<223> OTHER INFORMATION: attB2 site

<400> SEQUENCE: 41
accactttgt acaagaaagc tgggt                                    25

<210> SEQ ID NO 42
<211> LENGTH: 55
<212> TYPE: DNA
<213> ORGANISM: Artificial
<220> FEATURE:
<223> OTHER INFORMATION: At5g26030-5'attB forward primer

<400> SEQUENCE: 42
ttaaacaagt tgtacaaaa aagcaggctc aacaatgcag gcaacggctt tatca    55

<210> SEQ ID NO 43
<211> LENGTH: 50
<212> TYPE: DNA
<213> ORGANISM: Artificial
<220> FEATURE:
<223> OTHER INFORMATION: At5g26030-3'attB reverse primer

<400> SEQUENCE: 43
ttaaaccact ttgtacaaga aagctgggtc tataggttcc ggaacgcatg         50

<210> SEQ ID NO 44
<211> LENGTH: 55
<212> TYPE: DNA
<213> ORGANISM: Artificial
<220> FEATURE:
<223> OTHER INFORMATION: At2g30390-5'attB forward primer

<400> SEQUENCE: 44
ttaaacaagt tgtacaaaa aagcaggctc aacaatgaat tgcccagcca tgact    55

<210> SEQ ID NO 45
<211> LENGTH: 50
<212> TYPE: DNA
<213> ORGANISM: Artificial
<220> FEATURE:
<223> OTHER INFORMATION: At2g30390-3'attB reverse primer

<400> SEQUENCE: 45
ttaaaccact ttgtacaaga aagctgggtt tataatgaag gcaagatgcc         50

<210> SEQ ID NO 46
<211> LENGTH: 54
<212> TYPE: DNA
<213> ORGANISM: Artificial
<220> FEATURE:
<223> OTHER INFORMATION: VC062 primer

<400> SEQUENCE: 46
ttaaacaagt tgtacaaaa aagcaggctg caattaaccc tcactaaagg gaac     54

<210> SEQ ID NO 47
<211> LENGTH: 53
<212> TYPE: DNA
<213> ORGANISM: Artificial
<220> FEATURE:
<223> OTHER INFORMATION: VC063 primer

<400> SEQUENCE: 47
ttaaaccact tgtacaaga aagctgggtg cgtaatacga ctcactatag ggc    53

<210> SEQ ID NO 48
<211> LENGTH: 484
<212> TYPE: PRT
<213> ORGANISM: Hordeum vulgare

<400> SEQUENCE: 48

```
Met Glu Cys Val Arg Ser Gly Ala Leu Asp Leu Gly Arg Ser Gly Asn
1               5                   10                  15

Phe Leu Gly Lys Ser Gly Ser Thr Thr Ser Cys Gly Lys Val Arg Cys
            20                  25                  30

Ser Thr Asn Leu Ala Gly Ser Thr Lys Cys Glu Gln Asn Leu His Gly
        35                  40                  45

Lys Ala Lys Pro Leu Leu Leu Ser Ala Ser Gly Lys Ala Arg Gly Thr
    50                  55                  60

Ser Gly Leu Val His Arg Ser Pro Val Leu Lys His Gln His His Leu
65                  70                  75                  80

Ser Val Arg Ser Thr Ser Thr Asp Val Cys Thr Thr Phe Asp Glu Asp
                85                  90                  95

Val Lys Gly Val Ser Ser His Ala Val Glu Glu Lys Val Gly Val Leu
            100                 105                 110

Leu Leu Asn Leu Gly Gly Pro Glu Thr Leu Asn Asp Val Gln Pro Phe
        115                 120                 125

Leu Phe Asn Leu Phe Ala Asp Pro Asp Ile Ile Arg Leu Pro Arg Leu
    130                 135                 140

Phe Arg Phe Leu Gln Arg Pro Leu Ala Lys Leu Ile Ser Thr Phe Arg
145                 150                 155                 160

Ala Pro Lys Ser Lys Glu Gly Tyr Ala Ser Ile Gly Gly Gly Ser Pro
                165                 170                 175

Leu Arg Lys Ile Thr Asp Glu Gln Ala Asn Ala Leu Lys Val Ala Leu
            180                 185                 190

Lys Ser Lys Asn Leu Glu Ala Asp Ile Tyr Val Gly Met Arg Tyr Trp
        195                 200                 205

Tyr Pro Phe Thr Glu Glu Ala Ile Asp Gln Ile Lys Lys Asp Lys Ile
    210                 215                 220

Thr Lys Leu Val Val Leu Pro Leu Tyr Pro Gln Tyr Ser Ile Ser Thr
225                 230                 235                 240

Ser Gly Ser Ser Ile Arg Val Leu Gln Asn Ile Val Lys Glu Asp Pro
                245                 250                 255

Tyr Phe Ala Gly Leu Pro Ile Ser Ile Glu Ser Trp Tyr Gln Arg
            260                 265                 270

Glu Gly Tyr Val Lys Ser Met Ala Asp Leu Ile Glu Lys Glu Leu Ser
        275                 280                 285

Val Phe Ser Asn Pro Glu Glu Val Met Ile Phe Phe Ser Ala His Gly
    290                 295                 300

Val Pro Leu Thr Tyr Val Lys Asp Ala Gly Asp Pro Tyr Arg Asp Gln
305                 310                 315                 320
```

```
Met Glu Asp Cys Ile Ala Leu Ile Met Glu Glu Leu Lys Ser Arg Gly
                325                 330                 335
Thr Leu Asn Asp His Thr Leu Ala Tyr Gln Ser Arg Val Gly Pro Val
            340                 345                 350
Gln Trp Leu Lys Pro Tyr Thr Asp Glu Val Leu Val Glu Leu Gly Gln
        355                 360                 365
Lys Gly Val Lys Ser Leu Leu Ala Val Pro Val Ser Phe Val Ser Glu
    370                 375                 380
His Ile Glu Thr Leu Glu Glu Ile Asp Met Glu Tyr Arg Glu Leu Ala
385                 390                 395                 400
Leu Glu Ser Gly Ile Glu Asn Trp Gly Arg Val Pro Ala Leu Gly Cys
                405                 410                 415
Thr Ser Ser Phe Ile Ser Asp Leu Ala Asp Ala Val Val Glu Ala Leu
            420                 425                 430
Pro Ser Ala Ser Ala Met Ala Thr Arg Lys Val Lys Asp Thr Asp Ser
        435                 440                 445
Asp Met Asp Met Met His Tyr Leu Thr Lys Met Phe Leu Gly Ser Val
    450                 455                 460
Leu Ala Phe Phe Leu Leu Leu Ser Pro Arg Leu Val Ser Ala Phe Arg
465                 470                 475                 480
Asn Thr Leu Gln

<210> SEQ ID NO 49
<211> LENGTH: 482
<212> TYPE: PRT
<213> ORGANISM: Oryza sativa

<400> SEQUENCE: 49

Met Glu Cys Val Arg Ser Gly Ser Gly Val Leu Asp Pro Arg Cys Ser
1               5                   10                  15
Pro Arg Phe Leu Gly Lys Lys Gly Ser Leu Thr Ser Cys Gly Lys
            20                  25                  30
Ala Thr Ser Thr Asn Leu Ala Ile Cys Thr Lys His Glu Gln Asn Leu
        35                  40                  45
His Gly Asn Val Lys Pro Ser Gln Leu Ala Ala Ser Gly Ser Ser Tyr
    50                  55                  60
Ser Val His Arg Ser Pro Val Leu Lys Gln Arg Gln Asn Leu Ser Ala
65                  70                  75                  80
Arg Ser Thr Ser Ala Asp Val Tyr Thr Thr Phe Asp Glu Asn Val Arg
                85                  90                  95
Ala Val Ser Ser His Ala Ala Glu Glu Lys Val Gly Val Leu Leu Leu
            100                 105                 110
Asn Leu Gly Gly Pro Glu Thr Leu Asp Asp Val Gln Pro Phe Leu Phe
        115                 120                 125
Asn Leu Phe Ala Asp Pro Asp Ile Ile Arg Leu Pro Arg Leu Phe Arg
    130                 135                 140
Phe Leu Gln Arg Pro Leu Ala Lys Leu Ile Ser Thr Phe Arg Ala Pro
145                 150                 155                 160
Lys Ser Lys Glu Gly Tyr Ala Ser Ile Gly Gly Gly Ser Pro Leu Arg
                165                 170                 175
Lys Ile Thr Asp Glu Gln Ala Asn Ala Leu Lys Val Ala Leu Lys Lys
            180                 185                 190
Lys Asn Leu Asn Ala Asn Ile Tyr Val Gly Met Arg Tyr Trp Tyr Pro
        195                 200                 205
```

```
Phe Thr Glu Glu Ala Ile Asp Gln Ile Lys Lys Asp Lys Ile Thr Lys
    210                 215                 220

Leu Val Val Leu Pro Leu Tyr Pro Gln Tyr Ser Ile Ser Thr Ser Gly
225                 230                 235                 240

Ser Ser Ile Arg Val Leu Gln Asn Ile Val Lys Glu Asp Ser Tyr Phe
                245                 250                 255

Ala Gly Leu Pro Ile Ser Ile Ile Glu Ser Trp Tyr Gln Arg Asp Gly
            260                 265                 270

Tyr Val Lys Ser Met Ala Asp Leu Ile Glu Lys Glu Leu Ser Ile Phe
        275                 280                 285

Ser Asn Pro Glu Glu Val Met Ile Phe Phe Ser Ala His Gly Val Pro
    290                 295                 300

Leu Thr Tyr Val Thr Asp Ala Gly Asp Pro Tyr Arg Asp Gln Met Glu
305                 310                 315                 320

Asp Cys Ile Ala Leu Ile Met Gly Glu Leu Lys Ser Arg Gly Ile Leu
                325                 330                 335

Asn Ser His Thr Leu Ala Tyr Gln Ser Arg Val Gly Pro Val Gln Trp
            340                 345                 350

Leu Lys Pro Tyr Thr Asp Glu Val Leu Val Glu Leu Gly Gln Gln Gly
        355                 360                 365

Val Lys Ser Leu Leu Ala Val Pro Val Ser Phe Val Ser Glu His Ile
    370                 375                 380

Glu Thr Leu Glu Glu Ile Asp Met Glu Tyr Lys Glu Leu Ala Leu Glu
385                 390                 395                 400

Ser Gly Ile Glu Asn Trp Gly Arg Val Pro Ala Leu Gly Cys Thr Ser
                405                 410                 415

Ser Phe Ile Ser Asp Leu Ala Asp Ala Val Val Glu Ala Leu Pro Ser
            420                 425                 430

Ala Ser Ala Leu Val Thr Lys Lys Val Asp Glu Ser Asp Ser Asp Met
        435                 440                 445

Asp Leu Met His Tyr Leu Ser Lys Met Phe Phe Gly Ser Ile Leu Ala
    450                 455                 460

Phe Val Leu Leu Leu Ser Pro Arg Leu Ile Ser Ala Phe Arg Asn Thr
465                 470                 475                 480

Leu Leu

<210> SEQ ID NO 50
<211> LENGTH: 445
<212> TYPE: PRT
<213> ORGANISM: Vitis vinifera

<400> SEQUENCE: 50

Met Glu Ala Val Ser Thr Ser Ser Ile Leu Pro His Gly Lys Val Ser
1               5                   10                  15

Gly Leu Asn His Arg Ser Phe Asn Gln Lys Ser Ser Ile Arg Ser Ser
            20                  25                  30

Pro Trp Lys Gly Lys Gly Lys Glu Leu Ser Phe Val Leu Thr Phe
        35                  40                  45

Gln Arg Gly Ala Tyr Thr Tyr Val Gly Ser Ala Val Glu Ser Pro Thr
    50                  55                  60

His Ala Val Glu Glu Lys Val Gly Val Leu Leu Asn Leu Gly Gly
65                  70                  75                  80

Pro Glu Thr Leu His Asp Val Gln Pro Phe Leu Phe Asn Leu Phe Ala
                85                  90                  95
```

Asp Pro Asp Ile Ile Arg Leu Pro Arg Leu Phe Gln Phe Leu Gln Arg
            100                 105                 110

Pro Leu Ala Gln Leu Ile Ser Val Ile Arg Ala Pro Lys Ser Lys Glu
        115                 120                 125

Gly Tyr Ala Ala Ile Gly Gly Ser Pro Leu Arg Lys Ile Thr Asp
    130                 135                 140

Glu Gln Ala His Ala Ile Lys Ala Ala Leu Glu Ala Lys Asn Met His
145                 150                 155                 160

Val Asn Val Tyr Val Gly Met Arg Tyr Trp Tyr Pro Phe Thr Glu Glu
                165                 170                 175

Ala Ile Glu Gln Ile Lys Lys Asp Lys Ile Thr Arg Leu Val Val Leu
            180                 185                 190

Pro Leu Tyr Pro Gln Phe Ser Ile Ser Thr Thr Gly Ser Ser Ile Arg
        195                 200                 205

Val Leu Glu Ser Ile Phe Arg Glu Asp Ala Tyr Leu Ser Arg Leu Pro
    210                 215                 220

Val Ser Ile Ile Gln Cys Trp Tyr Gln Arg Gly Tyr Ile Asn Ser
225                 230                 235                 240

Met Ala Asp Leu Ile Glu Glu Glu Leu Gln Ile Phe Ser Lys Pro Lys
                245                 250                 255

Glu Val Met Ile Phe Phe Ser Ala His Gly Val Pro Val Ser Tyr Val
            260                 265                 270

Glu Asp Ala Gly Asp Pro Tyr Arg Asp Gln Met Glu Glu Cys Ile Tyr
        275                 280                 285

Leu Ile Met Gln Glu Leu Lys Ala Arg Gly Ile Ser Asn Lys His Thr
    290                 295                 300

Leu Ala Tyr Gln Ser Arg Val Gly Pro Val Gln Trp Leu Lys Pro Tyr
305                 310                 315                 320

Thr Asp Glu Val Leu Val Glu Leu Gly Gln Lys Gly Val Lys Ser Leu
                325                 330                 335

Leu Ala Val Pro Val Ser Phe Val Ser Glu His Ile Glu Thr Leu Glu
            340                 345                 350

Glu Ile Asp Met Glu Tyr Lys His Leu Ala Leu Glu Ser Gly Ile Glu
        355                 360                 365

Asn Trp Gly Arg Val Pro Ala Leu Gly Cys Thr Ser Ser Phe Ile Thr
    370                 375                 380

Asp Leu Ala Asp Ala Val Ile Glu Ala Leu Pro Ala Ala Lys Ala Met
385                 390                 395                 400

Thr Thr Gln Ser Thr Ser Lys Glu Phe Asn Met Asp Pro Val Asn Tyr
                405                 410                 415

Ala Ile Lys Met Phe Phe Gly Ser Ile Leu Ala Phe Val Leu Leu Leu
            420                 425                 430

Ser Pro Lys Met Ile Ser Lys Phe Lys Asn Gln Leu Phe
        435                 440                 445

<210> SEQ ID NO 51
<211> LENGTH: 526
<212> TYPE: PRT
<213> ORGANISM: Oryza sativa

<400> SEQUENCE: 51

Met Trp Ser Ser Ser Gln Ala Ser Thr Arg Gly Val Ile Glu Val Gly
1               5                   10                  15

Arg Val Glu Ala Gly Pro Ser His Phe Pro Lys Arg Pro Ala Pro Arg
            20                  25                  30

-continued

Asn Ser Ser Arg Val Asn Leu Ser Arg Thr Tyr Ala Ile Lys Ser Cys
        35                  40                  45

Ser Val Ser Ser Arg Thr Gly Leu Cys Leu Gly Gln Cys Tyr His Lys
50                  55                  60

Lys Ser Ser Ala Cys Lys Cys Lys Leu Gly Trp Ser Ser Gln Pro Leu
65                  70                  75                  80

Ser Ser Leu Arg His His Leu Arg Val His Ser Ser Ala Ser Glu Ala
                85                  90                  95

Val Leu Thr Ser Gln Ser Asp Phe Thr Lys Leu Leu Val Gly Asn Glu
            100                 105                 110

Lys Ile Gly Val Leu Leu Asn Leu Gly Gly Pro Glu Thr Leu Asp
        115                 120                 125

Asp Val Gln Pro Phe Leu Phe Asn Leu Phe Ala Asp Pro Asp Ile Ile
        130                 135                 140

Arg Leu Pro Arg Leu Phe Arg Phe Leu Gln Lys Pro Leu Ala Gln Phe
145                 150                 155                 160

Ile Ser Val Val Arg Ala Pro Lys Ser Lys Glu Gly Tyr Ala Ser Ile
                165                 170                 175

Gly Gly Gly Ser Pro Leu Arg Gln Ile Thr Asp Ala Gln Ala Glu Ala
            180                 185                 190

Leu Arg Lys Ala Leu Cys Asp Lys Asp Ile Pro Ala Lys Val Tyr Val
        195                 200                 205

Gly Met Arg Tyr Trp His Pro Phe Thr Glu Glu Ala Ile Glu Gln Ile
    210                 215                 220

Lys Arg Asp Gly Ile Thr Lys Leu Val Val Leu Pro Leu Tyr Pro Gln
225                 230                 235                 240

Phe Ser Ile Ser Thr Ser Gly Ser Ser Leu Arg Leu Leu Glu Gly Ile
                245                 250                 255

Phe Arg Glu Asp Glu Tyr Leu Val Asn Met Gln His Thr Val Ile Pro
            260                 265                 270

Ser Trp Tyr Gln Arg Glu Gly Tyr Ile Lys Ala Met Ala Thr Leu Ile
        275                 280                 285

Glu Lys Glu Leu Arg Thr Phe Ser Glu Pro Gln Lys Val Met Ile Phe
    290                 295                 300

Phe Ser Ala His Gly Val Pro Leu Ala Tyr Val Glu Glu Ala Gly Asp
305                 310                 315                 320

Pro Tyr Lys Ala Glu Met Glu Glu Cys Val Asp Leu Ile Met Glu Glu
                325                 330                 335

Leu Glu Lys Arg Gly Ile Thr Asn Ser Cys Thr Leu Ala Tyr Gln Ser
            340                 345                 350

Arg Val Gly Pro Val Glu Trp Leu Arg Pro Tyr Thr Asp Glu Thr Ile
        355                 360                 365

Ile Glu Leu Gly Gln Lys Gly Val Lys Ser Leu Leu Ala Val Pro Ile
    370                 375                 380

Ser Phe Val Ser Glu His Ile Glu Thr Leu Glu Glu Ile Asp Val Glu
385                 390                 395                 400

Tyr Lys Glu Leu Ala Leu Glu Ser Gly Ile Lys His Trp Gly Arg Val
                405                 410                 415

Pro Ala Leu Gly Cys Glu Pro Thr Phe Ile Thr Asp Leu Ala Asp Ala
            420                 425                 430

Val Ile Glu Ser Leu Pro Tyr Val Gly Ala Met Ala Val Ser Asn Leu
        435                 440                 445

```
Glu Ala Arg Gln Pro Leu Val Pro Leu Gly Ser Val Glu Leu Leu
450                 455                 460

Ala Ala Tyr Asp Ser Lys Arg Asp Glu Leu Pro Pro Val Thr Val
465                 470                 475                 480

Trp Glu Trp Gly Trp Thr Lys Ser Ala Glu Thr Trp Asn Gly Arg Ala
                485                 490                 495

Ala Met Leu Ala Val Leu Ala Leu Leu Val Leu Glu Val Thr Thr Gly
                500                 505                 510

Glu Gly Phe Leu His Gln Trp Gly Ile Leu Pro Leu Phe His
                515                 520                 525

<210> SEQ ID NO 52
<211> LENGTH: 522
<212> TYPE: PRT
<213> ORGANISM: Cucumis sativus

<400> SEQUENCE: 52

Met Asp Ser Ala Ile Gln Ala Ser Ser Pro Ala Ser Ser Ser Ala
1               5                   10                  15

Phe Arg Ser Pro Cys Leu Thr Ser Ala Ser Gln Asn Cys Lys Phe Pro
                20                  25                  30

Leu Pro Thr Ser Arg Val Val Gly Ser Lys Arg His Arg Ala Phe Arg
                35                  40                  45

Leu His Met Asp Ala Cys Pro Thr Lys Cys His Val Val Ser Arg Tyr
50                  55                  60

Ser Phe Glu Leu Pro Asp Ser Gln Ser Ile Phe Ser Lys Lys Ser Ile
65                  70                  75                  80

Asn Lys Phe Phe Pro Pro Arg Ala Leu Val Ala Ser Asn Thr Gln
                85                  90                  95

Asn Thr Ser Ala Ala Pro Leu Ile Gly Glu Asp Lys Val Gly Val Leu
                100                 105                 110

Leu Leu Asn Leu Gly Gly Pro Glu Thr Leu Asp Asp Val Gln Pro Phe
                115                 120                 125

Leu Phe Asn Leu Phe Ala Asp Pro Asp Ile Ile Arg Leu Pro Arg Leu
                130                 135                 140

Phe Arg Phe Leu Gln Arg Pro Leu Ala Arg Phe Ile Ser Val Leu Arg
145                 150                 155                 160

Ser Pro Lys Ser Arg Glu Gly Tyr Ala Ser Ile Gly Gly Gly Ser Pro
                165                 170                 175

Leu Arg Lys Ile Thr Asp Ala Gln Ala Glu Glu Leu Lys Lys Ala Leu
                180                 185                 190

Trp Gln Lys Asp Val Pro Ala Glu Val Tyr Val Gly Met Arg Tyr Trp
                195                 200                 205

His Pro Phe Thr Glu Glu Ala Ile Glu Gln Ile Lys Lys Asp Gly Ile
                210                 215                 220

Ser Lys Leu Val Val Leu Pro Leu Tyr Pro Gln Phe Ser Ile Ser Thr
225                 230                 235                 240

Ser Gly Ser Ser Leu Arg Leu Leu Glu Gly Ile Phe Arg Glu Asp Glu
                245                 250                 255

Tyr Leu Val Asn Met Gln His Thr Val Ile Pro Ser Trp Tyr Gln Arg
                260                 265                 270

Glu Gly Tyr Ile Lys Ala Met Ala Asp Leu Ile Glu Lys Glu Leu Lys
                275                 280                 285

Thr Phe Asp Phe Pro Glu Gln Val Met Val Phe Ser Ala His Gly
                290                 295                 300
```

```
Val Pro Leu Ala Tyr Val Glu Glu Ala Gly Asp Pro Tyr Lys Ala Glu
305                 310                 315                 320

Met Glu Glu Cys Val Asp Leu Ile Met Glu Glu Leu Glu Lys Arg Arg
            325                 330                 335

Ile Thr Asn Ser Tyr Thr Leu Ala Tyr Gln Ser Arg Val Gly Pro Val
            340                 345                 350

Glu Trp Leu Lys Pro Tyr Thr Asp Glu Thr Ile Ile Glu Leu Gly Gln
        355                 360                 365

Lys Gly Val Lys Ser Leu Leu Ala Val Pro Ile Ser Phe Val Ser Glu
370                 375                 380

His Ile Glu Thr Leu Glu Glu Ile Asp Val Glu Tyr Lys Glu Leu Ala
385                 390                 395                 400

Leu Lys Ser Gly Ile Glu Lys Trp Gly Arg Val Pro Ala Leu Gly Cys
                405                 410                 415

Glu Pro Thr Phe Ile Thr Asp Leu Ala Asp Ala Val Ile Glu Ser Leu
            420                 425                 430

Pro Tyr Val Gly Ala Met Ala Val Ser Asn Leu Glu Ala Arg Gln Pro
        435                 440                 445

Leu Val Pro Leu Gly Ser Val Glu Glu Leu Leu Ala Ala Tyr Asp Ser
450                 455                 460

Gln Arg Arg Gln Leu Pro Pro Val Thr Val Trp Glu Trp Gly Trp
465                 470                 475                 480

Thr Lys Ser Ala Glu Thr Trp Asn Gly Arg Ala Ala Met Leu Ala Val
                485                 490                 495

Leu Val Leu Leu Val Leu Glu Val Thr Thr Gly Glu Gly Phe Leu His
                500                 505                 510

Gln Trp Gly Ile Phe Pro Leu Phe His Gln
            515                 520

<210> SEQ ID NO 53
<211> LENGTH: 497
<212> TYPE: PRT
<213> ORGANISM: Nicotiana tabacum

<400> SEQUENCE: 53

Met Ala Gln Pro Val Ile Phe Cys Arg Glu Ile Ser Ala Ser Pro Ala
1               5                   10                  15

Asn Cys Thr Ser Tyr Ser Pro Phe His Gln Val Asp Gly Gln Ser Ser
            20                  25                  30

Val Pro Phe Ala Ala Ser Cys Leu Arg Val Pro Lys Asn Cys Ser Leu
        35                  40                  45

Val Ala Ala Arg Cys Ser Leu Lys Pro Ser Met Met Pro Ser Ala Leu
    50                  55                  60

Val Thr Ser Arg Pro Gln Gln Val Ser Thr Asp Pro Val Asn Val Val
65                  70                  75                  80

Cys Asp Gly Lys Ile Gly Val Leu Leu Leu Asn Leu Gly Gly Pro Glu
                85                  90                  95

Ser Leu Glu Asp Val Gln Pro Phe Leu Phe Asn Leu Phe Ala Asp Pro
            100                 105                 110

Asp Ile Ile Arg Leu Pro Arg Leu Phe Arg Phe Leu Gln Arg Pro Leu
        115                 120                 125

Ala Gln Phe Ile Ser Val Ala Arg Ala Pro Lys Ser Lys Glu Gly Tyr
    130                 135                 140

Ala Ser Ile Gly Gly Gly Ser Pro Leu Arg Arg Ile Thr Asp Ala Gln
```

```
            145                 150                 155                 160
Ala Glu Ala Leu Arg Lys Ala Leu Arg Glu Arg Asn Val Pro Ala Lys
                165                 170                 175

Val Tyr Val Gly Met Arg Tyr Trp His Pro Phe Thr Glu Glu Ala Ile
                180                 185                 190

Glu Leu Ile Lys Arg Asp Gly Ile Thr Lys Leu Val Leu Pro Leu
                195                 200                 205

Tyr Pro Gln Phe Ser Ile Ser Thr Ser Gly Ser Ser Leu Arg Leu Leu
    210                 215                 220

Glu Ser Ile Phe Arg Glu Asp Glu Tyr Leu Val Asn Met Gln His Thr
225                 230                 235                 240

Val Ile Pro Ser Trp Tyr Gln Arg Glu Gly Tyr Ile Lys Ala Met Ala
                245                 250                 255

Asp Leu Met Glu Lys Glu Leu Lys Ser Phe Glu Arg Pro Gly Glu Val
                260                 265                 270

Met Ile Phe Phe Ser Ala His Gly Val Pro Leu Ala Tyr Val Glu Glu
                275                 280                 285

Ala Gly Asp Pro Tyr Lys Ala Glu Met Glu Glu Cys Val Asp Leu Ile
    290                 295                 300

Met Glu Glu Leu Glu Lys Arg Arg Val Tyr Asn Ala Tyr Thr Leu Ala
305                 310                 315                 320

Tyr Gln Ser Arg Val Gly Pro Val Glu Trp Leu Lys Pro Tyr Thr Asp
                325                 330                 335

Glu Thr Ile Ile Glu Leu Gly Lys Lys Gly Val Lys Ser Ile Leu Ala
                340                 345                 350

Val Pro Ile Ser Phe Val Ser Glu His Ile Glu Thr Leu Glu Glu Ile
                355                 360                 365

Asp Val Glu Tyr Lys Glu Leu Ala Leu Glu Ser Gly Ile Gln Asn Trp
    370                 375                 380

Ala Arg Val Pro Ala Leu Gly Val Glu Pro Thr Phe Ile Ser Asp Leu
385                 390                 395                 400

Ala Asp Ala Val Ile Glu Ser Leu Pro Tyr Val Gly Ala Met Ala Val
                405                 410                 415

Ser Asn Leu Glu Ala Arg Gln Ser Leu Val Pro Leu Gly Ser Val Glu
                420                 425                 430

Glu Leu Leu Ala Ala Tyr Asp Ser His Gly Arg Glu Leu Pro Pro Pro
                435                 440                 445

Val Thr Val Trp Glu Trp Gly Trp Thr Lys Ser Ala Glu Thr Trp Asn
    450                 455                 460

Gly Arg Ala Ala Met Leu Ala Val Leu Val Leu Val Leu Glu Val
465                 470                 475                 480

Thr Thr Gly Glu Gly Phe Leu His Gln Trp Ile Leu Pro Leu Phe
                485                 490                 495

Arg

<210> SEQ ID NO 54
<211> LENGTH: 387
<212> TYPE: PRT
<213> ORGANISM: Synechocystis PCC6803

<400> SEQUENCE: 54

Met Gly Arg Val Gly Val Leu Leu Asn Leu Gly Gly Pro Glu Lys
1               5                   10                  15

Leu Glu Asp Val Arg Pro Phe Leu Phe Asn Leu Phe Ala Asp Pro Glu
```

```
            20                  25                  30
Ile Ile Arg Leu Pro Phe Pro Trp Leu Gln Lys Pro Leu Ala Trp Leu
         35                  40                  45
Ile Ser Thr Leu Arg Ala Lys Lys Ser Gln Ala Asn Tyr Ala Glu Ile
 50                  55                  60
Gly Gly Gly Ser Pro Leu Leu Gln Ile Thr Glu Ala Gln Ala Ser Ala
 65                  70                  75                  80
Leu Thr Thr Arg Leu Glu Arg Leu Gly Gln Asp Ala Lys Val Tyr Ile
                 85                  90                  95
Gly Met Arg Tyr Trp His Pro Phe Thr Glu Glu Ala Val Glu Lys Ile
                100                 105                 110
Lys Gly Asp Arg Leu Gln Arg Leu Val Ile Leu Pro Leu Tyr Pro His
                115                 120                 125
Phe Ser Ile Ser Thr Ser Gly Ser Ser Phe Arg Val Leu Glu Glu Met
            130                 135                 140
Trp His Asn Asp Pro Ser Leu Arg Gln Leu Asp Tyr Ser Leu Ile Pro
145                 150                 155                 160
Ser Trp Tyr Asp His Pro Gly Tyr Leu Gln Ala Met Ala Asp Leu Ile
                165                 170                 175
Ala Gln Glu Leu Lys Lys Phe Pro Asn Pro Asp Gln Ala His Ile Phe
                180                 185                 190
Phe Ser Ala His Gly Val Pro Gln Ser Tyr Val Asp Glu Ala Gly Asp
                195                 200                 205
Pro Tyr Gln Ala Glu Ile Glu Ala Cys Thr Arg Leu Ile Met Arg Thr
            210                 215                 220
Leu Asp Arg Pro Asn Gln Tyr Thr Leu Ala Tyr Gln Ser Arg Val Gly
225                 230                 235                 240
Pro Val Glu Trp Leu Lys Pro Tyr Thr Glu Glu Ala Leu Gln Lys Leu
                245                 250                 255
Gly Ala Glu Gly Ile Asp Asp Leu Leu Val Val Pro Ile Ser Phe Val
                260                 265                 270
Ser Glu His Ile Glu Thr Leu Gln Glu Ile Asp Ile Glu Tyr Arg Glu
            275                 280                 285
Ile Ala Glu Glu Ala Gly Ile Asp Asn Phe Gln Arg Val Pro Ala Leu
        290                 295                 300
Asn Thr His Pro Val Phe Ile Asp Ala Leu Ala Gln Met Val Met Asp
305                 310                 315                 320
Ser Leu Asn Asp Pro Pro Cys Thr Phe Glu Thr Val Pro His Pro Lys
                325                 330                 335
Lys Asn Met Lys Met Tyr Pro Gln Glu Arg Trp Glu Trp Gly Leu Thr
                340                 345                 350
Thr Ala Ala Glu Val Trp Asn Gly Arg Leu Ala Met Leu Gly Phe Ile
            355                 360                 365
Ala Leu Leu Val Glu Leu Ile Ser Gly Gln Gly Pro Leu His Phe Val
        370                 375                 380
Gly Leu Leu
385

<210> SEQ ID NO 55
<211> LENGTH: 4035
<212> TYPE: DNA
<213> ORGANISM: Artificial
<220> FEATURE:
<223> OTHER INFORMATION: Plasmid PHP30949, an entry clone containing the
      maize ferrochelatase-I protein.
```

<400> SEQUENCE: 55

```
aagggtgggc gcgccgaccc agctttcttg tacaaagttg gcattataag aaagcattgc      60
ttatcaattt gttgcaacga acaggtcact atcagtcaaa ataaaatcat tatttgccat     120
ccagctgata tccccatatag tgagtcgtat tacatggtca tagctgtttc ctggcagctc    180
tggcccgtgt ctcaaaatct ctgatgttac attgcacaag ataaaaatat atcatcatga    240
acaataaaac tgtctgctta cataaacagt aatacaaggg gtgttatgag ccatattcaa    300
cgggaaacgt cgaggccgcg attaaattcc aacatggatg ctgatttata tgggtataaa    360
tgggctcgcg ataatgtcgg gcaatcaggt gcgacaatct atcgcttgta tgggaagccc    420
gatgcgccag agttgtttct gaaacatggc aaaggtagcg ttgccaatga tgttacagat    480
gagatggtca gactaaactg gctgacggaa tttatgcctc ttccgaccat caagcatttt    540
atccgtactc ctgatgatgc atggttactc accactgcga tccccggaaa aacagcattc    600
caggtattag aagaatatcc tgattcaggt gaaaatattg ttgatgcgct ggcagtgttc    660
ctgcgccggt tgcattcgat tcctgtttgt aattgtcctt ttaacagcga tcgcgtattt    720
cgtctcgctc aggcgcaatc acgaatgaat aacggtttgg ttgatgcgag tgattttgat    780
gacgagcgta atggctggcc tgttgaacaa gtctggaaag aaatgcataa acttttgcca    840
ttctcaccgg attcagtcgt cactcatggt gatttctcac ttgataacct tattttttgac    900
gaggggaaat taataggttg tattgatgtt ggacgagtcg gaatcgcaga ccgataccag    960
gatcttgcca tcctatggaa ctgcctcggt gagttttctc cttcattaca gaaacggctt   1020
tttcaaaaat atggtattga taatcctgat atgaataaat tgcagtttca tttgatgctc   1080
gatgagtttt tctaatcaga attggttaat tggttgtaac actggcagag cattacgctg   1140
acttgacggg acggcgcaag ctcatgacca aaatccctta acgtgagtta cgcgtcgttc   1200
cactgagcgt cagacccgt agaaaagatc aaaggatctt cttgagatcc ttttttctg    1260
cgcgtaatct gctgcttgca acaaaaaaa ccaccgctac cagcggtggt ttgtttgccg   1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agcattgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg attttgtga    1800
tgctcgtcag gggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gctagccagg aagagtttgt agaaacgcaa   2160
aaaggccatc cgtcaggatg gccttctgct tagtttgatg cctggcagtt tatgcgggc    2220
gtcctgcccg ccaccctccg ggcgttgct tcacaacgtt caaatccgct cccggcggat    2280
```

```
ttgtcctact caggagagcg ttcaccgaca acaacagat aaaacgaaag gcccagtctt    2340
ccgactgagc ctttcgtttt atttgatgcc tggcagttcc ctactctcgc gttaacgcta    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520 tgcttttta taatgccaac tttgtacaaa aaagcaggct ccgcggccgc cccttcacc    2580 atgtcttcgt cgggccctc cccggcgacg ggaatccacg cgtcgccgcc gttgggcctt    2640 tgccggcga cgggaaccca tcacaccagg tcatgggca aaacaacctc cacaagtttt    2700
actggttcta ccaccaaaca tgagcagagc ttgcatggaa atgttaagcc gttgcaattg    2760
gcggcaaatg aatcctctcg tttggcttac agaagtccag cacttaaaaa ccagtggaat    2820
cttcctgcta gttcttcctc cactaatgtg gttaccacct ttgatgataa cgaacacgtg    2880
tcttccagtg ttattgaaga aaaagttgga gtactgttat aaaccttgg tggtccagag    2940 acacttgacg atgttcaacc attttattc aacctatttg ctgatccaga tatcattcga    3000
ctccctaggc tcttcaggtt tcttcaaaga ccactggcca aacttatttc tacttttaga    3060
gctcctaaga gtaaagaagg gtatgcttca attggtggtg ggtcgccgtt aaggaaaatt    3120
actgatgaac aggcgaatgc tttgaagatt gccctggaaa agaaaaaatt gaacgcaaac    3180
atatatgttg ggatgcggta ttggtaccct ttcacagaag aggccattga tcaaattaaa    3240
aaggataaga ttaccaagct cgttgttctt ccctttacc ctcagtactc catatcaaca    3300
agtgggtcaa gcattcgtgt tctccaagac attgtcaagg aagattcata tttttctggt    3360
ttgccaattt ccattattga atcatggtac caacgagatg gctatgtgaa atcaatgtct    3420
gacctaattg aaaaggagct ctccgccttc tccaatcctg aagaggttat gatattcttc    3480
agtgcacatg gtgtgccact tacctatgtt gaggatgctg agatcctta cagagatcag    3540 atggaggatt gtattgcttt gatcatgggg gagttaagat caagaggaat cttaaatagt    3600
cacactttgg cgtaccagag tcgggtgggg ccagttcaat ggctgaagcc atatactgat    3660
gaagttttag tagaacttgg tcaaaagggt gtgaagagcc tcctggctgt tccagtaagc    3720
tttgtgagtg agcacatcga gacattggaa gaaattgaca tggagtacaa ggagttggct    3780
ctggaatcag gcatcaagaa ctggggtcgg gttcctgctc ttggatgcac ttcaacattc    3840
atctccgacc ttgcagatgc tgtcgtcgaa gccctgccct ctgcttcagc gctcgcgacc    3900
agaaagcctg acgacatcga ttccagcatg gacctgacgc attacctcac caagatgctg    3960
tttggctcaa tcttggcatt tgtcctgctg ctatcaccaa ggctagtttc cgccttccgg    4020
agcaccatgc tttaa                                                    4035
```

<210> SEQ ID NO 56
<211> LENGTH: 1934
<212> TYPE: DNA
<213> ORGANISM: Zea mays

<400> SEQUENCE: 56

```
cgccactccc ccaatactca ggtgtcagga cagcgagcag gcacaagcag atctcactcc     60
acgttgctcc ttccgccctt cctctccgcc gctccccgaa aattcctgca ggaaggatca    120
tggagcgcgg gattcttggc tccaggggcg ccgtccaaat cttggggtcg aagaccgggg    180
ccgcgatgtc atgtggcaaa acaacctcta caagttttac ttgttctacc aaacacgagc    240
tgaacttgca tgtgaatgtt aagccgttgc aattggcaac agatggatcc tctcgtttgg    300
catacaaaac tccagtgctt aaaaatcagt ggaatctttc tgctagttct tcctctgcaa    360
```

-continued

```
atgtggttac cacttttgat gatgacaaag gtgtaccttc cagttttgct gaagaaaaga    420
tcggagtact gttattaaat cttggtggtc cagaaaccct agacgatgtt caaccattct    480
tgttcaacct atttgctgat ccagatatca ttcgactgcc taggctcttc aggttccttc    540
aaagaccact ggccaaactt atttctactt ttagagctcc taagagtaaa gaagggtatg    600
cttcaatcgg tggtgggtca ccattgagga aaattactga tgagcaggca atgctttga    660
agattgctct ggaaaagaaa aaattgaacg caaatatata tgttgggatg cggtattggt    720
atcctttcac agaagaagcc attgatcaga ttaagaagga taatatttcc aagctcgttg    780
ttcttccact ctaccctcag tactccatat caacaagtgg gtcaagcatt cgtgttctcc    840
aaaatgttgt caaggaagat tcatattttt ctggcttgcc aatctccatt atcgaatcat    900
ggtaccaacg tgatggctat gtgaaatcaa tggctgacct aattgaaaaa gagctatctg    960
cctttccaa tcctgaagag gtaatgatat tcttcagtgc acatggtgtg ccacttacct   1020
atgttcagga tgctggagat ccttacagag atcagatgga ggattgtatt tctttgatca   1080
tgggggagct gagatccaga ggaatcttaa atggtcacac tttggcgtat cagagtcggg   1140
tgggaccagt tcaatggctg aagccatata ctgatgaagt tttagtagaa cttggtcaga   1200
acggtgtgaa gagcctcctg gctgttccag taagcttcgt gagcgagcac attgagacac   1260
tggaagaaat agacatggag tacaaggagt tggctctgga atcaggcatt gagaactggg   1320
gccgggtccc tgctcttgga tgcacttcga ctttcatctc cgaccttgca gatgcggttg   1380
tcgaagccct cccatctgcc tcggcgctgg gaaccagaaa gcctgaagac accgattcca   1440
gcatggatct gatgcattac ctgaccaaga tgttcttcgg ctcaatcttg gcatttatcc   1500
tgctgttgtc accaagactg gtttctgctt tccggaacac catgctttag gtggttaggt   1560
aggtaagcaa aaagggaatg gtgtgatagg taattcttaa aaatttgaga ttaataatgg   1620
aaaaactgga gagagcttgg tgatagtaac tagagatcct ttaggctttg tttgggtact   1680
ctagtattga ccctaatccg tgtgttgaga tagattgagg tgtaaattag tttaagttat   1740
acctcaattc agctcagtac atatagattg agctcaatac tagaatactc aaactaggcc   1800
ttagtgcacg aggtagcagc ttgtaatttg ctgtttttga tattgttcac aggaaacatt   1860
ggtctcataa atgaatctgt gaaagcacat aacgttacaa atcaaaaaaa aaaaaaaaa    1920
aaaaaaaaaa aaaa                                                    1934
```

<210> SEQ ID NO 57
<211> LENGTH: 481
<212> TYPE: PRT
<213> ORGANISM: Glycine max

<400> SEQUENCE: 57

```
Met Asn Ala Thr Ser Tyr Ser Ala Leu Pro Ser Thr Phe Arg Ser Leu
1               5                   10                  15

His His Arg Asn Phe Ser Ala Phe Cys Ser Asp Ile Gln Asn Pro Gly
            20                  25                  30

Tyr Val Asp Cys His Ser Asn Cys Asn Lys Ser Thr Ser Gln Ala Ser
        35                  40                  45

Leu Phe Leu Cys Ser Asp Ser Asn Ser Arg Arg Asn Gly Val Phe Gly
    50                  55                  60

Arg Pro Leu Cys Val Asn Pro Ser Gly Arg Arg Asn Leu Val Gly Pro
65                  70                  75                  80

Ala Phe Tyr Ser Leu Glu Thr Ser Ala Tyr Asp Val Ala Ala Leu Glu
```

```
                    85                    90                    95
Ser Pro Ser Arg Val Ala Glu Glu Lys Val Gly Val Leu Leu Leu Asn
                100                  105                  110
Leu Gly Gly Pro Glu Thr Leu Ser Asp Val Gln Pro Phe Leu Phe Asn
                115                  120                  125
Leu Phe Ala Asp Pro Asp Ile Ile Arg Leu Pro Arg Leu Phe Arg Phe
130                  135                  140
Leu Gln Arg Pro Leu Ala Lys Leu Ile Ser Val Leu Arg Ala Pro Lys
145                  150                  155                  160
Ser Lys Glu Gly Tyr Ala Ala Ile Gly Gly Ser Pro Leu Arg Lys
                165                  170                  175
Ile Thr Asp Asp Gln Ala Leu Ala Ile Lys Met Ala Leu Glu Ala Lys
                180                  185                  190
Gly Ile Ser Ser Asn Val Tyr Val Gly Met Arg Tyr Trp Tyr Pro Phe
                195                  200                  205
Thr Glu Glu Ala Ile Gln Gln Ile Lys Arg Asp Arg Ile Thr Arg Leu
                210                  215                  220
Val Val Leu Pro Leu Tyr Pro Gln Phe Ser Ile Ser Thr Thr Gly Ser
225                  230                  235                  240
Ser Ile Arg Val Leu Glu His Ile Phe Arg Glu Asp Ala Tyr Leu Ser
                245                  250                  255
Lys Leu Pro Val Ser Ile Ile Asn Ser Trp Tyr Gln Arg Glu Gly Tyr
                260                  265                  270
Ile Lys Ser Met Ala Asn Leu Ile Gln Lys Glu Leu Gln Ser Phe Ser
                275                  280                  285
Glu Pro Lys Glu Val Met Ile Phe Phe Ser Ala His Gly Val Pro Val
                290                  295                  300
Ser Tyr Val Glu Glu Ala Gly Asp Pro Tyr Arg Asp Gln Met Glu Glu
305                  310                  315                  320
Cys Ile Phe Leu Ile Met Gln Glu Leu Lys Ala Arg Gly Ile Ser Asn
                325                  330                  335
Glu His Thr Leu Ala Tyr Gln Ser Arg Val Gly Pro Val Gln Trp Leu
                340                  345                  350
Lys Pro Tyr Thr Asp Glu Val Leu Val Glu Leu Gly Gln Lys Gly Val
                355                  360                  365
Lys Ser Leu Leu Ala Val Pro Val Ser Phe Val Ser Glu His Ile Glu
                370                  375                  380
Thr Leu Glu Glu Ile Asp Met Glu Tyr Lys Glu Leu Ala Leu Glu Ser
385                  390                  395                  400
Gly Ile Lys Asn Trp Ala Arg Val Pro Ala Leu Gly Val Thr Pro Ser
                405                  410                  415
Phe Ile Thr Asp Leu Ala Asp Ala Val Ile Glu Ala Leu Pro Ser Ala
                420                  425                  430
Thr Ala Ile Tyr Ala Pro Thr Arg Thr Ser Glu Asp Val Asp His Asp
                435                  440                  445
Pro Val Arg Tyr Phe Ile Lys Met Phe Phe Gly Ser Ile Leu Ala Phe
                450                  455                  460
Ile Leu Phe Leu Ser Pro Lys Met Ile Thr Ala Phe Arg Asn His Val
465                  470                  475                  480

Ile

<210> SEQ ID NO 58
<211> LENGTH: 466
```

<212> TYPE: PRT
<213> ORGANISM: Arabidopsis thaliana

<400> SEQUENCE: 58

```
Met Gln Ala Thr Ala Leu Ser Ser Gly Phe Asn Pro Leu Thr Lys Arg
1               5                   10                  15

Lys Asp His Arg Phe Pro Arg Ser Cys Ser Gln Arg Asn Ser Leu Ser
            20                  25                  30

Leu Ile Gln Cys Asp Ile Lys Glu Arg Ser Phe Gly Ser Met Thr
        35                  40                  45

Ile Thr Asn Arg Gly Leu Ser Phe Lys Thr Asn Val Phe Glu Gln Ala
    50                  55                  60

Arg Ser Val Thr Gly Asp Cys Ser Tyr Asp Glu Thr Ser Ala Lys Ala
65                  70                  75                  80

Arg Ser His Val Val Ala Glu Asp Lys Ile Gly Val Leu Leu Leu Asn
                85                  90                  95

Leu Gly Gly Pro Glu Thr Leu Asn Asp Val Gln Pro Phe Leu Tyr Asn
            100                 105                 110

Leu Phe Ala Asp Pro Asp Ile Ile Arg Leu Pro Arg Pro Phe Gln Phe
        115                 120                 125

Leu Gln Gly Thr Ile Ala Lys Phe Ile Ser Val Val Arg Ala Pro Lys
    130                 135                 140

Ser Lys Glu Gly Tyr Ala Ala Ile Gly Gly Ser Pro Leu Arg Lys
145                 150                 155                 160

Ile Thr Asp Glu Gln Ala Asp Ala Ile Lys Met Ser Leu Gln Ala Lys
                165                 170                 175

Asn Ile Ala Ala Asn Val Tyr Val Gly Met Arg Tyr Trp Tyr Pro Phe
            180                 185                 190

Thr Glu Glu Ala Val Gln Gln Ile Lys Lys Asp Lys Ile Thr Arg Leu
        195                 200                 205

Val Val Leu Pro Leu Tyr Pro Gln Tyr Ser Ile Ser Thr Thr Gly Ser
    210                 215                 220

Ser Ile Arg Val Leu Gln Asp Leu Phe Arg Lys Asp Pro Tyr Leu Ala
225                 230                 235                 240

Gly Val Pro Val Ala Ile Ile Lys Ser Trp Tyr Gln Arg Gly Tyr
                245                 250                 255

Val Asn Ser Met Ala Asp Leu Ile Glu Lys Glu Leu Gln Thr Phe Ser
            260                 265                 270

Asp Pro Lys Glu Val Met Ile Phe Phe Ser Ala His Gly Val Pro Val
        275                 280                 285

Ser Tyr Val Glu Asn Ala Gly Asp Pro Tyr Gln Lys Gln Met Glu Glu
    290                 295                 300

Cys Ile Asp Leu Ile Met Glu Glu Leu Lys Arg Gly Val Leu Asn
305                 310                 315                 320

Asp His Lys Leu Ala Tyr Gln Ser Arg Val Gly Pro Val Gln Trp Leu
                325                 330                 335

Lys Pro Tyr Thr Asp Glu Val Leu Val Asp Leu Gly Lys Ser Gly Val
            340                 345                 350

Lys Ser Leu Leu Ala Val Pro Val Ser Phe Val Ser Glu His Ile Glu
        355                 360                 365

Thr Leu Glu Glu Ile Asp Met Glu Tyr Arg Glu Leu Ala Leu Glu Ser
    370                 375                 380

Gly Val Glu Asn Trp Gly Arg Val Pro Ala Leu Gly Leu Thr Pro Ser
385                 390                 395                 400
```

-continued

```
Phe Ile Thr Asp Leu Ala Asp Ala Val Ile Glu Ser Leu Pro Ser Ala
                405                 410                 415
Glu Ala Met Ser Asn Pro Asn Ala Val Val Asp Ser Glu Asp Ser Glu
            420                 425                 430
Ser Ser Asp Ala Phe Ser Tyr Ile Val Lys Met Phe Phe Gly Ser Ile
        435                 440                 445
Leu Ala Phe Val Leu Leu Ser Pro Lys Met Phe His Ala Phe Arg
    450                 455                 460
Asn Leu
465

<210> SEQ ID NO 59
<211> LENGTH: 476
<212> TYPE: PRT
<213> ORGANISM: Zea mays

<400> SEQUENCE: 59

Met Glu Arg Gly Ile Leu Gly Ser Arg Gly Ala Val Gln Ile Leu Gly
1               5                   10                  15
Ser Lys Thr Gly Ala Ala Met Ser Cys Gly Lys Thr Thr Ser Thr Ser
            20                  25                  30
Phe Thr Cys Ser Thr Lys His Glu Leu Asn Leu His Val Asn Val Lys
        35                  40                  45
Pro Leu Gln Leu Val Thr Asp Gly Ser Ser Arg Leu Ala Tyr Lys Thr
    50                  55                  60
Pro Val Leu Lys Asn Gln Trp Asn Leu Ser Ala Ser Ser Ser Ser Ala
65                  70                  75                  80
Asn Val Val Thr Thr Phe Asp Asp Lys Gly Val Pro Ser Ser Phe
                85                  90                  95
Ala Glu Glu Lys Ile Gly Val Leu Leu Leu Asn Leu Gly Gly Pro Glu
            100                 105                 110
Thr Leu Asp Asp Val Gln Pro Phe Leu Phe Asn Leu Phe Ala Asp Pro
        115                 120                 125
Asp Ile Ile Arg Leu Pro Arg Leu Phe Arg Phe Leu Gln Arg Pro Leu
    130                 135                 140
Ala Lys Leu Ile Ser Thr Phe Arg Ala Pro Lys Ser Lys Glu Gly Tyr
145                 150                 155                 160
Ala Ser Ile Gly Gly Gly Ser Pro Leu Arg Lys Ile Thr Asp Glu Gln
                165                 170                 175
Ala Asn Ala Leu Lys Ile Ala Leu Glu Lys Lys Leu Asn Ala Asn
            180                 185                 190
Ile Tyr Val Gly Met Arg Tyr Trp Tyr Pro Phe Thr Glu Glu Ala Ile
        195                 200                 205
Asp Gln Ile Lys Lys Asp Asn Ile Ser Lys Leu Val Val Leu Pro Leu
    210                 215                 220
Tyr Pro Gln Tyr Ser Ile Ser Thr Ser Gly Ser Ser Ile Arg Val Leu
225                 230                 235                 240
Gln Asn Val Val Lys Glu Asp Ser Tyr Phe Ser Gly Leu Pro Ile Ser
                245                 250                 255
Ile Ile Glu Ser Trp Tyr Gln Arg Asp Gly Tyr Val Lys Ser Met Ala
            260                 265                 270
Asp Leu Ile Glu Lys Glu Leu Ser Ala Phe Ser Asn Pro Glu Glu Val
        275                 280                 285
Met Ile Phe Phe Ser Ala His Gly Val Pro Leu Thr Tyr Val Gln Asp
```

```
                    290                 295                 300
Ala Gly Asp Pro Tyr Arg Asp Gln Met Glu Asp Cys Ile Ser Leu Ile
305                 310                 315                 320

Met Gly Glu Leu Arg Ser Arg Gly Ile Leu Asn Gly His Thr Leu Ala
                325                 330                 335

Tyr Gln Ser Arg Val Gly Pro Val Gln Trp Leu Lys Pro Tyr Thr Asp
                340                 345                 350

Glu Val Leu Val Glu Leu Gly Gln Asn Gly Val Lys Ser Leu Leu Ala
                355                 360                 365

Val Pro Val Ser Phe Val Ser Glu His Ile Glu Thr Leu Glu Glu Ile
370                 375                 380

Asp Met Glu Tyr Lys Glu Leu Ala Leu Glu Ser Gly Ile Glu Asn Trp
385                 390                 395                 400

Gly Arg Val Pro Ala Leu Gly Cys Thr Ser Thr Phe Ile Ser Asp Leu
                405                 410                 415

Ala Asp Ala Val Val Glu Ala Leu Pro Ser Ala Ser Ala Leu Gly Thr
                420                 425                 430

Arg Lys Pro Glu Asp Thr Gly Ser Ser Met Asp Leu Met His Tyr Leu
                435                 440                 445

Thr Lys Met Phe Phe Gly Ser Ile Leu Ala Phe Ile Leu Leu Leu Ser
                450                 455                 460

Pro Arg Leu Val Ser Ala Phe Arg Asn Thr Thr Leu
465                 470                 475

<210> SEQ ID NO 60
<211> LENGTH: 484
<212> TYPE: PRT
<213> ORGANISM: Zea mays

<400> SEQUENCE: 60

Met Ser Ser Ser Gly Pro Ser Pro Ala Thr Gly Ile His Ala Ser Pro
1               5                   10                  15

Pro Leu Gly Leu Leu Pro Ala Thr Gly Thr His His Thr Arg Ser Trp
                20                  25                  30

Gly Lys Thr Thr Ser Thr Ser Phe Thr Gly Ser Thr Thr Lys His Glu
                35                  40                  45

Gln Ser Leu His Gly Asn Val Lys Pro Leu Gln Leu Ala Ala Asn Glu
            50                  55                  60

Ser Ser Arg Leu Ala Tyr Arg Ser Pro Ala Leu Lys Asn Gln Trp Asn
65              70                  75                  80

Leu Pro Ala Ser Ser Ser Thr Asn Val Val Thr Thr Phe Asp Asp
                85                  90                  95

Asn Glu His Val Ser Ser Val Ile Glu Lys Val Gly Val Leu
                100                 105                 110

Leu Leu Asn Leu Gly Gly Pro Glu Thr Leu Asp Asp Val Gln Pro Phe
                115                 120                 125

Leu Phe Asn Leu Phe Ala Asp Pro Asp Ile Ile Arg Leu Pro Arg Leu
                130                 135                 140

Phe Arg Phe Leu Gln Arg Pro Leu Ala Lys Leu Ile Ser Thr Phe Arg
145                 150                 155                 160

Ala Pro Lys Ser Lys Glu Gly Tyr Ala Ser Ile Gly Gly Gly Ser Pro
                165                 170                 175

Leu Arg Lys Ile Thr Asp Glu Gln Ala Asn Ala Leu Lys Ile Ala Leu
                180                 185                 190
```

```
Glu Lys Lys Lys Leu Asn Ala Asn Ile Tyr Val Gly Met Arg Tyr Trp
            195                 200                 205

Tyr Pro Phe Thr Glu Glu Ala Ile Asp Gln Ile Lys Lys Asp Lys Ile
        210                 215                 220

Thr Lys Leu Val Val Leu Pro Leu Tyr Pro Gln Tyr Ser Ile Ser Thr
225                 230                 235                 240

Ser Gly Ser Ser Ile Arg Val Leu Gln Asp Ile Val Lys Glu Asp Ser
                245                 250                 255

Tyr Phe Ser Gly Leu Pro Ile Ser Ile Glu Ser Trp Tyr Gln Arg
            260                 265                 270

Asp Gly Tyr Val Lys Ser Met Ser Asp Leu Ile Glu Lys Glu Leu Ser
        275                 280                 285

Ala Phe Ser Asn Pro Glu Glu Val Met Ile Phe Ser Ala His Gly
    290                 295                 300

Val Pro Leu Thr Tyr Val Glu Asp Ala Gly Asp Pro Tyr Arg Asp Gln
305                 310                 315                 320

Met Glu Asp Cys Ile Ala Leu Ile Met Gly Glu Leu Arg Ser Arg Gly
                325                 330                 335

Ile Leu Asn Ser His Thr Leu Ala Tyr Gln Ser Arg Val Gly Pro Val
            340                 345                 350

Gln Trp Leu Lys Pro Tyr Thr Asp Glu Val Leu Val Glu Leu Gly Gln
        355                 360                 365

Lys Gly Val Lys Ser Leu Leu Ala Val Pro Val Ser Phe Val Ser Glu
    370                 375                 380

His Ile Glu Thr Leu Glu Glu Ile Asp Met Glu Tyr Lys Glu Leu Ala
385                 390                 395                 400

Leu Glu Ser Gly Ile Lys Asn Trp Gly Arg Val Pro Ala Leu Gly Cys
                405                 410                 415

Thr Ser Thr Phe Ile Ser Asp Leu Ala Asp Ala Val Val Glu Ala Leu
            420                 425                 430

Pro Ser Ala Ser Ala Leu Ala Thr Arg Lys Pro Asp Asp Ile Asp Ser
        435                 440                 445

Ser Met Asp Leu Thr His Tyr Leu Thr Lys Met Leu Phe Gly Ser Ile
    450                 455                 460

Leu Ala Phe Val Leu Leu Ser Pro Arg Leu Val Ser Ala Phe Arg
465                 470                 475                 480

Ser Thr Met Leu

<210> SEQ ID NO 61
<211> LENGTH: 482
<212> TYPE: PRT
<213> ORGANISM: Oryza sativa

<400> SEQUENCE: 61

Met Glu Cys Val Arg Ser Gly Ser Gly Val Leu Asp Pro Arg Cys Ser
1               5                   10                  15

Pro Arg Phe Leu Gly Lys Lys Gly Gly Ser Leu Thr Ser Cys Gly Lys
            20                  25                  30

Ala Thr Ser Thr Asn Leu Ala Ile Cys Thr Lys His Glu Gln Asn Leu
        35                  40                  45

His Gly Asn Val Lys Pro Ser Gln Leu Ala Ala Ser Gly Ser Ser Tyr
    50                  55                  60

Ser Val His Arg Ser Pro Val Leu Lys Gln Arg Gln Asn Leu Ser Ala
65                  70                  75                  80
```

-continued

```
Arg Ser Thr Ser Ala Asp Val Tyr Thr Thr Phe Asp Glu Asn Val Arg
             85                  90                  95
Ala Val Ser Ser His Ala Ala Glu Glu Lys Val Gly Val Leu Leu Leu
            100                 105                 110
Asn Leu Gly Gly Pro Glu Thr Leu Asp Asp Val Gln Pro Phe Leu Phe
            115                 120                 125
Asn Leu Phe Ala Asp Pro Asp Ile Ile Arg Leu Pro Arg Leu Phe Arg
130                 135                 140
Phe Leu Gln Arg Pro Leu Ala Lys Leu Ile Ser Thr Phe Arg Ala Pro
145                 150                 155                 160
Lys Ser Lys Glu Gly Tyr Ala Ser Ile Gly Gly Ser Pro Leu Arg
            165                 170                 175
Lys Ile Thr Asp Glu Gln Ala Asn Ala Leu Lys Val Ala Leu Lys Lys
            180                 185                 190
Lys Asn Leu Asn Ala Asn Ile Tyr Val Gly Met Arg Tyr Trp Tyr Pro
            195                 200                 205
Phe Thr Glu Glu Ala Ile Asp Gln Ile Lys Lys Asp Lys Ile Thr Lys
            210                 215                 220
Leu Val Val Leu Pro Leu Tyr Pro Gln Tyr Ser Ile Ser Thr Ser Gly
225                 230                 235                 240
Ser Ser Ile Arg Val Leu Gln Asn Ile Val Lys Glu Asp Ser Tyr Phe
            245                 250                 255
Ala Gly Leu Pro Ile Ser Ile Glu Ser Trp Tyr Gln Arg Asp Gly
            260                 265                 270
Tyr Val Lys Ser Met Ala Asp Leu Ile Glu Lys Glu Leu Ser Ile Phe
            275                 280                 285
Ser Asn Pro Glu Glu Val Met Ile Phe Phe Ser Ala His Gly Val Pro
            290                 295                 300
Leu Thr Tyr Val Thr Asp Ala Gly Asp Pro Tyr Arg Asp Gln Met Glu
305                 310                 315                 320
Asp Cys Ile Ala Leu Ile Met Gly Glu Leu Lys Ser Arg Gly Ile Leu
            325                 330                 335
Asn Ser His Thr Leu Ala Tyr Gln Ser Arg Val Gly Pro Val Gln Trp
            340                 345                 350
Leu Lys Pro Tyr Thr Asp Glu Val Leu Val Glu Leu Gly Gln Gln Gly
            355                 360                 365
Val Lys Ser Leu Leu Ala Val Pro Val Ser Phe Val Ser Glu His Ile
            370                 375                 380
Glu Thr Leu Glu Glu Ile Asp Met Glu Tyr Lys Glu Leu Ala Leu Glu
385                 390                 395                 400
Ser Gly Ile Glu Asn Trp Gly Arg Val Pro Ala Leu Gly Cys Thr Ser
            405                 410                 415
Ser Phe Ile Ser Asp Leu Ala Asp Ala Val Glu Ala Leu Pro Ser
            420                 425                 430
Ala Ser Ala Leu Val Thr Lys Lys Val Asp Glu Ser Asp Ser Asp Met
            435                 440                 445
Asp Leu Met His Tyr Leu Ser Lys Met Phe Phe Gly Ser Ile Leu Ala
            450                 455                 460
Phe Val Leu Leu Leu Ser Pro Arg Leu Ile Ser Ala Phe Arg Asn Thr
465                 470                 475                 480
Leu Leu
```

```
<210> SEQ ID NO 62
<211> LENGTH: 526
<212> TYPE: PRT
<213> ORGANISM: Oryza sativa

<400> SEQUENCE: 62

Met Trp Ser Ser Ser Gln Ala Ser Thr Arg Gly Val Ile Glu Val Gly
1               5                   10                  15

Arg Val Glu Ala Gly Pro Ser His Phe Pro Lys Arg Pro Ala Pro Arg
            20                  25                  30

Asn Ser Ser Arg Val Asn Leu Ser Arg Thr Tyr Ala Ile Lys Ser Cys
        35                  40                  45

Ser Val Ser Ser Arg Thr Gly Leu Cys Leu Gly Gln Cys Tyr His Lys
    50                  55                  60

Lys Ser Ser Ala Cys Lys Cys Lys Leu Gly Trp Ser Ser Gln Pro Leu
65                  70                  75                  80

Ser Ser Leu Arg His His Leu Arg Val His Ser Ser Ala Ser Glu Ala
                85                  90                  95

Val Leu Thr Ser Gln Ser Asp Phe Thr Lys Leu Leu Val Gly Asn Glu
            100                 105                 110

Lys Ile Gly Val Leu Leu Leu Asn Leu Gly Gly Pro Glu Thr Leu Asp
        115                 120                 125

Asp Val Gln Pro Phe Leu Phe Asn Leu Phe Ala Asp Pro Asp Ile Ile
    130                 135                 140

Arg Leu Pro Arg Leu Phe Arg Phe Leu Gln Lys Pro Leu Ala Gln Phe
145                 150                 155                 160

Ile Ser Val Val Arg Ala Pro Lys Ser Lys Glu Gly Tyr Ala Ser Ile
                165                 170                 175

Gly Gly Gly Ser Pro Leu Arg Gln Ile Thr Asp Ala Gln Ala Glu Ala
            180                 185                 190

Leu Arg Lys Ala Leu Cys Asp Lys Asp Ile Pro Ala Lys Val Tyr Val
        195                 200                 205

Gly Met Arg Tyr Trp His Pro Phe Thr Glu Glu Ala Ile Glu Gln Ile
    210                 215                 220

Lys Arg Asp Gly Ile Thr Lys Leu Val Val Leu Pro Leu Tyr Pro Gln
225                 230                 235                 240

Phe Ser Ile Ser Thr Ser Gly Ser Ser Leu Arg Leu Leu Glu Gly Ile
                245                 250                 255

Phe Arg Glu Asp Glu Tyr Leu Val Asn Met Gln His Thr Val Ile Pro
            260                 265                 270

Ser Trp Tyr Gln Arg Glu Gly Tyr Ile Lys Ala Met Ala Thr Leu Ile
        275                 280                 285

Glu Lys Glu Leu Arg Thr Phe Ser Pro Gln Lys Val Met Ile Phe
        290                 295                 300

Phe Ser Ala His Gly Val Pro Leu Ala Tyr Val Glu Glu Ala Gly Asp
305                 310                 315                 320

Pro Tyr Lys Ala Glu Met Glu Glu Cys Val Asp Leu Ile Met Glu Glu
                325                 330                 335

Leu Glu Lys Arg Gly Ile Thr Asn Ser Cys Thr Leu Ala Tyr Gln Ser
            340                 345                 350

Arg Val Gly Pro Val Glu Trp Leu Arg Pro Tyr Thr Asp Glu Thr Ile
        355                 360                 365

Ile Glu Leu Gly Gln Lys Gly Val Lys Ser Leu Leu Ala Val Pro Ile
    370                 375                 380
```

```
Ser Phe Val Ser Glu His Ile Glu Thr Leu Glu Ile Asp Val Glu
385                 390                 395                 400

Tyr Lys Glu Leu Ala Leu Glu Ser Gly Ile Lys His Trp Gly Arg Val
                405                 410                 415

Pro Ala Leu Gly Cys Glu Pro Thr Phe Ile Thr Asp Leu Ala Asp Ala
            420                 425                 430

Val Ile Glu Ser Leu Pro Tyr Val Gly Ala Met Ala Val Ser Asn Leu
        435                 440                 445

Glu Ala Arg Gln Pro Leu Val Pro Leu Gly Ser Val Glu Glu Leu Leu
    450                 455                 460

Ala Ala Tyr Asp Ser Lys Arg Asp Glu Leu Pro Pro Val Thr Val
465                 470                 475                 480

Trp Glu Trp Gly Trp Thr Lys Ser Ala Glu Thr Trp Asn Gly Arg Ala
                485                 490                 495

Ala Met Leu Ala Val Leu Ala Leu Leu Val Leu Glu Val Thr Thr Gly
                500                 505                 510

Glu Gly Phe Leu His Gln Trp Gly Ile Leu Pro Leu Phe His
            515                 520                 525

<210> SEQ ID NO 63
<211> LENGTH: 591
<212> TYPE: PRT
<213> ORGANISM: Zea mays

<400> SEQUENCE: 63

Phe Pro Leu Val Ser Ser Arg Leu Val Pro Tyr Ser Arg Pro Val Arg
1               5                   10                  15

Leu His Leu Arg Ser Pro Gly Pro Asp Thr Pro Leu Tyr Gln Ser Arg
                20                  25                  30

Pro Pro Ala His Phe Ser His Pro Arg Ala Ala Ser Gly Ala Gly Glu
            35                  40                  45

Pro Ser Arg Arg Ser Ser Asn Asp Pro Ser Leu Ser Arg Pro Val Ser
    50                  55                  60

Leu Pro Leu Pro Ala Gln Gly Glu Glu Arg Glu Arg Met Trp Ser Ser
65                  70                  75                  80

Ser Gln Ala Ser Thr Arg Gly Val Val Glu Met Gly Arg Val Glu Ala
                85                  90                  95

Gly Pro Ser His Phe Pro Lys Arg Pro Ala Pro Gln Asn Ser Ala Arg
            100                 105                 110

Val Asn Leu Ser Arg Thr His Thr Val Lys Pro Thr Ser Ala Gly Asp
        115                 120                 125

Arg Ser Gly Ile Ser Val Lys Cys Asn Leu Gly Trp Ser Ser Gln Pro
    130                 135                 140

Ser Pro Asp Leu Arg His His Phe Arg Gly Tyr Ser Ser Ala Ser Glu
145                 150                 155                 160

Ala Val Leu Thr Ser Gln Ser Asp Val Arg Lys Leu Phe Val Gly Asn
                165                 170                 175

Glu Lys Ile Gly Val Leu Leu Asn Leu Gly Gly Pro Glu Thr Leu
            180                 185                 190

Asp Asp Val Gln Pro Phe Leu Phe Asn Leu Phe Ala Asp Pro Asp Ile
        195                 200                 205

Ile Arg Leu Pro Arg Leu Phe Arg Phe Leu Gln Lys Pro Leu Ala Lys
    210                 215                 220
```

-continued

```
Phe Ile Ser Glu Val Arg Ala Pro Lys Ser Lys Glu Gly Tyr Ala Ser
225                 230                 235                 240

Ile Gly Gly Ser Pro Leu Arg Gln Ile Thr Asp Ala Gln Ala Glu
                245                 250                 255

Ala Leu Arg Glu Ala Leu His Gly Lys Asp Val Pro Ala Asn Val Tyr
            260                 265                 270

Val Gly Met Arg Tyr Trp His Pro Phe Thr Glu Ala Ile Glu Gln
            275                 280                 285

Ile Lys Arg Asp Gly Ile Thr Lys Leu Val Val Leu Pro Leu Tyr Pro
        290                 295                 300

Gln Phe Ser Ile Ser Thr Ser Gly Ser Ser Leu Arg Leu Leu Glu Ser
305                 310                 315                 320

Ile Ser Arg Glu Asp Glu Tyr Leu Val Asn Met Gln His Thr Val Ile
                325                 330                 335

Pro Ser Trp Tyr Gln Arg Glu Gly Tyr Ile Lys Ala Met Ala Thr Leu
            340                 345                 350

Ile Glu Asn Glu Leu Thr Lys Phe Gln Glu Pro Gln Lys Val Met Ile
            355                 360                 365

Phe Phe Ser Ala His Gly Val Pro Leu Ala Tyr Val Glu Glu Ala Gly
370                 375                 380

Asp Pro Tyr Lys Ala Glu Met Glu Glu Cys Ile Asp Leu Ile Met Glu
385                 390                 395                 400

Glu Leu Glu Lys Arg Gly Ile Thr Asn Pro Cys Ile Leu Ala Tyr Gln
                405                 410                 415

Ser Arg Val Gly Pro Val Glu Trp Leu Lys Pro Tyr Thr Asp Glu Thr
            420                 425                 430

Ile Ile Glu Leu Gly Gln Lys Gly Val Lys Ser Leu Leu Ala Val Pro
            435                 440                 445

Ile Ser Phe Val Ser Glu His Ile Lys Thr Leu Glu Glu Ile Asp Val
    450                 455                 460

Glu Tyr Lys Glu Leu Ala Leu Glu Ser Gly Ile Lys His Trp Gly Arg
465                 470                 475                 480

Val Pro Ala Leu Gly Cys Glu Pro Thr Phe Ile Ser Asp Leu Ala Asp
            485                 490                 495

Ala Val Ile Glu Ser Leu Pro Tyr Val Gly Ala Met Ala Val Ser Asn
            500                 505                 510

Leu Glu Ala Arg Gln Ser Leu Val Pro Leu Gly Ser Val Glu Glu Leu
            515                 520                 525

Leu Ala Ala Tyr Asp Ser Lys Arg Asp Glu Leu Pro Pro Pro Val Ile
        530                 535                 540

Val Trp Glu Trp Gly Trp Thr Lys Ser Ala Glu Thr Trp Asn Gly Arg
545                 550                 555                 560

Ala Ala Met Leu Ala Val Leu Ala Leu Leu Val Leu Glu Val Thr Thr
            565                 570                 575

Gly Glu Gly Phe Leu His Gln Trp Gly Ile Leu Pro Leu Phe Arg
            580                 585                 590
```

DROUGHT TOLERANT PLANTS AND RELATED CONSTRUCTS AND METHODS INVOLVING GENES ENCODING FERROCHELATASES This application is a divisional of U.S. patent application Ser. No. 12/887,724, filed Sep. 22, 2010, now U.S. Pat. No. 8,158,859, which is a divisional of U.S. patent application Ser. No. 12/326,206, filed Dec. 2, 2008, now U.S. Pat. No. 7,812,223, which claims the benefit of U.S. Provisional Application No. 60/991,859, filed Dec. 3, 2007, the entire content of each is herein incorporated by reference.

FIELD OF THE INVENTION

The field of invention relates to plant breeding and genetics and, in particular, relates to recombinant DNA constructs useful in plants for conferring tolerance to drought.

BACKGROUND OF THE INVENTION

Abiotic stressors significantly limit crop production worldwide. Cumulatively, these factors are estimated to be responsible for an average 70% reduction in agricultural production (Bresson, 1999).

Drought stress, in particular, not only causes a reduction in the average yield for crops but also causes yield instability through high interannual yield variation. Globally, about 35-40% of arable land falls under arid or semiarid classification. Even in non-arid regions where soils are nutrient-rich, drought stress occurs regularly for brief periods or at moderate levels. Moreover, it has been predicted that in the coming years rainfall patterns will shift and become more variable due to increased global temperatures.

U.S. studies have shown that the ten most important kinds of cultivated plants (corn, soybeans, wheat, tomatoes, etc.) produced only about 50% of the genetically possible yields on average per year; two thirds of the losses were due to the frequent combination of heat stress and water shortage (G. Schütte, S. Stirn, and V. Beusmann, Transgene Pflanzen—Sicherheitsforschung, Risikoabschätzung and Nachzulassungs-Monitoring. Birkhäuser Verlag A G, Basel-Boston-Berlin, 2001).

Plants are sessile and have to adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors. Some of the molecular responses to abiotic stress factors such as drought are specific, but it has also been shown that similar genes are activated by several stressors (Royal Society of London, *Transgenic Plants and World Agriculture*, 2000, National Academy Press, Washington, D.C.). It is believed that about 15 percent of a plant's genome is devoted to stress perception and adaptation (see e.g., Cushman and Bohnert, 2000).

Earlier work on molecular aspects of abiotic stress responses was accomplished by differential and/or subtractive analysis (e.g., see Bray, 1993, Shinozaki and Yamaguchi-Shinozaki, 1997, Zhu et al., 1997, Thomashow, 1999). Other methods include selection of candidate genes (e.g., selection of genes from a particular known module and analyzing expression of such a gene or its active product under stresses, or by functional complementation in a stressor system that is well defined, see Xiong and Zhu, 2001). Additionally, forward and reverse genetic studies involving the identification and isolation of mutations in regulatory genes have also been used to provide evidence for observed changes in gene expression under stress or exposure (Xiong and Zhu, 2001).

Activation tagging can be utilized to identify genes with the ability to affect a trait. This approach has been used in the model plant species *Arabidopsis thaliana* (Weigel et al., *Plant Physiol.* 122:1003-1013 (2000)). Insertions of transcriptional enhancer elements can dominantly activate and/or elevate the expression of nearby endogenous genes. This method can be used to select genes involved in agronomically important phenotypes, including stress tolerance.

SUMMARY OF THE INVENTION

The present invention includes:

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO:2, 4, 6, 8, 10, 12, 14, 16, 18, 20, 22, 24, 26, 28 or 30, and wherein said plant exhibits increased drought tolerance when compared to a control plant not comprising said recombinant DNA construct.

In another embodiment, a method of increasing drought tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct; and optionally, (c) obtaining a progeny plant derived from the transgenic plant, wherein said progeny plant comprises in its genome the recombinant DNA construct and exhibits increased drought tolerance when compared to a control plant not comprising the recombinant DNA construct.

In another embodiment, a method of evaluating drought tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct; and (c) evaluating the transgenic plant for drought tolerance compared to a control plant not comprising the recombinant DNA construct; and optionally, (d) obtaining a progeny plant derived from the transgenic plant, wherein the progeny plant comprises in its genome the recombinant DNA construct; and optionally, (e) evaluating the progeny plant for drought tolerance compared to a control plant not comprising the recombinant DNA construct.

In another embodiment, a method of evaluating drought tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for drought tolerance compared to a control plant not comprising the recombinant DNA construct.

In another embodiment, the present invention includes any of the methods of the present invention wherein the plant is a maize plant or a soybean plant.

In another embodiment, the present invention includes an isolated polynucleotide comprising: (a) a nucleotide sequence encoding a ferrochelatase, wherein the polypeptide has an amino acid sequence of at least 90% or 95% sequence identity, based on the Clustal V method of alignment, when compared to one of SEQ ID NO:4, 6, 8, 10, 12, 14, 16, 18, 24, 26, 28 or 30, or (b) a full complement of the nucleotide sequence, wherein the full complement and the nucleotide sequence consist of the same number of nucleotides and are 100% complementary. The polypeptide may comprise the amino acid sequence of SEQ ID NO:4, 6, 8, 10, 12, 14, 16, 18, 24, 26, 28 or 30. The nucleotide sequence may comprise the nucleotide sequence of SEQ ID NO:3, 5, 7, 9, 11, 13, 15, 17, 23, 25, 27 or 29.

In another embodiment, the present invention concerns a recombinant DNA construct comprising any of the isolated polynucleotides of the present invention operably linked to at least one regulatory sequence, and a cell, a plant, and a seed comprising the recombinant DNA construct.

In another embodiment, the present invention includes a vector comprising any of the isolated polynucleotides of the present invention.

In another embodiment, the present invention concerns a cell, plant or seed comprising any of the recombinant DNA constructs of the present invention. The cell may be eukaryotic, e.g., a yeast, insect or plant cell, or prokaryotic, e.g., a bacterium.

BRIEF DESCRIPTION OF THE FIGURES AND SEQUENCE LISTING

The invention can be more fully understood from the following detailed description and the accompanying drawings and Sequence Listing which form a part of this application.

Figure 10A:
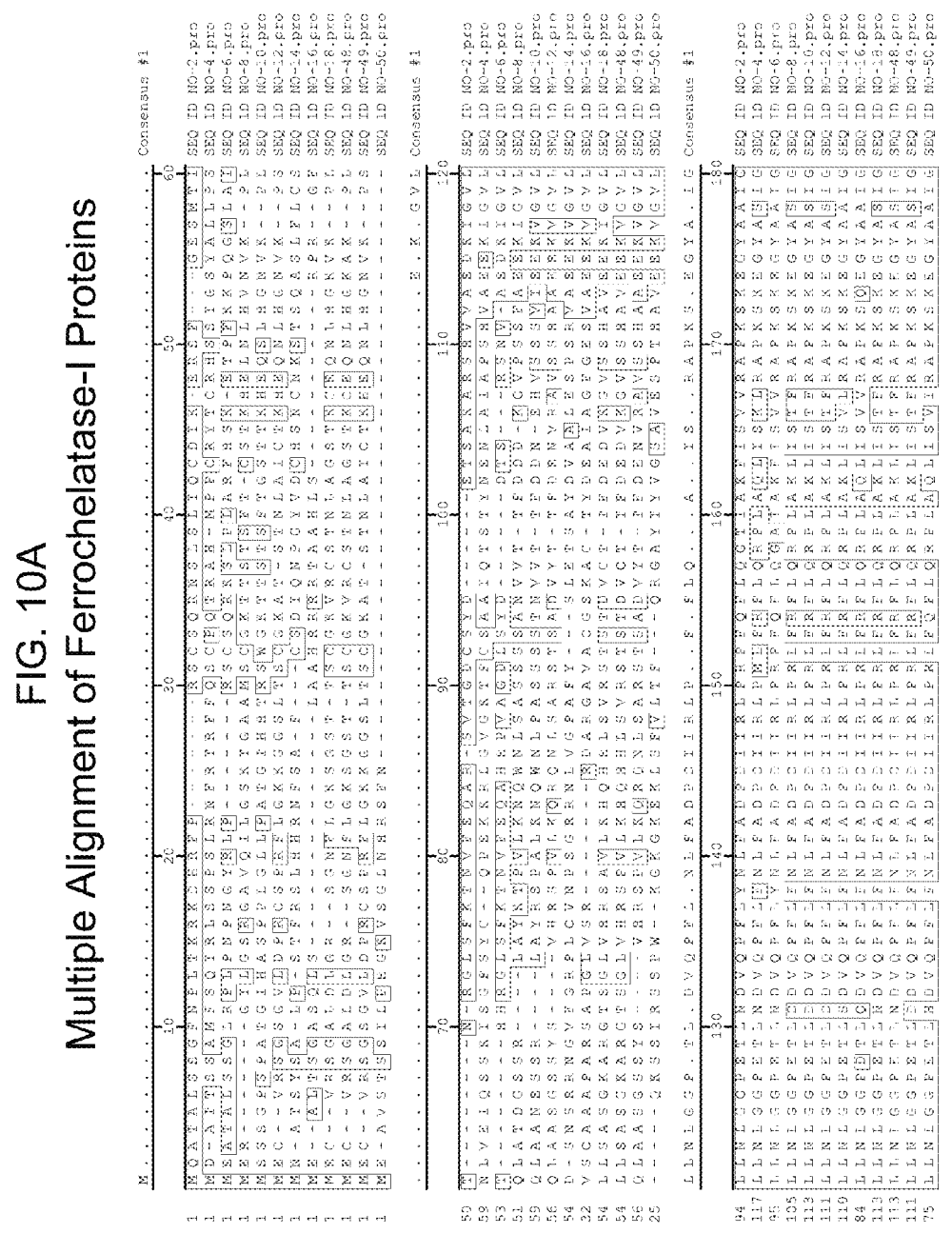
Figure 10B:
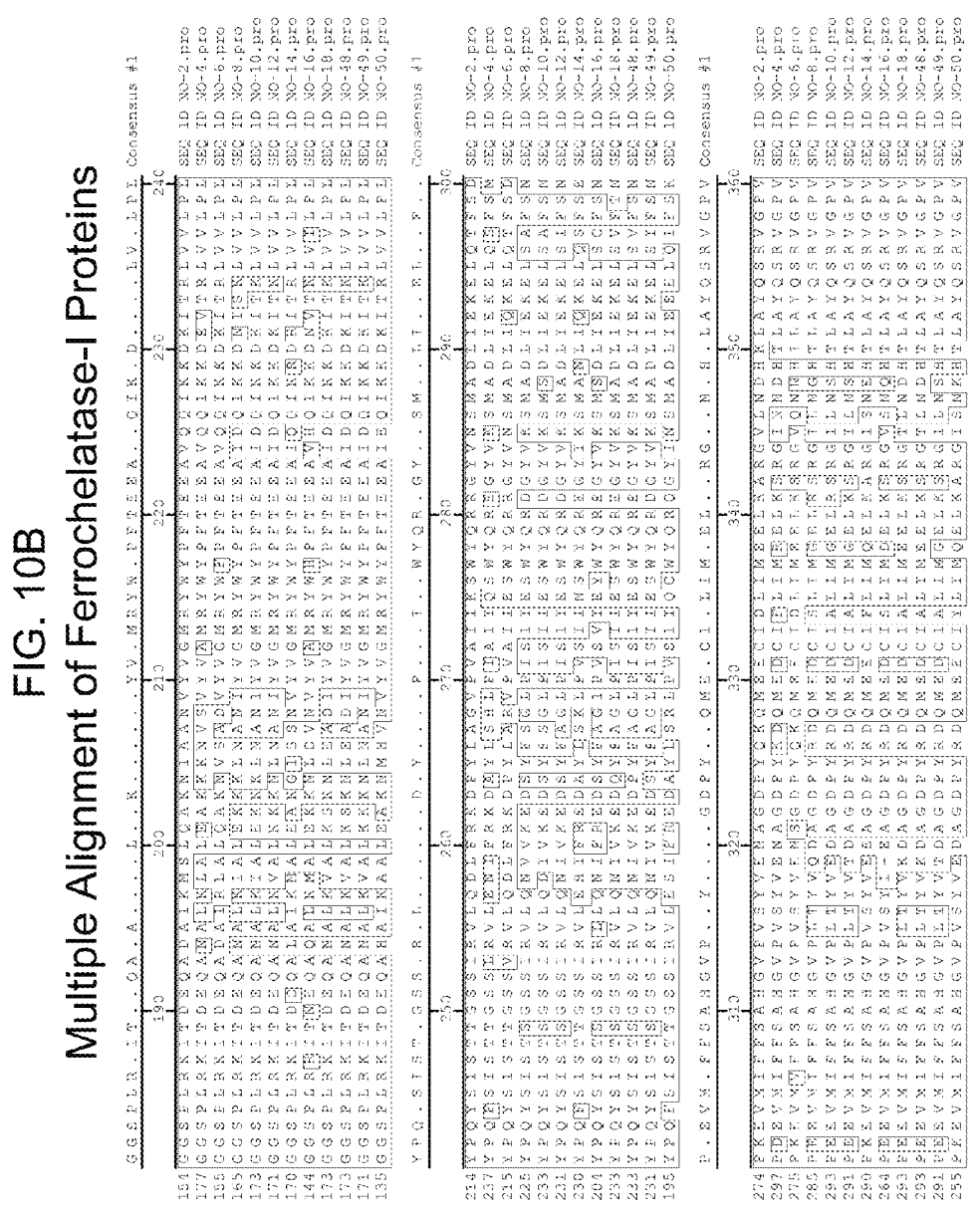
Figure 10C:
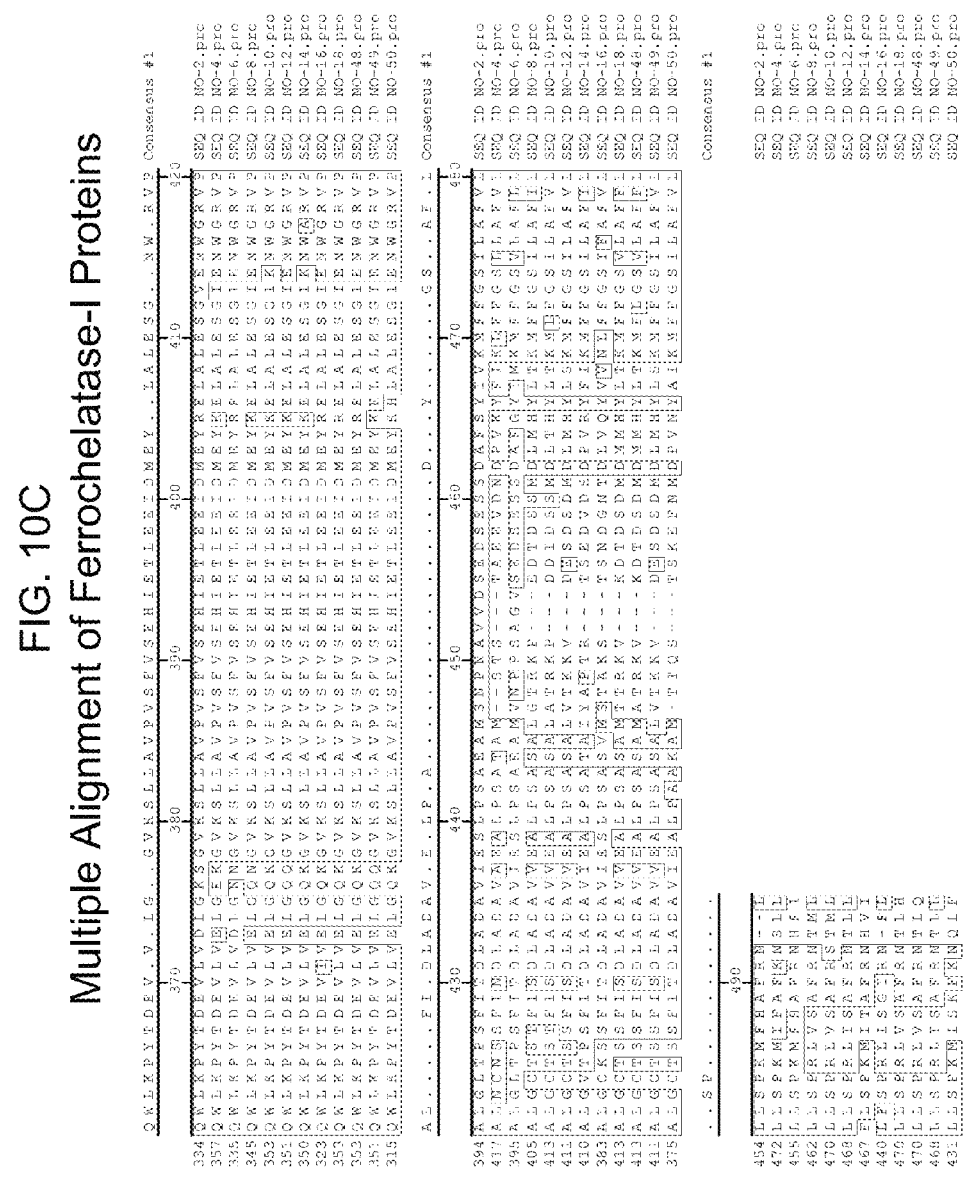

FIGS. 10A-10C show the multiple alignment of the amino acid sequences of the ferrochelatase-I proteins of SEQ ID NOs:2, 4, 6, 8, 10, 12, 14, 16, 18, 48, 49 and 50. Residues that are identical to the residue of SEQ ID NO:2 at a given position are enclosed in a box. A consensus sequence is presented where a residue is shown if identical in all sequences, otherwise, a period is shown.

Figure 11:
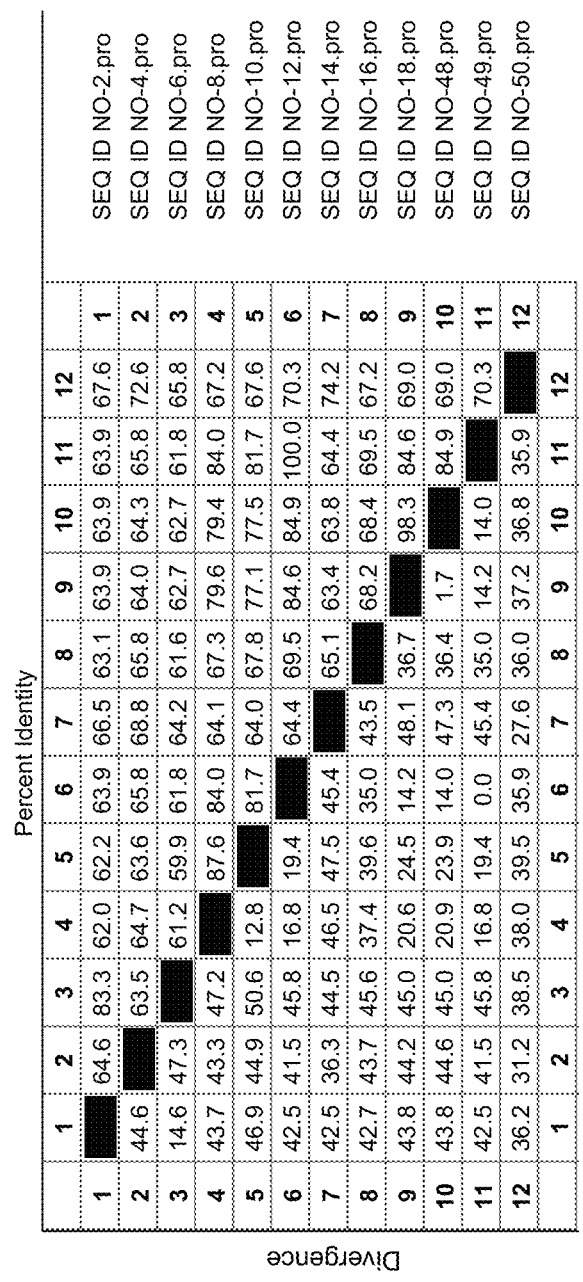

FIG. 11 shows the percent sequence identity and the divergence values for each pair of amino acids sequences of ferrochelatases displayed in FIGS. 10A-10C.

Figure 12A:
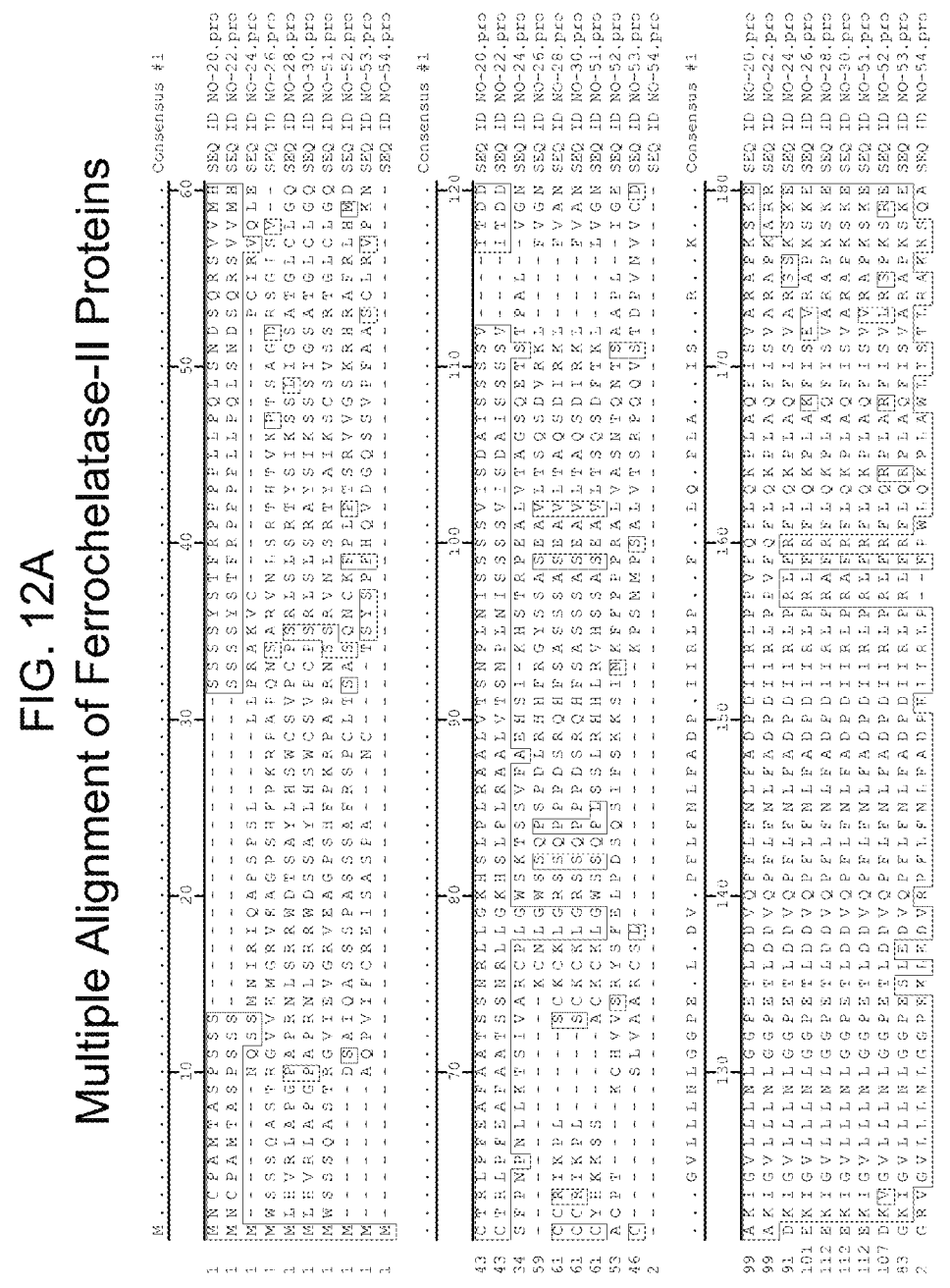
Figure 12B:
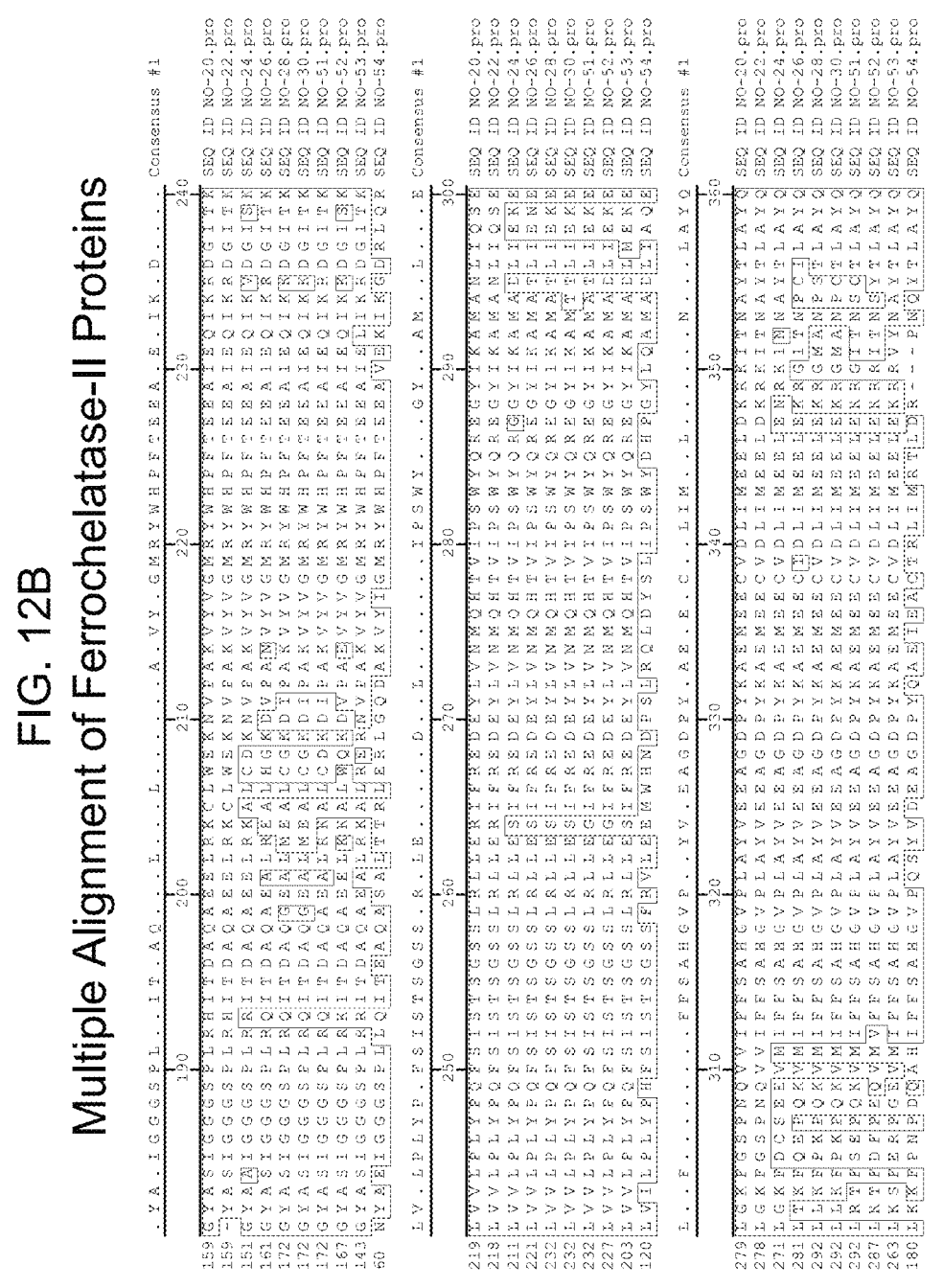
Figure 12C:
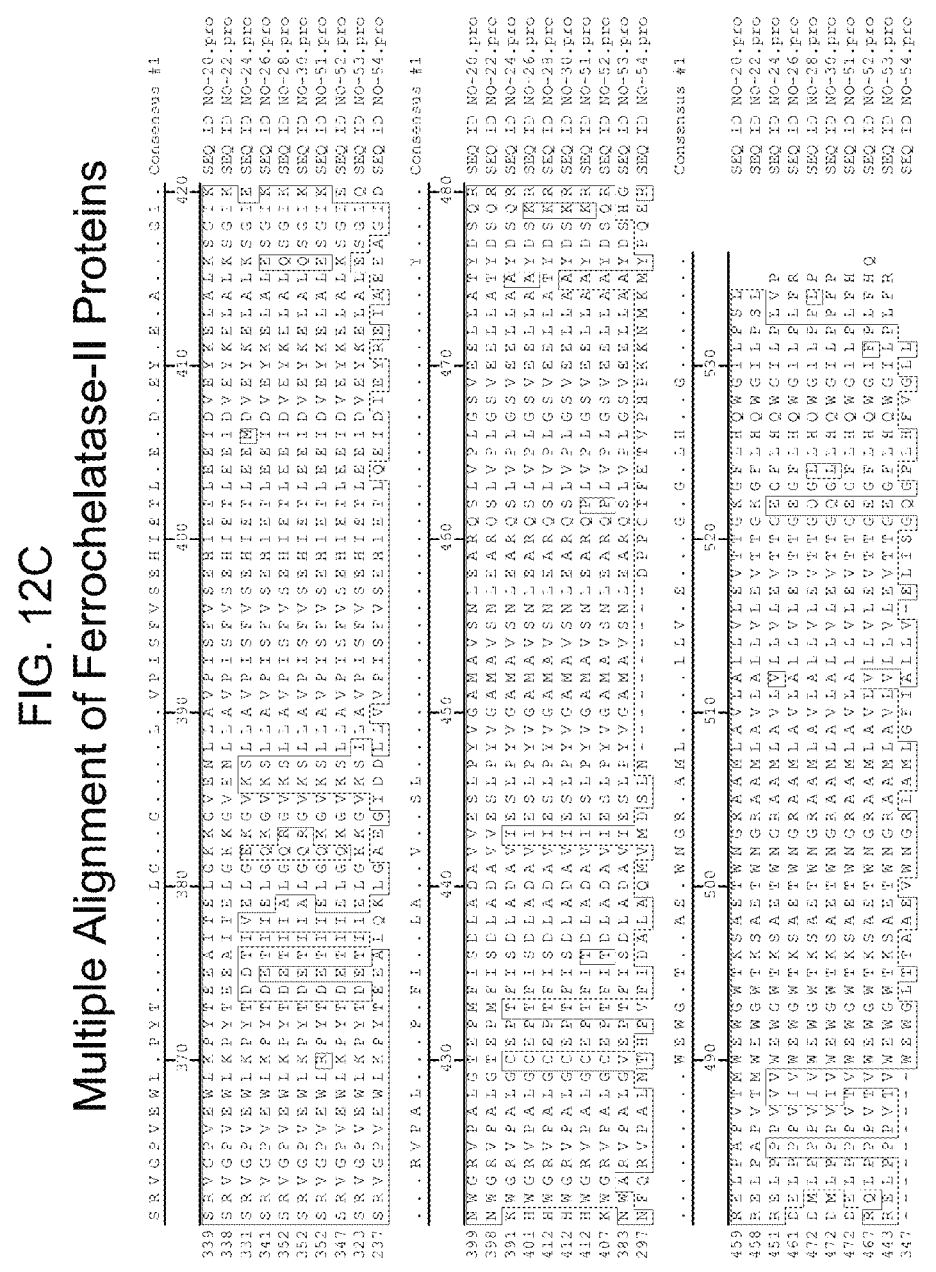

FIGS. 12A-12C show the multiple alignment of the amino acid sequences of the ferrochelatase-II proteins of SEQ ID NOs:20, 22, 24, 26, 28, 30, 51, 52, 53 and 54. Residues that are identical to the residue of SEQ ID NO:20 at a given position are enclosed in a box. A consensus sequence is presented where a residue is shown if identical in all sequences, otherwise, a period is shown.

Figure 13:
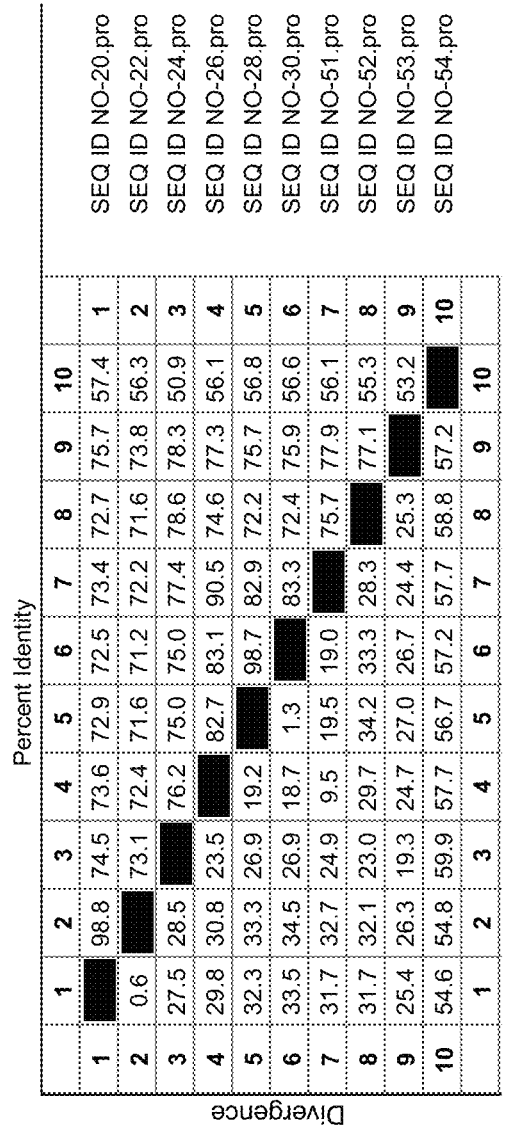

FIG. 13 shows the percent sequence identity and the divergence values for each pair of amino acids sequences of ferrochelatases displayed in FIGS. 12A-12C.

FIGS. 14A-14B show an evaluation of individual Gaspe Flint derived maize lines transformed with PHP31419.

FIG. 15 shows a summary evaluation of Gaspe Flint derived maize lines transformed with PHP31419.

FIGS. 16A-16B show an evaluation of individual Gaspe Flint derived maize lines transformed with PHP33089.

FIG. 17 shows a summary evaluation of Gaspe Flint derived maize lines transformed with PHP33089.

FIGS. 18A-18B show an evaluation of individual Gaspe Flint derived maize lines transformed with PHP30829.

FIG. 19 shows a summary evaluation of Gaspe Flint derived maize lines transformed with PHP30829.

FIGS. 20A-20B show an evaluation of individual Gaspe Flint derived maize lines transformed with PHP30745.

FIG. 21 shows a summary evaluation of Gaspe Flint derived maize lines transformed with PHP30745.

FIGS. 22A-22B show an evaluation of individual Gaspe Flint derived maize lines transformed with PHP30761.

FIG. 23 shows a summary evaluation of Gaspe Flint derived maize lines transformed with PHP30761.

SEQ ID NO:1 corresponds to NCBI GI No. 511080 which is the nucleotide sequence of a cDNA fragment encoding an *Arabidopsis* ferrochelatase-I protein (locus At5g26030).

SEQ ID NO:2 corresponds to NCBI GI No. 511081, which is the amino acid sequence of the *Arabidopsis* ferrochelatase-I protein encoded by SEQ ID NO:1.

TABLE 1 cDNAs Encoding Ferrochelatase-I (FeC-I)

| Plant | Clone Designation | SEQ ID NO: (Nucleotide) | SEQ ID NO: (Amino Acid) |
|---|---|---|---|
| Sugar Beet | ebs1c.pk002.n16 (FIS) | 3 | 4 |
| Brassica | ebb1c.pk006.j11 (FIS) | 5 | 6 |
| Maize | cfp3n.pk004.f12 (FIS) | 7 | 8 |
| Maize | cfp5n.pk009.j16 (FIS) | 9 | 10 |
| Rice | rl0n.pk117.h21 (FIS) | 11 | 12 |
| Soybean | se3.pk0034.e10 (FIS) | 13 | 14 |
| Tulip | etb1n.pk002.n16 (FIS) | 15 | 16 |
| Wheat | wlp1c.pk002.p10 (FIS) | 17 | 18 |

SEQ ID NO:19 corresponds to NCBI GI No. 30684569 which is the nucleotide sequence of a cDNA fragment encoding a first allele of an *Arabidopsis* ferrochelatase-II protein (locus At2g30390).

SEQ ID NO:20 corresponds to NCBI GI No. 15227742, which is the amino acid sequence of the *Arabidopsis* ferrochelatase-II protein encoded by SEQ ID NO:19.

SEQ ID NO:21 corresponds to NCBI GI No. 2623989, which is the nucleotide sequence of a cDNA fragment encoding a second allele of an *Arabidopsis* ferrochelatase-II protein (locus At2g30390).

SEQ ID NO:22 corresponds to NCBI GI No. 2623990, which is the amino acid sequence of the *Arabidopsis* ferrochelatase-II protein encoded by SEQ ID NO:21.

TABLE 2 cDNAs Encoding Ferrochelatase-II (FeC-II)

| Plant | Clone Designation | SEQ ID NO: (Nucleotide) | SEQ ID NO: (Amino Acid) |
|---|---|---|---|
| Catmint | ecl1c.pk005.l15 (FIS) | 23 | 24 |
| Maize | cfp6n.pk072.n9 (FIS) | 25 | 26 |
| Wheat | Wlp1c.pk004.d13 (FIS) | 27 | 28 |
| Wheat | wpa1c.pk014.g4 (FIS) | 29 | 30 |

SEQ ID NO:31 is the nucleotide sequence of the pHSbarENDs2 activation tagging vector.

SEQ ID NO:32 is the nucleotide sequence of the GATEWAY® donor vector pDONR™/Zeo.

SEQ ID NO:33 is the nucleotide sequence of the GATEWAY® donor vector pDONR™221.

SEQ ID NO:34 is the nucleotide sequence of pBC-yellow, a destination vector for use with *Arabidopsis*.

SEQ ID NO:35 is the nucleotide sequence of PHP27840, a destination vector for use with soybean.

SEQ ID NO:36 is the nucleotide sequence of PHP23236, a destination vector for use with Gaspe Flint derived maize lines.

SEQ ID NO:37 is the nucleotide sequence of PHP10523 (Komari et al., *Plant J.* 10:165-174 (1996); NCBI General Identifier No. 59797027).

SEQ ID NO:38 is the nucleotide sequence of PHP23235, a destination vector for use with Gaspe Flint derived lines.

SEQ ID NO:39 is the nucleotide sequence of PHP28647, a destination vector for use with maize inbred-derived lines.

SEQ ID NO:40 is the nucleotide sequence of the attB1 site.

SEQ ID NO:41 is the nucleotide sequence of the attB2 site.

SEQ ID NO:42 is the nucleotide sequence of the At5g26030-5'attB forward primer, containing the attB1 sequence, used to amplify the At5g26030 protein-coding region.

SEQ ID NO:43 is the nucleotide sequence of the At5g26030-3'attB reverse primer, containing the attB2 sequence, used to amplify the At5g26030 protein-coding region.

SEQ ID NO:44 is the nucleotide sequence of the At2g30390-5'attB forward primer, containing the attB1 sequence, used to amplify the At2g30390 protein-coding region.

SEQ ID NO:45 is the nucleotide sequence of the At2g30390-3'attB reverse primer, containing the attB2 sequence, used to amplify the At2g30390 protein-coding region.

SEQ ID NO:46 is the nucleotide sequence of the VC062 primer, containing the T3 promoter and attB1 site, useful to amplify cDNA inserts cloned into a Bluescript® II SK(+) vector (Stratagene).

SEQ ID NO:47 is the nucleotide sequence of the VC063 primer, containing the T7 promoter and attB2 site, useful to amplify cDNA inserts cloned into a Bluescript® II SK(+) vector (Stratagene).

SEQ ID NO:48 is the amino acid sequence of a *Hordeum vulgare* ferrochelatase-I protein (NCBI GI NO. 2460251).

SEQ ID NO:49 is the amino acid sequence of a rice ferrochelatase-I protein (NCBI GI NO. 113631036).

SEQ ID NO:50 is the amino acid sequence of a *Vitis vinifera* ferrochelatase-I protein (NCBI GI NO. 147818793).

SEQ ID NO:51 is the amino acid sequence of a rice ferrochelatase-II protein (NCBI GI NO. 115463419).

SEQ ID NO:52 is the amino acid sequence of a *Cucumis sativus* ferrochelatase-II protein (NCBI GI NO. 12082085).

SEQ ID NO:53 is the amino acid sequence of a *Nicotiana tabacum* ferrochelatase-II protein (NCBI GI NO. 15147828).

SEQ ID NO:54 is the amino acid sequence of a *Synechocystis* ferrochelatase protein (NCBI GI NO. 1708186).

SEQ ID NO:55 is the nucleotide acid sequence of plasmid PHP30949, an entry clone containing the maize ferrochelatase-I protein (SEQ ID NO:10).

SEQ ID NO:56 is the nucleotide sequence of the cDNA insert of cfp5n.pk064.n7 and encodes a maize ferrochelatase-II protein (SEQ ID NO:8). SEQ ID NO:56 differs from the nucleotide sequence of cfp3n.pk004.f12 (SEQ ID NO:7) in that it contains a 12 base pair insertion in the 5'-UTR, 8 nucleotides before the ATG start codon.

SEQ ID NO:57 is the amino acid sequence presented in SEQ ID NO:240025 of US Patent Publication No. US2004031072.

SEQ ID NO:58 is the amino acid sequence presented in SEQ ID NO:20 of Japanese Patent Publication No. JP2001190168-A.

SEQ ID NO:59 is the amino acid sequence presented in SEQ ID NO:13029 of US Patent Publication No. US2006150283.

SEQ ID NO:60 is the amino acid sequence presented in SEQ ID NO:7745 of US Patent Publication No. US2006150283.

SEQ ID NO:61 is the amino acid sequence presented in SEQ ID NO:46156 of Japanese Patent Publication No. JP2005185101.

SEQ ID NO:62 is the amino acid sequence presented in SEQ ID NO:52154 of Japanese Patent Publication No. JP2005185101.

SEQ ID NO:63 is the amino acid sequence presented in SEQ ID NO:72746 of US Patent Publication No. US2004034888-A1.

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF EMBODIMENTS

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

"Ferrochelatase" (protoheme ferrolyase; EC 4.99.1.1) is the terminal enzyme of the biosynthetic pathway of heme; it catalyses the chelation of ferrous ion into the protoporphyrin IX ring to form protoheme In higher plants there is evidence for two isoforms of this enzyme, ferrochelatase-1 and ferrochelatase-2 (Suzuki et al. 2002 J Biol Chem 277:4731-4737). The terms "ferrochelatase-I", "ferrochelatase-1", "FeC-I" and "FeC-1" are used interchangeably herein. The terms "ferrochelatase-II", "ferrochelatase-2", "FeC-II" and "FeC-2" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height and ear length.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs useful for conferring drought tolerance, compositions (such as plants or seeds) comprising these recombinant DNA constructs, and methods utilizing these recombinant DNA constructs.

Isolated Polynucleotides and Polypeptides:

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:4, 6, 8, 10, 12, 14, 16, 18, 24, 26, 28 or 30; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide is preferably a ferrochelatase.

An isolated polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:4, 6, 8, 10, 12, 14, 16, 18, 24, 26, 28 or 30. The polypeptide is preferably a ferrochelatase.

An isolated polynucleotide comprising (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:3, 5, 7, 9, 11, 13, 15, 17, 23, 25, 27 or 29; or (ii) a full complement of the nucleic acid sequence of (i). Any of the foregoing isolated polynucleotides may be utilized in any recombinant DNA constructs (including suppression DNA constructs) of the present invention. The isolated polynucleotide preferably encodes a ferrochelatase.

Recombinant DNA Constructs and Suppression DNA Constructs:

In one aspect, the present invention includes recombinant DNA constructs (including suppression DNA constructs).

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 1, 3, 5, 7, 9, 11, 13, 15, 17, 19, 21, 23, 25, 27 or 29; or (ii) a full complement of the nucleic acid sequence of (i).

FIGS. 10A-10C show the multiple alignment of the amino acid sequences of the ferrochelatases of SEQ ID NO:2, 4, 6, 8, 10, 12, 14, 16, 18, 48, 49 and 50. The multiple alignment of the sequences was performed using the Megalign® program of the LASERGENE® bioinformatics computing suite (DNASTAR® Inc., Madison, Wis.); in particular, using the Clustal V method of alignment (Higgins and Sharp (1989) *CABIOS.* 5:151-153) with the multiple alignment default parameters of GAP PENALTY=10 and GAP LENGTH PENALTY=10, and the pairwise alignment default parameters of KTUPLE=1, GAP PENALTY=3, WINDOW=5 and DIAGONALS SAVED=5.

FIG. 11 shows the percent sequence identity and the divergence values for each pair of amino acids sequences displayed in FIGS. 10A-10C.

FIGS. 12A-12C show the multiple alignment of the amino acid sequences of the ferrochelatases of SEQ ID NO:20, 22, 24, 26, 28, 30, 51, 52, 53 and 54. The multiple alignment of the sequences was performed using the Megalign® program of the LASERGENE® bioinformatics computing suite (DNASTAR® Inc., Madison, Wis.); in particular, using the Clustal V method of alignment (Higgins and Sharp (1989) *CABIOS.* 5:151-153) with the multiple alignment default parameters of GAP PENALTY=10 and GAP LENGTH PENALTY=10, and the pairwise alignment default parameters of KTUPLE=1, GAP PENALTY=3, WINDOW=5 and DIAGONALS SAVED=5.

FIG. 13 shows the percent sequence identity and the divergence values for each pair of amino acids sequences displayed in FIGS. 12A-12C.

In another embodiment, a recombinant DNA construct comprises a polynucleotide operably linked to at least one regulatory sequence (e.g., a promoter functional in a plant), wherein said polynucleotide encodes a ferrochelatase. The ferrochelatase may be from *Arabidopsis thaliana, Zea mays, Glycine max, Glycine tabacina, Glycine soja* and *Glycine tomentella.*

In another aspect, the present invention includes suppression DNA constructs.

A suppression DNA construct may comprise at least one regulatory sequence (e.g., a promoter functional in a plant) operably linked to (a) all or part of: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; or (c) all or part of: (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 1, 3, 5, 7, 9, 11, 13, 15, 17, 19, 21, 23, 25, 27 or 29, or (ii) a full complement of the nucleic acid sequence of (c)(i). The suppression DNA construct may comprise a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107, 065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., Plant J. 16:651-659 (1998); and Gura, Nature 404:804-808 (2000)).

Another variation describes the use of plant viral sequences to direct the suppression of proximal mRNA encoding sequences (PCT Publication No. WO 98/36083 published on Aug. 20, 1998).

Previously described is the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see Wesley, S. V. et al. (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication No. WO 99/61632 published on Dec. 2, 1999).

The use of poly-T and poly-A sequences to generate the stem in the stem-loop structure has also been described (PCT Publication No. WO 02/00894 published Jan. 3, 2002).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication No. WO 02/00904, published Jan. 3, 2002.

RNA interference refers to the process of sequence-specific post-transcriptional gene silencing in animals mediated by short interfering RNAs (siRNAs) (Fire et al., Nature 391: 806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., Trends Genet. 15:358 (1999)). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., Nature 409:363 (2001)). Short interfering RNAs derived from dicer activity are typically about 21 to about 23 nucleotides in length and comprise about 19 base pair duplexes (Elbashir et al., Genes Dev. 15:188 (2001)). Dicer has also been implicated in the excision of 21- and 22-nucleotide small temporal RNAs (stRNAs) from precursor RNA of conserved structure that are implicated in translational control (Hutvagner et al., Science 293:834 (2001)). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex. In addition, RNA interference can also involve small RNA (e.g., miRNA) mediated gene silencing, presumably through cellular mechanisms that regulate chromatin structure and thereby prevent transcription of target gene sequences (see, e.g., Allshire, Science 297:1818-1819 (2002); Volpe et al., Science 297:1833-1837 (2002); Jenuwein, Science 297:2215-2218 (2002); and Hall et al., Science 297:2232-2237 (2002)). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (Nature 391:806 (1998)) were the first to observe RNAi in Caenorhabditis elegans. Wianny and Goetz (Nature Cell Biol. 2:70 (1999)) describe RNAi mediated by dsRNA in mouse embryos. Hammond et al. (Nature 404:293 (2000)) describe RNAi in Drosophila cells transfected with dsRNA. Elbashir et al., (Nature 411:494 (2001)) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity causes RNA cleavage, whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al., Science 294:853-858 (2001), Lagos-Quintana et al., Curr. Biol. 12:735-739 (2002); Lau et al., Science 294:858-862 (2001); Lee and Ambros, Science 294:862-864 (2001); Llave et al., Plant Cell 14:1605-1619 (2002); Mourelatos et al., Genes. Dev. 16:720-728 (2002); Park et al., Curr. Biol. 12:1484-1495 (2002); Reinhart et al., Genes. Dev. 16:1616-1626 (2002)). They are processed from longer precursor transcripts that range in size from approximately 70 to 200 nt, and these precursor transcripts have the ability to form stable hairpin structures. In animals, the enzyme involved in processing miRNA precursors is called dicer, an RNAse III-like protein (Grishok et al., Cell 106:23-34 (2001); Hutvagner et al., Science 293:834-838 (2001); Ketting et al., Genes. Dev. 15:2654-2659 (2001)). Plants also have a dicer-like enzyme, DCL1 (previously named CARPEL FACTORY/SHORT INTEGUMENTS1/SUSPENSOR1), and recent evidence indicates that it, like dicer, is involved in processing the hairpin precursors to generate mature miRNAs (Park et al., Curr. Biol. 12:1484-1495 (2002); Reinhart et al., Genes Dev. 16:1616-1626 (2002)). Furthermore, it is becoming clear from recent work that at least some miRNA hairpin precursors originate as longer polyadenylated transcripts, and several different miRNAs and associated hairpins can be present in a single transcript (Lagos-Quintana et al., Science 294:853-858 (2001); Lee et al., EMBO J. 21:4663-4670 (2002)). Recent work has also examined the selection of the miRNA strand from the dsRNA product arising from processing of the hairpin by DICER (Schwartz et al., Cell 115:199-208 (2003)). It appears that the stability (i.e. G:C versus A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

MicroRNAs (miRNAs) appear to regulate target genes by binding to complementary sequences located in the transcripts produced by these genes. In the case of lin-4 and let-7, the target sites are located in the 3' UTRs of the target mRNAs (Lee et al., Cell 75:843-854 (1993); Wightman et al., Cell 75:855-862 (1993); Reinhart et al., Nature 403:901-906 (2000); Slack et al., Mol. Cell. 5:659-669 (2000)), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, Dev. Biol. 216:671-680 (1999)). On the other hand, recent evidence suggests that miRNAs can in some cases cause specific RNA cleavage of the target transcript within the target site, and this cleavage step appears to require 100% complementarity between the miRNA and the target transcript (Hutvagner and Zamore, Science 297:2056-2060 (2002); Llave et al., *Plant Cell* 14:1605-1619 (2002)). It seems likely that miRNAs can enter at least two pathways of target gene regulation: (1) protein downregulation when target complementarity is <100%; and (2) RNA cleavage when target complementarity is 100%. MicroRNAs entering the RNA cleavage pathway are analogous to the 21-25 nt short interfering RNAs (siRNAs) generated during RNA interference (RNAi) in animals and post-transcriptional gene silencing (PTGS) in plants, and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., *Plant Cell* 14:1605-1619 (2002); Park et al., *Curr. Biol.* 12:1484-1495 (2002); Rhoades et al., *Cell* 110:513-520 (2002)), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

Regulatory Sequences:

A recombinant DNA construct (including a suppression DNA construct) of the present invention may comprise at least one regulatory sequence.

A regulatory sequence may be a promoter.

A number of promoters can be used in recombinant DNA constructs of the present invention. The promoters can be selected based on the desired outcome, and may include constitutive, tissue-specific, inducible, or other promoters for expression in the host organism.

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) Nature Biotechnol. 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include soybean Kunitz trypsin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J. 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current invention include the following: 1) the stress-inducible RD29A promoter (Kasuga et al. (1999) Nature Biotechnol. 17:287-91); 2) the barley promoter, B22E; expression of B22E is specific to the pedicel in developing maize kernels ("Primary Structure of a Novel Barley Gene Differentially Expressed in Immature Aleurone Layers". Klemsdal, S. S. et al., Mol. Gen. Genet. 228(½):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993); "Structural characterization, chromosomal localization and phylogenetic evaluation of two pairs of AGAMOUS-like MADS-box genes from maize", Theissen et al. Gene 156(2):155-166 (1995); NCBI GenBank Accession No. X80206)). Zag2 transcripts can be detected 5 days prior to pollination to 7 to 8 days after pollination ("DAP"), and directs expression in the carpel of developing female inflorescences and CimI which is specific to the nucleus of developing maize kernels. CimI transcript is detected 4 to 5 days before pollination to 6 to 8 DAP. Other useful promoters include any promoter which can be derived from a gene whose expression is maternally associated with developing female florets.

Additional promoters for regulating the expression of the nucleotide sequences of the present invention in plants are stalk-specific promoters. Such stalk-specific promoters include the alfalfa S2A promoter (GenBank Accession No.

EF030816; Abrahams et al., Plant Mol. Biol. 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B., Biochemistry of Plants 15:1-82 (1989).

Promoters for use in the current invention may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*. Other promoters include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790; GI No. 1063664), Recombinant DNA constructs of the present invention may also include other regulatory sequences, including but not limited to, translation leader sequences, introns, and polyadenylation recognition sequences. In another embodiment of the present invention, a recombinant DNA construct of the present invention further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell. Biol.* 8:4395-4405 (1988); Callis et al., *Genes Dev.* 1:1183-1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or from a non-plant eukaryotic gene.

A translation leader sequence is a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Molecular Biotechnology 3:225).

Any plant can be selected for the identification of regulatory sequences and ferrochelatase genes to be used in recombinant DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions:

A composition of the present invention is a plant comprising in its genome any of the recombinant DNA constructs (including any of the suppression DNA constructs) of the present invention (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct may be stably integrated into the genome of the plant.

Particularly embodiments include but are not limited to the following:

1. A plant (for example, a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, and wherein said plant exhibits increased drought tolerance when compared to a control plant not comprising said recombinant DNA construct. The plant may further exhibit an alteration of at least one agronomic characteristic when compared to the control plant.

2. A plant (for example, a maize or soybean plant) comprising in its genome a recombinant DNA construct comprising a polynucleotide operably linked to at least one regulatory sequence, wherein said polynucleotide encodes a ferrochelatase, and wherein said plant exhibits increased drought tolerance when compared to a control plant not comprising said recombinant DNA construct. The plant may further exhibit an alteration of at least one agronomic characteristic when compared to the control plant.

3. A plant (for example, a maize or soybean plant) comprising in its genome a recombinant DNA construct comprising a polynucleotide operably linked to at least one regulatory sequence, wherein said polynucleotide encodes a ferrochelatase, and wherein said plant exhibits an alteration of at least one agronomic characteristic when compared to a control plant not comprising said recombinant DNA construct.

4. A plant (for example, a maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, and wherein said plant exhibits an alteration of at least one agronomic characteristic when compared to a control plant not comprising said recombinant DNA construct.

5. A plant (for example, a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase, and wherein said plant exhibits an alteration of at least one agronomic characteristic when compared to a control plant not comprising said suppression DNA construct.

6. A plant (for example, a maize or soybean plant) comprising in its genome a suppression DNA construct comprising at least one regulatory element operably linked to all or part of (a) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (b) a full complement of the nucleic acid sequence of (a), and wherein said plant exhibits an alteration of at least one agronomic characteristic when compared to a control plant not comprising said suppression DNA construct.

7. Any progeny of the above plants in embodiments 1-6, any seeds of the above plants in embodiments 1-6, any seeds of progeny of the above plants in embodiments 1-6, and cells from any of the above plants in embodiments 1-6 and progeny thereof.

In any of the foregoing embodiments 1-7 or any other embodiments of the present invention, the ferrochelatase may be from *Arabidopsis thaliana*, *Zea mays*, *Glycine max*, *Glycine tabacina*, *Glycine soja* or *Glycine tomentella*.

In any of the foregoing embodiments 1-7 or any other embodiments of the present invention, the recombinant DNA construct (or suppression DNA construct) may comprise at least a promoter functional in a plant as a regulatory sequence.

In any of the foregoing embodiments 1-7 or any other embodiments of the present invention, the alteration of at least one agronomic characteristic is either an increase or decrease.

In any of the foregoing embodiments 1-7 or any other embodiments of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height and ear length. For example, the alteration of at least one agronomic characteristic may be an increase in yield, greenness or biomass.

In any of the foregoing embodiments 1-7 or any other embodiments of the present invention, the plant may exhibit the alteration of at least one agronomic characteristic when compared, under water limiting conditions, to a control plant not comprising said recombinant DNA construct (or said suppression DNA construct).

"Drought" refers to a decrease in water availability to a plant that, especially when prolonged, can cause damage to the plant or prevent its successful growth (e.g., limiting plant growth or seed yield).

"Drought tolerance" is a trait of a plant to survive under drought conditions over prolonged periods of time without exhibiting substantial physiological or physical deterioration.

"Increased drought tolerance" of a plant is measured relative to a reference or control plant, and is a trait of the plant to survive under drought conditions over prolonged periods of time, without exhibiting the same degree of physiological or physical deterioration relative to the reference or control plant grown under similar drought conditions. Typically, when a transgenic plant comprising a recombinant DNA construct or suppression DNA construct in its genome exhibits increased drought tolerance relative to a reference or control plant, the reference or control plant does not comprise in its genome the recombinant DNA construct or suppression DNA construct.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

A drought stress experiment may involve a chronic stress (i.e., slow dry down) and/or may involve two acute stresses (i.e., abrupt removal of water) separated by a day or two of recovery. Chronic stress may last 8-10 days. Acute stress may last 3-5 days. The following variables may be measured during drought stress and well watered treatments of transgenic plants and relevant control plants:

The variable "% area chg_start chronic–acute2" is a measure of the percent change in total area determined by remote visible spectrum imaging between the first day of chronic stress and the day of the second acute stress The variable "% area chg_start chronic–end chronic" is a measure of the percent change in total area determined by remote visible spectrum imaging between the first day of chronic stress and the last day of chronic stress The variable "% area chg_start chronic–harvest" is a measure of the percent change in total area determined by remote visible spectrum imaging between the first day of chronic stress and the day of harvest The variable "% area chg_start chronic–recovery24 hr" is a measure of the percent change in total area determined by remote visible spectrum imaging between the first day of chronic stress and 24 hrs into the recovery (24 hrs after acute stress 2)

The variable "psii_acute1" is a measure of Photosystem II (PSII) efficiency at the end of the first acute stress period. It provides an estimate of the efficiency at which light is absorbed by PSII antennae and is directly related to carbon dioxide assimilation within the leaf.

The variable "psii_acute2" is a measure of Photosystem II (PSII) efficiency at the end of the second acute stress period. It provides an estimate of the efficiency at which light is absorbed by PSII antennae and is directly related to carbon dioxide assimilation within the leaf.

The variable "fv/fm_acute1" is a measure of the optimum quantum yield (Fv/Fm) at the end of the first acute stress–(variable fluorescence difference between the maximum and minimum fluorescence/maximum fluorescence)

The variable "fv/fm_acute2" is a measure of the optimum quantum yield (Fv/Fm) at the end of the second acute stress–(variable fluorescence difference between the maximum and minimum fluorescence/maximum fluorescence)

The variable "leaf rolling_harvest" is a measure of the ratio of top image to side image on the day of harvest.

The variable "leaf rolling_recovery24 hr" is a measure of the ratio of top image to side image 24 hours into the recovery.

The variable "Specific Growth Rate (SGR)" represents the change in total plant surface area (as measured by Lemna Tec Instrument) over a single day ($Y(t)=Y0*e^{r*t}$). $Y(t)=Y0*e^{r*t}$ is equivalent to % change in $Y/\Delta t$ where the individual terms are as follows: Y(t)=Total surface area at t; Y0=Initial total surface area (estimated); r=Specific Growth Rate day$^{-1}$, and t=Days After Planting ("DAP")

The variable "shoot dry weight" is a measure of the shoot weight 96 hours after being placed into a 104° C. oven The variable "shoot fresh weight" is a measure of the shoot weight immediately after being cut from the plant The Examples below describe some representative protocols and techniques for simulating drought conditions and/or evaluating drought tolerance.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to a control or reference plant).

One of ordinary skill in the art would readily recognize a suitable control or reference plant to be utilized when assessing or measuring an agronomic characteristic or phenotype of a transgenic plant in any embodiment of the present invention in which a control plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or the suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods:

Methods include but are not limited to methods for increasing drought tolerance in a plant, methods for evaluating drought tolerance in a plant, methods for altering an agronomic characteristic in a plant, methods for determining an alteration of an agronomic characteristic in a plant, and methods for producing seed. The plant may be a monocotyledonous or dicotyledonous plant, for example, a maize or soybean plant. The plant may also be sunflower, sorghum, canola, wheat, alfalfa, cotton, rice, barley or millet. The seed is may be a maize or soybean seed, for example, a maize hybrid seed or maize inbred seed.

Methods include but are not limited to the following:

A method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

A method for isolating a polypeptide of the invention from a cell or culture medium of the cell, wherein the cell comprises a recombinant DNA construct comprising a polynucleotide of the invention operably linked to at least one regulatory sequence, and wherein the transformed host cell is grown under conditions that are suitable for expression of the recombinant DNA construct.

A method of altering the level of expression of a polypeptide of the invention in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the polypeptide of the invention in the transformed host cell.

A method of increasing drought tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of increasing drought tolerance in a plant, comprising: (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (a) (i); and (b) regenerating a transgenic plant from the regenerable plant cell after step (a), wherein the transgenic plant comprises in its genome the suppression DNA construct and exhibits increased drought tolerance when compared to a control plant not comprising the suppression DNA construct. The method may further comprise (c) obtaining a progeny plant derived from the transgenic plant, wherein said progeny plant comprises in its genome the suppression DNA construct and exhibits increased drought tolerance when compared to a control plant not comprising the suppression DNA construct.

A method of increasing drought tolerance in a plant, comprising: (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; and (b) regenerating a transgenic plant from the regenerable plant cell after step (a), wherein the transgenic plant comprises in its genome the suppression DNA construct and exhibits increased drought tolerance when compared to a control plant not comprising the suppression DNA construct. The method may further comprise (c) obtaining a progeny plant derived from the transgenic plant, wherein said progeny plant comprises in its genome the suppression DNA construct and exhibits increased drought tolerance when compared to a control plant not comprising the suppression DNA construct.

A method of evaluating drought tolerance in a plant, comprising (a) introducing into a regenerable plant cell a recombinant DNA construct comprising a polynucleotide operably linked to at least on regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct; and (c) evaluating the transgenic plant for drought tolerance compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for drought tolerance compared to a control plant not comprising the recombinant DNA construct.

A method of evaluating drought tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (a)(i); (b) regenerating a transgenic plant from the regenerable plant cell after step (a), wherein the transgenic plant comprises in its genome the suppression DNA construct; and (c) evaluating the transgenic plant for drought tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for drought tolerance compared to a control plant not comprising the suppression DNA construct.

A method of evaluating drought tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; (b) regenerating a transgenic plant from the regenerable plant cell after step (a), wherein the transgenic plant comprises in its genome the suppression DNA construct; and (c) evaluating the transgenic plant for drought tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for drought tolerance compared to a control plant not comprising the suppression DNA construct.

A method of evaluating drought tolerance in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome the recombinant DNA construct; (c) obtaining a progeny plant derived from said transgenic plant, wherein the progeny plant comprises in its genome the recombinant DNA construct; and (d) evaluating the progeny plant for drought tolerance compared to a control plant not comprising the recombinant DNA construct.

A method of evaluating drought tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (a)(i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) evaluating the progeny plant for drought tolerance compared to a control plant not comprising the suppression DNA construct.

A method of evaluating drought tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) evaluating the progeny plant for drought tolerance compared to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least on regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome said recombinant DNA construct; and (c) determining whether the transgenic plant exhibits an alteration in at least one agronomic characteristic when compared, optionally under water limiting conditions, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (i); (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared, optionally under water limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared, optionally under water limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30; (b) regenerating a transgenic plant from the regenerable plant cell after step (a), wherein the transgenic plant comprises in its genome said recombinant DNA construct; (c) obtaining a progeny plant derived from said transgenic plant, wherein the progeny plant comprises in its genome the recombinant DNA construct; and (d) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, 4, 6, 8, 10, 12, 14, 16, 18, 20, 22, 24, 26, 28 or 30, or (ii) a full complement of the nucleic acid sequence of (i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a ferrochelatase; (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared, optionally under water limiting conditions, to a control plant not comprising the suppression DNA construct.

A method of producing seed (for example, seed that can be sold as a drought tolerant product offering) comprising any of the preceding methods, and further comprising obtaining seeds from said progeny plant, wherein said seeds comprise in their genome said recombinant DNA construct (or suppression DNA construct).

In any of the preceding methods or any other embodiments of methods of the present invention, in said introducing step said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present invention, said regenerating step may comprise the following: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, amino acid content in a vegetative tissue, total plant protein content, fruit protein content, seed protein content, protein content in a vegetative tissue, drought tolerance, nitrogen uptake, root lodging, harvest index, stalk lodging, plant height, ear height and ear length. The alteration of at least one agronomic characteristic may be an increase in yield, greenness or biomass.

In any of the preceding methods or any other embodiments of methods of the present invention, the plant may exhibit the alteration of at least one agronomic characteristic when compared, under water limiting conditions, to a control plant not comprising said recombinant DNA construct (or said suppression DNA construct).

In any of the preceding methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation.

Techniques are set forth below in the Examples below for transformation of maize plant cells and soybean plant cells.

Other methods for transforming dicots, primarily by use of *Agrobacterium tumefaciens*, and obtaining transgenic plants include those published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., Bio/Technology 6:923 (1988), Christou et al., Plant Physiol. 87:671 674 (1988)); *Brassica* (U.S. Pat. No. 5,463,174); peanut (Cheng et al., Plant Cell Rep. 15:653 657 (1996), McKently et al., Plant Cell Rep. 14:699 703 (1995)); papaya; and pea (Grant et al., Plant Cell Rep. 15:254 258, (1995)).

Transformation of monocotyledons using electroporation, particle bombardment, and *Agrobacterium* have also been reported, for example, transformation and plant regeneration as achieved in asparagus (Bytebier et al., Proc. Natl. Acad. Sci. (USA) 84:5354, (1987)); barley (Wan and Lemaux, Plant Physiol 104:37 (1994)); maize (Rhodes et al., Science 240: 204 (1988), Gordon-Kamm et al., Plant Cell 2:603 618 (1990), Fromm et al., Bio/Technology 8:833 (1990), Koziel et al., Bio/Technology 11: 194, (1993), Armstrong et al., Crop Science 35:550 557 (1995)); oat (Somers et al., Bio/Technology 10: 15 89 (1992)); orchard grass (Horn et al., Plant Cell Rep. 7:469 (1988)); rice (Toriyama et al., TheorAppl. Genet. 205:34, (1986); Part et al., Plant Mol. Biol. 32:1135 1148, (1996); Abedinia et al., Aust. J. Plant Physiol. 24:133 141 (1997); Zhang and Wu, Theor. Appl. Genet. 76:835 (1988); Zhang et al. Plant Cell Rep. 7:379, (1988); Battraw and Hall, Plant Sci. 86:191 202 (1992); Christou et al., Bio/Technology 9:957 (1991)); rye (De la Pena et al., Nature 325:274 (1987)); sugarcane (Bower and Birch, Plant J. 2:409 (1992)); tall fescue (Wang et al., Bio/Technology 10:691 (1992)), and wheat (Vasil et al., Bio/Technology 10:667 (1992); U.S. Pat. No. 5,631,152).

There are a variety of methods for the regeneration of plants from plant tissue. The particular method of regeneration will depend on the starting plant tissue and the particular plant species to be regenerated.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

Figure 1:
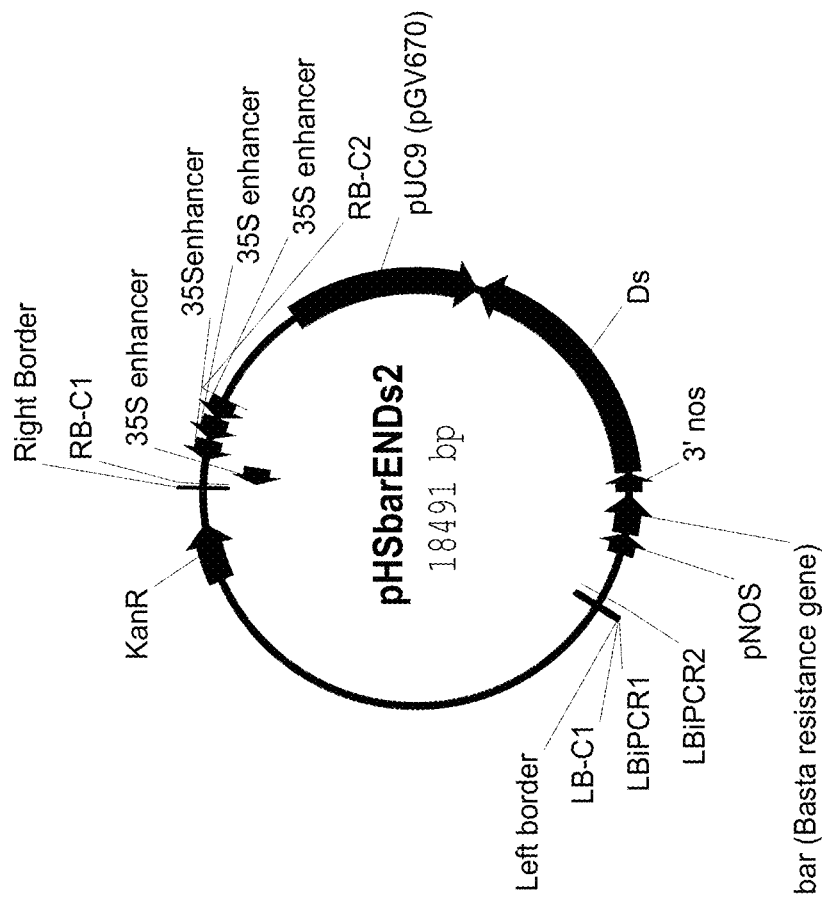
FIG. 1 shows a schematic of the pHSbarENDs2 activation tagging construct (SEQ ID NO:31) used to make the *Arabidopsis* populations.

An 18.5-kb T-DNA based binary construct was created, pHSbarENDs2 (FIG. 1; SEQ ID NO:31), that contains four multimerized enhancer elements derived from the Cauliflower Mosaic Virus 35S promoter (corresponding to sequences −341 to −64, as defined by Odell et al., *Nature* 313:810-812 (1985)). The construct also contains vector sequences (pUC9) and a polylinker to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

*Arabidopsis* activation-tagged populations were created by whole plant *Agrobacterium* transformation. The pHSbarENDs2 construct was transformed into *Agrobacterium tumefaciens* strain C58, grown in LB at 25° C. to OD600~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting T1 seed were sown on soil, and transgenic seedlings were selected by spraying with glufosinate (Finale®; AgrEvo; Bayer Environmental Science). A total of 100,000 glufosinate resistant T1 seedlings were selected. T2 seed from each line was kept separate.

Example 2

Screens to Identify Lines with Enhanced Drought Tolerance

Quantitative Drought Screen:

From each of 96,000 separate T1 activation-tagged lines, nine glufosinate resistant T2 plants are sown, each in a single pot on Scotts® Metro-Mix® 200 soil. Flats are configured with 8 square pots each. Each of the square pots is filled to the top with soil. Each pot (or cell) is sown to produce 9 glufosinate resistant seedlings in a 3×3 array.

The soil is watered to saturation and then plants are grown under standard conditions (i.e., 16 hour light, 8 hour dark cycle; 22° C.; ~60% relative humidity). No additional water is given.

Digital images of the plants are taken at the onset of visible drought stress symptoms. Images are taken once a day (at the same time of day), until the plants appear dessicated. Typically, four consecutive days of data is captured.

Color analysis is employed for identifying potential drought tolerant lines. Color analysis can be used to measure the increase in the percentage of leaf area that falls into a yellow color bin. Using hue, saturation and intensity data ("HSI"), the yellow color bin consists of hues 35 to 45.

Maintenance of leaf area is also used as another criterion for identifying potential drought tolerant lines, since *Arabidopsis* leaves wilt during drought stress. Maintenance of leaf area can be measured as reduction of rosette leaf area over time.

Leaf area is measured in terms of the number of green pixels obtained using the LemnaTec imaging system. Activation-tagged and control (e.g., wild-type) plants are grown side by side in flats that contain 72 plants (9 plants/pot). When wilting begins, images are measured for a number of days to monitor the wilting process. From these data wilting profiles are determined based on the green pixel counts obtained over four consecutive days for activation-tagged and accompanying control plants. The profile is selected from a series of measurements over the four day period that gives the largest degree of wilting. The ability to withstand drought is measured by the tendency of activation-tagged plants to resist wilting compared to control plants.

LemnaTec HTSBonitUV software is used to analyze CCD images. Estimates of the leaf area of the *Arabidopsis* plants are obtained in terms of the number of green pixels. The data for each image is averaged to obtain estimates of mean and standard deviation for the green pixel counts for activation-tagged and wild-type plants. Parameters for a noise function are obtained by straight line regression of the squared deviation versus the mean pixel count using data for all images in a batch. Error estimates for the mean pixel count data are calculated using the fit parameters for the noise function. The mean pixel counts for activation-tagged and wild-type plants are summed to obtain an assessment of the overall leaf area for each image. The four-day interval with maximal wilting is obtained by selecting the interval that corresponds to the maximum difference in plant growth. The individual wilting responses of the activation-tagged and wild-type plants are obtained by normalization of the data using the value of the green pixel count of the first day in the interval. The drought tolerance of the activation-tagged plant compared to the wild-type plant is scored by summing the weighted difference between the wilting response of activation-tagged plants and wild-type plants over day two to day four; the weights are estimated by propagating the error in the data. A positive drought tolerance score corresponds to an activation-tagged plant with slower wilting compared to the wild-type plant. Significance of the difference in wilting response between activation-tagged and wild-type plants is obtained from the weighted sum of the squared deviations.

Lines with a significant delay in yellow color accumulation and/or with significant maintenance of rosette leaf area, when compared to the average of the whole flat, are designated as Phase 1 hits. Phase 1 hits are re-screened in duplicate under the same assay conditions. When either or both of the Phase 2 replicates show a significant difference (score of greater than 0.9) from the whole flat mean, the line is then considered a validated drought tolerant line.

Example 3

Identification of Activation-Tagged Genes

Genes flanking the T-DNA insert in drought tolerant lines are identified using one, or both, of the following two standard procedures: (1) thermal asymmetric interlaced (TAIL) PCR (Liu et al., (1995), *Plant J.* 8:457-63); and (2) SAIFF PCR (Siebert et al., (1995) *Nucleic Acids Res.* 23:1087-1088). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence.

Once a tag of genomic sequence flanking a T-DNA insert is obtained, candidate genes are identified by alignment to publicly available *Arabidopsis* genome sequence.

Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4A

Identification of Activation-Tagged

Ferrochelatase-I (FeC-I) Gene

An activation-tagged line (No. 105998) showing drought tolerance was further analyzed. DNA from the line was extracted, and genes flanking the T-DNA insert in the mutant line were identified using SAIFF PCR (Siebert et al., *Nucleic Acids Res.* 23:1087-1088 (1995)). A PCR amplified fragment was identified that contained T-DNA border sequence and *Arabidopsis* genomic sequence. Genomic sequences flanking the T-DNA insert was obtained, and the candidate gene was identified by alignment to the completed *Arabidopsis* genome. For a given T-DNA integration event, the annotated gene nearest the 35S enhancer elements/T-DNA RB was the candidate for gene that is activated in the line. In the case of line 105998, the gene nearest the 35S enhancers at the integration site was At5g26030 (SEQ ID NO:1; NCBI GI No. 511080), encoding a ferrochelatase-I protein (SEQ ID NO:2; NCBI GI No. 511081).

Example 4B

Assay for Expression Level of Candidate Drought Tolerance Genes

A functional activation-tagged allele should result in either up-regulation of the candidate gene in tissues where it is normally expressed, ectopic expression in tissues that do not normally express that gene, or both.

Expression levels of the candidate genes in the cognate mutant line vs. wild-type are compared. A standard RT-PCR procedure, such as the QuantiTect® Reverse Transcription Kit from Qiagen®, is used. RT-PCR of the actin gene is used as a control to show that the amplification and loading of samples from the mutant line and wild-type are similar.

Assay conditions are optimized for each gene. Expression levels are checked in mature rosette leaves. If the activation-tagged allele results in ectopic expression in other tissues (e.g., roots), it is not detected by this assay. As such, a positive result is useful but a negative result does not eliminate a gene from further analysis.

Example 5A

Validation of *Arabidopsis* Candidate Gene At5g26030 (Ferrochelatase-I) Via Transformation into *Arabidopsis*

Candidate genes can be transformed into *Arabidopsis* and overexpressed under the 35S promoter. If the same or similar phenotype is observed in the transgenic line as in the parent activation-tagged line, then the candidate gene is considered to be a validated "lead gene" in *Arabidopsis*.

The candidate *Arabidopsis* ferrochelatase-I gene (At5g26030; SEQ ID NO:1; NCBI GI No. 511080) was tested for its ability to confer drought tolerance in the following manner.

Figure 4:
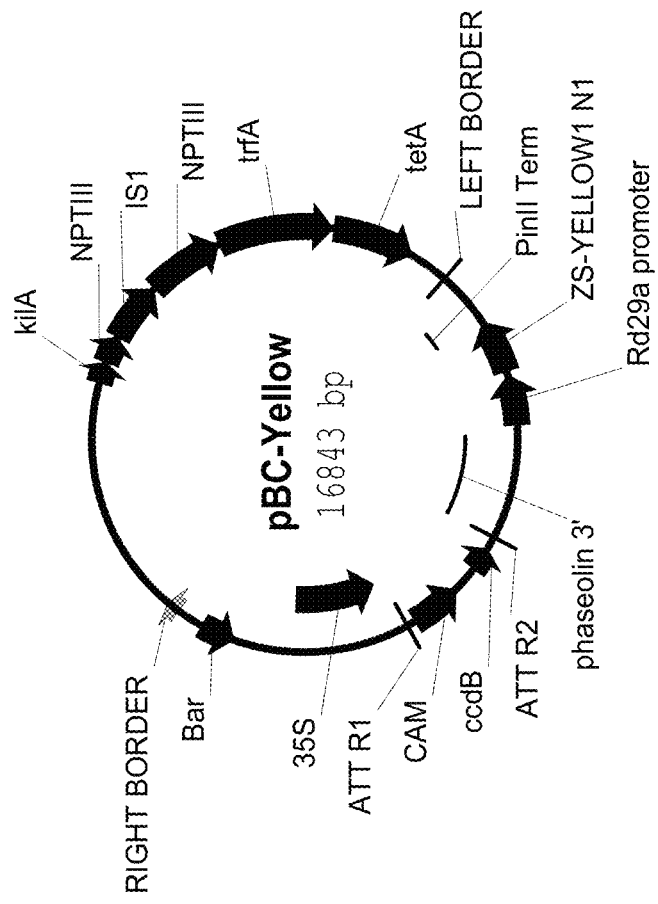
FIG. 4 shows a map of the vector pBC-yellow (SEQ ID NO:34), a destination vector for use in construction of expression vectors for *Arabidopsis*. The attR1 site is at nucleotides 11276-11399 (complementary strand); the attR2 site is at nucleotides 9695-9819 (complementary strand).

A 16.8-kb T-DNA based binary vector, called pBC-yellow (SEQ ID NO:34; FIG. 4), was constructed with a 1.3-kb 35S promoter immediately upstream of the INVITROGEN™ GATEWAY® C1 conversion insert. The vector also contains the RD29a promoter driving expression of the gene for ZS-Yellow (INVITROGEN™), which confers yellow fluorescence to transformed seed.

The At5g26030 cDNA protein-coding region was amplified by RT-PCR with the following primers:

```
(1) At5g26030-5'attB forward primer
(SEQ ID NO: 42):
TTAAACAAGTTTGTACAAAAAAGCAGGCTCAACAATGCAGGCAACGG

CTTTATCA (2) At5g26030-3'attB reverse primer
(SEQ ID NO: 43):
TTAAACCACTTTGTACAAGAAAGCTGGGTCTATAGGTTCCGGAACGC

ATG
```

The forward primer contains the attB1 sequence (ACAAGTTTGTACAAAAAAGCAGGCT; SEQ ID NO:40) and a consensus Kozak sequence (CAACA) adjacent to the first 21 nucleotides of the protein-coding region, beginning with the ATG start codon, of said cDNA.

The reverse primer contains the attB2 sequence (AC-CACTTTGTACAAGAAAGCTGGGT; SEQ ID NO:41) adjacent to the reverse complement of the last 21 nucleotides of the protein-coding region, beginning with the reverse complement of the stop codon, of said cDNA.

Figure 2:
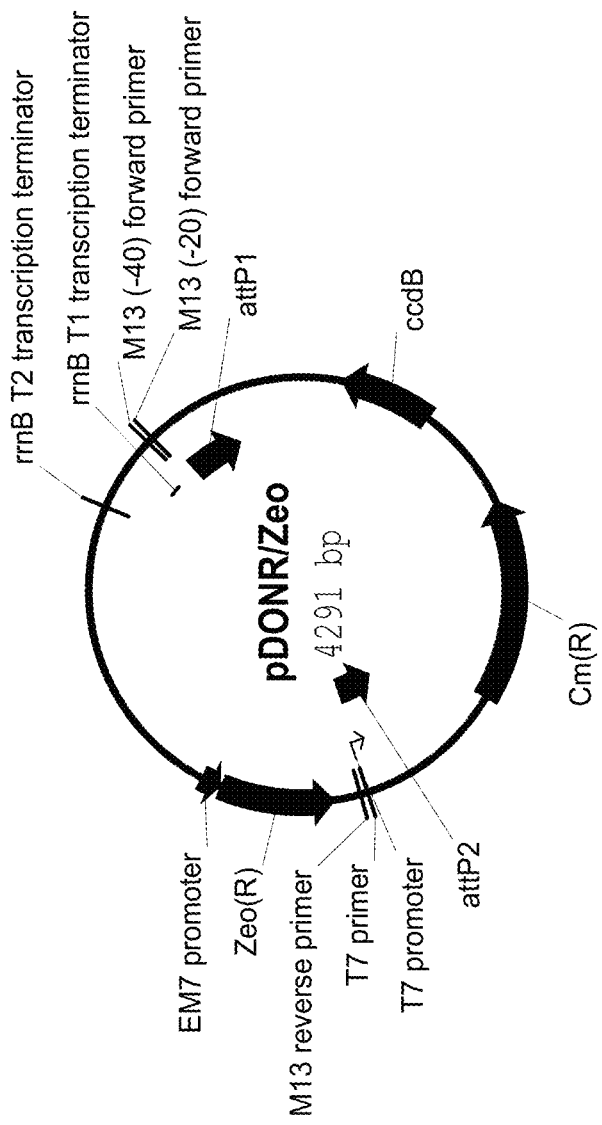
FIG. 2 shows a map of the vector pDONR™/Zeo (SEQ ID NO:32). The attP1 site is at nucleotides 570-801; the attP2 site is at nucleotides 2754-2985 (complementary strand).

Using the INVITROGEN™ GATEWAY® CLONASE™ technology, a BP Recombination Reaction was performed with pDONR™/Zeo (SEQ ID NO:32; FIG. 2). This process removed the bacteria lethal ccdB gene, as well as the chloramphenicol resistance gene (CAM) from pDONR™/Zeo and directionally cloned the PCR product with flanking attB1 and attB2 sites creating an entry clone, PHP31052. This entry clone was used for a subsequent LR Recombination Reaction with a destination vector, as follows.

A 16.8-kb T-DNA based binary vector (destination vector), called pBC-yellow (SEQ ID NO:34; FIG. 4), was constructed with a 1.3-kb 35S promoter immediately upstream of the INVITROGEN™ GATEWAY® C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed on the PHP31052 entry clone, containing the directionally cloned PCR product, and pBC-yellow. This allowed for rapid and directional cloning of the candidate gene behind the 35S promoter in pBC-yellow to create the 35S promoter::At5g26030 expression construct, pBC-Yellow-At5g26030.

Applicants then introduced the 35S promoter::At5g26030 expression construct into wild-type *Arabidopsis* ecotype Col-0, using the same *Agrobacterium*-mediated transformation procedure described in Example 1. Transgenic T1 seeds were selected by yellow fluorescence, and T1 seeds were plated next to wild-type seeds and grown under water limiting conditions. Growth conditions and imaging analysis were as described in Example 2. It was found that the original drought tolerance phenotype from activation tagging could be recapitulated in wild-type *Arabidopsis* plants that were transformed with a construct where At5g26030 was directly expressed by the 35S promoter. The drought tolerance score, as determined by the method of Example 2, was 5.3.

Example 5B

Validation of *Arabidopsis* Candidate Gene At2g30390 (Ferrochelatase-II) Via Transformation into *Arabidopsis*

A cDNA encoding ferrochelatase-I from *Arabidopsis* was previously cloned by functional complementation of a yeast mutant (Smith et al. 1994 J Biol Chem 269:13405-13413). Subsequently, a second ferrochelatase isoform, ferrochelatase-II, was found in *Arabidopsis* (Chow et al. 1998 Plant J 15:531-541). Two forms of ferrochelatase also have been identified in cucumber, *Cucumis sativus* (Miyamoto et al. 1994 Plant Physiol 105:769-770; and Suzuki et al. 2002 J Biol Chem 277:4731-4737). The C-terminal region of ferrochelatase-II, but not ferrochelatase-I, contains a conserved motif found in light-harvesting chlorophyll proteins (Suzuki et al. 2002 J Biol Chem 277:4731-4737). The C-terminal region of the ferrochelatase from the cyanobacteria *Synechocystis* (NCBI GI NO. 1708186) has sequence homology to this conserved motif.

The *Arabidopsis* ferrochelatase-II gene (At2g30390) was selected as a second candidate gene, and was tested for its ability to confer drought tolerance in the following manner.

A 16.8-kb T-DNA based binary vector, called pBC-yellow (SEQ ID NO:34; FIG. 4), was constructed with a 1.3-kb 35S promoter immediately upstream of the INVITROGEN™ GATEWAY® C1 conversion insert. The vector also contains the RD29a promoter driving expression of the gene for ZS-Yellow (INVITROGEN™), which confers yellow fluorescence to transformed seed.

The At2g30390 cDNA protein-coding region was amplified by RT-PCR with the following primers:

```
(3) At2g30390-5'attB forward primer
(SEQ ID NO: 44):
TTAAACAAGTTTGTACAAAAAAGCAGGCTCAACAATGAATTGCCCAG

CCATGACT (4) At2g30390-3'attB reverse primer
(SEQ ID NO: 45):
TTAAACCACTTTGTACAAGAAAGCTGGGTTTATAATGAAGGCAAGAT

GCC
```

The forward primer contains the attB1 sequence (ACAAGTTTGTACAAAAAAGCAGGCT; SEQ ID NO:40) and a consensus Kozak sequence (CAACA) adjacent to the first 21 nucleotides of the protein-coding region, beginning with the ATG start codon, of said cDNA.

The reverse primer contains the attB2 sequence (AC-CACTTTGTACAAGAAAGCTGGGT; SEQ ID NO:41) adjacent to the reverse complement of the last 21 nucleotides of the protein-coding region, beginning with the reverse complement of the stop codon, of said cDNA.

Using the INVITROGEN™ GATEWAY® CLONASE™ technology, a BP Recombination Reaction was performed with pDONR™/Zeo (SEQ ID NO:32; FIG. 2). This process removed the bacteria lethal ccdB gene, as well as the chloramphenicol resistance gene (CAM) from pDONR™/Zeo and directionally cloned the PCR product with flanking attB1 and attB2 sites creating an entry clone, PHP-Entry-At2g30390. This entry clone was used for a subsequent LR Recombination Reaction with a destination vector, as follows.

A 16.8-kb T-DNA based binary vector (destination vector), called pBC-yellow (SEQ ID NO:34; FIG. 4), was constructed with a 1.3-kb 35S promoter immediately upstream of the INVITROGEN™ GATEWAY® C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed on the PHP-Entry-At2g30390 entry clone, containing the directionally cloned PCR product, and pBC-yellow. This allowed for rapid and directional cloning of the candidate gene behind the 35S promoter in pBC-yellow to create the 35S promoter::At2g30390 expression construct, pBC-Yellow-At2g30390.

Applicants then introduced the 35S promoter::At2g30390 expression construct into wild-type *Arabidopsis* ecotype Col-0, using the same *Agrobacterium*-mediated transformation procedure described in Example 1. Transgenic T1 seeds were selected by yellow fluorescence, and T1 seeds were plated next to wild-type seeds and grown under water limiting conditions. Growth conditions and imaging analysis were as described in Example 2. It was found that the original drought tolerance phenotype from activation tagging could be recapitulated in wild-type *Arabidopsis* plants that were transformed with a construct where At2g30390 was directly expressed by the 35S promoter. The drought tolerance score, as determined by the method of Example 2, was 3.7.

Example 6A

Preparation of cDNA Libraries and Isolation and Sequencing of cDNA Clones cDNA libraries may be prepared by any one of many methods available. For example, the cDNAs may be introduced into plasmid vectors by first preparing the cDNA libraries in UNI-ZAP™ XR vectors according to the manufacturer's protocol (Stratagene Cloning Systems, La Jolla, Calif.). The UNI-ZAP™ XR libraries are converted into plasmid libraries according to the protocol provided by Stratagene. Upon conversion, cDNA inserts will be contained in the plasmid vector pBluescript®. In addition, the cDNAs may be introduced directly into precut Bluescript® II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism® dye-terminator ReadyReaction mix) outward from the transposition event site, utilizing unique primers specific to the binding sites within the transposon.

Sequence data is collected (ABI Prism® Collections) and assembled using Phred and Phrap (Ewing et al. (1998) *Genome Res.* 8:175-185; Ewing and Green (1998) *Genome Res.* 8:186-194). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al. (1998) *Genome Res.* 8:195-202).

In some of the clones the cDNA fragment may correspond to a portion of the 3'-terminus of the gene and does not cover the entire open reading frame. In order to obtain the upstream information one of two different protocols is used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript® vector using a commercial kit and following the manufacturer's protocol. This kit is selected from many available from several vendors including INVITROGEN™ (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 7

Identification of cDNA Clones cDNA clones encoding ferrochelatases can be identified by conducting BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health) searches for similarity to amino acid sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences from clones can be translated in all reading frames and compared for similarity to all publicly available protein sequences contained in the "nr" database using the BLASTX algorithm (Gish and States (1993) *Nat. Genet.* 3:266-272) provided by the NCBI. The polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expectation) of observing a match of a cDNA-encoded sequence to a sequence contained in the searched databases merely by chance as calculated by BLAST are reported herein as "pLog" values, which represent the negative of the logarithm of the reported P-value or E-value. Accordingly, the greater the pLog value, the greater the likelihood that the cDNA-encoded sequence and the BLAST "hit" represent homologous proteins.

ESTs sequences can be compared to the Genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described above. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 8

Characterization of cDNA Clones Encoding Ferrochetalases cDNA libraries representing mRNAs from various tissues of Sugar Beet, Canola, Maize, Rice, Soybean, Wheat and Catmint were prepared and cDNA clones encoding ferrochelatases were identified. The characteristics of the libraries are described below.

TABLE 3 cDNA Libraries from Sugar Beet, Canola, Maize, Rice, Soybean, Wheat and Catmint

| Library | Description | Clone |
|---------|-------------|-------|
| ebs1c | Sugar Beet, shoot and phloem specific genes | ebs1c.pk002.n16:fis |
| ebb1c | Immature buds of Canola, Rf gene knock out mutant line, 02SM2 | ebb1c.pk006.j11:fis |
| cfp3n | Maize Ear, pooled V10-V14-v16-VT, Full-length enriched normalized | cfp3n.pk004.f12:fis |
| cfp5n | Maize Kernel, pooled stages, Full-length enriched, normalized | cfp5n.pk009.j16:fis |
| rl0n | Rice 15 Day Old Leaf* | rl0n.pk117.h21:fis |
| se3 | Soybean Embryo, 17 Days After Flowering | se3.pk0034.e10:fis |
| etb1n | Normalized tulip bulb library | etb1n.pk002.n16:fis |
| wlp1c | Wheat (*Triticum aestivum*, Hi Line) lemma and palea | wlp1c.pk002.p10:fis |
| ecl1c | Catmint (*Nepeta racemosa*) cDNA library from young leaf tissue | ecl1c.pk005.l15:fis |
| cfp6n | Maize Leaf and Seed pooled, Full-length enriched normalized | cfp6n.pk072.n9:fis |
| wlp1c | Wheat (*Triticum aestivum*, Hi Line) lemma and palea | wlp1c.pk004.d13:fis |
| wpa1c | Wheat (*Triticum aestivum*) pre-meiotic anthers | wpa1c.pk014.g4:fis |

*These libraries were normalized essentially as described in U.S. Pat. No. 5,482,845

Two of the cDNA clones listed in Table 3 had anomalies. The clone ebb1c.pk006.j11:fis contains an unspliced intron at nucleotides 386-481 of SEQ ID NO:5. The polypeptide encoded by the two exons surrounding the intron is given in SEQ ID NO:6. Additionally, the clone ecl1c.pk005.l15:fis has a single base deletion at nucleotide 442, which results in a frame-shift in the corresponding translation. Based on comparison to a highly similar clone cDNA clone from grape, veb1c.pk008.p6 (411 base pairs), a "T" nucleotide was added to the ecl1c.pk005.l15:fis sequence at position 442. The modified nucleotide sequence is presented in SEQ ID NO:23, which encodes the amino acid sequence of SEQ ID NO:24.

The BLAST search using the sequences from clones listed in Table 3 revealed similarity of the polypeptides encoded by the cDNAs to the ferrochelatases from various organisms. As shown in Table 4 and FIGS. 10A-10C, certain cDNAs encoded polypeptides similar to ferrochelatase-I proteins from *Arabidopsis* (GI No. 511081; SEQ ID NO:2; FeC-I), barley (GI No. 2460251; SEQ ID NO:48; FeC-I), rice (GI No. 113631036; SEQ ID NO:49; FeC-I), and grape (GI No. 147818793; SEQ ID NO:50; FeC-I). As shown in Table 6 and FIGS. 12A-12C, certain cDNAs encoded polypeptides similar to ferrochelatase-II proteins from *Arabidopsis* (GI No. 15227742; SEQ ID NO:20; FeC-II), rice (GI No. 115463419; SEQ ID NO:51; FeC-II), cucumber (GI No. 12082085; SEQ ID NO:52; FeC-II), tobacco (GI No. 15147828; SEQ ID NO:53; FeC-II) and a ferrochelatse-II-like protein from *Synechocystis* (GI No. 1708186; SEQ ID NO:54; FeC-II-like).

Shown in Tables 4 and 6 (non-patent literature) and Tables 5 and 7 (patent literature) are the BLASTP results for the amino acid sequences derived from the nucleotide sequences of the entire cDNA inserts ("Full-Insert Sequence" or "FIS") of the clones listed in Table 3. Each cDNA insert encodes an entire or functional protein ("Complete Gene Sequence" or "CGS"). Also shown in Tables 4-7 are the percent sequence identity values for each pair of amino acid sequences:

TABLE 4

BLASTP Results for Ferrochelatase-I Polypeptides

| Sequence (SEQ ID NO) | Status | NCBI GI No. (SEQ ID NO) | BLASTP pLog of E-value | Percent Sequence Identity |
|---|---|---|---|---|
| ebs1c.pk002.n16 (FIS) (SEQ ID NO: 4) | CGS | 147818793 (SEQ ID NO: 50) | >180 | 72.6 |
| ebb1c.pk006.j11 (FIS) (SEQ ID NO: 6) | CGS | 511081 (SEQ ID NO: 2) | >180 | 83.3 |
| cfp3n.pk004.f12 (FIS) (SEQ ID NO: 8) | CGS | 113631036 (SEQ ID NO: 49) | >180 | 84.0 |
| cfp5n.pk009.j16 (FIS) (SEQ ID NO: 10) | CGS | 113631036 (SEQ ID NO: 49) | >180 | 81.7 |
| rl0n.pk117.h21 (FIS) (SEQ ID NO: 12) | CGS | 113631036 (SEQ ID NO: 49) | >180 | 100 |
| se3.pk0034.e10 (FIS) (SEQ ID NO: 14) | CGS | 147818793 (SEQ ID NO: 50) | >180 | 74.2 |
| etb1n.pk002.n16 (FIS) (SEQ ID NO: 16) | CGS | 113631036 (SEQ ID NO: 49) | 180 | 69.5 |
| wlp1c.pk002.p10 (FIS) (SEQ ID NO: 18) | CGS | 2460251 (SEQ ID NO: 48) | >180 | 98.3 |

TABLE 5

BLASTP Results for Ferrochelatase-I Polypeptides

| Sequence (SEQ ID NO) | Status | Reference (SEQ ID NO) | BLASTP pLog of E-value | Percent Sequence Identity |
|---|---|---|---|---|
| ebs1c.pk002.n16 (FIS) (SEQ ID NO: 4) | CGS | SEQ ID NO: 240025 of US2004031072 (SEQ ID NO: 57) | >180 | 68.8 |
| ebb1c.pk006.j11 (FIS) (SEQ ID NO: 6) | CGS | SEQ ID NO: 20 of JP2001190168-A (SEQ ID NO: 58) | >180 | 83.3 |
| cfp3n.pk004.f12 (FIS) (SEQ ID NO: 8) | CGS | SEQ ID NO: 13029 of US2006150283 (SEQ ID NO: 59) | >180 | 99.4 |
| cfp5n.pk009.j16 (FIS) (SEQ ID NO: 10) | CGS | SEQ ID NO: 7745 of US2006150283 (SEQ ID NO: 60) | >180 | 100 |
| rl0n.pk117.h21 (FIS) (SEQ ID NO: 12) | CGS | SEQ ID NO: 46156 of JP2005185101 (SEQ ID NO: 61) | >180 | 100 |
| se3.pk0034.e10 (FIS) (SEQ ID NO: 14) | CGS | SEQ ID NO: 240025 of US2004031072 (SEQ ID NO: 57) | >180 | 100 |
| etb1n.pk002.n16 (FIS) (SEQ ID NO: 16) | CGS | SEQ ID NO: 46156 of JP2005185101 (SEQ ID NO: 61) | >180 | 69.5 |
| wlp1c.pk002.p10 (FIS) (SEQ ID NO: 18) | CGS | SEQ ID NO: 46156 of JP2005185101 (SEQ ID NO: 61) | >180 | 84.6 |

TABLE 6

BLASTP Results for Ferrochelatase-II Polypeptides

| Sequence (SEQ ID NO) | Status | NCBI GI No. (SEQ ID NO) | BLASTP pLog of E-value | Percent Sequence Identity |
|---|---|---|---|---|
| ecl1c.pk005.l15 (FIS) (SEQ ID NO: 24) | CGS | 12082085 (SEQ ID NO: 52) | >180 | 78.6 |
| cfp6n.pk072.n9 (FIS) (SEQ ID NO: 26) | CGS | 115463419 (SEQ ID NO: 51) | >180 | 90.5 |
| wlp1c.pk004.d13 (FIS) (SEQ ID NO: 28) | CGS | 115463419 (SEQ ID NO: 51) | >180 | 82.9 |
| wpa1c.pk014.g4 (FIS) (SEQ ID NO: 30) | CGS | 115463419 (SEQ ID NO: 51) | >180 | 83.3 |

TABLE 7

BLASTP Results for Ferrochelatase-II Polypeptides

| Sequence (SEQ ID NO) | Status | Reference (SEQ ID NO) | BLASTP pLog of E-value | Percent Sequence Identity |
|---|---|---|---|---|
| ecl1c.pk005.l15 (FIS) (SEQ ID NO: 24) | CGS | SEQ ID NO: 52154 of JP2005185101 (SEQ ID NO: 62) | >180 | 77.4 |
| cfp6n.pk072.n9 (FIS) (SEQ ID NO: 26) | CGS | SEQ ID NO: 72746 of US2004034888 (SEQ ID NO: 63) | >180 | 99.6 |
| wlp1c.pk004.d13 (FIS) (SEQ ID NO: 28) | CGS | SEQ ID NO: 52154 of JP2005185101 (SEQ ID NO: 62) | >180 | 82.9 |
| wpa1c.pk014.g4 (FIS) (SEQ ID NO: 30) | CGS | SEQ ID NO: 52154 of JP2005185101 (SEQ ID NO: 62) | >180 | 83.3 |

FIGS. 10A-10C present an alignment of the amino acid sequences of ferrochelatase-I proteins set forth in SEQ ID NOs:2, 4, 6, 8, 10, 12, 14, 16, 18, 48, 49 and 50. FIG. 11 presents the percent sequence identities and divergence values for each sequence pair presented in FIGS. 10A and 10B.

FIGS. 12A-12C present an alignment of the amino acid sequences of ferrochelatase-II proteins set forth in SEQ ID NOs:20, 22, 24, 26, 28, 30, 51, 52, 53 and 54. FIG. 13 presents the percent sequence identities and divergence values for each sequence pair presented in FIGS. 12A and 12B.

Sequence alignments and percent identity calculations were performed using the Megalign® program of the LASERGENE® bioinformatics computing suite (DNASTAR® Inc., Madison, Wis.). Multiple alignment of the sequences was performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

Import experiments into isolated chloroplasts and mitochondria showed that the *Arabidopsis* ferrochelatase-II gene encodes a precursor which is imported solely into the chloroplast, in contrast to *Arabidopsis* ferrochelatase-I which is targeted to both organelles (Chow et al. 1997 J Biol Chem 272:27565-27571; Chow et al. 1998 Plant J 15:531-541). The ferrochelatase from *Synechocystis* (GI No. 1708186; SEQ ID NO:54) is more similar to the ferrechelatase-II isoform.

Sequence alignments and BLAST scores and probabilities indicate that the nucleic acid fragments comprising the instant cDNA clones encode ferrochelatases.

Example 9

Preparation of a Plant Expression Vector Containing a Homolog to the *Arabidopsis* Lead Gene Sequences homologous to the *Arabidopsis* ferrochelatase-I polypeptide can be identified using sequence comparison algorithms such as BLAST (Basic Local Alignment Search Tool; Altschul et al., J. Mol. Biol. 215:403-410 (1993); see also the explanation of the BLAST algorithm on the world wide web site for the National Center for Biotechnology Information at the National Library of Medicine of the National Institutes of Health). Sequences encoding homologous ferrochelatases can be PCR-amplified by either of the following methods.

Method 1 (RNA-based): If the 5' and 3' sequence information for the protein-coding region of a gene encoding a ferrochelatase homolog is available, gene-specific primers can be designed as outlined in Example 5. RT-PCR can be used with plant RNA to obtain a nucleic acid fragment containing the protein-coding region flanked by attB1 (SEQ ID NO:40) and attB2 (SEQ ID NO:41) sequences. The primer may contain a consensus Kozak sequence (CAACA) upstream of the start codon.

Method 2 (DNA-based): Alternatively, if a cDNA clone is available for a gene encoding a ferrochelatase homolog, the entire cDNA insert (containing 5' and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBulescript SK+, the forward primer VC062 (SEQ ID NO:46) and the reverse primer VC063 (SEQ ID NO:47) can be used.

Methods 1 and 2 can be modified according to procedures known by one skilled in the art. For example, the primers of Method 1 may contain restriction sites instead of attB1 and attB2 sites, for subsequent cloning of the PCR product into a vector containing attB1 and attB2 sites. Additionally, Method 2 can involve amplification from a cDNA clone, a lambda clone, a BAC clone or genomic DNA.

Figure 3:
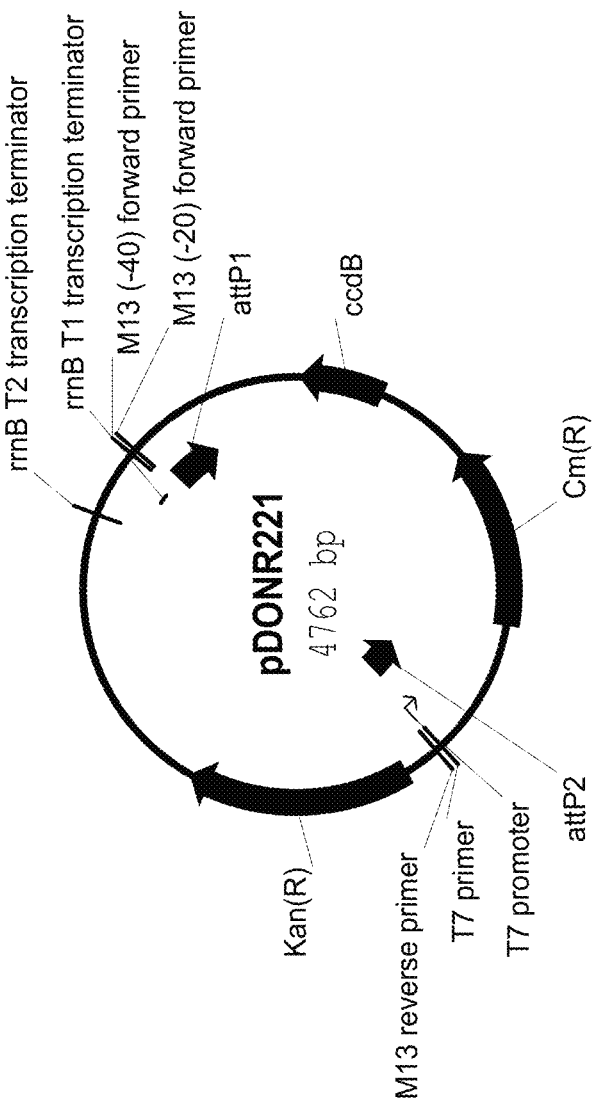
FIG. 3 shows a map of the vector pDONR™221 (SEQ ID NO:33). The attP1 site is at nucleotides 570-801; the attP2 site is at nucleotides 2754-2985 (complementary strand).

A PCR product obtained by either method above can be combined with the GATEWAY® donor vector, such as pDONR™/Zeo (INVITROGEN™; FIG. 2; SEQ ID NO:32) or pDONR™221 (INVITROGEN™; FIG. 3; SEQ ID NO:33), using a BP Recombination Reaction. This process removes the bacteria lethal ccdB gene, as well as the chloramphenicol resistance gene (CAM) from pDONR™221 and directionally clones the PCR product with flanking attB1 and attB2 sites to create an entry clone. Using the INVITROGEN™ GATEWAY® CLONASE™ technology, the sequence encoding the homologous ferrochelatase from the entry clone can then be transferred to a suitable destination vector, such as pBC-Yellow (FIG. 4; SEQ ID NO:34), PHP27840 (FIG. 5; SEQ ID NO:35) or PHP23236 (FIG. 6; SEQ ID NO:36), to obtain a plant expression vector for use with *Arabidopsis*, soybean and corn, respectively.

Figure 5:
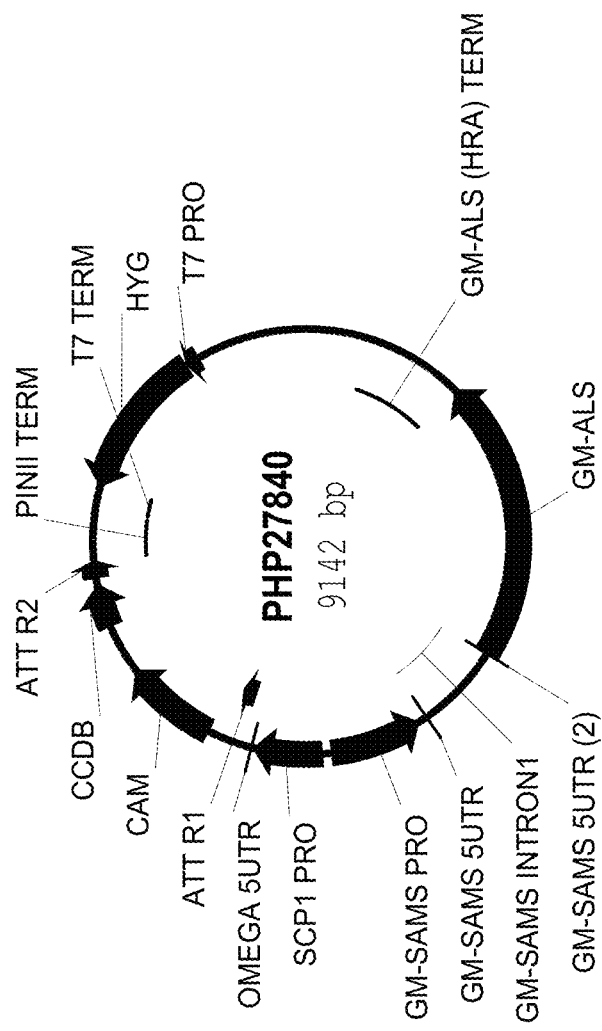
FIG. 5 shows a map of PHP27840 (SEQ ID NO:35), a destination vector for use in construction of expression vectors for soybean. The attR1 site is at nucleotides 7310-7434; the attR2 site is at nucleotides 8890-9014.
Figure 6:
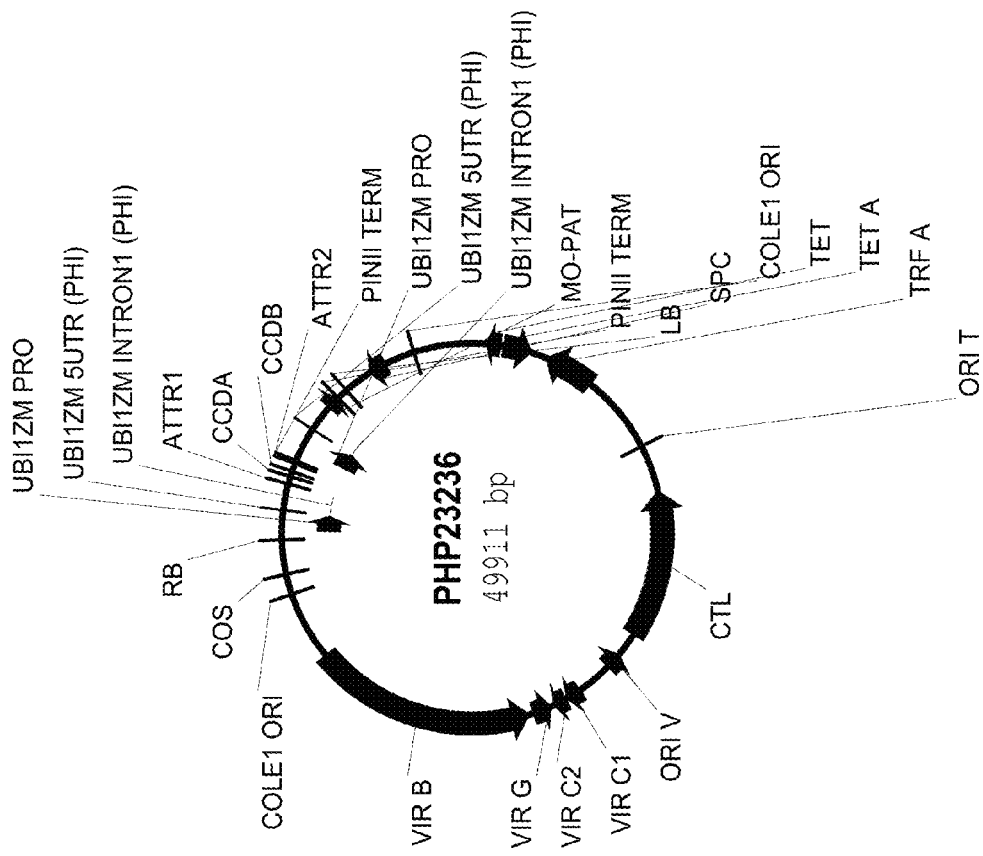
FIG. 6 shows a map of PHP23236 (SEQ ID NO:36), a destination vector for use in construction of expression vectors for Gaspe Flint derived maize lines. The attR1 site is at nucleotides 2006-2130; the attR2 site is at nucleotides 2899-3023.

The attP1 and attP2 sites of donor vectors pDONR™/Zeo or pDONR™221 are shown in FIGS. 2 and 3, respectively. The attR1 and attR2 sites of destination vectors pBC-Yellow, PHP27840 and PHP23236 are shown in FIGS. 4, 5 and 6, respectively.

Alternatively a MultiSite GATEWAY® LR recombination reaction between multiple entry clones and a suitable destination vector can be performed to create an expression vector.

Example 10

Preparation of Soybean Expression Vectors and Transformation of Soybean with Validated *Arabidopsis* Lead Genes Soybean plants can be transformed to overexpress a validated *Arabidopsis* lead gene or the corresponding homologs from various species in order to examine the resulting phenotype.

The same GATEWAY® entry clone described in Example 5 can be used to directionally clone each gene into the PHP27840 vector (SEQ ID NO:35; FIG. 5) such that expression of the gene is under control of the SCP1 promoter.

Soybean embryos may then be transformed with the expression vector comprising sequences encoding the instant polypeptides.

To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos, which produce secondary embryos, are then excised and placed into a suitable liquid medium. After repeated selection for clusters of somatic embryos which multiply as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium. Soybean embryogenic suspension cultures may then be transformed by the method of particle gun bombardment (Klein et al. (1987) *Nature* (London) 327:70-73, U.S. Pat. No. 4,945,050). A DUPONT™ BIOLISTIC™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. Another selectable marker gene which can be used to facilitate soybean transformation is an herbicide-resistant acetolactate synthase (ALS) gene from soybean or *Arabidopsis*. ALS is the first common enzyme in the biosynthesis of the branched-chain amino acids valine, leucine and isoleucine. Mutations in ALS have been identified that convey resistance to some or all of three classes of inhibitors of ALS (U.S. Pat. No. 5,013,659; the entire contents of which are herein incorporated by reference). Expression of the herbicide-resistant ALS gene can be under the control of a SAM synthetase promoter (U.S. Patent Application No. US-2003-0226166-A1; the entire contents of which are herein incorporated by reference).

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

T1 plants can be subjected to a soil-based drought stress. Using image analysis, plant area, volume, growth rate and color analysis can be taken at multiple times before and during drought stress. Overexpression constructs that result in a significant delay in wilting or leaf area reduction, yellow color accumulation and/or increased growth rate during drought stress will be considered evidence that the *Arabidopsis* gene functions in soybean to enhance drought tolerance.

Soybean plants transformed with validated genes can then be assayed under more vigorous field-based studies to study yield enhancement and/or stability under well-watered and water-limiting conditions.

Example 11

Transformation of Maize with Validated *Arabidopsis* Lead Genes Using Particle Bombardment Maize plants can be transformed to overexpress a validated *Arabidopsis* lead gene or the corresponding homologs from various species in order to examine the resulting phenotype.

The same GATEWAY® entry clone described in Example 5 can be used to directionally clone each gene into a maize transformation vector. Expression of the gene in the maize transformation vector can be under control of a constitutive promoter such as the maize ubiquitin promoter (Christensen et al., (1989) *Plant Mol. Biol.* 12:619-632 and Christensen et al., (1992) *Plant Mol. Biol.* 18:675-689)

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a KAPTON™ flying disc (Bio-Rad Labs). The particles are then accelerated into the corn tissue with a DUPONT™ BIOLISTIC™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional 2 weeks the tissue can be transferred to fresh N6 medium containing bialaphos. After 6 weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839). Transgenic T0 plants can be regenerated and their phenotype determined following high throughput ("HTP") procedures. T1 seed can be collected.

T1 plants can be subjected to a soil-based drought stress. Using image analysis, plant area, volume, growth rate and color analysis can be taken at multiple times before and during drought stress. Overexpression constructs that result in a significant delay in wilting or leaf area reduction, yellow color accumulation and/or increased growth rate during drought stress will be considered evidence that the *Arabidopsis* gene functions in maize to enhance drought tolerance.

Example 12

Electroporation of *Agrobacterium tumefaciens* LBA4404

Figure 7:
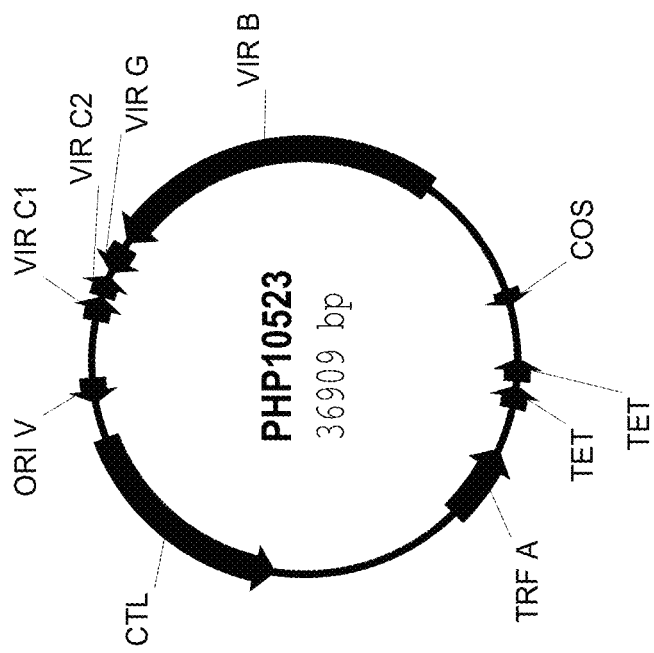
FIG. 7 shows a map of PHP10523 (SEQ ID NO:37), a plasmid DNA present in *Agrobacterium* strain LBA4404 (Komari et al., *Plant J.* 10:165-174 (1996); NCBI General Identifier No. 59797027).

Electroporation competent cells (40 4), such as *Agrobacterium tumefaciens* LBA4404 containing PHP10523 (FIG. 7; SEQ ID NO:37), are thawed on ice (20-30 min). PHP10523 contains VIR genes for T-DNA transfer, an *Agrobacterium* low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 µL parental DNA at a concentration of 0.2 µg-1.0 µg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., FALCON™ tube). The cells are incubated at 28-30° C., 200-250 rpm for 3 h.

Aliquots of 250 µL are spread onto plates containing YM medium and 50 µg/mL spectinomycin and incubated three days at 28-30° C. To increase the number of transformants one of two optional steps can be performed:

Option 1: Overlay plates with 30 µL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 µg/mL spectinomycin for isolation of single colonies. The plates are incubated at 28° C. for two to three days. A single colony for each putative co-integrate is picked and inoculated with 4 mL of 10 g/L bactopeptone, 10 g/L yeast extract, 5 g/L sodium chloride and 50 mg/L spectinomycin. The mixture is incubated for 24 h at 28° C. with shaking. Plasmid DNA from 4 mL of culture is isolated using Qiagen® Miniprep and an optional Buffer PB wash. The DNA is eluted in 30 µL. Aliquots of 2 µL are used to electroporate 20 µL of DH10b+20 µL of twice distilled $H_2O$ as per above. Optionally a 15 µL aliquot can be used to transform 75-100 µL of INVITROGEN™ Library Efficiency DH5α. The cells are spread on plates containing LB medium and 50 µg/mL spectinomycin and incubated at 37° C. overnight.

Three to four independent colonies are picked for each putative co-integrate and inoculated 4 mL of 2×YT medium (10 g/L bactopeptone, 10 g/L yeast extract, 5 g/L sodium chloride) with 50 µg/mL spectinomycin. The cells are incubated at 37° C. overnight with shaking. Next, isolate the plasmid DNA from 4 mL of culture using QIAprep® Miniprep with optional Buffer PB wash (elute in 50 4). Use 8 µL for digestion with SalI (using parental DNA and PHP10523 as controls). Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Example 13

Transformation of Maize Using *Agrobacterium*

Maize plants can be transformed to overexpress a validated *Arabidopsis* lead gene or the corresponding homologs from various species in order to examine the resulting phenotype. *Agrobacterium*-mediated transformation of maize is performed essentially as described by Zhao et al. in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-Culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 Plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:
1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplemente with 0.85 mg/L silver nitrate (filter-sterilized), 3.0 g/L Gelrite®, 100 µM acetosyringone (filter-sterilized), pH 5.8.
3. PHI-C: PHI-B without Gelrite® and acetosyringonee, reduce 2,4-D to 1.5 mg/L and supplemente with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).

5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.

6. PHI-F: PHI-E without zeatin, IAA, ABA; reduce sucrose to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

Furthermore, a recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under water limiting and water non-limiting conditions.

Subsequent yield analysis can be done to determine whether plants that contain the validated *Arabidopsis* lead gene have an improvement in yield performance (under water limiting or non-limiting conditions), when compared to the control (or reference) plants that do not contain the validated *Arabidopsis* lead gene. Specifically, water limiting conditions can be imposed during the flowering and/or grain fill period for plants that contain the validated *Arabidopsis* lead gene and the control plants. Plants containing the validated *Arabidopsis* lead gene would have less yield loss relative to the control plants, for example, at least 50% less yield loss, under water limiting conditions, or would have increased yield relative to the control plants under water non-limiting conditions.

Example 14A

Preparation of *Arabidopsis* Lead Gene (At5g26030) Expression Vector for Transformation of Maize Using INVITROGEN's™ GATEWAY® technology, an LR Recombination Reaction was performed with an entry clone (PHP31052) and a destination vector (PHP28647) to create the precursor plasmid PHP31079. The vector PHP31079 contains the following expression cassettes:

1. Ubiquitin promoter::moPAT::PinII terminator; cassette expressing the PAT herbicide resistance gene used for selection during the transformation process.

2. LTP2 promoter::DS-RED2::PinII terminator; cassette expressing the DS-RED color marker gene used for seed sorting.

3. Ubiquitin promoter::At5g26030::PinII terminator; cassette overexpressing the gene of interest, *Arabidopsis* ferrochelatase-I.

Example 14B

Transformation of Maize with the *Arabidopsis* Lead Gene (At5g26030) Using *Agrobacterium*

The ferrochelatase-I expression cassette present in vector PHP31079 can be introduced into a maize inbred line, or a transformable maize line derived from an elite maize inbred line, using *Agrobacterium*-mediated transformation as described in Examples 12 and 13.

Vector PHP31079 can be electroporated into the LBA4404 *Agrobacterium* strain containing vector PHP10523 (FIG. 7; SEQ ID NO:37) to create the co-integrate vector PHP31217. The co-integrate vector is formed by recombination of the 2 plasmids, PHP31079 and PHP10523, through the COS recombination sites contained on each vector. The co-integrate vector PHP31217 contains the same 3 expression cassettes as above (Example 14A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation.

Example 15

Figure 8:
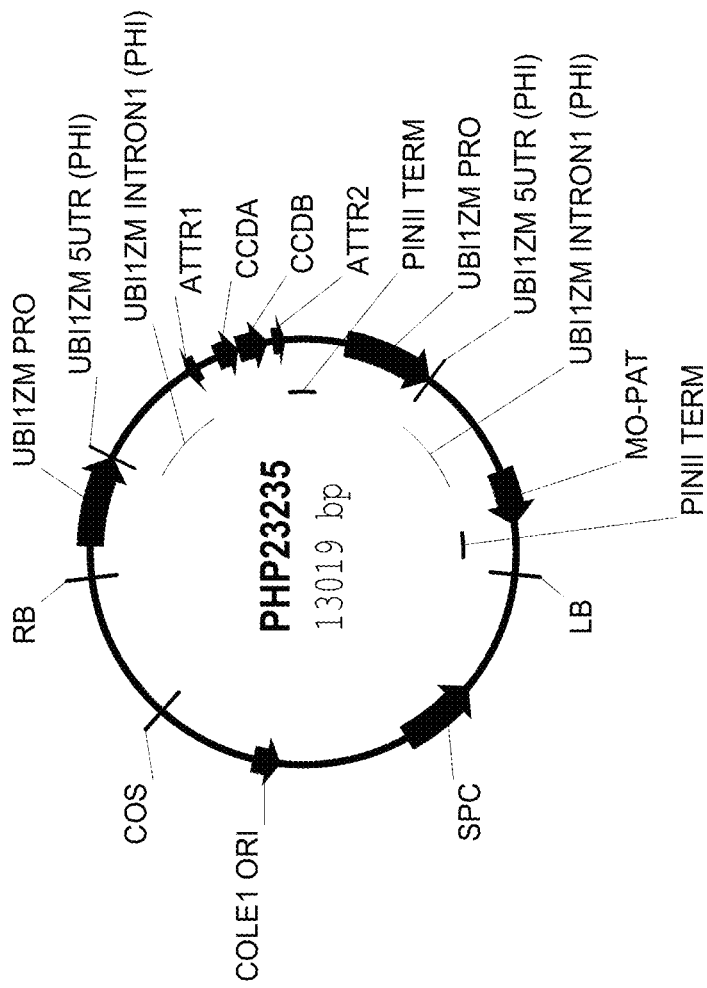
FIG. 8 shows a map of PHP23235 (SEQ ID NO:38), a vector used to construct the destination vector PHP23236.
Figure 9:
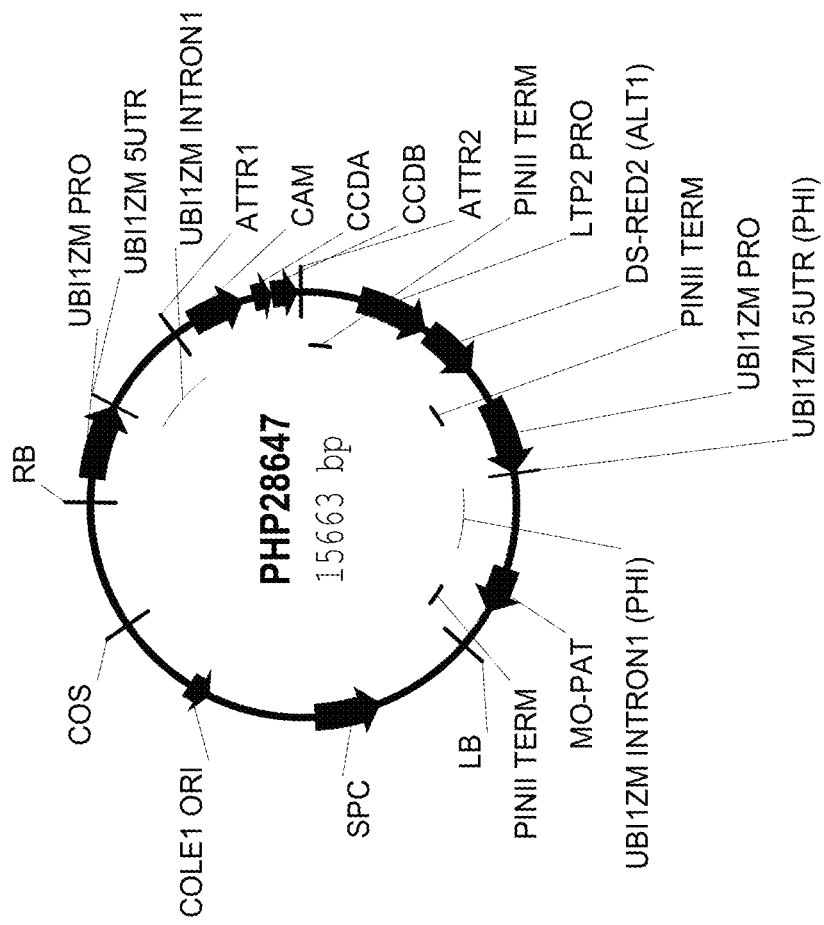
FIG. 9 shows a map of PHP28647 (SEQ ID NO:39), a destination vector for use with maize inbred-derived lines. The attR1 site is at nucleotides 2289-2413; the attR2 site is at nucleotides 3869-3993.

Preparation of the Destination Vector PHP23236 for Transformation into Gaspe Flint Derived Maize Lines Destination vector PHP23236 (FIG. 6, SEQ ID NO:36) was obtained by transformation of *Agrobacterium* strain LBA4404 containing plasmid PHP10523 (FIG. 7, SEQ ID NO:37) with plasmid PHP23235 (FIG. 8, SEQ ID NO:38) and isolation of the resulting co-integration product. Destination vector PHP23236, can be used in a recombination reaction with an entry clone as described in Example 16 to create a maize expression vector for transformation of Gaspe Flint-derived maize lines.

Example 16

Preparation of Plasmids for Transformation into Gaspe Flint Derived Maize Lines

Using the INVITROGEN™ GATEWAY® LR Recombination technology, the same entry clone described in Example 5A, PHP31052, was directionally cloned into the destination vector PHP23236 (SEQ ID NO:36; FIG. 6) to create an expression vector, PHP31419. This expression vector contains the cDNA of interest, encoding AtFeC-I, under control of the UBI promoter and is a T-DNA binary vector for *Agrobacterium*-mediated transformation into corn as described, but not limited to, the examples described herein.

Using the INVITROGEN™ GATEWAY® LR Recombination technology, the same entry clone described in Example 5B, PHP-Entry-At2g30390, was directionally cloned into the destination vector PHP29634 to create an expression vector, PHP33089. Destination vector PHP29634 is similar to destination vector PHP23236, however, destination vector PHP29634 has site-specific recombination sites FRT1 and FRT87 and also encodes the GAT4602 selectable marker protein for selection of transformants using glyphosate. This expression vector contains the cDNA of interest, encoding AtFeC-II, under control of the UBI promoter and is a T-DNA binary vector for *Agrobacterium*-mediated transformation into corn as described, but not limited to, the examples described herein.

Example 17

Transformation of Gaspe Flint Derived Maize Lines with a Validated *Arabidopsis* Lead Gene Maize plants can be transformed to overexpress the *Arabidopsis* lead gene or the corresponding homologs from other species in order to examine the resulting phenotype.

Recipient Plants:

Recipient plant cells can be from a uniform maize line having a short life cycle ("fast cycling"), a reduced size, and high transformation potential. Typical of these plant cells for maize are plant cells from any of the publicly available Gaspe Flint (GBF) line varieties. One possible candidate plant line variety is the F1 hybrid of GBF×QTM (Quick Turnaround Maize, a publicly available form of Gaspe Flint selected for growth under greenhouse conditions) disclosed in Tomes et al. U.S. Patent Application Publication No. 2003/0221212. Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line is a double haploid line of GS3 (a highly transformable line) X Gaspe Flint. Yet another suitable line is a transformable elite inbred line carrying a transgene which causes early flowering, reduced stature, or both.

Transformation Protocol:

Any suitable method may be used to introduce the transgenes into the maize cells, including but not limited to inoculation type procedures using *Agrobacterium* based vectors. Transformation may be performed on immature embryos of the recipient (target) plant.

Precision Growth and Plant Tracking:

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location with the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. Published Patent Application No. 2004/0122592, incorporated herein by reference.

Phenotypic Analysis Using Three-Dimensional Imaging:

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. A digital imaging analyzer may be used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate the biomass, size and morphology of each plant.

Due to the change in size of the plants from the time the first leaf appears from the soil to the time the plants are at the end of their development, the early stages of plant development are best documented with a higher magnification from the top. This may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation:

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture and motor focus. All camera settings may be made using LemnaTec software. For example, the instrumental variance of the imaging analyzer is less than about 5% for major components and less than about 10% for minor components.

Software:

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g. Matlab, others) can be used for quantitative interpretation of the imaging data, and any of these software systems can be applied to the image data set.

Conveyor System:

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination:

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores.

Biomass Estimation Based on Three-Dimensional Imaging:

For best estimation of biomass the plant images should be taken from at least three axes, for example, the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification:

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis:

Transgenes which modify plant architecture parameters may also be identified using the present invention, including such parameters as maximum height and width, internodal distances, angle between leaves and stem, number of leaves starting at nodes and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date:

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g. pollination date, first silk date) can be recorded by the personnel responsible for performing plant care. To maximize data integrity and process efficiency this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants:

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 18

Screening of Gaspe Flint Derived Maize Lines for Drought Tolerance

Transgenic Gaspe Flint derived maize lines containing the candidate gene can be screened for tolerance to drought stress in the following manner.

Transgenic maize plants are subjected to well-watered conditions (control) and to drought-stressed conditions. Transgenic maize plants are screened at the T1 stage or later.

Stress is imposed starting at 10 to 14 days after sowing (DAS) or 7 days after transplanting, and is continued through to silking. Pots are watered by an automated system fitted to timers to provide watering at 25 or 50% of field capacity during the entire period of drought-stress treatment. The intensity and duration of this stress will allow identification of the impact on vegetative growth as well as on the anthesis-silking interval.

Potting Mixture:

A mixture of ⅓ TURFACE® (Profile Products LLC, IL, USA), ⅓ sand and ⅓ SB300 (Sun Gro Horticulture, WA, USA) can be used. The SB300 can be replaced with Fafard Fine-Germ (Conrad Fafard, Inc., MA, USA) and the proportion of sand in the mixture can be reduced. Thus, a final potting mixture can be ⅜ (37.5%) TURFACE®, ⅜ (37.5%) Fafard and ¼ (25%) sand.

Field Capacity Determination:

The weight of the soil mixture (w1) to be used in one S200 pot (minus the pot weight) is measured. If all components of the soil mix are not dry, the soil is dried at 100° C. to constant weight before determining w1. The soil in the pot is watered to full saturation and all the gravitational water is allowed to drain out. The weight of the soil (w2) after all gravitational water has seeped out (minus the pot weight) is determined. Field capacity is the weight of the water remaining in the soil obtained as w2-w1. It can be written as a percentage of the oven-dry soil weight.

Stress Treatment:

During the early part of plant growth (10 DAS to 21 DAS), the well-watered control has a daily watering of 75% field capacity and the drought-stress treatment has a daily watering of 25% field capacity, both as a single daily dose at or around 10 AM. As the plants grow bigger, by 21 DAS, it will become necessary to increase the daily watering of the well-watered control to full field capacity and the drought stress treatment to 50% field capacity.

Nutrient Solution:

A modified Hoagland's solution at 1/16 dilution with tap water is used for irrigation.

TABLE 8

Preparation of 20 L of Modified Hoagland's Solution Using the Following Recipe:

| Component | Amount/20 L |
|---|---|
| 10X Micronutrient Solution | 16 mL |
| KH$_2$PO$_4$ (MW: 136.02) | 22 g |
| MgSO$_4$ (MW: 120.36) | 77 g |
| KNO$_3$ (MW: 101.2) | 129.5 g |
| Ca(NO$_3$)$_2$•4H$_2$0 (MW: 236.15) | 151 g |
| NH$_4$NO$_3$ (MW: 80.04) | 25.6 g |
| Sprint 330 (Iron chelate) | 32 g |

TABLE 9

Preparation of 1 L of 10X Micronutrient Solution Using the Following Recipe:

| Component | mg/L | Concentration |
|---|---|---|
| H$_3$BO$_3$ | 1854 | 30 mM |
| MnCl$_2$•4H$_2$0 | 1980 | 10 mM |
| ZnSO$_4$•7H$_2$0 | 2874 | 10 mM |
| CuSO$_4$•5H$_2$0 | 250 | 1 mM |
| H$_2$MoO$_4$•H$_2$0 | 242 | 1 mM |

Fertilizer grade KNO$_3$ is used.

It is useful to add half a teaspoon of OSMOCOTE® (NPK 15:9:12) to the pot at the time of transplanting or after emergence (The Scotts Miracle-Gro Company, OH, USA).

Border Plants:

Place a row of border plants on bench-edges adjacent to the glass walls of the greenhouse or adjacent to other potential causes of microenvironment variability such as a cooler fan.

Automation:

Watering can be done using PVC pipes with drilled holes to supply water to systematically positioned pots using a siphoning device. Irrigation scheduling can be done using timers.

Statistical Analysis:

Mean values for plant size, color and chlorophyll fluorescence recorded on transgenic events under different stress treatments will be exported to Spotfire (Spotfire, Inc., MA, USA). Treatment means will be evaluated for differences using Analysis of Variance.

Replications:

Eight to ten individual plants are used per treatment per event.

Observations Made:

Lemnatec measurements are made three times a week throughout growth to capture plant-growth rate. Leaf color determinations are made three times a week throughout the stress period using Lemnatec. Chlorophyll fluorescence is recorded as PhiPSII (which is indicative of the operating quantum efficiency of photosystem II photochemistry) and Fv'/Fm' (which is the maximum efficiency of photosystem II) two to four times during the experimental period, starting at 11 AM on the measurement days, using the Hansatech FMS2 instrument (LemnaTec GmbH, Wurselen, Germany). Measurements are started during the stress period at the beginning of visible drought stress symptoms, namely, leaf greying and the start of leaf rolling until the end of the experiment and measurements are recorded on the youngest most fully expanded leaf. The dates of tasseling and silking on individual plants are recorded, and the ASI is computed.

The above methods may be used to select transgenic plants with increased drought tolerance when compared to a control plant not comprising said recombinant DNA construct.

Example 19

Yield Analysis of Maize Lines with the *Arabidopsis* Lead Gene

A recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under well-watered and water-limiting conditions.

Subsequent yield analysis can be done to determine whether plants that contain the validated *Arabidopsis* lead gene have an improvement in yield performance under water-limiting conditions, when compared to the control plants that do not contain the validated *Arabidopsis* lead gene. Specifically, drought conditions can be imposed during the flowering and/or grain fill period for plants that contain the validated *Arabidopsis* lead gene and the control plants. Reduction in yield can be measured for both. Plants containing the validated *Arabidopsis* lead gene have less yield loss relative to the control plants, for example, at least 50% less yield loss.

The above method may be used to select transgenic plants with increased yield, under water-limiting conditions and/or well-watered conditions, when compared to a control plant not comprising said recombinant DNA construct.

Example 20A

Preparation of Maize Ferrochelatase-I Lead Gene Expression Vector for Transformation of Maize Clone cfp5n.pk009.j16 encodes a maize ferrochelatase-I protein designated "ZmFeC-Ia" (SEQ ID NO:10). The protein-coding region of clone cfp5n.pk009.j16 was introduced into the INVITROGEN™ vector pENTR/D-TOPO® to create entry clone PHP30949 (SEQ ID NO:55).

Using INVITROGEN's™ GATEWAY® technology, an LR Recombination Reaction was performed with an entry clone (PHP30949) and a destination vector (PHP28647) to create the precursor plasmid PHP30963. The vector PHP30963 contains the following expression cassettes:

1. Ubiquitin promoter::moPAT::PinII terminator; cassette expressing the PAT herbicide resistance gene used for selection during the transformation process.

2. LTP2 promoter::DS-RED2::PinII terminator; cassette expressing the DS-RED color marker gene used for seed sorting.

3. Ubiquitin promoter::ZmFeC-Ia::PinII terminator; cassette overexpressing the gene of interest, maize ferrochelatase-I.

Example 20B

Transformation of Maize with Maize Ferrochelatase-I Lead Gene Using *Agrobacterium*

The ZmFeC-Ia expression cassette present in vector PHP30963 can be introduced into a maize inbred line, or a transformable maize line derived from an elite maize inbred line, using *Agrobacterium*-mediated transformation as described in Examples 12 and 13.

Vector PHP30963 can be electroporated into the LBA4404 *Agrobacterium* strain containing vector PHP10523 (FIG. 7; SEQ ID NO:37) to create the co-integrate vector PHP30976. The co-integrate vector is formed by recombination of the 2 plasmids, PHP30963 and PHP10523, through the COS recombination sites contained on each vector. The co-integrate vector PHP30976 contains the same 3 expression cassettes as above (Example 14A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation.

Example 21

Preparation of Maize Expression Plasmids for Transformation into Gaspe Flint Derived Maize Lines Clone cfp5n.pk009.j16 encodes a complete maize ferrochelatase-I homolog designated "ZmFeC-Ia" (SEQ ID NO:10). Clone cfp3n.pk004.f12 encodes a different complete maize ferrochelatase-I homolog designated "ZmFeC-Ib" (SEQ ID NO:8). Clone cfp5n.pk064.n7 also encodes the ZmFeC-Ib protein (SEQ ID NO:8), however the nucleotide sequence of cfp5n.pk064.n7 (SEQ ID NO:56) differs from the nucleotide sequence of cfp3n.pk004.f12 (SEQ ID NO:7) in that it contains a 12 base pair insertion in the 5'-UTR, 8 nucleotides before the ATG start codon.

Using the INVITROGEN™ GATEWAY® Recombination technology described in Example 9, the three clones encoding maize ferrochelatase-I homologs were directionally cloned into the destination vector PHP23236 (SEQ ID NO:36; FIG. 6) to create the expression vectors listed in Table 10. Each expression vector contains the cDNA of interest under control of the UBI promoter and is a T-DNA binary vector for *Agrobacterium*-mediated transformation into corn as described, but not limited to, the examples described herein.

TABLE 10

Maize Ferrochelatase-I Expression Vectors

| Protein | Clone Origin | SEQ ID NO: (Amino Acid) | Expression Vector |
|---------|--------------|--------------------------|-------------------|
| ZmFeC-Ia | cfp5n.pk009.j16 (FIS) | 10 | PHP30829 |
| ZmFeC-Ib | cfp3n.pk004.f12 (FIS) | 8 | PHP30745 |
| ZmFeC-Ib | cfp5n.pk064.n7 (FIS) | 8 | PHP30761 |

Example 22

Transformation and Evaluation of Gaspe Flint Derived Maize Lines for Drought Tolerance Gaspe Flint derived maize lines were transformed via *Agrobacterium* using the following plasmid DNAs: PHP31419 (AtFeC-I; At5g26030); PHP33089 (AtFeC-II; At2g30390); PHP30829 (ZmFeC-Ia; cfp5n.pk009.j16); PHP30745 (ZmFeC-Ib; cfp3n.pk004.f12) and PHP30761 (ZmFeC-Ib; cfp5n.pk064.n7). Four transformation events for each plasmid construct were evaluated for drought tolerance in the following manner. For plant growth, the soil mixture consisted of ⅓ TURFACE®, ⅓ SB300 and ⅓ sand. All pots were filled with the same amount of soil±10 grams. Pots were brought up to 100% field capacity ("FC") by hand watering. All plants were maintained at 60% FC using a 20-10-20 (N-P-K) 125 ppm N nutrient solution. Throughout the experiment pH was monitored at least three times weekly for each table. Starting at 13 days after planting (DAP), the experiment was divided into two treatment groups, well watered and reduce watered. All plants comprising the reduced watered treatment were maintained at 40% FC while plants in the well watered treatment were maintained at 80% FC. Reduced watered plants were grown for 10 days under chronic drought stress conditions (40% FC). All plants were imaged daily throughout chronic stress period. Plants were sampled for metabolic profiling analyses at the end of chronic drought period, 22 DAP. At the conclusion of the chronic stress period all plants were imaged and measured for chlorophyll fluorescence. Reduced watered plants were subjected to a severe drought stress period followed by a recovery period, 23-31 DAP and 32-34 DAP respectively. During the severe drought stress, water and nutrients were withheld until the plants reached 8% FC. At the conclusion of severe stress and recovery periods all plants were again imaged and measured for chlorophyll fluorescence. The probability of a greater Student's t Test was calculated for each transgenic mean compared to the appropriate null mean (either segregant null or construct null). A minimum (P<t) of 0.1 was used as a cut off for a statistically significant result.

Tables 11-20 show the variables for each transgenic event that were significantly altered, as compared to the segregant nulls. A "positive effect" was defined as statistically significant improvement in that variable for the transgenic event relative to the null control. A "negative effect" was defined as a statistically significant improvement in that variable for the null control relative to the transgenic event. Tables 11, 13, 15, 17, and 19 present the number of variable with a significant change for individual events transformed with each of the five plasmid DNA constructs. Tables 12, 14, 16, 18 and 20 present the number of events for each construct that showed a significant change for each individual variable.

TABLE 11

Number of Variables with a Significant Change* for Individual Events Transformed with PHP31419 Encoding AtFeC-I (At5g26030)

| | Reduced Water | | Well Watered | |
|---|---|---|---|---|
| Event | Positive Effect | Negative Effect | Positive Effect | Negative Effect |
| EA2392.498.1.2 | 2 | 1 | 4 | 0 |
| EA2392.498.1.3 | 3 | 1 | 1 | 3 |
| EA2392.498.1.5 | 0 | 0 | 3 | 0 |
| EA2392.498.1.6 | 12 | 0 | 3 | 0 |

*P-value less than or equal to 0.1

TABLE 12

Number of Events Transformed with PHP31419 Encoding AtFeC-I (At5g26030) with a Significant Change* for Individual Variables

| | Reduced Water | | Well Watered | |
|---|---|---|---|---|
| Variable | Positive Effect | Negative Effect | Positive Effect | Negative Effect |
| % area chg__start chronic - acute2 | 1 | 0 | 1 | 0 |
| % area chg__start chronic - end chronic | 1 | 0 | 2 | 0 |
| % area chg__start chronic - harvest | 1 | 0 | 1 | 0 |
| % area chg__start chronic - recovery24hr | 1 | 0 | 1 | 1 |
| fv/fm__acute1 | 2 | 0 | 2 | 0 |
| fv/fm__acute2 | 1 | 0 | 1 | 0 |
| leaf rolling__harvest | 2 | 0 | 0 | 0 |
| leaf rolling__recovery24hr | 2 | 0 | 1 | 0 |
| psii__acute1 | 2 | 0 | 2 | 0 |
| psii__acute2 | 1 | 0 | 0 | 0 |
| sgr - r2 > 0.9 | 2 | 0 | 0 | 0 |
| shoot dry weight | 0 | 1 | 0 | 1 |
| shoot fresh weight | 1 | 1 | 0 | 1 |

*P-value less than or equal to 0.1

TABLE 13

Number of Variables with a Significant Change* for Individual Events Transformed with PHP33089 Encoding AtFeC-II (At2g30390)

| | Reduced Water | | Well Watered | |
|---|---|---|---|---|
| Event | Positive Effect | Negative Effect | Positive Effect | Negative Effect |
| EA2534.088.2.2 | 0 | 3 | 1 | 0 |
| EA2534.088.2.4 | 3 | 1 | 2 | 2 |
| EA2534.088.2.5 | 6 | 0 | 2 | 2 |
| EA2534.088.2.8 | 1 | 3 | 0 | 2 |

*P-value less than or equal to 0.1

TABLE 14

Number of Events Transformed with PHP33089 Encoding AtFeC-II (At2g30390) with a Significant Change* for Individual Variables

| | Reduced Water | | Well Watered | |
|---|---|---|---|---|
| Variable | Positive Effect | Negative Effect | Positive Effect | Negative Effect |
| % area chg__start chronic - end chronic | 2 | 0 | 1 | 0 |
| % area chg__start chronic - end severe | 1 | 2 | 0 | 0 |
| % area chg__start chronic - recovery48hr | 0 | 1 | 0 | 0 |
| fv/fm__end severe | 1 | 2 | 1 | 0 |
| fv/fm__recovery48hr | 1 | 0 | 0 | 1 |
| fv/fm__start severe | 1 | 0 | 0 | 0 |
| leaf rolling__recovery24hr | 0 | 0 | 1 | 1 |
| psii__end severe | 1 | 2 | 1 | 0 |
| psii__recovery48hr | 1 | 0 | 0 | 2 |
| psii__start severe | 1 | 0 | 1 | 2 |
| sgr - r2 > 0.9 | 0 | 0 | 0 | 0 |
| shoot dry weight | 1 | 0 | 0 | 0 |
| shoot fresh weight | 0 | 0 | 0 | 0 |

*P-value less than or equal to 0.1

TABLE 15

Number of Variables with a Significant Change* for Individual Events Transformed with PHP30829 Encoding MzFeC-Ia (cfp5n.pk009.j16)

| | Reduced Water | | Well Watered | |
|---|---|---|---|---|
| Event | Positive Effect | Negative Effect | Positive Effect | Negative Effect |
| EA2391.472.1.10 | 0 | 5 | 3 | 3 |
| EA2391.472.1.2 | 0 | 2 | 6 | 1 |
| EA2391.472.1.3 | 0 | 4 | 2 | 0 |
| EA2391.472.1.4 | 2 | 2 | 3 | 0 |

*P-value less than or equal to 0.1

TABLE 16

Number of Events Transformed with PHP30829 Encoding MzFeC-Ia (cfp5n.pk009.j16) with a Significant Change* for Individual Variables

| | Reduced Water | | Well Watered | |
|---|---|---|---|---|
| Variable | Positive Effect | Negative Effect | Positive Effect | Negative Effect |
| % area chg__start chronic - end chronic | 0 | 2 | 0 | 0 |
| % area chg__start chronic - harvest | 0 | 1 | 3 | 0 |

TABLE 16-continued

Number of Events Transformed with PHP30829 Encoding MzFeC-Ia (cfp5n.pk009.j16) with a Significant Change* for Individual Variables

| Variable | Reduced Water | | Well Watered | |
|---|---|---|---|---|
| | Positive Effect | Negative Effect | Positive Effect | Negative Effect |
| % area chg_start chronic - recovery24hr | 0 | 0 | 0 | 0 |
| % area chg_start chronic - recovery48hr | 0 | 1 | 0 | 0 |
| fv/fm_acute1 | 0 | 0 | 2 | 1 |
| fv/fm_acute2 | 1 | 1 | 2 | 0 |
| leaf rolling_recovery24hr | 0 | 1 | 1 | 0 |
| leaf rolling_recovery48hr | 0 | 2 | 1 | 0 |
| psii_acute1 | 0 | 0 | 2 | 1 |
| psii_acute2 | 1 | 1 | 1 | 1 |
| sgr - r2 > 0.9 | 0 | 2 | 1 | 0 |
| shoot dry weight | 0 | 1 | 0 | 1 |
| shoot fresh weight | 0 | 1 | 1 | 0 |

*P-value less than or equal to 0.1

TABLE 17

Number of Variables with a Significant Change* for Individual Events Transformed with PHP30745 Encoding MzFeC-Ib (cfp3n.pk004.f12)

| Event | Reduced Water | | Well Watered | |
|---|---|---|---|---|
| | Positive Effect | Negative Effect | Positive Effect | Negative Effect |
| EA2392.447.1.1 | 4 | 1 | 4 | 0 |
| EA2392.447.1.3 | 0 | 3 | 2 | 7 |
| EA2392.447.1.5 | 0 | 0 | 2 | 1 |
| EA2392.447.1.9 | 2 | 4 | 4 | 1 |

*P-value less than or equal to 0.1

TABLE 18

Number of Events Transformed with PHP30745 Encoding MzFeC-Ib (cfp3n.pk004.f12) with a Significant Change* for Individual Variables

| Variable | Reduced Water | | Well Watered | |
|---|---|---|---|---|
| | Positive Effect | Negative Effect | Positive Effect | Negative Effect |
| % area chg_start chronic - end chronic | 1 | 0 | 3 | 1 |
| % area chg_start chronic - end severe | 0 | 0 | 2 | 1 |
| % area chg_start chronic - recovery48hr | 0 | 0 | 2 | 1 |
| fv/fm_end severe | 2 | 0 | 0 | 0 |
| fv/fm_recovery48hr | 1 | 1 | 0 | 1 |
| fv/fm_start severe | 0 | 1 | 0 | 1 |
| leaf rolling_recovery48hr | 0 | 0 | 0 | 0 |
| psii_end severe | 0 | 0 | 0 | 0 |
| psii_recovery48hr | 0 | 1 | 1 | 2 |
| psii_start severe | 0 | 2 | 0 | 1 |
| shoot dry weight | 2 | 0 | 2 | 1 |
| shoot fresh weight | 2 | 1 | 2 | 0 |

*P-value less than or equal to 0.1

TABLE 19

Number of Variables with a Significant Change* for Individual Events Transformed with PHP30761 Encoding MzFeC-Ib (cfp5n.pk064.n7)

| Event | Reduced Water | | Well Watered | |
|---|---|---|---|---|
| | Positive Effect | Negative Effect | Positive Effect | Negative Effect |
| EA2392.441.1.1 | 0 | 0 | 0 | 1 |
| EA2392.441.1.2 | 0 | 0 | 2 | 0 |
| EA2392.441.1.4 | 5 | 0 | 7 | 3 |
| EA2392.441.1.7 | 5 | 3 | 0 | 0 |

*P-value less than or equal to 0.1

TABLE 20

Number of Events Transformed with PHP30761 Encoding MzFeC-Ib (cfp5n.pk064.n7) with a Significant Change* for Individual Variables

| Variable | Reduced Water | | Well Watered | |
|---|---|---|---|---|
| | Positive Effect | Negative Effect | Positive Effect | Negative Effect |
| % area chg_start chronic - end chronic | 0 | 1 | 0 | 1 |
| % area chg_start chronic - end severe | 0 | 1 | 0 | 0 |
| % area chg_start chronic - recovery48hr | 0 | 0 | 0 | 0 |
| fv/fm_end severe | 2 | 0 | 1 | 0 |
| fv/fm_recovery48hr | 2 | 0 | 1 | 0 |
| fv/fm_start severe | 0 | 0 | 2 | 0 |
| leaf rolling_recovery48hr | 1 | 0 | 1 | 0 |
| psii_end severe | 2 | 0 | 1 | 0 |
| psii_recovery48hr | 2 | 0 | 1 | 0 |
| psii_start severe | 1 | 0 | 1 | 0 |
| sgr - r2 > 0.9 | 0 | 0 | 0 | 1 |
| shoot dry weight | 0 | 1 | 1 | 2 |
| shoot fresh weight | 0 | 0 | 0 | 0 |

*P-value less than or equal to 0.1

For each of the five constructs evaluated, the statistical value associated with each improved variable is presented in FIGS. 14A-23. A significant positive result had a P-value of less than or equal to 0.1. The results for individual transformed maize lines are presented in FIGS. 14A-14B, 16A-16B, 18A-18B, 20A-20B and 22A-22B. The summary evaluations for each of the five constructs are presented in FIGS. 15, 17, 19, 21, and 23.

Example 23

Screening of Inbred Derived Maize Lines for Drought Tolerance

A transformable maize line derived from an elite maize inbred line was transformed with PHP30829 which encodes the maize ferrochelatase-I protein, MzFeC-1a (SEQ ID NO:10). Seed of transgenic events from the PHP30829 transformation were separated into transgenic and null seed using a seed color marker. The Fv'/Fm' and Phi PSII data were collected from a drought seedling assay following a procedure similar to the one described in Example 18 with the following modifications: an elite maize hybrid seedling was used for the assay instead of a Gaspe Flint derived maize line; and the chlorophyll fluorescence data were collected only during recovery from moderate drought stress (or chronic drought stress). The experiment was designed and analyzed as a Randomized Complete Block Design with the events including the construct null as treatments. A number of individual events were found to have higher Fv'/Fm' and/or Phi PSII values during drought stress relative to the null segregant control. The data is presented in the Table below.

TABLE 21

Fv'/Fm' and Phi PSII Values For Individual Events Transformed
With PHP30829 Encoding MzFeC-Ia (cfp5n.pk009.j16)

| Event | Fv'/Fm' | Phi PSII |
|---|---|---|
| E7733.78.1.1 | 0.421 | 0.330[a] |
| E7733.78.1.2 | 0.462 | 0.407[a] |
| E7733.78.2.20 | 0.520[a] | 0.420[a] |
| E7733.78.4.1 | 0.428 | 0.339[a] |
| E7733.78.2.10 | 0.475[a] | 0.398[a] |
| E7733.78.2.2 | 0.360[b] | 0.284 |
| E7733.78.2.6 | 0.373[b] | 0.289 |
| E7733.78.2.7 | 0.469[a] | 0.392[a] |
| 30976-CN[c] | 0.392 | 0.314 |

[a]Positive and statistically significant at the 0.1 level of confidence
[b]Negative and statistically significant at the 0.1 level of confidence
[c]Null segregant used as a control Example 24

Transformation and Evaluation of Soybean with Soybean Homologs of Validated Lead Genes Based on homology searches, one or several candidate soybean homologs of validated *Arabidopsis* lead genes can be identified and also be assessed for their ability to enhance drought tolerance in soybean. Vector construction, plant transformation and phenotypic analysis will be similar to that in previously described Examples.

Example 25

Transformation of *Arabidopsis* with Maize and Soybean Homologs of Validated Lead Genes Soybean and maize homologs to validated *Arabidopsis* lead genes can be transformed into *Arabidopsis* under control of the 35S promoter and assessed for their ability to enhance drought tolerance in *Arabidopsis*. Vector construction, plant transformation and phenotypic analysis will be similar to that in previously described Examples.

What is claimed is:

1. A recombinant DNA construct comprising a polynucleotide operably linked to at least one heterologous regulatory sequence, wherein the polynucleotide comprises:

(a) a nucleotide sequence encoding a polypeptide with ferrochelatase activity, wherein the polypeptide has an amino acid sequence of at least 92% sequence identity, based on the Clustal V method of alignment with pairwise alignment default parameters of KTUPLE=1, GAP PENALTY=3, WINDOW=5 and DIAGONALS SAVED=5, when compared to SEQ ID NO:24; or (b) the full complement of the nucleotide sequence of (a).

2. The recombinant DNA construct of claim 1, wherein the polypeptide has an amino acid sequence of at least 95% sequence identity, based on the Clustal V method of alignment with the pairwise alignment default parameters, when compared to SEQ ID NO:24.

3. The recombinant DNA construct of claim 1, wherein the amino acid sequence of the polypeptide comprises SEQ ID NO:24.

4. The recombinant DNA construct of claim 1 wherein the nucleotide sequence comprises SEQ ID NO:23.

5. A vector comprising the recombinant DNA construct of claim 1.

6. A cell comprising the recombinant DNA construct of claim 1, wherein the cell is selected from the group consisting of: a bacterial cell, a yeast cell, an insect cell and a plant cell.

7. A plant or seed comprising the recombinant DNA construct of claim 1.

8. The plant or seed of claim 7, wherein the plant or seed is selected from the group consisting of: maize, soybean, sunflower, sorghum, canola, wheat, alfalfa, cotton, rice, barley and millet.

* * * * *